US008026241B2

(12) United States Patent
Balan et al.

(10) Patent No.: US 8,026,241 B2
(45) Date of Patent: Sep. 27, 2011

(54) VANILLOID RECEPTOR LIGANDS AND THEIR USE IN TREATMENTS

(75) Inventors: Chenera Balan, Thousand Oaks, CA (US); Yunxin Bo, Thousand Oaks, CA (US); Celia Dominguez, Thousand Oaks, CA (US); Christopher H. Fotsch, Thousand Oaks, CA (US); Vijay K. Gore, Thousand Oaks, CA (US); Vu Van Ma, Simi Valley, CA (US); Mark H. Norman, Thousand Oaks, CA (US); Vassil I. Ognyanov, Thousand Oaks, CA (US); Yi-xin Qian, Thousand Oaks, CA (US); Xianghong Wang, Moorpark, CA (US); Ning Xi, Thousand Oaks, CA (US); Shimin Xu, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 177 days.

(21) Appl. No.: 12/367,352

(22) Filed: Feb. 6, 2009

(65) Prior Publication Data
US 2009/0143575 A1 Jun. 4, 2009

Related U.S. Application Data

(63) Continuation of application No. 10/688,246, filed on Oct. 16, 2003, now Pat. No. 7,582,761.

(60) Provisional application No. 60/419,791, filed on Oct. 17, 2002.

(51) Int. Cl.
*A61K 31/497* (2006.01)
*C07D 403/04* (2006.01)
*C07D 401/04* (2006.01)

(52) U.S. Cl. .......... 514/252.19; 514/254.06; 514/253.1; 544/295; 544/360; 544/370

(58) Field of Classification Search .............. 544/295, 544/360, 370; 514/252.19, 253.1, 254.06
See application file for complete search history.

(56) References Cited

U.S. PATENT DOCUMENTS
4,093,726 A * 6/1978 Winn et al. .............. 514/254.06

FOREIGN PATENT DOCUMENTS

| CA | 2 319 824 | * 5/1999 |
|---|---|---|
| WO | WO 03/004023 | 1/2003 |
| WO | WO 03/006438 | 1/2003 |
| WO | WO 03/066595 | 8/2003 |

OTHER PUBLICATIONS

Hori et al., Design and Syntheses of a series of novel serotonin S3 antagonists; Chemical and Pharmaceutical Bulletin (1993), 41(10), pp. 1832-1841. (Abstrac).*
Valenzano, et al., N-(4-Tertiarybutylphenyl)-4-(3-chloropyridin-2-yl)tetrahydropyrazine-1(2H)-carbox-amide (BCTC), a Novel,Orally Effective Vanilloid Receptor 1 Antagonist with Analgesic Properties: I. In Vitro Characterization and Pharmacokinetic Properties, JPET, 306: 377-386 (2003).
Pomonis, et al., N-(4-Tertiarybutylphenyl)-4-(3-cholorphyridin-2-yl)tetrahydropyrazine-1(2H)-carbox-amide (BCTC), a Novel, Orally Effective Vanilloid Receptor 1 Antagonist with Analgesic Properties: II. In Vivo Characterization in Rat Models of Inflammatory and Neuropathic Pain, JPET, 306: 387-393 (2003).

* cited by examiner

*Primary Examiner* — James O Wilson
*Assistant Examiner* — Ebenezer O Sackey
(74) *Attorney, Agent, or Firm* — Richard V. Person

(57) ABSTRACT

Therapeutic benzimidazoles and compositions containing them, for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotizing agents, hair growth, vasomotor or allergic rhinitis, bronchial disorders or bladder disorders.

17 Claims, No Drawings

VANILLOID RECEPTOR LIGANDS AND THEIR USE IN TREATMENTS

This application is a continuation of application Ser. No. 10/688,246, filed on Oct. 16, 2003 now U.S. Pat. No. 7,582,761, which claims the benefit of U.S. Provisional Application No. 60/419,791, filed Oct. 17, 2002, which are hereby incorporated by reference.

BACKGROUND

The vanilloid receptor 1 (VR1) is the molecular target of capsaicin, the active ingredient in hot peppers. Julius et al. reported the molecular cloning of VR1 (Caterina et al., 1997). VR1 is a non-selective cation channel which is activated or sensitized by a series of different stimuli including capsaicin and resiniferatoxin (exogenous activators), heat & acid stimulation and products of lipid bilayer metabolism, anandamide (Premkumar et al., 2000, Szabo et al., 2000, Gauldie et al., 2001, Olah et al., 2001) and lipoxygenase metabolites (Hwang et al., 2000). VR1 is highly expressed in primary sensory neurons (Caterina et al., 1997) in rats, mice and humans (Onozawa et al., 2000, Mezey et al., 2000, Helliwell et al., 1998, Cortright et al., 2001). These sensory neurons innervate many visceral organs including the dermis, bones, bladder, gastrointestinal tract and lungs; VR1 is also expressed in other neuronal and non-neuronal tissues including but not limited to, CNS nuclei, kidney, stomach and T-cells (Nozawa et al., 2001, Yiangou et al., 2001, Birder et al., 2001). Presumably expression in these various cells and organs may contribute to their basic properties such as cellular signaling and cell division.

Prior to the molecular cloning of VR1, experimentation with capsaicin indicated the presence of a capsaicin sensitive receptor, which could increase the activity of sensory neurons in humans, rats and mice (Holzer, 1991; Dray, 1992, Szallasi and Blumberg 1996, 1999). The results of acute activation by capsaicin in humans was pain at injection site and in other species increased behavioral sensitivity to sensory stimuli (Szallasi and Blumberg, 1999). Capsaicin application to the skin in humans causes a painful reaction characterized not only by the perception of heat and pain at the site of administration but also by a wider area of hyperalgesia and allodynia, two characteristic symptoms of the human condition of neuropathic pain (Holzer, 1991). Taken together, it seems likely that increased activity of VR1 plays a significant role in the establishment and maintenance of pain conditions. Topical or intradermal injection of capsaicin has also been shown to produce localized vasodilation and edema production (Szallasi and Blumberg 1999, Singh et al., 2001). This evidence indicates that capsaicin through it's activation of VR1 can regulate afferent and efferent function of sensory nerves. Sensory nerve involvement in diseases could therefore be modified by molecules which effect the function of the vanilloid receptor to increase or decrease the activity of sensory nerves.

VR1 gene knockout mice have been shown to have reduced sensory sensitivity to thermal and acid stimuli (Caterina et al., 2000)). This supports the concept that VR1 contributes not only to generation of pain responses (i.e. via thermal, acid or capsaicin stimuli) but also to the maintenance of basal activity of sensory nerves. This evidence agrees with studies demonstrating capsaicin sensitive nerve involvement in disease. Primary sensory nerves in humans and other species can be made inactive by continued capsaicin stimulation. This paradigm causes receptor activation induced desensitization of the primary sensory nerve—such reduction in sensory nerve activity in vivo makes subjects less sensitive to subsequent painful stimuli. In this regard both capsaicin and resinferatoxin (exogenous activators of VR1), produce desensitization and they have been used for many proof of concept studies in in vivo models of disease (Holzer, 1991, Dray 1992, Szallasi and Blumberg 1999).

BIBLIOGRAPHY

Birder-L A. Kanai-A J. de-Groat-W C. Kiss-S, Nealen-M L. Burke-N E. Dineley-K E. Watkins-S. Reynolds-I J. Caterina-M J. (2001) Vanilloid receptor expression suggests a sensory role for urinary bladder epithelial cells. PNAS 98: 23: 13396-13401.

Caterina, M. J., Schumacher, M. A., Tominaga, M., Rosen, T. A., Levine, J. D., and Julius, D, (1997). The capsaicin receptor: a heat-activated ion channel in the pain pathway. Nature 389: 816-824.

Caterina-M J. Leffler-A. Malmberg-A B. Martin-W J. Trafton-J. Petersen-Zeitz K R. Koltzenburg-M. Basbaum-A I. Julius-D (2000) Impaired nociception and pain sensation in mice lacking the capsaicin receptor. Science- (WASH-DC). 288: 5464: 306-313.

Cortright-D N. Crandall-M. Sanchez-J F. Zou-T. Krause-J E. White-G (2001) The tissue distribution and functional characterization of human VR1. Biochemical and Biophysical Research Communications 281: 5: 1183-1189

Dray, A., (1992). Therapeutic potential of capsaicin-like molecules. Life Sciences 51: 1759-1765.

Gauldie-S D. McQueen-D S. Pertwee-R. Chessell-I P. (2001) Anandamide activates peripheral nociceptors in normal and arthritic rat knee joints. British Journal of Pharmacology 132: 3: 617-621.

Helliwell-R J A. McLatchie-L M. Clarke-M. Winter-J. Bevan-S. McIntyre-P (1998) Capsaicin sensitivity is associated with expression of the vanilloid (capsaicin) receptor (VR1) mRNA in adult rat sensory ganglia. Neuroscience Lett. 250: 3: 177-180.

Holzer, P. (1991) Capsaicin: Cellular targets, Mechanisms of Action and selectivity for thin sensory neurons. Pharmacological reviews 43: 2: 143-201

Hwang-S W. Cho-H. Kwak-J. Lee-S Y. Kang-C J. Jung-J. Cho-S. Min-K H. Suh-Y G. Kim-D. Oh-U. (2000) Direct activation of capsaicin receptors by products of lipoxygenases: Endogenous capsaicin-like substances. PNAS 97: 11: 6155-6160.

Mezey-E. Toth-Z E. Cortright-D N. Arzubi-M K. Krause-J E. Elde-R. Guo-A. Blumberg-P M. Szallasi-A (2000) Distribution of mRNA for vanilloid receptor subtype 1 (VR1), and VR1-like immunoreactivity, in the central nervous system of the rat and human. PNAS 97: 7: 3655-3660.

Nozawa-Y. Nishihara-K. Yamamoto-A. Nakano-M. Ajioka-H.

Matsuura-N. (2001) Distribution and characterization of vanilloid receptors in the rat stomach. Neuroscience Letters 309: 1: 33-36.

Olah-Z. Karai-L. Iadarola-M J. (2001) Anandamide activates vanilloid receptor 1 (VR1) at acidic pH in dorsal root ganglia neurons and cells ectopically expressing VR1. Journal of Biological Chemistry 276: 33, 31163-31170.

Onozawa-K. Nakamura-A. Tsutsumi-S. Yao-J. Ishikawa-R. Kohama-K. (2000) Tissue distribution of capsaicin receptor in the various organs of rats. Proc. Jpn. Acad. Ser. B, Phys.-Biol. Sci. 76: 5: 68-72.

Premkumar-L S. Ahern-G P. (2000) Induction of vanilloid receptor channel activity by protein kinase C. Nature (London) 408: 6815: 985-990.

Singh-L K. Pang-X. Alexacos-N. Letourneau-R. Theoharides-T C. (1999) Acute immobilization stress triggers skin mast cell degranulation via corticotropin releasing hormone, neurotensin, and substance P: A link to neurogenic skin disorders. Brain Behav. Immun. 13: 3: 225-239.

Szallasi, A. Blumberg-P M (1996) Vanilloid receptors: New insights enhance potential as a therapeutic target. Pain 68: 195-208

Szallasi-A. Blumberg-P M. (1999) Vanilloid (capsaicin) receptors and mechanisms. Pharmacol. Rev. 51: 2: 159-211.

Szabo-T. Wang-J. Gonzalez-A. Kedei-N. Lile-J. Treanor-J. Blumberg-P M. (2000) Pharmacological characterization of the human vanilloid receptor type-1 (hVR1). Society for Neuroscience Abstracts. 26:1-2: 634.18.

Tominaga, M., Caterina, M. J., Malmberg, A. B., Rosen, T. A., Gilbert, H., Skinner, K., Raumann, B. E., Basbaum, A. I., and Julius, D., (1998). The cloned capsaicin receptor integrates multiple pain-producing stimuli. Neuron 21: 531-543.

Yiangou-Y. Facer-P. Dyer-N H C. Chan-C L H. Knowles-C. Williams-N S. Anand-P. (2001) Vanilloid receptor 1 immunoreactivity in inflamed human bowel. Lancet (North American Edition) 357: 9265: 1338-1339.

Yiangou-Y. Facer-P. Ford-A. Brady-C. Wiseman-O. Fowler-C J. Anand-P. (2001) Capsaicin receptor VR1 and ATP-gated ion channel P2X3 in human urinary bladder. BJU International 87: 9: 774-779.

Wang-H. Bian-D. Zhu-D. Zajic-G. Loeloff-R. Lile-J. Wild-K. Treanor-J. Curran-E. (2000) Inflammation-induced upregulation of VR1 in rat spinal cord and DRG correlates with enhanced nociceptive processing. Society for Neuroscience Abstracts 26:1-2: 632.15.

SUMMARY

The present invention comprises a new class of compounds useful in the treatment of diseases, such as vanilloid-receptor-mediated diseases and other maladies, such as inflammatory or neuropathic pain and diseases involving sensory nerve function such as asthma, rheumatoid arthritis, osteoarthritis, inflammatory bowel disorders, urinary incontinence, migraine and psoriasis. In particular, the compounds of the invention are useful for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders. Accordingly, the invention also comprises pharmaceutical compositions comprising the compounds, methods for the treatment of vanilloid-receptor-mediated diseases, such as inflammatory or neuropathic pain, asthma, rheumatoid arthritis, osteoarthritis, inflammatory bowel disorders, urinary incontinence, migraine and psoriasis diseases, using the compounds and compositions of the invention, and intermediates and processes useful for the preparation of the compounds of the invention.

The compounds of the invention are represented by the following general structure:

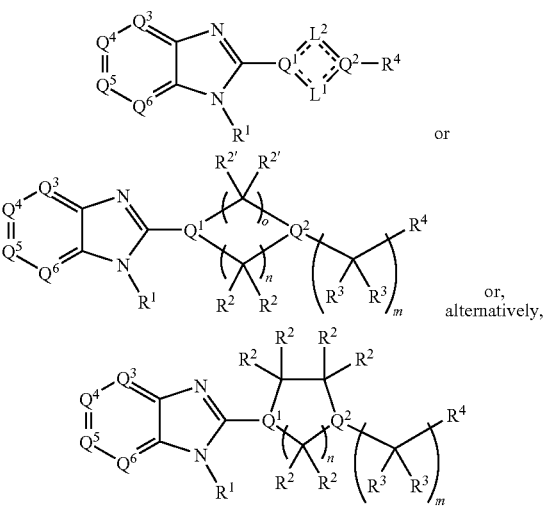

or a pharmaceutically acceptable salt thereof, wherein m, n, o, $L^1$, $L^2$, $Q^1$, $Q^2$, $Q^3$, $Q^4$, $Q^5$, $Q^6$, $R^1$, $R^2$, $R^{2'}$, $R^3$ and $R^4$ are defined herein.

The foregoing merely summarizes certain aspects of the invention and is not intended, nor should it be construed, as limiting the invention in any way. All patents, patent applications and other publications recited herein are hereby incorporated by reference in their entirety.

DETAILED DESCRIPTION

One aspect of the current invention relates to compounds having the general structure:

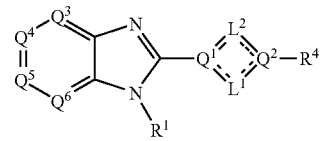

or any pharmaceutically-acceptable salt thereof, wherein:

$L^1$ is a saturated, unsaturated, or partially-saturated chain of 1, 2 or 3 carbon atoms substituted at each open position by $R^2$;

$L^2$ is a saturated, unsaturated, or partially-saturated chain of 1, 2 or 3 carbon atoms substituted at each open position by $R^2$; wherein the combined number of carbon atoms in the $L^1$ and $L^2$ chains is 3, 4 or 5; wherein, when $L^1$ is a one carbon chain and $Q^1$ and $Q^2$ are both N, then $L^1$ is carbonyl, and when $L^2$ is a one carbon chain and $Q^1$ and $Q^2$ are both N, then $L^2$ is carbonyl;

m is independently at each instance 0, 1 or 2;

$Q^1$ is N or C($R^2$);

$Q^2$ is N or $C(R^2)$; wherein at least one of $Q^1$ and $Q^2$ is N;
$Q^3$ is N or $C(R^5)$;
$Q^4$ is N or $C(R^6)$;
$Q^5$ is N or $C(R^{6'})$;
$Q^6$ is N or $C(R^{5'})$;
$R^1$ is H or $—(C(R^2)(R^{2'}))_m—R^g$;

$R^2$ is, independently, in each instance, H, $C_{1-8}$alkyl, $C_{1-4}$haloalkyl, $—O(C_{1-7}$alkyl), $—N(C_{1-7}$alkyl)$R^a$, or a $C_{1-6}$alkyl substituted by 1, 2 or 3 substituents selected from halo, cyano, $—OR^a$, $—OC(=O)R^b$, $—SR^a$, $—S(=O)R^b$, $—S(=O)_2R^b$, $—S(=O)_2NR^aR^a$, $—NR^aR^a$, $—N(R^a)C(=O)R^b$, $—N(R^a)C(=O)OR^b$, $—N(R^a)C(=O)NR^aR^a$, $—N(R^a)C(=NR^a)NR^aR^a$, $—N(R^a)S(=O)_2R^b$, $—NR^aC_{2-6}$alkylNR$^aR^a$ and $—NR^aC_{2-6}$alkylOR$^a$; wherein any two geminal $R^2$ groups may additionally be oxo;

$R^{2'}$ is, independently, in each instance, H, $C_{1-8}$alkyl, $C_{1-4}$haloalkyl, $—O(C_{1-7}$alkyl), $—N(C_{1-7}$alkyl)$R^a$, or a $C_{1-6}$alkyl substituted by 1, 2 or 3 substituents selected from halo, cyano, $—OR^a$, $—OC(=O)R^b$, $—SR^a$, $—S(=O)R^b$, $—S(=O)_2R^b$, $—S(=O)_2NR^aR^a$, $—NR^aR^a$, $—N(R^a)C(=O)R^b$, $—N(R^a)C(=O)OR^b$, $—N(R^a)C(=O)NR^aR^a$, $—N(R^a)C(=NR^a)NR^aR^a$, $—N(R^a)S(=O)_2R^b$, $—NR^aC_{2-6}$alkylNR$^aR^a$ and $—NR^aC_{2-6}$alkylOR$^a$; wherein any two geminal $R^{2'}$ groups may additionally be oxo;

$R^4$ is phenyl or naphthyl, wherein the phenyl and naphthyl are substituted by 1, 2, 3 or 4 substituents selected from $R^c$, $R^e$, halo, $C_{1-4}$haloalkyl, cyano, nitro, $—C(=O)R^e$, $—C(=O)OR^h$, $—C(=O)NR^aR^h$, $—C(=NR^a)NR^aR^h$, $—OR^h$, $—OC(=O)R^e$, $—OC(=O)NR^aR^h$, $—OC(=O)N(R^a)S(=O)_2R^e$, $—OC_{2-6}$alkylNR$^aR^h$, $—OC_{2-6}$alkylOR$^h$, $—SR^e$, $—S(=O)R^e$, $—S(=O)_2R^e$, $—S(=O)_2NR^aR^h$, $—S(=O)_2N(R^a)C(=O)R^e$, $—S(=O)_2N(R^a)C(=O)OR^h$, $—S(=O)_2N(R^a)C(=O)NR^aR^h$, $—NR^aR^h$, $—N(R^a)C(=O)R^e$, $—N(R^a)C(=O)OR^h$, $—N(R^a)C(=O)NR^aR^h$, $—N(R^a)C(=NR^a)NR^aR^h$, $—N(R^a)S(=O)_2R^e$, $—N(R^a)S(=O)_2NR^aR^h$, $—NR^aC_{2-6}$alkylNR$^aR^h$, $—NR^aC_{2-6}$alkylOR$^h$, $—C(=O)R^g$, $—C(=O)OR^g$, $—C(=O)NR^gR^g$, $—C(=NR^a)NR^aR^g$, $—OR^g$, $—OC(=O)R^g$, $—OC(=O)NR^gR^g$, $—OC(=O)N(R^a)S(=O)_2R^g$, $—OC(=O)N(R^g)S(=O)_2R^e$, $—OC_{2-6}$alkylNR$^aR^g$, $—OC_{2-6}$alkylOR$^g$, $—SR^g$, $—S(=O)R^g$, $—S(=O)_2R^g$, $—S(=O)_2NR^aR^g$, $—S(=O)_2N(R^g)C(=O)R^e$, $—S(=O)_2N(R^a)C(=O)R^g$, $—S(=O)_2N(R^g)C(=O)OR^h$, $—S(=O)_2N(R^a)C(=O)OR^g$, $—S(=O)_2N(R^g)C(=O)NR^aR^h$, $—S(=O)_2N(R^a)C(=O)NR^aR^g$, $—NR^aR^g$, $—N(R^g)C(=O)R^e$, $—N(R^a)C(=O)R^g$, $—N(R^g)C(=O)OR^h$, $—N(R^a)C(=O)OR^g$, $—N(R^g)C(=O)NR^aR^h$, $—N(R^a)C(=O)NR^aR^g$, $—N(R^g)C(=NR^a)NR^aR^h$, $—N(R^a)C(=NR^a)NR^aR^g$, $—N(R^g)S(=O)_2R^e$, $—N(R^a)S(=O)_2R^g$, $—N(R^g)S(=O)_2NR^aR^h$, $—N(R^a)S(=O)_2NR^aR^g$, $—NR^hC_{2-6}$alkylNR$^aR^g$, $—NR^aC_{2-6}$alkylNR$^aR^g$, $—NR^gC_{2-6}$alkylOR$^h$ and $—NR^aC_{2-6}$alkylOR$^g$; or $R^4$ is $R^c$ substituted by 0, 1, 2, 3 or 4 substituents selected from $R^c$, $R^e$, halo, $C_{1-4}$haloalkyl, cyano, nitro, $—C(=O)R^e$, $—C(=O)OR^h$, $—C(=O)NR^aR^h$, $—C(=NR^a)NR^aR^h$, $—OR^h$, $—OC(=O)R^e$, $—OC(=O)NR^aR^h$, $—OC(=O)N(R^a)S(=O)_2R^e$, $—OC_{2-6}$alkylNR$^aR^h$, $—OC_{2-6}$alkylOR$^h$, $—SR^e$, $—S(=O)R^e$, $—S(=O)_2R^e$, $—S(=O)_2NR^aR^h$, $—S(=O)_2N(R^a)C(=O)R^e$, $—S(=O)_2N(R^a)C(=O)OR^h$, $—S(=O)_2N(R^a)C(=O)NR^aR^h$, $—NR^aR^h$, $—N(R^a)C(=O)R^e$, $—N(R^a)C(=O)OR^h$, $—N(R^a)C(=O)NR^aR^h$, $—N(R^a)C(=NR^a)NR^aR^h$, $—N(R^a)S(=O)_2R^e$, $—N(R^a)S(=O)_2NR^aR^h$, $—NR^aC_{2-6}$alkylNR$^aR^h$, $—NR^aC_{2-6}$alkylOR$^h$, $—C(=O)R^g$, $—C(=O)OR^g$, $—C(=O)NR^gR^g$, $—C(=NR^a)NR^aR^g$, $—OR^g$, $—OC(=O)R^g$, $—OC(=O)NR^gR^g$, $—OC(=O)N(R^a)S(=O)_2R^g$, $—OC_{2-6}$alkylNR$^aR^g$, $—OC_{2-6}$alkylOR$^g$, $—SR^g$, $—S(=O)R^g$, $—S(=O)_2R^g$, $—S(=O)_2NR^aR^g$, $—S(=O)_2N(R^a)C(=O)R^g$, $—S(=O)_2N(R^a)C(=O)OR^g$, $—S(=O)_2N(R^a)C(=O)NR^aR^g$, $—NR^aR^g$, $—N(R^a)C(=O)R^g$, $—N(R^a)C(=O)OR^g$, $—N(R^a)C(=O)NR^aR^g$, $—N(R^a)C(=NR^a)NR^aR^g$, $—N(R^a)S(=O)_2R^g$, $—N(R^a)S(=O)_2NR^aR^g$, $—NR^aC_{2-6}$alkylNR$^aR^g$ and $—NR^aC_{2-6}$alkylOR$^g$, wherein $R^4$ is not imidazole or any substituted derivative thereof, $R^5$ is H, $R^e$, $C_{1-4}$haloalkyl, halo, cyano, nitro, $—C(=O)R^e$, $—C(=O)OR^e$, $—C(=O)NR^eR^a$, $—C(=NR^a)NR^hR^a$, $—OR^h$, $—OC(=O)R^e$, $—OC(=O)NR^aR^h$, $—OC(=O)N(R^a)S(=O)_2R^e$, $—OC_{2-6}$alkylNR$^aR^h$, $—OC_{2-6}$alkylOR$^h$, $—SR^h$, $—S(=O)R^e$, $—S(=O)_2R^e$, $—S(=O)_2NR^aR^h$, $—S(=O)_2N(R^a)C(=O)R^e$, $—S(=O)_2N(R^a)C(=O)OR^e$, $—S(=O)_2N(R^a)C(=O)NR^aR^h$, $—NR^aR^h$, $—N(R^a)C(=O)R^e$, $—N(R^a)C(=O)OR^e$, $—N(R^a)C(=O)NR^aR^h$, $—N(R^a)C(=NR^a)NR^aR^h$, $—N(R^a)S(=O)_2R^e$, $—N(R^a)S(=O)_2NR^aR^h$, $—NR^aC_{2-6}$alkylNR$^aR^h$, $—NR^aC_{2-6}$alkylOR$^h$, $—C(=O)R^g$, $—C(=O)OR^g$, $—C(=O)NR^gR^a$, $—C(=NR^a)NR^aR^g$, $—OR^g$, $—OC(=O)R^g$, $—OC(=O)NR^gR^g$, $—OC(=O)N(R^a)S(=O)_2R^g$, $—OC_{2-6}$alkylNR$^aR^g$, $—OC_{2-6}$alkylOR$^g$, $—SR^g$, $—S(=O)R^g$, $—S(=O)_2R^g$, $—S(=O)_2NR^aR^g$, $—S(=O)_2N(R^a)C(=O)R^g$, $—S(=O)_2N(R^a)C(=O)OR^g$, $—S(=O)_2N(R^a)C(=O)NR^aR^g$, $—NR^aR^g$, $—N(R^a)C(=O)R^g$, $—N(R^a)C(=O)OR^g$, $—N(R^a)C(=O)NR^aR^g$, $—N(R^a)C(=NR^a)NR^aR^g$, $—N(R^a)S(=O)_2R^g$, $—N(R^a)S(=O)_2NR^aR^g$, $—NR^aC_{2-6}$alkylNR$^aR^g$ or $—NR^aC_{2-6}$alkylOR$^g$; or $R^5$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2, 3 or 4 substituents selected from $R^e$, $C_{1-4}$haloalkyl, halo, cyano, nitro, $—C(=O)R^e$, $—C(=O)OR^e$, $—C(=O)NR^eR^a$, $—C(=NR^a)NR^hR^a$, $—OR^h$, $—OC(=O)R^e$, $—OC(=O)NR^aR^h$, $—OC(=O)N(R^a)S(=O)_2R^e$, $—OC_{2-6}$alkylNR$^aR^h$, $—OC_{2-6}$alkylOR$^h$, $—SR^h$, $—S(=O)R^e$, $—S(=O)_2R^e$, $—S(=O)_2NR^aR^h$, $—S(=O)_2N(R^a)C(=O)R^e$, $—S(=O)_2N(R^a)C(=O)OR^e$, $—S(=O)_2N(R^a)C(=O)NR^aR^h$, $—NR^aR^h$, $—N(R^a)C(=O)R^e$, $—N(R^a)C(=O)OR^e$, $—N(R^a)C(=O)NR^aR^h$, $—N(R^a)C(=NR^a)NR^aR^h$, $—N(R^a)S(=O)_2R^e$, $—N(R^a)S(=O)_2NR^aR^h$, $—NR^aC_{2-6}$alkylNR$^aR^h$, $—NR^aC_{2-6}$alkylOR$^h$, $—C(=O)R^g$, $—C(=O)OR^g$, $—C(=O)NR^gR^a$, $—C(=NR^a)NR^aR^g$, $—OR^g$, $—OC(=O)R^g$, $—OC(=O)NR^gR^g$, $—OC(=O)N(R^a)S(=O)_2R^g$, $—OC_{2-6}$alkylNR$^aR^g$, $—OC_{2-6}$alkylOR$^g$, $—SR^g$, $—S(=O)R^g$, $—S(=O)_2R^g$, $—S(=O)_2NR^aR^g$, $—S(=O)_2N(R^a)C(=O)R^g$, $—S(=O)_2N(R^a)C(=O)OR^g$, $—S(=O)_2N(R^a)C(=O)NR^aR^g$, $—NR^aR^g$, $—N(R^a)C(=O)R^g$, $—N(R^a)C(=O)OR^g$, $—N(R^a)C(=O)NR^aR^g$, $—N(R^a)C(=NR^a)NR^aR^g$, $—N(R^a)S(=O)_2R^g$, $—N(R^a)S(=O)_2NR^aR^g$, $—NR^aC_{2-6}$alkylNR$^aR^g$ and $—NR^aC_{2-6}$alkylOR$^g$;

$R^{5'}$ is H, $R^e$, $C_{1-4}$haloalkyl, halo, cyano, nitro, $—C(=O)R^e$, $—C(=O)OR^e$, $—C(=O)NR^eR^a$, $—C(=NR^a)NR^hR^a$, $—OR^h$, $—OC(=O)R^e$, $—OC(=O)NR^aR^h$, $—OC(=O)N(R^a)S(=O)_2R^e$, $—OC_{2-6}$alkylNR$^aR^h$, $—OC_{2-6}$alkylOR$^h$, $—SR^h$, $—S(=O)R^e$, $—S(=O)_2R^e$, $—S(=O)_2NR^aR^h$, $—S(=O)_2N(R^a)C(=O)R^e$, $—S(=O)_2N(R^a)C(=O)OR^e$, $—S(=O)_2N(R^a)C(=O)NR^aR^h$, $—NR^aR^h$, $—N(R^a)C(=O)R^e$, $—N(R^a)C(=O)OR^e$, $—N(R^a)C(=O)NR^aR^h$, $—N(R^a)C(=NR^a)NR^aR^h$, $—N(R^a)S(=O)_2R^e$, $—N(R^a)S(=O)_2NR^aR^h$, $—NR^aC_{2-6}$alkylNR$^aR^h$, $—NR^aC_{2-6}$alkylOR$^h$, $—C(=O)R^g$, $—C(=O)OR^g$, $—C(=O)NR^gR^a$, —C(=NR$^a$)NR$^a$R$^g$, —OR$^g$, —OC(=O)R$^g$, —OC(=O)NR$^a$R$^g$, —OC(=O)N(R$^a$)S(=O)$_2$R$^g$, —OC$_{2-6}$alkylNR$^a$R$^g$, —OC$_{2-6}$alkylOR$^g$, —SR$^g$, —S(=O)R$^g$, —S(=O)$_2$R$^g$, —S(=O)$_2$NR$^a$R$^g$, —S(=O)$_2$N(R$^a$)C(=O)R$^g$, —S(=O)$_2$N(R$^a$)C(=O)OR$^g$, —S(=O)$_2$N(R$^a$)C(=O)NR$^a$R$^g$, —NR$^a$R$^g$, —N(R$^a$)C(=O)R$^g$, —N(R$^a$)C(=O)OR$^g$, —N(R$^a$)C(=O)NR$^a$R$^g$, —N(R$^a$)C(=NR$^a$)NR$^a$R$^g$, —N(R$^a$)S(=O)$_2$R$^g$, —N(R$^a$)S(=O)$_2$NR$^a$R$^g$, —NR$^a$C$_{2-6}$alkylNR$^a$R$^g$ or —NR$^a$C$_{2-6}$alkylOR$^g$; or R$^{5'}$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2, 3 or 4 substituents selected from R$^e$, C$_{1-4}$haloalkyl, halo, cyano, nitro, —C(=O)R$^e$, —C(=O)OR$^e$, —C(=O)NR$^e$R$^a$, —C(=NR$^a$)NR$^h$R$^a$, —OR$^h$, —OC(=O)R$^e$, —OC(=O)NR$^e$R$^h$, —OC(=O)N(R$^a$)S(=O)$_2$R$^e$, —OC$_{2-6}$alkylNR$^e$R$^h$, —OC$_{2-6}$alkylOR$^h$, —SR$^h$, —S(=O)R$^e$, —S(=O)$_2$R$^e$, —S(=O)$_2$NR$^a$R$^h$, —S(=O)$_2$N(R$^a$)C(=O)R$^e$, —S(=O)$_2$N(R$^a$)C(=O)OR$^e$, —S(=O)$_2$N(R$^a$)C(=O)NR$^a$R$^h$, —NR$^a$R$^h$, —N(R$^a$)C(=O)R$^e$, —N(R$^a$)C(=O)OR$^e$, —N(R$^a$)C(=O)NR$^a$R$^h$, —N(R$^a$)C(=NR$^a$)NR$^a$R$^h$, —N(R$^a$)S(=O)$_2$R$^e$, —N(R$^a$)S(=O)$_2$NR$^a$R$^h$, —NR$^a$C$_{2-6}$alkylNR$^a$R$^h$, —NR$^a$C$_{2-6}$alkylOR$^h$, —C(=O)R$^g$, —C(=O)OR$^g$, —C(=O)NR$^a$R$^g$, —C(=NR$^a$)NR$^a$R$^g$, —OR$^g$, —OC(=O)R$^g$, —OC(=O)NR$^a$R$^g$, —OC(=O)N(R$^a$)S(=O)$_2$R$^g$, —OC$_{2-6}$alkylNR$^a$R$^g$, —OC$_{2-6}$alkylOR$^g$, —SR$^g$, —S(=O)R$^g$, —S(=O)$_2$R$^g$, —S(=O)$_2$NR$^a$R$^g$, —S(=O)$_2$N(R$^a$)C(=O)R$^g$, —S(=O)$_2$N(R$^a$)C(=O)OR$^g$, —S(=O)$_2$N(R$^a$)C(=O)NR$^a$R$^g$, —NR$^a$R$^g$, —N(R$^a$)C(=O)R$^g$, —N(R$^a$)C(=O)OR$^g$, —N(R$^a$)C(=O)NR$^a$R$^g$, —N(R$^a$)C(=NR$^a$)NR$^a$R$^g$, —N(R$^a$)S(=O)$_2$R$^g$, —N(R$^a$)S(=O)$_2$NR$^a$R$^g$, —NR$^a$C$_{2-6}$alkylNR$^a$R$^g$ and —NR$^a$C$_{2-6}$alkylOR$^g$;

R$^6$ is H, C$_{1-4}$haloalkyl, halo, cyano, —C(=O)R$^b$, —C(=O)OR$^b$, —C(=O)NR$^a$R$^a$, —C(=NR$^a$)NR$^a$R$^a$, —OC$_{2-6}$alkyl, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^b$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$ and R$^e$;

R$^{6'}$ is H, C$_{1-4}$haloalkyl, halo, cyano, —C(=O)R$^b$, —C(=O)OR$^b$, —C(=O)NR$^a$R$^a$, —C(=NR$^a$)NR$^a$R$^a$, —OC$_{2-6}$alkyl, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^b$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$ and R$^e$; wherein at least one of R$^6$ and R$^{6'}$ is other than H;

R$^a$ is independently, at each instance, H or R$^b$;

R$^b$ is independently, at each instance, phenyl, benzyl or C$_{1-6}$alkyl, the phenyl, benzyl and C$_{1-6}$alkyl being substituted by 0, 1, 2 or 3 substituents selected from halo, C$_{1-4}$alkyl, C$_{1-3}$haloalkyl, —OC$_{1-4}$alkyl, —NH$_2$, —NHC$_{1-4}$alkyl, —N(C$_{1-4}$alkyl)C$_{1-4}$alkyl;

R$^c$ is independently at each instance a saturated, partially saturated or unsaturated 5-, 6- or 7-membered monocyclic or 6-, 7-, 8-, 9-, 10- or 11-membered bicyclic ring containing 1, 2, 3 or 4 atoms selected from N, O and S, wherein the carbon atoms of the ring are substituted by 0, 1 or 2 oxo groups;

R$^d$ is independently at each instance C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^b$;

R$^e$ is independently at each instance C$_{1-6}$alkyl substituted by 0, 1, 2 or 3 substituents independently selected from R$^d$ and additionally substituted by 0 or 1 substituents selected from R$^g$;

R$^g$ is independently at each instance a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; and R$^h$ is independently at each instance R$^e$ or H.

In another embodiment, in conjunction with any one of the above and below embodiments, L$^1$ is a saturated, unsaturated, or partially-saturated chain of 2 or 3 carbon atoms substituted at each open position by R$^2$.

In another embodiment, in conjunction with any one of the above and below embodiments, L$^1$ is a saturated, unsaturated, or partially-saturated chain of 2 carbon atoms substituted at each open position by R$^2$.

In another embodiment, in conjunction with any one of the above and below embodiments, L$^2$ is a saturated, unsaturated, or partially-saturated chain of 2 or 3 carbon atoms substituted at each open position by R$^{2'}$.

In another embodiment, in conjunction with any one of the above and below embodiments, L$^2$ is a saturated, unsaturated, or partially-saturated chain of 2 carbon atoms substituted at each open position by R$^{2'}$.

In another embodiment, in conjunction with any one of the above and below embodiments, the combined number of carbon atoms in the L$^1$ and L$^2$ chains is 3.

In another embodiment, in conjunction with any one of the above and below embodiments, the combined number of carbon atoms in the L$^1$ and L$^2$ chains is 4.

In another embodiment, in conjunction with any one of the above and below embodiments, the combined number of carbon atoms in the L$^1$ and L$^2$ chains is 5.

In another embodiment, in conjunction with any one of the above and below embodiments, the group:

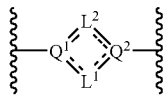

is selected from

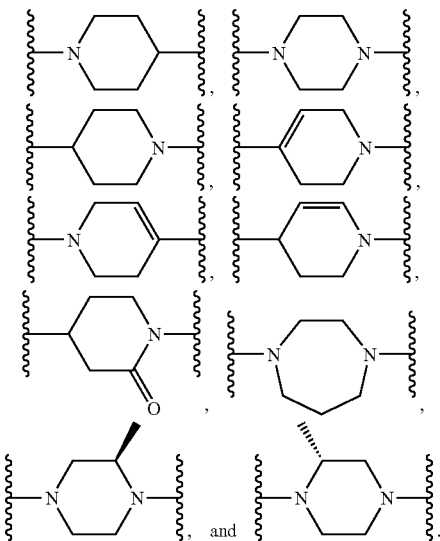

In another embodiment, in conjunction with any one of the above and below embodiments, m is independently at each instance 0.

In another embodiment, in conjunction with any one of the above and below embodiments, m is independently at each instance 1 or 2.

In another embodiment, in conjunction with any one of the above and below embodiments, $Q^1$ is N.

In another embodiment, in conjunction with any one of the above and below embodiments, $Q^2$ is N.

In another embodiment, in conjunction with any one of the above and below embodiments, $Q^3$ is $C(R^5)$.

In another embodiment, in conjunction with any one of the above and below embodiments, $Q^4$ is $C(R^6)$.

In another embodiment, in conjunction with any one of the above and below embodiments, $Q^5$ is $C(R^{6'})$.

In another embodiment, in conjunction with any one of the above and below embodiments, $Q^6$ is $C(R^{5'})$.

In another embodiment, in conjunction with any one of the above and below embodiments, $R^1$ is H.

In another embodiment, in conjunction with any one of the above and below embodiments, $R^1$ is $R^g$.

In another embodiment, in conjunction with any one of the above and below embodiments, $R^1$ is $—(C(R^2)(R^2))—R^g$.

In another embodiment, in conjunction with any one of the above and below embodiments, $R^1$ is $—(C(R^2)(R^2))_2—R^g$.

In another embodiment, in conjunction with any one of the above and below embodiments, $R^2$ is H.

In another embodiment, in conjunction with any one of the above and below embodiments, $R^{2'}$ is H.

In another embodiment, in conjunction with any one of the above and below embodiments, $R^4$ is phenyl or naphthyl, wherein the phenyl and naphthyl are substituted by 1, 2, 3 or 4 substituents selected from $R^e$, $R^e$, halo, $C_{1-4}$haloalkyl, cyano, nitro, $—C(=O)R^e$, $—C(=O)OR^h$, $—C(=O)NR^aR^h$, $—C(=NR^a)NR^aR^h$, $—OR^h$, $—OC(=O)R^e$, $—OC(=O)NR^aR^h$, $—OC(=O)N(R^a)S(=O)_2R^e$, $—OC_{2-6}$alkylNR^aR^h$, $—OC_{2-6}$alkylOR^h$, $—SR^e$, $—S(=O)R^e$, $—S(=O)_2R^e$, $—S(=O)_2NR^aR^h$, $—S(=O)_2N(R^a)C(=O)R^e$, $—S(=O)_2N(R^a)C(=O)OR^h$, $—S(=O)_2N(R^a)C(=O)NR^aR^h$, $—NR^aR^h$, $—N(R^a)C(=O)R^e$, $—N(R^a)C(=O)OR^h$, $—N(R^a)C(=O)NR^aR^h$, $—N(R^a)C(=NR^a)NR^aR^h$, $—N(R^a)S(=O)_2R^e$, $—N(R^a)S(=O)_2NR^aR^h$, $—NR^aC_{2-6}$alkylNR^aR^h$, $—NR^aC_{2-6}$alkylOR^h$, $—C(=O)R^g$, $—C(=O)OR^g$, $—C(=O)NR^aR^g$, $—C(=NR^a)NR^aR^g$, $—OR^g$, $—OC(=O)R^g$, $—OC(=O)NR^aR^g$, $—OC(=O)N(R^a)S(=O)_2R^g$, $—OC(=O)N(R^g)S(=O)_2R^e$, $—OC_{2-6}$alkylNR^aR^g$, $—OC_{2-6}$alkylOR^g$, $—SR^g$, $—S(=O)R^g$, $—S(=O)_2R^g$, $—S(=O)_2NR^aR^g$, $—S(=O)_2N(R^g)C(=O)R^e$, $—S(=O)_2N(R^a)C(=O)R^g$, $—S(=O)_2N(R^g)C(=O)OR^h$, $—S(=O)_2N(R^a)C(=O)OR^g$, $—S(=O)_2N(R^g)C(=O)NR^aR^h$, $—S(=O)_2N(R^a)C(=O)NR^aR^g$, $—NR^aR^g$, $—N(R^g)C(=O)R^e$, $—N(R^a)C(=O)R^g$, $—N(R^g)C(=O)OR^h$, $—N(R^a)C(=O)OR^g$, $—N(R^g)C(=O)NR^aR^h$, $—N(R^a)C(=O)NR^aR^g$, $—N(R^g)C(=NR^a)NR^aR^h$, $—N(R^a)C(=NR^a)NR^aR^g$, $—N(R^g)S(=O)_2R^e$, $—N(R^a)S(=O)_2R^g$, $—N(R^g)S(=O)_2NR^aR^h$, $—N(R^a)S(=O)_2NR^aR^g$, $—NR^hC_{2-6}$alkylNR^aR^g$, $—NR^aC_{2-6}$alkylNR^aR^g$, $—NR^gC_{2-6}$alkylOR^h$ and $—NR^aC_{2-6}$alkylOR^g$.

In another embodiment, in conjunction with any one of the above and below embodiments, $R^4$ is $R^c$ substituted by 0, 1, 2, 3 or 4 substituents selected from $R^c$, $R^e$, halo, $C_{1-4}$haloalkyl, cyano, nitro, $—C(=O)R^e$, $—C(=O)OR^h$, $—C(=O)NR^aR^h$, $—C(=NR^a)NR^aR^a$, $—OR^h$, $—OC(=O)R^e$, $—OC(=O)NR^aR^h$, $—OC(=O)N(R^a)S(=O)_2R^e$, $—OC_{2-6}$alkylNR^aR^h$, $—OC_{2-6}$alkylOR^h$, $—SR^e$, $—S(=O)R^e$, $—S(=O)_2R^e$, $—S(=O)_2NR^aR^h$, $—S(=O)_2N(R^a)C(=O)R^e$, $—S(=O)_2N(R^a)C(=O)OR^h$, $—S(=O)_2N(R^a)C(=O)NR^aR^h$, $—NR^aR^h$, $—N(R^a)C(=O)R^e$, $—N(R^a)C(=O)OR^h$, $—N(R^a)C(=O)NR^aR^h$, $—N(R^a)C(=NR^a)NR^aR^h$, $—N(R^a)S(=O)_2R^e$, $—N(R^a)S(=O)_2NR^aR^h$, $—NR^aC_{2-6}$alkylNR^aR^h$, $—NR^aC_{2-6}$alkylOR^h$, $—C(=O)R^g$, $—C(=O)OR^g$, $—C(=O)NR^aR^g$, $—C(=NR^a)NR^aR^g$, $—OR^g$, $—OC(=O)R^g$, $—OC(=O)NR^aR^g$, $—OC(=O)N(R^a)S(=O)_2R^g$, $—OC(=O)N(R^g)S(=O)_2R^e$, $—OC_{2-6}$alkylNR^aR^g$, $—OC_{2-6}$alkylOR^g$, $—SR^g$, $—S(=O)R^g$, $—S(=O)_2R^g$, $—S(=O)_2NR^aR^g$, $—S(=O)_2N(R^g)C(=O)R^e$, $—S(=O)_2N(R^a)C(=O)R^g$, $—S(=O)_2N(R^g)C(=O)OR^h$, $—S(=O)_2N(R^a)C(=O)OR^g$, $—S(=O)_2N(R^g)C(=O)NR^aR^h$, $—S(=O)_2N(R^a)C(=O)NR^aR^g$, $—NR^aR^g$, $—N(R^g)C(=O)R^e$, $—N(R^a)C(=O)R^g$, $—N(R^g)C(=O)OR^h$, $—N(R^a)C(=O)OR^g$, $—N(R^g)C(=O)NR^aR^h$, $—N(R^a)C(=O)NR^aR^g$, $—N(R^g)C(=NR^a)NR^aR^h$, $—N(R^a)C(=NR^a)NR^aR^g$, $—N(R^g)S(=O)_2R^e$, $—N(R^a)S(=O)_2R^g$, $—N(R^g)S(=O)_2NR^aR^h$, $—N(R^a)S(=O)_2NR^aR^g$, $—NR^hC_{2-6}$alkylNR^aR^g$, $—NR^aC_{2-6}$alkylNR^aR^g$, $—NR^gC_{2-6}$alkylOR^h$ and $—NR^aC_{2-6}$alkylOR^g$, wherein $R^4$ is not imidazole or any substituted derivative thereof.

In another embodiment, in conjunction with any one of the above and below embodiments, $R^4$ is $R^e$ substituted by 1, 2, 3 or 4 substituents selected from $R^c$, $R^e$, halo, $C_{1-4}$haloalkyl, cyano, nitro, $—C(=O)R^e$, $—C(=O)OR^h$, $—C(=O)NR^aR^h$, $—C(=NR^a)NR^aR^h$, $—OR^h$, $—OC(=O)R^e$, $—OC(=O)NR^aR^h$, $—OC(=O)N(R^a)S(=O)_2R^e$, $—OC_{2-6}$alkylNR^aR^h$, $—OC_{2-6}$alkylOR^h$, $—SR^e$, $—S(=O)R^e$, $—S(=O)_2R^e$, $—S(=O)_2NR^aR^h$, $—S(=O)_2N(R^a)C(=O)R^e$, $—S(=O)_2N(R^a)C(=O)OR^h$, $—NR^aR^h$, $—N(R^a)C(=O)R^e$, $—N(R^a)C(=O)OR^h$, $—N(R^a)C(=O)NR^aR^h$, $—N(R^a)C(=NR^a)NR^aR^h$, $—N(R^a)$ $S(=O)_2R^e$, $—N(R^a)S(=O)_2NR^aR^h$, $—NR^aC_{2-6}$alkylN- $R^aR^h$, —$NR^aC_{2-6}$alkyl$OR^h$, —C(=O)$R^g$, —C(=O)$OR^g$, —C(=O)$NR^aR^g$, —C(=$NR^a$)$NR^aR^g$, —$OR^g$, —OC(=O)$R^g$, —OC(=O)$NR^aR^g$, —OC(=O)N($R^a$)S(=O)$_2R^g$, —OCN($R^g$)S(=O)$_2R^e$, —$OC_{2-6}$alkylN$R^aR^g$, —$OC_{2-6}$alkyl$OR^g$, —$SR^g$, —S(=O)$R^g$, —S(=O)$_2R^g$, —S(=O)$_2NR^aR^g$, —S(=O)$_2$N($R^g$)C(=O)$R^e$, —S(=O)$_2$N($R^a$)C(=O)$R^g$, —S(=O)$_2$N($R^g$)C(=O)$OR^h$, —S(=O)$_2$N($R^a$)C(=O)$OR^g$, —S(=O)$_2$N($R^g$)C(=O)$NR^aR^h$, —S(=O)$_2$N($R^a$)C(=O)$NR^aR^g$, —$NR^aR^g$, —N($R^g$)C(=O)$R^e$, —N($R^a$)C(=O)$R^g$, —N($R^g$)C(=O)$OR^h$, —N($R^a$)C(=O)$OR^g$, —N($R^g$)C(=O)$NR^aR^h$, —N($R^a$)C(=O)$NR^aR^g$, —N($R^g$)C(=$NR^a$)$NR^aR^h$, —N($R^a$)C(=$NR^a$)$NR^aR^g$, —N($R^g$)S(=O)$_2R^e$, —N($R^a$)S(=O)$_2R^g$, —N($R^g$)S(=O)$_2NR^aR^h$, —N($R^a$)S(=O)$_2NR^aR^g$, —$NR^hC_{2-6}$alkyl-$NR^aR^g$, —$NR^aC_{2-6}$alkyl$NR^aR^g$, —$NR^gC_{2-6}$alkyl$OR^h$ and —$NR^aC_{2-6}$alkyl$OR^g$, wherein $R^4$ is not imidazole or any substituted derivative thereof.

In another embodiment, in conjunction with any one of the above and below embodiments, $R^4$ is $R^c$, wherein $R^4$ is not imidazole or any substituted derivative thereof.

In another embodiment, in conjunction with any one of the above and below embodiments, $R^4$ is a ring selected from thiophene, pyrrole, 1,3-oxazole, 1,3-thiazole, 1,3,4-oxadiazole, 1,3,4-thiadiazole, 1,2,3-oxadiazole, 1,2,3-thiadiazole, 1H-1,2,3-triazole, isothiazole, 1,2,4-oxadiazole, 1,2,4-thiadiazole, 1,2,3,4-oxatriazole, 1,2,3,4-thiatriazole, 1H-1,2,3,4-tetraazole, 1,2,3,5-oxatriazole, 1,2,3,5-thiatriazole, furan, imidazol-1-yl, imidazol-4-yl, 1,2,4-triazol-4-yl, 1,2,4-triazol-5-yl, isoxazol-3-yl, isoxazol-5-yl, thiolane, pyrrolidine, tetrahydrofuran, 4,5-dihydrothiophene, 2-pyrroline, 4,5-dihydrofuran, pyridazine, pyrimidine, pyrazine, 1,2,3-triazine, 1,2,4-triazine, 1,2,4-triazine, 1,3,5-triazine, pyridine, 2H-3,4,5,6-tetrahydropyran, thiane, 1,2-diazaperhydroine, 1,3-diazaperhydroine, piperazine, 1,3-oxazaperhydroine, morpholine, 1,3-thiazaperhydroine, 1,4-thiazaperhydroine, piperidine, 2H-3,4-dihydropyran, 2,3-dihydro-4H-thiin, 1,4,5,6-tetrahydropyridine, 2H-5,6-dihydropyran, 2,3-dihydro-6H-thiin, 1,2,5,6-tetrahydropyridine, 3,4,5,6-tetrahydropyridine, 4H-pyran, 4H-thiin, 1,4-dihydropyridine, 1,4-dithiane, 1,4-dioxane, 1,4-oxathiane, 1,2-oxazolidine, 1,2-thiazolidine, pyrazolidine, 1,3-oxazolidine, 1,3-thiazolidine, imidazolidine, 1,2,4-oxadiazolidine, 1,3,4-oxadiazolidine, 1,2,4-thiadiazolidine, 1,3,4-thiadiazolidine, 1,2,4-triazolidine, 2-imidazoline, 3-imidazoline, 2-pyrazoline, 4-imidazoline, 2,3-dihydroisothiazole, 4,5-dihydroisoxazole, 4,5-dihydroisothiazole, 2,5-dihydroisoxazole, 2,5-dihydroisothiazole, 2,3-dihydroisoxazole, 4,5-dihydrooxazole, 2,3-dihydrooxazole, 2,5-dihydrooxazole, 4,5-dihydrothiazole, 2,3-dihydrothiazole, 2,5-dihydrothiazole, 1,3,4-oxathiazolidine, 1,4,2-oxathiazolidine, 2,3-dihydro-1H-[1,2,3]triazole, 2,5-dihydro-1H-[1,2,3]triazole, 4,5-dihydro-1H-[1,2,3]triazole, 2,3-dihydro-1H-[1,2,4]triazole, 4,5-dihydro-1H-[1,2,4]triazole, 2,3-dihydro-[1,2,4]oxadiazole, 2,5-dihydro-[1,2,4]oxadiazole, 4,5-dihydro-[1,2,4]thiadiazole, 2,3-dihydro-[1,2,4]thidiazole, 2,5-dihydro-[1,2,4]thiadiazole, 4,5-dihydro-[1,2,4]thiadiazole, 2,5-dihydro-[1,2,4]oxadiazole, 2,3-dihydro-[1,2,4]oxadiazole, 4,5-dihydro-[1,2,4]oxadiazole, 2,5-dihydro-[1,2,4]thiadiazole, 2,3-dihydro-[1,2,4]thiadiazole, 4,5-dihydro-[1,2,4]thiadiazole, 2,3-dihydro-[1,3,4]oxadiazole, 2,3-dihydro-[1,3,4]thiadiazole, [1,4,2]oxathiazole, [1,3,4]oxathiazole, 1,3,5-triazaperhydroine, 1,2,4-triazaperhydroine, 1,4,2-dithiazaperhydroine, 1,4,2-dioxazaperhydroine, 1,3,5-oxadiazaperhydroine, 1,2,5-oxadiazaperhydroine, 1,3,4-thiadiazaperhydroine, 1,3,5-thiadiazaperhydroine, 1,2,5-thiadiazaperhydroine, 1,3,4-oxadiazaperhydroine, 1,4,3-oxathiazaperhydroine, 1,4,2-oxathiazaperhydroine, 1,4,5,6-tetrahydropyridazine, 1,2,3,4-tetrahydropyridazine, 1,2,3,6-tetrahydropyridazine, 1,2,5,6-tetrahydropyrimidine, 1,2,3,4-tetrahydropyrimidine, 1,4,5,6-tetrahydropyrimidine, 1,2,3,6-tetrahydropyrazine, 1,2,3,4-tetrahydropyrazine, 5,6-dihydro-4H-[1,2]oxazine, 5,6-dihydro-2H-[1,2]oxazine, 3,6-dihydro-2H-[1,2]oxazine, 3,4-dihydro-2H-[1,2]oxazine, 5,6-dihydro-4H-[1,2]thiazine, 5,6-dihydro-2H-[1,2]thiazine, 3,6-dihydro-2H-[1,2]thiazine, 3,4-dihydro-2H-[1,2]thiazine, 5,6-dihydro-2H-[1,3]oxazine, 5,6-dihydro-4H-[1,3]oxazine, 3,6-dihydro-2H-[1,3]oxazine, 3,4-dihydro-2H-[1,3]oxazine, 3,6-dihydro-2H-[1,4]oxazine, 3,4-dihydro-2H-[1,4]oxazine, 5,6-dihydro-2H-[1,3]thiazine, 5,6-dihydro-4H-[1,3]thiazine, 3,6-dihydro-2H-[1,3]thiazine, 3,4-dihydro-2H-[1,3]thiazine, 3,6-dihydro-2H-[1,4]thiazine, 3,4-dihydro-2H-[1,4]thiazine, 1,2,3,6-tetrahydro-[1,2,4]triazine, 1,2,3,4-tetrahydro-[1,2,4]triazine, 1,2,3,4-tetrahydro-[1,3,5]triazine, 2,3,4,5-tetrahydro-[1,2,4]triazine, 1,4,5,6-tetrahydro-[1,2,4]triazine, 5,6-dihydro-[1,4,2]dioxazine, 5,6-dihydro-[1,4,2]dioxazine, 5,6-dihydro-[1,4,2]dithiazine, 2,3-dihydro-[1,4,2]dioxazine, 3,4-dihydro-2H-[1,3,4]oxadiazine, 3,6-dihydro-2H-[1,3,4]oxadiazine, 3,4-dihydro-2H-[1,3,5]oxadiazine, 3,6-dihydro-2H-[1,3,5]oxadiazine, 5,6-dihydro-2H-[1,2,5]oxadiazine, 5,6-dihydro-4H-[1,2,5]oxadiazine, 3,4-dihydro-2H-[1,3,4]thiadiazine, 3,6-dihydro-2H-[1,3,4]thiadiazine, 3,4-dihydro-2H-[1,3,5]thiadiazine, 3,6-dihydro-2H-[1,3,5]thiadiazine, 5,6-dihydro-2H-[1,2,5]thiadiazine, 5,6-dihydro-4H-[1,2,5]thiadiazine, 5,6-dihydro-2H-[1,2,3]oxadiazine, 3,6-dihydro-2H-[1,2,5]oxadiazine, 5,6-dihydro-4H-[1,3,4]oxadiazine, 3,4-dihydro-2H-[1,2,5]oxadiazine, 5,6-dihydro-2H-[1,2,3]thiadiazine, 3,6-dihydro-2H-[1,2,5]thiadiazine, 5,6-dihydro-4H-[1,3,4]thiadiazine, 3,4-dihydro-2H-[1,2,5]thiadiazine, 5,6-dihydro-[1,4,3]oxathiazine, 5,6-dihydro-[1,4,2]oxathiazine, 2,3-dihydro-[1,4,3]oxathiazine, 2,3-dihydro-[1,4,2]oxathiazine, 4,5-dihydropyridine, 1,6-dihydropyridine, 5,6-dihydropyridine, 2H-pyran, 2H-thiin, 3,6-dihydropyridine, 2,3-dihydropyridazine, 2,5-dihydropyridazine, 4,5-dihydropyridazine, 1,2-dihydropyridazine, 2,3-dihydropyrimidine, 2,5-dihydropyrimidine, 5,6-dihydropyrimidine, 3,6-dihydropyrimidine, 4,5-dihydropyrazine, 5,6-dihydropyrazine, 3,6-dihydropyrazine, 4,5-dihydropyrazine, 1,4-dihydropyrazine, 1,4-dithiin, 1,4-dioxin, 2H-1,2-oxazine, 6H-1,2-oxazine, 4H-1,2-oxazine, 2H-1,3-oxazine, 4H-1,3-oxazine, 6H-1,3-oxazine, 2H-1,4-oxazine, 4H-1,4-oxazine, 2H-1,3-thiazine, 2H-1,4-thiazine, 4H-1,2-thiazine, 6H-1,3-thiazine, 4H-1,4-thiazine, 2H-1,2-thiazine, 6H-1,2-thiazine, 1,4-oxathiin, 2H,5H-1,2,3-triazine, 1H,4H-1,2,3-triazine, 4,5-dihydro-1,2,3-triazine, 1H,6H-1,2,3-triazine, 1,2-dihydro-1,2,3-triazine, 2,3-dihydro-1,2,4-triazine, 3H,6H-1,2,4-triazine, 1H,6H-1,2,4-triazine, 3,4-dihydro-1,2,4-triazine, 1H,4H-1,2,4-triazine, 5,6-dihydro-1,2,4-triazine, 4,5-dihydro-1,2,4-triazine, 2H,5H-1,2,4-triazine, 1,2-dihydro-1,2,4-triazine, 1H,4H-1,3,5-triazine, 1,2-dihydro-1,3,5-triazine, 1,4,2-dithiazine, 1,4,2-dioxazine, 2H-1,3,4-oxadiazine, 2H-1,3,5-oxadiazine, 6H-1,2,5-oxadiazine, 4H-1,3,4-oxadiazine, 4H-1,3,5-oxadiazine, 4H-1,2,5-oxadiazine, 2H-1,3,5-thiadiazine, 6H-1,2,5-thiadiazine, 4H-1,3,4-thiadiazine, 4H-1,3,5-thiadiazine, 4H-1,2,5-thiadiazine, 2H-1,3,4-thiadiazine, 6H-1,3,4-thiadiazine, 6H-1,3,4-oxadiazine, 1,4,2-oxathiazine and any bicyclic derivative of any of the above rings containing a vicinally-fused phenyl, pyridine or pyrimidine, wherein the carbon atoms of the ring and bicyclic derivative are substituted by 0, 1 or 2 oxo or thioxo groups; wherein the ring or bicyclic derivative there of is substituted by 0, 1, 2, 3 or 4 substituents selected from $R^c$, $R^e$, halo, $C_{1-4}$haloalkyl, cyano, nitro, —C(=O)$R^e$, —C(=O)$OR^h$, —C(=O)$NR^aR^h$, —C(=$NR^a$)$NR^aR^h$, —$OR^h$, —OC(=O)$R^e$, —OC(=O)$NR^aR^h$, —OC(=O)N($R^a$)S(=O)$_2R^e$, —$OC_{2-6}$alkyl$NR^aR^h$, —$OC_{2-6}$alkyl$OR^h$, —$SR^e$, —S(=O)

R$^e$, —S(=O)$_2$R$^e$, —S(=O)$_2$NR$^a$R$^h$, —S(=O)$_2$N(R$^a$)C(=O)R$^e$, —S(=O)$_2$N(R$^a$)C(=O)OR$^h$, —S(=O)$_2$N(R$^a$)C(=O)NR$^a$R$^e$, —NR$^a$R$^h$, —N(R$^a$)C(=O)R$^e$, —N(R$^a$)C(=O)OR$^h$, —N(R$^a$)C(=O)NR$^a$R$^h$, —N(R$^a$)C(=NR$^a$)NR$^a$R$^h$, —N(R$^a$)S(=O)$_2$R$^e$, —N(R$^a$)S(=O)$_2$NR$^a$R$^h$, —NR$^a$C$_{2-6}$alkylNR$^a$R$^h$, —NR$^a$C$_{2-6}$alkylOR$^h$, —C(=O)R$^g$, —C(=O)OR$^g$, —C(=O)NR$^a$R$^g$, —C(=NR$^a$)NR$^a$R$^g$, —OR$^g$, —OC(=O)R$^g$, —OC(=O)NR$^a$R$^g$, —OC(=O)N(R$^a$)S(=O)$_2$R$^g$, —OC(=O)N(R$^g$)S(=O)$_2$R$^e$, —OC$_{2-6}$alkylNR$^a$R$^g$, —OC$_{2-6}$alkylOR$^g$, —SR$^g$, —S(=O)R$^g$, —S(=O)$_2$R$^g$, —S(=O)$_2$NR$^a$R$^g$, —S(=O)$_2$N(R$^g$)C(=O)R$^e$, —S(=O)$_2$N(R$^a$)C(=O)R$^g$, —S(=O)$_2$N(R$^g$)C(=O)OR$^h$, —S(=O)$_2$N(R$^a$)C(=O)OR$^g$, —S(=O)$_2$N(R$^g$)C(=O)NR$^a$R$^h$, —S(=O)$_2$N(R$^a$)C(=O)NR$^a$R$^g$, —NR$^a$R$^g$, —N(R$^g$)C(=O)R$^e$, —N(R$^a$)C(=O)R$^g$, —N(R$^g$)C(=O)OR$^h$, —N(R$^a$)C(=O)OR$^g$, —N(R$^g$)C(=O)NR$^a$R$^h$, —N(R$^a$)C(=O)NR$^a$R$^g$, —N(R$^g$)C(=NR$^a$)NR$^a$R$^h$, —N(R$^a$)C(=NR$^a$)NR$^a$R$^g$, —N(R$^g$)S(=O)$_2$R$^e$, —N(R$^a$)S(=O)$_2$R$^g$, —N(R$^g$)S(=O)$_2$NR$^a$R$^h$, —N(R$^a$)S(=O)$_2$NR$^a$R$^g$, —NR$^h$C$_{2-6}$alkylNR$^a$R$^g$, —NR$^a$C$_{2-6}$alkylNR$^a$R$^g$, —NR$^g$C$_{2-6}$alkylOR$^h$ and —NR$^a$C$_{2-6}$alkylOR$^g$.

In another embodiment, in conjunction with any one of the above and below embodiments, R$^5$ is H.

In another embodiment, in conjunction with any one of the above and below embodiments, R$^5$ is R$^e$, C$_{1-4}$haloalkyl, halo, cyano, —C(=O)R$^e$, —C(=O)OR$^e$, —C(=O)NR$^e$R$^a$, —C(=NR$^a$)NR$^h$R$^a$, —OR$^h$, —OC(=O)R$^e$, —OC(=O)NR$^a$R$^h$, —OC(=O)N(R$^a$)S(=O)$_2$R$^e$, —OC$_{2-6}$alkylNR$^a$R$^h$, —OC$_{2-6}$alkylOR$^h$, —SR$^h$, —S(=O)R$^e$, —S(=O)$_2$R$^e$, —S(=O)$_2$NR$^a$R$^h$, —S(=O)$_2$N(R$^a$)C(=O)R$^e$, —S(=O)$_2$N(R$^a$)C(=O)O R$^e$, —S(=O)$_2$N(R$^a$)C(=O)NR$^a$R$^h$, —NR$^a$R$^h$, —N(R$^a$)C(=O)R$^e$, —N(R$^a$)C(=O)OR$^e$, —N(R$^a$)C(=O)NR$^a$R$^h$, —N(R$^a$)C(=NR$^a$)NR$^a$R$^h$, —N(R$^a$)S(=O)$_2$R$^e$, —N(R$^a$)S(=O)$_2$NR$^a$R$^h$, —NR$^a$C$_{2-6}$alkylNR$^a$R$^h$, —NR$^a$C$_{2-6}$alkylOR$^h$, —C(=O)R$^g$, —C(=O)OR$^g$, —C(=O)NR$^g$R$^a$, —C(=NR$^a$)NR$^a$R$^g$, —OR$^g$, —OC(=O)R$^g$, —OC(=O)NR$^a$R$^g$, —OC(=O)N(R$^a$)S(=O)$_2$R$^g$, —OC$_{2-6}$alkylNR$^a$R$^g$, —OC$_{2-6}$alkylOR$^g$, —SR$^g$, —S(=O)R$^g$, —S(=O)$_2$R$^g$, —S(=O)$_2$NR$^a$R$^g$, —S(=O)$_2$N(R$^a$)C(=O)R$^g$, —S(=O)$_2$N(R$^a$)C(=O)OR$^g$, —S(=O)$_2$N(R$^a$)C(=O)NR$^a$R$^g$, —NR$^a$R$^g$, —N(R$^a$)C(=O)R$^g$, —N(R$^a$)C(=O)OR$^g$, —N(R$^a$)C(=O)NR$^a$R$^g$, —N(R$^a$)C(=NR$^a$)NR$^a$R$^g$, —N(R$^a$)S(=O)$_2$R$^g$, —N(R$^a$)S(=O)$_2$NR$^a$R$^g$, —NR$^a$C$_{2-6}$alkylNR$^a$R$^g$ or —NR$^a$C$_{2-6}$alkylOR$^g$; or R$^5$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2, 3 or 4 substituents selected from R$^e$, C$_{1-4}$haloalkyl, halo, cyano, nitro, —C(=O)R$^e$, —C(=O)OR$^e$, —C(=O)NR$^e$R$^a$, —C(=NR$^a$)NR$^h$R$^a$, —OR$^h$, —OC(=O)R$^e$, —OC(=O)NR$^a$R$^h$, —OC(=O)N(R$^a$)S(=O)$_2$R$^e$, —OC$_{2-6}$alkylNR$^a$R$^h$, —OC$_{2-6}$alkylOR$^h$, —SR$^h$, —S(=O)R$^e$, —S(=O)$_2$R$^e$, —S(=O)$_2$NR$^a$R$^h$, —S(=O)$_2$N(R$^a$)C(=O)R$^e$, —S(=O)$_2$N(R$^a$)C(=O)O(R$^a$)C(=O)OR$^e$, —S(=O)$_2$N(R$^a$)C(=O)NR$^a$R$^h$, —NR$^a$R$^h$, —N(R$^a$)C(=O)R$^e$, —N(R$^a$)C(=O)OR$^e$, —N(R$^a$)C(=O)NR$^a$R$^h$, —N(R$^a$)C(=NR$^a$)NR$^a$R$^h$, —N(R$^a$)S(=O)$_2$R$^e$, —N(R$^a$)S(=O)$_2$NR$^a$R$^h$, —NR$^a$C$_{2-6}$alkylNR$^a$R$^h$, —NR$^a$C$_{2-6}$alkylOR$^h$, —C(=O)R$^g$, —C(=O)OR$^g$, —C(=O)NR$^g$R$^a$, —C(=NR$^a$)NR$^a$R$^g$, —OR$^g$, —OC(=O)R$^g$, —OC(=O)NR$^a$R$^g$, —OC(=O)N(R$^a$)S(=O)$_2$R$^g$, —OC$_{2-6}$alkylNR$^a$R$^g$, —OC$_{2-6}$alkylOR$^g$, —SR$^g$, —S(=O)R$^g$, —S(=O)$_2$R$^g$, —S(=O)$_2$NR$^a$R$^g$, —S(=O)$_2$N(R$^a$)C(=O)R$^g$, —S(=O)$_2$N(R$^a$)C(=O)OR$^g$, —S(=O)$_2$N(R$^a$)C(=O)NR$^a$R$^g$, —NR$^a$R$^g$, —N(R$^a$)S(=O)$_2$R$^g$, —N(R$^a$)S(=O)$_2$NR$^a$R$^g$, —NR$^a$C$_{2-6}$alkylNR$^a$R$^g$ and —NR$^a$C$_{2-6}$alkylOR$^g$.

In another embodiment, in conjunction with any one of the above and below embodiments, R$^5$ is R$^e$.

In another embodiment, in conjunction with any one of the above and below embodiments, R$^5$ is halo, cyano, —C(=O)R$^e$, —C(=O)OR$^e$, —C(=O)NR$^e$R$^a$, —C(=NR$^a$)NR$^h$R$^a$, —OR$^h$, —OC(=O)R$^e$, —OC(=O)NR$^a$R$^h$, —OC(=O)N(R$^a$)S(=O)$_2$R$^e$, —OC$_{2-6}$alkylNR$^a$R$^h$, —OC$_{2-6}$alkylOR$^h$, —SR$^h$, —S(=O)R$^e$, —S(=O)$_2$R$^e$, —S(=O)$_2$NR$^a$R$^h$, —S(=O)$_2$N(R$^a$)C(=O)R$^e$, —S(=O)$_2$N(R$^a$)C(=O)OR$^e$, —S(=O)$_2$N(R$^a$)C(=O)NR$^a$R$^h$, —NR$^a$R$^h$, —N(R$^a$)C(=O)R$^e$, —N(R$^a$)C(=O)OR$^e$, —N(R$^a$)C(=O)NR$^a$R$^h$, —N(R$^a$)C(=NR$^a$)NR$^a$R$^h$, —N(R$^a$)S(=O)$_2$R$^e$, —N(R$^a$)S(=O)$_2$NR$^a$R$^h$, —NR$^a$C$_{2-6}$alkylNR$^a$R$^h$, —NR$^a$C$_{2-6}$alkylOR$^h$, —C(=O)R$^g$, —C(=O)OR$^g$, —C(=O)NR$^g$R$^a$, —C(=NR$^a$)NR$^a$R$^g$, —OR$^g$, —OC(=O)R$^g$, —OC(=O)NR$^a$R$^g$, —OC(=O)N(R$^a$)S(=O)$_2$R$^g$, —OC$_{2-6}$alkylNR$^a$R$^g$, —OC$_{2-6}$alkylOR$^g$, —SR$^g$, —S(=O)R$^g$, —S(=O)$_2$R$^g$, —S(=O)$_2$NR$^a$R$^g$, —S(=O)$_2$N(R$^a$)C(=O)R$^g$, —S(=O)$_2$N(R$^a$)C(=O)OR$^g$, —S(=O)$_2$N(R$^a$)C(=O)NR$^a$R$^g$, —NR$^a$R$^g$, —N(R$^a$)C(=O)R$^g$, —N(R$^a$)C(=O)OR$^g$, —N(R$^a$)C(=O)NR$^a$R$^g$, —N(R$^a$)C(=NR$^a$)NR$^a$R$^g$, —N(R$^a$)S(=O)$_2$R$^g$, —N(R$^a$)S(=O)$_2$NR$^a$R$^g$, —NR$^a$C$_{2-6}$alkylNR$^a$R$^g$ or —NR$^a$C$_{2-6}$alkylOR$^g$.

In another embodiment, in conjunction with any one of the above and below embodiments, R$^5$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2, 3 or 4 substituents selected from R$^e$, C$_{1-4}$haloalkyl, halo, cyano, nitro, —C(=O)R$^e$, —C(=O)OR$^e$, —C(=O)NR$^e$R$^a$, —C(=NR$^a$)NR$^h$R$^a$, —OR$^h$, —OC(=O)R$^e$, —OC(=O)NR$^a$R$^h$, —OC(=O)N(R$^a$)S(=O)$_2$R$^e$, —OC$_{2-6}$alkylNR$^a$R$^h$, —OC$_{2-6}$alkylOR$^h$, —SR$^h$, —S(=O)R$^e$, —S(=O)$_2$R$^e$, —S(=O)$_2$NR$^a$R$^h$, —S(=O)$_2$N(R$^a$)C(=O)R$^e$, —S(=O)$_2$N(R$^a$)C(=O)OR$^e$, —S(=O)$_2$N(R$^a$)C(=O)NR$^a$R$^h$, —NR$^a$R$^h$, —N(R$^a$)C(=O)R$^e$, —N(R$^a$)C(=O)OR$^e$, —N(R$^a$)C(=O)NR$^a$R$^h$, —N(R$^a$)C(=NR$^a$)NR$^a$R$^h$, —N(R$^a$)S(=O)$_2$R$^e$, —N(R$^a$)S(=O)$_2$NR$^a$R$^h$, —NR$^a$C$_{2-6}$alkylNR$^a$R$^h$, —NR$^a$C$_{2-6}$alkylOR$^h$, —C(=O)R$^g$, —C(=O)OR$^g$, —C(=O)NR$^g$R$^a$, —C(=NR$^a$)NR$^a$R$^g$, —OR$^g$, —OC(=O)R$^g$, —OC(=O)NR$^a$R$^g$, —OC(=O)N(R$^a$)S(=O)$_2$R$^g$, —OC$_{2-6}$alkylNR$^a$R$^g$, —OC$_{2-6}$alkylOR$^g$, —SR$^g$, —S(=O)R$^g$, —S(=O)$_2$R$^g$, —S(=O)$_2$NR$^a$R$^g$, —S(=O)$_2$N(R$^a$)C(=O)R$^g$, —S(=O)$_2$N(R$^a$)C(=O)OR$^g$, —S(=O)$_2$N(R$^a$)C(=O)NR$^a$R$^g$, —NR$^a$R$^g$, —N(R$^a$)C(=O)R$^g$, —N(R$^a$)C(=O)OR$^g$, —N(R$^a$)C(=O)NR$^a$R$^g$, —N(R$^a$)C(=NR$^a$)NR$^a$R$^g$, —N(R$^a$)S(=O)$_2$R$^g$, —N(R$^a$)S(=O)$_2$NR$^a$R$^g$, —NR$^a$C$_{2-6}$alkylNR$^a$R$^g$ and —NR$^a$C$_{2-6}$alkylOR$^g$.

In another embodiment, in conjunction with any one of the above and below embodiments, R$^{5'}$ is H.

In another embodiment, in conjunction with any one of the above and below embodiments, R$^{5'}$ is R$^e$, C$_{1-4}$haloalkyl, halo, cyano, —C(=O)R$^e$, —C(=O)OR$^e$, —C(=O)NR$^e$R$^a$, —C(=NR$^a$)NR$^h$R$^a$, —OR$^h$, —OC(=O)R$^e$, —OC(=O)NR$^a$R$^h$, —OC(=O)N(R$^a$)S(=O)$_2$R$^e$, —OC$_{2-6}$alkylNR$^a$R$^h$, —OC$_{2-6}$alkylOR$^h$, —SR$^h$, —S(=O)R$^e$, —S(=O)$_2$R$^e$, —S(=O)$_2$NR$^a$R$^h$, —S(=O)$_2$N(R$^a$)C(=O)R$^e$, —S(=O)$_2$N(R$^a$)C(=O)OR$^e$, —S(=O)$_2$N(R$^a$)C(=O)NR$^a$R$^h$, —NR$^a$R$^h$, —N(R$^a$)C(=O)R$^e$, —N(R$^a$)C(=O)OR$^e$, —N(R$^a$)C(=O)NR$^a$R$^h$, —N(R$^a$)C(=NR$^a$)NR$^a$R$^h$, —N(R$^a$)S(=O)$_2$R$^e$, —N(R$^a$)S(=O)$_2$NR$^a$R$^h$, —NR$^a$C$_{2-6}$alkylNR$^a$R$^h$, —NR$^a$C$_{2-6}$alkylOR$^h$, —C(=O)R$^g$, —C(=O)OR$^g$, —C(=O)NR$^g$R$^a$, —C(=NR$^a$)NR$^a$R$^g$, —OR$^g$, —OC(=O)

R$^g$, —OC(=O)NR$^a$R$^g$, —OC(=O)N(R$^a$)S(=O)$_2$R$^g$, —OC$_{2-6}$alkylNR$^a$R$^g$, —OC$_{2-6}$alkylOR$^g$, —SR$^g$, —S(=O)R$^g$, —S(=O)$_2$R$^g$, —S(=O)$_2$NR$^a$R$^g$, —S(=O)$_2$N(R$^a$)C(=O)R$^g$, —S(=O)$_2$N(R$^a$)C(=O)OR$^g$, —S(=O)$_2$N(R$^a$)C(=O)NR$^a$R$^g$, —NR$^a$R$^g$, —N(R$^a$)C(=O)R$^g$, —N(R$^a$)C(=O)OR$^g$, —N(R$^a$)C(=O)NR$^a$R$^g$, —N(R$^a$)C(=NR$^a$)NR$^a$R$^g$, —N(R$^a$)S(=O)$_2$R$^g$, —N(R$^a$)S(=O)$_2$NR$^a$R$^g$, —NR$^a$C$_{2-6}$alkylNR$^a$R$^g$ or —NR$^a$C$_{2-6}$alkylOR$^g$; or R$^{5'}$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2, 3 or 4 substituents selected from R$^e$, C$_{1-4}$haloalkyl, halo, cyano, nitro, —C(=O)R$^e$, —C(=O)OR$^e$, —C(=O)NR$^e$R$^a$, —C(=NR$^a$)NR$^h$R$^a$, —OR$^h$, —OC(=O)R$^e$, —OC(=O)NR$^a$R$^h$, —OC(=O)N(R$^a$)S(=O)$_2$R$^e$, —OC$_{2-6}$alkylNR$^a$R$^h$, —OC$_{2-6}$alkylOR$^h$, —SR$^h$, —S(=O)R$^e$, —S(=O)$_2$R$^e$, —S(=O)$_2$NR$^a$R$^h$, —S(=O)$_2$N(R$^a$)C(=O)R$^e$, —S(=O)$_2$N(R$^a$)C(=O)OR$^e$, —S(=O)$_2$N(R$^a$)C(=O)NR$^a$R$^h$, —NR$^a$R$^h$, —N(R$^a$)C(=O)R$^e$, —N(R$^a$)C(=O)OR$^e$, —N(R$^a$)C(=O)NR$^a$R$^h$, —N(R$^a$)C(=NR$^a$)NR$^a$R$^h$, —N(R$^a$)S(=O)$_2$R$^e$, —N(R$^a$)S(=O)$_2$NR$^a$R$^h$, —NR$^a$C$_{2-6}$alkylNR$^a$R$^h$, —NR$^a$C$_{2-6}$alkylOR$^h$, —C(=O)R$^g$, —C(=O)OR$^g$, —C(=O)NR$^g$R$^a$, —C(=NR$^a$)NR$^a$R$^g$, —OR$^g$, —OC(=O)R$^g$, —OC(=O)NR$^a$R$^g$, —OC(=O)N(R$^a$)S(=O)$_2$R$^g$, —OC$_{2-6}$alkylNR$^a$R$^g$, —OC$_{2-6}$alkylOR$^g$, —SR$^g$, —S(=O)R$^g$, —S(=O)$_2$R$^g$, —S(=O)$_2$NR$^a$R$^g$, —S(=O)$_2$N(R$^a$)C(=O)R$^g$, —S(=O)$_2$N(R$^a$)C(=O)OR$^g$, —S(=O)$_2$N(R$^a$)C(=O)NR$^a$R$^g$, —NR$^a$R$^g$, —N(R$^a$)C(=O)R$^g$, —N(R$^a$)C(=O)OR$^g$, —N(R$^a$)C(=O)NR$^a$R$^g$, —N(R$^a$)C(=NR$^a$)NR$^a$R$^g$, —N(R$^a$)S(=O)$_2$R$^g$, —N(R$^a$)S(=O)$_2$NR$^a$R$^g$, —NR$^a$C$_{2-6}$alkylNR$^a$R$^g$ and —NR$^a$C$_{2-6}$alkylOR$^g$.

In another embodiment, in conjunction with any one of the above and below embodiments, R$^{5'}$ is R$^e$ or C$_{1-4}$haloalkyl.

In another embodiment, in conjunction with any one of the above and below embodiments, R$^{5'}$ is halo, cyano, —C(=O)R$^e$, —C(=O)OR$^e$, —C(=O)NR$^e$R$^a$, —C(=NR$^a$)NR$^e$R$^a$, —OR$^h$, —OC(=O)R$^e$, —OC(=O)NR$^a$R$^h$, —OC(=O)N(R$^a$)S(=O)$_2$R$^e$, —OC$_{2-6}$alkylNR$^a$R$^h$, —OC$_{2-6}$alkylOR$^h$, —SR$^h$, —S(=O)R$^e$, —S(=O)$_2$R$^e$, —S(=O)$_2$NR$^a$R$^h$, —S(=O)$_2$N(R$^a$)C(=O)R$^e$, —S(=O)$_2$N(R$^a$)C(=O)OR$^e$, —S(=O)$_2$N(R$^a$)C(=O)NR$^a$R$^h$, —NR$^a$R$^h$, —N(R$^a$)C(=O)R$^e$, —N(R$^a$)C(=O)OR$^e$, —N(R$^a$)C(=O)NR$^a$R$^h$, —N(R$^a$)C(=NR$^a$)NR$^a$R$^h$, —N(R$^a$)S(=O)$_2$R$^e$, —N(R$^a$)S(=O)$_2$NR$^a$R$^h$, —NR$^a$C$_{2-6}$alkylNR$^a$R$^h$, —NR$^a$C$_{2-6}$alkylOR$^h$, —C(=O)R$^g$, —C(=O)OR$^g$, —C(=O)NR$^g$R$^a$, —C(=NR$^a$)NR$^a$R$^g$, —OR$^g$, —OC(=O)R$^g$, —OC(=O)NR$^a$R$^g$, —OC(=O)N(R$^a$)S(=O)$_2$R$^g$, —OC$_{2-6}$alkylNR$^a$R$^g$, —OC$_{2-6}$alkylOR$^g$, —SR$^g$, —S(=O)R$^g$, —S(=O)$_2$R$^g$, —S(=O)$_2$NR$^a$R$^g$, —S(=O)$_2$N(R$^a$)C(=O)R$^g$, —S(=O)$_2$N(R$^a$)C(=O)OR$^g$, —S(=O)$_2$N(R$^a$)C(=O)NR$^a$R$^g$, —NR$^a$R$^g$, —N(R$^a$)C(=O)R$^g$, —N(R$^a$)C(=O)OR$^g$, —N(R$^a$)C(=O)NR$^a$R$^g$, —N(R$^a$)C(=NR$^a$)NR$^a$R$^g$, —N(R$^a$)S(=O)$_2$R$^g$, —N(R$^a$)S(=O)$_2$NR$^a$R$^g$, —NR$^a$C$_{2-6}$alkylNR$^a$R$^g$ or —NR$^a$C$_{2-6}$alkylOR$^g$.

In another embodiment, in conjunction with any one of the above and below embodiments, R$^{5'}$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2, 3 or 4 substituents selected from R$^e$, C$_{1-4}$haloalkyl, halo, cyano, nitro, —C(=O)R$^e$, —C(=O)OR$^e$, —C(=O)NR$^e$R$^a$, —C(=NR$^a$)NR$^h$R$^a$, —OR$^h$, —OC(=O)R$^e$, —OC(=O)NR$^a$R$^h$, —OC(=O)N(R$^a$)S(=O)$_2$R$^e$, —OC$_{2-6}$alkylNR$^a$R$^h$, —OC$_{2-6}$alkylOR$^h$, —SR$^h$, —S(=O)R$^e$, —S(=O)$_2$R$^e$, —S(=O)$_2$NR$^a$R$^h$, —S(=O)$_2$N(R$^a$)C(=O)R$^e$, —S(=O)$_2$N(R$^a$)C(=O)OR$^e$, —S(=O)$_2$N(R$^a$)C(=O)NR$^a$R$^h$, —NR$^a$R$^h$, —N(R$^a$)C(=O)R$^e$, —N(R$^a$)C(=O)OR$^e$, —N(R$^a$)C(=O)NR$^a$R$^h$, —N(R$^a$)C(=NR$^a$)NR$^a$R$^h$, —N(R$^a$)S(=O)$_2$R$^e$, —N(R$^a$)S(=O)$_2$NR$^a$R$^h$, —NR$^a$C$_{2-6}$alkylNR$^a$R$^h$, —NR$^a$C$_{2-6}$alkylOR$^h$, —C(=O)R$^g$, —C(=O)OR$^g$, —C(=O)NR$^g$R$^a$, —C(=NR$^a$)NR$^a$R$^g$, —OR$^g$, —OC(=O)R$^g$, —OC(=O)NR$^a$R$^g$, —OC(=O)N(R$^a$)S(=O)$_2$R$^g$, —OC$_{2-6}$alkylNR$^a$R$^g$, —OC$_{2-6}$alkylOR$^g$, —SR$^g$, —S(=O)R$^g$, —S(=O)$_2$R$^g$, —S(=O)$_2$NR$^a$R$^g$, —S(=O)$_2$N(R$^a$)C(=O)R$^g$, —S(=O)$_2$N(R$^a$)C(=O)OR$^g$, —S(=O)$_2$N(R$^a$)C(=O)NR$^a$R$^g$, —NR$^a$R$^g$, —N(R$^a$)C(=O)R$^g$, —N(R$^a$)C(=O)OR$^g$, —N(R$^a$)C(=O)NR$^a$R$^g$, —N(R$^a$)C(=NR$^a$)NR$^a$R$^g$, —N(R$^a$)S(=O)$_2$R$^g$, —N(R$^a$)S(=O)$_2$NR$^a$R$^g$, —NR$^a$C$_{2-6}$alkylNR$^a$R$^g$ and —NR$^a$C$_{2-6}$alkylOR$^g$.

In another embodiment, in conjunction with any one of the above and below embodiments, R$^6$ is H.

In another embodiment, in conjunction with any one of the above and below embodiments, R$^6$ is C$_{1-4}$haloalkyl, halo, cyano, —C(=O)R$^b$, —C(=O)OR$^b$, —C(=O)NR$^a$R$^a$, —C(=NR$^a$)NR$^a$R$^a$, —OH, —OC$_{2-6}$alkyl, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^b$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$ and R$^e$.

In another embodiment, in conjunction with any one of the above and below embodiments, R$^6$ is R$^e$ or C$_{1-4}$haloalkyl.

In another embodiment, in conjunction with any one of the above and below embodiments, R$^6$ is R$^e$.

In another embodiment, in conjunction with any one of the above and below embodiments, R$^{6'}$ is H.

In another embodiment, in conjunction with any one of the above and below embodiments, R$^{6'}$ is C$_{1-4}$haloalkyl, halo, cyano, —C(=O)R$^b$, —C(=O)OR$^b$, —C(=O)NR$^a$R$^a$, —C(=NR$^a$)NR$^a$R$^a$, —OH, —OC$_{2-6}$alkyl, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^b$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$ and R$^e$.

In another embodiment, in conjunction with any one of the above and below embodiments, R$^{6'}$ is R$^e$ or C$_{1-4}$haloalkyl.

In another embodiment, in conjunction with any one of the above and below embodiments, R$^{6'}$ is R$^e$.

In another embodiment, in conjunction with any one of the above and below embodiments, R$^b$ is independently, at each instance, phenyl, benzyl or C$_{1-6}$alkyl, the phenyl, benzyl and C$_{1-6}$alkyl being substituted by 0, 1, 2 or 3 substituents selected from halo, C$_{1-4}$alkyl, C$_{1-3}$haloalkyl, —OC$_{1-4}$alkyl, —NH$_2$, —NHC$_{1-4}$alkyl, —N(C$_{1-4}$alkyl)C$_{1-4}$alkyl.

In another embodiment, in conjunction with any one of the above and below embodiments, R$^b$ is independently, at each instance, C$_{1-6}$alkyl substituted by 0, 1, 2 or 3 substituents selected from halo, C$_{1-4}$alkyl, C$_{1-3}$haloalkyl, —OC$_{1-4}$alkyl, —NH$_2$, —NHC$_{1-4}$alkyl, —N(C$_{1-4}$alkyl)C$_{1-4}$alkyl.

In another embodiment, in conjunction with any one of the above and below embodiments, R$^b$ is independently, at each instance, C$_{1-6}$alkyl substituted by 1, 2 or 3 substituents selected from halo, $C_{1-4}$alkyl, $C_{1-3}$haloalkyl, —$OC_{1-4}$alkyl, —$NH_2$, —$NHC_{1-4}$alkyl, —$N(C_{1-4}alkyl)C_{1-4}$alkyl.

In another embodiment, in conjunction with any one of the above and below embodiments, $R^b$ is independently, at each instance, $C_{1-6}$alkyl.

In another embodiment, in conjunction with any one of the above and below embodiments, $R^c$ is independently, at each instance, a ring selected from thiophene, pyrrole, 1,3-oxazole, 1,3-thiazole, 1,3,4-oxadiazole, 1,3,4-thiadiazole, 1,2,3-oxadiazole, 1,2,3-thiadiazole, 1H-1,2,3-triazole, isothiazole, 1,2,4-oxadiazole, 1,2,4-thiadiazole, 1,2,3,4-oxatriazole, 1,2,3,4-thiatriazole, 1H-1,2,3,4-tetraazole, 1,2,3,5-oxatriazole, 1,2,3,5-thiatriazole, furan, 1,2,4-triazol-4-yl, 1,2,4-triazol-5-yl, isoxazol-3-yl, isoxazol-5-yl, thiolane, pyrrolidine, tetrahydrofuran, 4,5-dihydrothiophene, 2-pyrroline, 4,5-dihydrofuran, pyridazine, pyrimidine, pyrazine, 1,2,3-triazine, 1,2,4-triazine, 1,2,4-triazine, 1,3,5-triazine, pyridine, 2H-3,4,5,6-tetrahydropyran, thiane, 1,2-diazaperhydroine, 1,3-diazaperhydroine, piperazine, 1,3-oxazaperhydroine, morpholine, 1,3-thiazaperhydroine, 1,4-thiazaperhydroine, piperidine, 2H-3,4-dihydropyran, 2,3-dihydro-4H-thiin, 1,4,5,6-tetrahydropyridine, 2H-5,6-dihydropyran, 2,3-dihydro-6H-thiin, 1,2,5,6-tetrahydropyridine, 3,4,5,6-tetrahydropyridine, 4H-pyran, 4H-thiin, 1,4-dihydropyridine, 1,4-dithiane, 1,4-dioxane, 1,4-oxathiane, 1,2-oxazolidine, 1,2-thiazolidine, pyrazolidine, 1,3-oxazolidine, 1,3-thiazolidine, imidazolidine, 1,2,4-oxadiazolidine, 1,3,4-oxadiazolidine, 1,2,4-thiadiazolidine, 1,3,4-thiadiazolidine, 1,2,4-triazolidine, 2-imidazoline, 3-imidazoline, 2-pyrazoline, 4-imidazoline, 2,3-dihydroisothiazole, 4,5-dihydroisoxazole, 4,5-dihydroisothiazole, 2,5-dihydroisoxazole, 2,5-dihydroisothiazole, 2,3-dihydroisoxazole, 4,5-dihydrooxazole, 2,3-dihydrooxazole, 2,5-dihydrooxazole, 4,5-dihydrothiazole, 2,3-dihydrothiazole, 2,5-dihydrothiazole, 1,3,4-oxathiazolidine, 1,4,2-oxathiazolidine, 2,3-dihydro-1H-[1,2,3]triazole, 2,5-dihydro-1H-[1,2,3]triazole, 4,5-dihydro-1H-[1,2,3]triazole, 2,3-dihydro-1H-[1,2,4]triazole, 4,5-dihydro-1H-[1,2,4]triazole, 2,3-dihydro-[1,2,4]oxadiazole, 2,5-dihydro-[1,2,4]oxadiazole, 4,5-dihydro-[1,2,4]thiadiazole, 2,3-dihydro-[1,2,4]thidiazole, 2,5-dihydro-[1,2,4]thiadiazole, 4,5-dihydro-[1,2,4]thiadiazole, 2,5-dihydro-[1,2,4]oxadiazole, 2,3-dihydro-[1,2,4]oxadiazole, 4,5-dihydro-[1,2,4]oxadiazole, 2,5-dihydro-[1,2,4]thiadiazole, 2,3-dihydro-[1,2,4]thiadiazole, 4,5-dihydro-[1,2,4]thiadiazole, 2,3-dihydro-[1,3,4]oxadiazole, 2,3-dihydro-[1,3,4]thiadiazole, [1,4,2]oxathiazole, [1,3,4]oxathiazole, 1,3,5-triazaperhydroine, 1,2,4-triazaperhydroine, 1,4,2-dithiazaperhydroine, 1,4,2-dioxazaperhydroine, 1,3,5-oxadiazaperhydroine, 1,2,5-oxadiazaperhydroine, 1,3,4-thiadiazaperhydroine, 1,3,5-thiadiazaperhydroine, 1,2,5-thiadiazaperhydroine, 1,3,4-oxadiazaperhydroine, 1,4,3-oxathiazaperhydroine, 1,4,2-oxathiazaperhydroine, 1,4,5,6-tetrahydropyridazine, 1,2,3,4-tetrahydropyridazine, 1,2,3,6-tetrahydropyridazine, 1,2,5,6-tetrahydropyrimidine, 1,2,3,4-tetrahydropyrimidine, 1,4,5,6-tetrahydropyrimidine, 1,2,3,6-tetrahydropyrazine, 1,2,3,4-tetrahydropyrazine, 5,6-dihydro-4H-[1,2]oxazine, 5,6-dihydro-2H-[1,2]oxazine, 3,6-dihydro-2H-[1,2]oxazine, 3,4-dihydro-2H-[1,2]oxazine, 5,6-dihydro-4H-[1,2]thiazine, 5,6-dihydro-2H-[1,2]thiazine, 3,6-dihydro-2H-[1,2]thiazine, 3,4-dihydro-2H-[1,2]thiazine, 5,6-dihydro-2H-[1,3]oxazine, 5,6-dihydro-4H-[1,3]oxazine, 3,6-dihydro-2H-[1,3]oxazine, 3,4-dihydro-2H-[1,3]oxazine, 3,6-dihydro-2H-[1,4]oxazine, 3,4-dihydro-2H-[1,4]oxazine, 5,6-dihydro-2H-[1,3]thiazine, 5,6-dihydro-4H-[1,3]thiazine, 3,6-dihydro-2H-[1,3]thiazine, 3,4-dihydro-2H-[1,3]thiazine, 3,6-dihydro-2H-[1,4]thiazine, 3,4-dihydro-2H-[1,4]thiazine, 1,2,3,6-tetrahydro-[1,2,4]triazine, 1,2,3,4-tetrahydro-[1,2,4]triazine, 1,2,3,4-tetrahydro-[1,3,5]triazine, 2,3,4,5-tetrahydro-[1,2,4]triazine, 1,4,5,6-tetrahydro-[1,2,4]triazine, 5,6-dihydro-[1,4,2]dioxazine, 5,6-dihydro-[1,4,2]dioxazine, 5,6-dihydro-[1,4,2]dithiazine, 2,3-dihydro-[1,4,2]dioxazine, 3,4-dihydro-2H-[1,3,4]oxadiazine, 3,6-dihydro-2H-[1,3,4]oxadiazine, 3,4-dihydro-2H-[1,3,5]oxadiazine, 3,6-dihydro-2H-[1,3,5]oxadiazine, 5,6-dihydro-2H-[1,2,5]oxadiazine, 5,6-dihydro-4H-[1,2,5]oxadiazine, 3,4-dihydro-2H-[1,3,4]thiadiazine, 3,6-dihydro-2H-[1,3,4]thiadiazine, 3,4-dihydro-2H-[1,3,5]thiadiazine, 3,6-dihydro-2H-[1,3,5]thiadiazine, 5,6-dihydro-2H-[1,2,5]thiadiazine, 5,6-dihydro-4H-[1,2,5]thiadiazine, 5,6-dihydro-2H-[1,2,3]oxadiazine, 3,6-dihydro-2H-[1,2,5]oxadiazine, 5,6-dihydro-4H-[1,3,4]oxadiazine, 3,4-dihydro-2H-[1,2,5]oxadiazine, 5,6-dihydro-2H-[1,2,3]thiadiazine, 3,6-dihydro-2H-[1,2,5]thiadiazine, 5,6-dihydro-4H-[1,3,4]thiadiazine, 3,4-dihydro-2H-[1,2,5]thiadiazine, 5,6-dihydro-[1,4,3]oxathiazine, 5,6-dihydro-[1,4,2]oxathiazine, 2,3-dihydro-[1,4,3]oxathiazine, 2,3-dihydro-[1,4,2]oxathiazine, 4,5-dihydropyridine, 1,6-dihydropyridine, 5,6-dihydropyridine, 2H-pyran, 2H-thiin, 3,6-dihydropyridine, 2,3-dihydropyridazine, 2,5-dihydropyridazine, 4,5-dihydropyridazine, 1,2-dihydropyridazine, 2,3-dihydropyrimidine, 2,5-dihydropyrimidine, 5,6-dihydropyrimidine, 3,6-dihydropyrimidine, 4,5-dihydropyrazine, 5,6-dihydropyrazine, 3,6-dihydropyrazine, 4,5-dihydropyrazine, 1,4-dihydropyrazine, 1,4-dithiin, 1,4-dioxin, 2H-1,2-oxazine, 6H-1,2-oxazine, 4H-1,2-oxazine, 2H-1,3-oxazine, 4H-1,3-oxazine, 6H-1,3-oxazine, 2H-1,4-oxazine, 4H-1,4-oxazine, 2H-1,3-thiazine, 2H-1,4-thiazine, 4H-1,2-thiazine, 6H-1,3-thiazine, 4H-1,4-thiazine, 2H-1,2-thiazine, 6H-1,2-thiazine, 1,4-oxathiin, 2H,5H-1,2,3-triazine, 1H,4H-1,2,3-triazine, 4,5-dihydro-1,2,3-triazine, 1H,6H-1,2,3-triazine, 1,2-dihydro-1,2,3-triazine, 2,3-dihydro-1,2,4-triazine, 3H,6H-1,2,4-triazine, 1H,6H-1,2,4-triazine, 3,4-dihydro-1,2,4-triazine, 1H,4H-1,2,4-triazine, 5,6-dihydro-1,2,4-triazine, 4,5-dihydro-1,2,4-triazine, 2H,5H-1,2,4-triazine, 1,2-dihydro-1,2,4-triazine, 1H,4H-1,3,5-triazine, 1,2-dihydro-1,3,5-triazine, 1,4,2-dithiazine, 1,4,2-dioxazine, 2H-1,3,4-oxadiazine, 2H-1,3,5-oxadiazine, 6H-1,2,5-oxadiazine, 4H-1,3,4-oxadiazine, 4H-1,3,5-oxadiazine, 4H-1,2,5-oxadiazine, 2H-1,3,5-thiadiazine, 6H-1,2,5-thiadiazine, 4H-1,3,4-thiadiazine, 4H-1,3,5-thiadiazine, 4H-1,2,5-thiadiazine, 2H-1,3,4-thiadiazine, 6H-1,3,4-thiadiazine, 6H-1,3,4-oxadiazine, 1,4,2-oxathiazine and any bicyclic derivative of any of the above rings containing a vicinally-fused phenyl, pyridine or pyrimidine, wherein the carbon atoms of the ring and bicyclic derivative are substituted by 0, 1 or 2 oxo or thioxo groups.

In another embodiment, in conjunction with any one of the above and below embodiments, $R^e$ is independently at each instance $C_{1-6}$alkyl substituted by 1, 2 or 3 substituents independently selected from $R^d$ and additionally substituted by 0 or 1 substituents selected from $R^g$.

In another embodiment, in conjunction with any one of the above and below embodiments, $R^e$ is independently at each instance $C_{1-6}$alkyl substituted by 0, 1, 2 or 3 substituents independently selected from $R^d$ and additionally substituted by 1 substituent selected from $R^g$.

In another embodiment, in conjunction with any one of the above and below embodiments, $R^e$ is independently at each instance $C_{1-6}$alkyl.

In another embodiment, in conjunction with any one of the above and below embodiments, $R^g$ is independently at each instance a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$alkylN$R^aR^a$ and —N$R^a$C$_{2-6}$alkylO$R^a$.

In another embodiment, in conjunction with any one of the above and below embodiments, $R^g$ is independently at each instance a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$alkylN$R^aR^a$ and —N$R^a$C$_{2-6}$alkylO$R^a$.

In another embodiment, in conjunction with any one of the above and below embodiments, $R^g$ is independently at each instance a saturated, partially saturated or unsaturated 5-, 6- or 7-membered monocyclic or 6-, 7-, 8-, 9-, 10- or 11-membered bicyclic ring containing 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$alkylN$R^aR^a$ and —N$R^a$C$_{2-6}$alkylO$R^a$.

In another embodiment, in conjunction with any one of the above and below embodiments, $R^g$ is phenyl substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$alkylN$R^aR^a$ and —N$R^a$C$_{2-6}$alkylO$R^a$.

In another embodiment, in conjunction with any one of the above and below embodiments, $R^g$ is phenyl substituted by 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$alkylN$R^aR^a$ and —N$R^a$C$_{2-6}$alkylO$R^a$.

Another embodiment of the invention involves a compound having the structure:

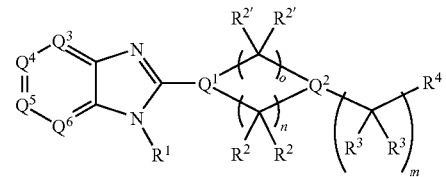

or any pharmaceutically-acceptable salt thereof, wherein:

n is 1, 2 or 3 and o is 1, 2 or 3; wherein n+o=4 or 5 and when n is 1 and $Q^1$ and $Q^2$ are both N, then both $R^2$ groups together are oxo, and when o is 1 and $Q^1$ and $Q^2$ are both N, then both $R^{2'}$ groups together are oxo;

m is independently at each instance 0, 1 or 2;

$Q^1$ is N or C($R^2$);

$Q^2$ is N or C($R^2$); wherein at least one of $Q^1$ and $Q^2$ is N;

$Q^3$ is N or C($R^{25}$);

$Q^4$ is N or C($R^6$);

$Q^5$ is N or C($R^6$);

$Q^6$ is N or C($R^5$);

—$R^1$ is H or (C($R^2$)($R^2$))$_m$—$R^g$;

$R^2$ is, independently, in each instance, H, $C_{1-8}$alkyl, $C_{1-4}$haloalkyl, —O($C_{1-7}$alkyl), —N($C_{1-7}$alkyl)$R^a$, or a $C_{1-6}$alkyl substituted by 1, 2 or 3 substituents selected from halo, cyano, —O$R^a$, —OC(=O)$R^b$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N$R^a$C$_{2-6}$alkylN$R^aR^a$ and —N$R^a$C$_{2-6}$alkylO$R^a$; wherein any two geminal $R^2$ groups may additionally be oxo;

$R^{2'}$ is, independently, in each instance, H, $C_{1-8}$alkyl, $C_{1-4}$haloalkyl, —O($C_{1-7}$alkyl), —N($C_{1-7}$alkyl)$R^a$, or a $C_{1-6}$alkyl substituted by 1, 2 or 3 substituents selected from halo, cyano, —O$R^a$, —OC(=O)$R^b$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N$R^a$C$_{2-6}$alkylN$R^aR^a$ and —N$R^a$C$_{2-6}$alkylO$R^a$; wherein any two geminal $R^{2'}$ groups may additionally be oxo;

$R^3$ is, independently, in each instance, H, $C_{1-8}$alkyl, $C_{1-4}$haloalkyl, —O($C_{1-7}$alkyl), —N($C_{1-7}$alkyl)$R^a$, or a $C_{1-6}$alkyl substituted by 0, 1, 2 or 3 substituents selected from halo, cyano, —O$R^a$, —OC(=O)$R^b$, —S$R^a$, —S(=O)$R^b$, —S(=O)$_2R^b$, —S(=O)$_2$N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —($R^a$)S(=O)$_2R^b$, —N$R^a$C$_{2-6}$alkylN$R^aR^a$ and —N$R^a$C$_{2-6}$alkylO$R^a$; wherein any two geminal $R^3$ groups may additionally be oxo;

$R^4$ is phenyl or naphthyl, wherein the phenyl and naphthyl are substituted by 1, 2, 3 or 4 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$) S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N (R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$ and R$^e$; or R$^4$ is R$^c$ substituted by 0, 1, 2, 3 or 4 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)NR$^a$R$^a$, —NR$^a$C$_{2-6}$alkylNR$^a$R$^a$, —NR$^a$C$_{2-6}$alkylOR$^a$ and R$^e$;

R$^5$ is independently, at each instance, H, C$_{1-8}$alkyl, C$_{1-4}$haloalkyl, halo, cyano, —C(=O)R$^b$, —C(=O)OR$^b$, —C(=O)NR$^b$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)NR$^a$R$^a$, —NR$^a$C$_{2-6}$alkylNR$^a$R$^a$, —NR$^a$C$_{2-6}$alkylOR$^a$, C$_{1-3}$alkylR$^c$, C$_{1-3}$alkylR$^f$ and R$^e$; or R$^5$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2, 3 or 4 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$ and R$^e$;

R$^6$ is independently, at each instance, H, C$_{1-8}$alkyl, C$_{1-4}$haloalkyl, halo, cyano, —C(=O)R$^b$, —C(=O)OR$^b$, —C(=O)NR$^a$R$^a$, —C(=NR$^a$)NR$^a$R$^a$, —OH, —OC$_{2-6}$alkyl, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^b$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$ and R$^a$;

R$^a$ is independently, at each instance, H or R$^b$;

R$^b$ is independently, at each instance, phenyl, benzyl or C$_{1-6}$alkyl, the phenyl, benzyl and C$_{1-6}$alkyl being substituted by 0, 1, 2 or 3 substituents selected from halo, C$_{1-4}$alkyl, C$_{1-3}$haloalkyl, —OC$_{1-4}$alkyl, —NH$_2$, —NHC$_{1-4}$alkyl, —N(C$_{1-4}$alkyl)C$_{1-4}$alkyl;

R$^c$ is independently at each instance a saturated, partially saturated or unsaturated 5-, 6- or 7-membered monocyclic or 6-, 7-, 8-, 9-, 10- or 11-membered bicyclic ring containing 1, 2, 3 or 4 atoms selected from N, O and S, wherein the carbon atoms of the ring are substituted by 0, 1 or 2 oxo groups;

R$^d$ is independently at each instance C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)R$^a$R$^a$, —OR$^a$, —C(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

R$^e$ is independently at each instance C$_{1-6}$alkyl substituted by 1, 2 or 3 substituents independently selected from R$^d$;

R$^f$ is independently at each instance R$^c$ substituted by 1, 2 or 3 substituents independently selected from R$^d$; and R$^g$ is independently at each instance a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$.

Another embodiment of the invention involves a compound having the structure:

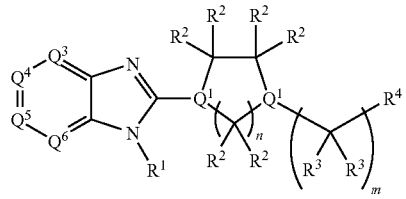

or any pharmaceutically-acceptable salt thereof, wherein:
n is 2 or 3;
m is independently at each instance 0, 1 or 2;
Q$^1$ is N or C(R$^2$);
Q$^2$ is N or C(R$^2$); wherein at least one of Q$^1$ and Q$^2$ is N;
Q$^3$ is N or C(R$^5$);
Q$^4$ is N or C(R$^6$);
Q$^5$ is N or C(R$^6$);
Q$^6$ is N or C(R$^5$);
R$^1$ is H or (C(R$^2$)(R$^2$))$_m$—R$^g$;
R$^2$ is, independently, in each instance, H, C$_{1-8}$alkyl, C$_{1-4}$haloalkyl, —O(C$_{1-7}$alkyl), —N(C$_{1-7}$alkyl)R$^a$, or a C$_{1-6}$alkyl substituted by 1, 2 or 3 substituents selected from halo, cyano, —OR$^a$, —OC(=O)R$^b$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —NR$^a$C$_{2-6}$alkylNR$^a$R$^a$ and —NR$^a$C$_{2-6}$alkylOR$^a$; wherein any two geminal R$^2$ groups may additionally be oxo;

R$^3$ is, independently, in each instance, H, C$_{1-8}$alkyl, C$_{1-4}$haloalkyl, —O(C$_{1-7}$alkyl), —N(C$_{1-7}$alkyl)R$^a$, or a C$_{1-6}$alkyl substituted by 0, 1, 2 or 3 substituents selected from halo, cyano, —OR$^a$, —OC(=O)R$^b$, —SR$^a$, —S(=O)R$^b$, —S(=O)$_2$R$^b$, —S(=O)$_2$NR$^a$R$^a$, —NR$^a$R$^a$, —N(R$^a$)C (=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —NR$^a$C$_{2-6}$alkylNR$^a$R$^a$ and —NR$^a$C$_{2-6}$alkylOR$^a$; wherein any two geminal R$^3$ groups may additionally be oxo;

R$^4$ is phenyl or naphthyl, wherein the phenyl and naphthyl are substituted by 1, 2, 3 or 4 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —C(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$ and R$^e$; or R$^4$ is R$^c$ substituted by 0, 1, 2, 3 or 4 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$ and R$^e$;

R$^5$ is independently, at each instance, H, C$_{1-8}$alkyl, C$_{1-4}$haloalkyl, halo, cyano, —C(=O)R$^b$, —C(=O)OR$^b$, —C(=O)NR$^b$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, C$_{1-3}$alkylR$^c$, C$_{1-3}$alkylR$^f$ and R$^e$; or R$^5$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2, 3 or 4 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$ and R$^e$;

R$^6$ is independently, at each instance, H, C$_{1-8}$alkyl, C$_{1-4}$haloalkyl, halo, cyano, —C(=O)R$^b$, —C(=O)OR$^b$, —C(=O)NR$^a$R$^a$, —C(=NR$^a$)NR$^a$R$^a$, —OH, —OC$_{2-6}$alkyl, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^b$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$ and R$^e$;

R$^a$ is independently, at each instance, H or R$^b$;

R$^b$ is independently, at each instance, phenyl, benzyl or C$_{1-6}$alkyl, the phenyl, benzyl and C$_{1-6}$alkyl being substituted by 0, 1, 2 or 3 substituents selected from halo, C$_{1-4}$alkyl, C$_{1-3}$haloalkyl, —OC$_{1-4}$alkyl, —NH$_2$, —NHC$_{1-4}$alkyl, —N(C$_{1-4}$alkyl)C$_{1-4}$alkyl;

R$^c$ is independently at each instance a saturated, partially saturated or unsaturated 5-, 6- or 7-membered monocyclic or 6-, 7-, 8-, 9-, 10- or 11-membered bicyclic ring containing 1, 2, 3 or 4 atoms selected from N, O and S, wherein the carbon atoms of the ring are substituted by 0, 1 or 2 oxo groups;

R$^d$ is independently at each instance C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

R$^e$ is independently at each instance C$_{1-6}$alkyl substituted by 1, 2 or 3 substituents independently selected from R$^d$;

R$^f$ is independently at each instance R$^e$ substituted by 1, 2 or 3 substituents independently selected from R$^d$; and R$^g$ is independently at each instance a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, Q$^1$ is N.

In another embodiment, in conjunction with any one of the above and below embodiments, Q$^2$ is N.

In another embodiment, in conjunction with any one of the above and below embodiments, Q$^1$ is N, and Q$^2$ is N.

In another embodiment, in conjunction with any one of the above and below embodiments, Q$^3$ is C(R$^5$); Q$^4$ is C(R$^6$); Q$^5$ is C(R$^6$); and Q$^6$ is C(R$^5$).

In another embodiment, in conjunction with any one of the above and below embodiments, any one of Q$^3$, Q$^4$, Q$^5$ and Q$^6$ is N.

In another embodiment, in conjunction with any one of the above and below embodiments, Q$^3$ is N; Q$^4$ is C(R$^6$); Q$^5$ is C(R$^6$); and Q$^6$ is C(R$^5$).

In another embodiment, in conjunction with any one of the above and below embodiments, Q$^3$ is C(R$^5$); Q$^4$ is N; Q$^5$ is C(R$^6$); and Q$^6$ is C(R$^5$)

In another embodiment, in conjunction with any one of the above and below embodiments, Q$^3$ is C(R$^5$); Q$^4$ is C(R$^6$); Q$^5$ is N; and Q$^6$ is C(R$^5$).

In another embodiment, in conjunction with any one of the above and below embodiments, Q$^3$ is C(R$^{25}$); Q$^4$ is C(R$^6$); Q$^5$ is C(R$^6$); and Q$^6$ is N.

In another embodiment, in conjunction with any one of the above and below embodiments, $Q^3$ is N; $Q^4$ is N; $Q^5$ is $C(R^6)$; and $Q^6$ is $C(R^5)$.

In another embodiment, in conjunction with any one of the above and below embodiments, $Q^3$ is N; $Q^4$ is $C(R^6)$; $Q^5$ is N; and $Q^6$ is $C(R^5)$.

In another embodiment, in conjunction with any one of the above and below embodiments, $Q^3$ is N; $Q^4$ is $C(R^6)$; $Q^5$ is $C(R^5)$; and $Q^6$ is N.

In another embodiment, in conjunction with any one of the above and below embodiments, $Q^3$ is $C(R^5)$; $Q^4$ is N; $Q^5$ is N; and $Q^6$ is $C(R^5)$.

In another embodiment, in conjunction with any one of the above and below embodiments, $Q^3$ is $C(R^5)$; $Q^4$ is $C(R^6)$; $Q^5$ is N; and $Q^6$ is N.

In another embodiment, in conjunction with any one of the above and below embodiments, $Q^3$ is $C(R^5)$; $Q^4$ is N; $Q^5$ is $C(R^6)$; and $Q^6$ is N.

In another embodiment, in conjunction with any one of the above and below embodiments, any two of $Q^3$, $Q^4$, $Q^5$ and $Q^6$ are N.

In another embodiment, in conjunction with any one of the above and below embodiments, $R^1$ is H.

In another embodiment, in conjunction with any one of the above and below embodiments, $R^1$ is $-(C(R^2)(R^{2'}))_m-R^g$.

In another embodiment, in conjunction with any one of the above and below embodiments, $R^g$ is independently at each instance an unsaturated 5-, 6- or 7-membered monocyclic ring containing 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, $-C(=O)R^b$, $-C(=O)OR^b$, $-C(=O)NR^aR^a$, $-C(=NR^a)NR^aR^a$, $-OR^a$, $-OC(=O)R^b$, $-OC(=O)NR^aR^a$, $-OC(=O)N(R^a)S(=O)_2R^b$, $-OC_{2-6}$alkylNR$^a$R$^a$, $-OC_{2-6}$alkylOR$^a$, $-SR^a$, $-S(=O)R^b$, $-S(=O)_2R^b$, $-S(=O)_2NR^aR^a$, $-S(=O)_2N(R^a)C(=O)R^b$, $-S(=O)_2N(R^a)C(=O)OR^b$, $-S(=O)_2N(R^a)C(=O)NR^aR^a$, $-NR^aR^a$, $-N(R^a)C(=O)R^b$, $-N(R^a)C(=O)OR^b$, $-N(R^a)C(=O)NR^aR^a$, $-N(R^a)C(=NR^a)NR^aR^a$, $-N(R^a)S(=O)_2R^b$, $-N(R^a)S(=O)NR^aR^a$, $-NR^aC_{2-6}$alkylNR$^a$R$^a$ and $-NR^aC_{2-6}$alkylOR$^a$.

In another embodiment, in conjunction with any one of the above and below embodiments, $R^g$ is independently at each instance naphthyl or phenyl substituted by 0, 1, 2 or 3 substituents selected from $C_{1-8}$alkyl, $C_{1-4}$haloalkyl, halo, cyano, nitro, $-C(=O)R^b$, $-C(=O)OR^b$, $-C(=O)NR^aR^a$, $-C(=NR^a)NR^aR^a$, $-OR^a$, $-OC(=O)R^b$, $-OC(=O)NR^aR^a$, $-OC(=O)N(R^a)S(=O)_2R^b$, $-OC_{2-6}$alkylNR$^a$R$^a$, $-OC_{2-6}$alkylOR$^a$, $-SR^a$, $-S(=O)R^b$, $-S(=O)_2R^b$, $-S(=O)_2NR^aR^a$, $-S(=O)_2N(R^a)C(=O)R^b$, $-S(=O)_2N(R^a)C(=O)OR^b$, $-S(=O)_2N(R^a)C(=O)NR^aR^a$, $-NR^aR^a$, $-N(R^a)C(=O)R^b$, $-N(R^a)C(=O)OR^b$, $-N(R^a)C(=O)NR^aR^a$, $-N(R^a)C(=NR^a)NR^aR^a$, $-N(R^a)S(=O)_2R^b$, $-N(R^a)S(=O)NR^aR^a$, $-NR^aC_{2-6}$alkylNR$^a$R$^a$ and $-NR^aC_{2-6}$alkylOR$^a$.

In another embodiment, in conjunction with any one of the above and below embodiments, $R^2$ is, in each instance, H.

In another embodiment, in conjunction with any one of the above and below embodiments, at least one $R^2$ group is selected from $C_{1-8}$alkyl, $C_{1-4}$haloalkyl, $-O(C_{1-7}$alkyl), $-N(C_{1-7}$alkyl)$R^a$, oxo and $C_{1-6}$alkyl substituted by 0, 1, 2 or 3 substituents selected from halo, cyano, $-OR^a$, $-OC(=O)R^b$, $-SR^a$, $-S(=O)R^b$, $-S(=O)_2R^b$, $-S(=O)_2NR^aR^a$, $-NR^aR^a$, $-N(R^a)C(=O)R^b$, $-N(R^a)C(=O)OR^b$, $-N(R^a)C(=O)NR^aR^a$, $-N(R^a)C(=NR^a)NR^aR^a$, $-N(R^a)S(=O)_2R^b$, $-NR^aC_{2-6}$alkylNR$^a$R$^a$ and $-NR^aC_{2-6}$alkylOR$^a$.

In another embodiment, in conjunction with any one of the above and below embodiments, at least one $R^2$ group is $C_{1-8}$alkyl or $C_{1-4}$haloalkyl.

In another embodiment, in conjunction with any one of the above and below embodiments, one $R^2$ group is selected from $C_{1-8}$alkyl and $C_{1-4}$haloalkyl, wherein the remaining $R^2$ groups are H.

In another embodiment, in conjunction with any one of the above and below embodiments, two geminal $R^2$ or $R^{2'}$ groups are oxo.

In another embodiment, in conjunction with any one of the above and below embodiments, $R^3$ is, in each instance, H.

In another embodiment, in conjunction with any one of the above and below embodiments, at least one $R^3$ group is selected from $C_{1-8}$alkyl, $C_{1-4}$haloalkyl, $-O(C_{1-7}$alkyl), $-N(C_{1-7}$alkyl)$R^a$, oxo and $C_{1-6}$alkyl substituted by 0, 1, 2 or 3 substituents selected from halo, cyano, $-OR^a$, $-OC(=O)R^b$, $-SR^a$, $-S(=O)R^b$, $-S(=O)_2R^b$, $-S(=O)_2NR^aR^a$, $-NR^aR^a$, $-N(R^a)C(=O)R^b$, $-N(R^a)C(=O)OR^b$, $-N(R^a)C(=O)NR^aR^a$, $-N(R^a)C(=NR^a)NR^aR^a$, $-N(R^a)S(=O)_2R^b$, $-NR^aC_{2-6}$alkylNR$^a$R$^a$ and $-NR^aC_{2-6}$alkylOR$^a$.

In another embodiment, in conjunction with any one of the above and below embodiments, at least one $R^3$ group is selected from $C_{1-8}$alkyl and $C_{1-4}$haloalkyl.

In another embodiment, in conjunction with any one of the above and below embodiments, one $R^3$ group is selected from $C_{1-8}$alkyl and $C_{1-4}$haloalkyl, wherein the remaining $R^3$ groups are H.

In another embodiment, in conjunction with any one of the above and below embodiments, two geminal $R^3$ groups are oxo.

In another embodiment, in conjunction with any one of the above and below embodiments, $R^4$ is phenyl or naphthyl, wherein the phenyl and naphthyl are substituted by 1, 2, 3 or 4 substituents selected from $C_{1-8}$alkyl, $C_{1-4}$haloalkyl, halo, cyano, nitro, $-C(=O)R^b$, $-C(=O)OR^b$, $-C(=O)NR^aR^a$, $-C(=NR^a)NR^aR^a$, $-OR^a$, $-OC(=O)R^b$, $-OC(=O)NR^aR^a$, $-OC(=O)N(R^a)S(=O)_2R^b$, $-OC_{2-6}$alkylNR$^a$R$^a$, $-OC_{2-6}$alkylOR$^a$, $-SR^a$, $-S(=O)R^b$, $-S(=O)_2R^b$, $-S(=O)_2NR^aR^a$, $-S(=O)_2N(R^a)C(=O)R^b$, $-S(=O)_2N(R^a)C(=O)OR^b$, $-S(=O)_2N(R^a)C(=O)NR^aR^a$, $-NR^aR^a$, $-N(R^a)C(=O)R^b$, $-N(R^a)C(=O)OR^b$, $-N(R^a)C(=O)NR^aR^a$, $-N(R^a)C(=NR^a)NR^aR^a$, $-N(R^a)S(=O)_2R^b$, $-N(R^a)S(=O)_2NR^aR^a$, $-NR^aC_{2-6}$alkylNR$^a$R$^a$, $-NR^aC_{2-6}$alkylOR$^a$ and $R^e$.

In another embodiment, in conjunction with any one of the above and below embodiments, $R^4$ is phenyl substituted by 1, 2, 3 or 4 substituents selected from $C_{1-8}$alkyl, $C_{1-4}$haloalkyl, halo, cyano, nitro, $-C(=O)R^b$, $-C(=O)OR^b$, $-C(=O)NR^aR^a$, $-C(=NR^a)NR^aR^a$, $-OR^a$, $-OC(=O)R^b$, $-OC(=O)NR^aR^a$, $-OC(=O)N(R^a)S(=O)_2R^b$, $-OC_{2-6}$alkylNR$^a$R$^a$, $-OC_{2-6}$alkylOR$^a$, $-SR^a$, $-S(=O)R^b$, $-S(=O)_2R^b$, $-S(=O)_2NR^aR^a$, $-S(=O)_2N(R^a)C(=O)R^b$, $-S(=O)_2N(R^a)C(=O)OR^b$, $-S(=O)_2N(R^a)C(=O)NR^aR^a$, $-NR^aR^a$, $-N(R^a)C(=O)R^b$, $-N(R^a)C(=O)OR^b$, $-N(R^a)C(=O)NR^aR^a$, $-N(R^a)C(=NR^a)NR^aR^a$, $-N(R^a)S(=O)_2R^b$, $-N(R^a)S(=O)_2NR^aR^a$, $-NR^aC_{2-6}$alkylNR$^a$R$^a$, $-NR^aC_{2-6}$alkylOR$^a$ and $R^e$.

In another embodiment, in conjunction with any one of the above and below embodiments, $R^4$ is phenyl substituted by 1, 2 or 3 substituents selected from $C_{1-4}$haloalkyl and halo.

In another embodiment, in conjunction with any one of the above and below embodiments, $R^4$ is 2,4-dichlorophenyl, 2,6-dichlorophenyl, 2-bromophenyl, 2-chloro-4-trifluoromethylphenyl, 2-chloro-6-trifluoromethylphenyl, 2-chlorophenyl, 2-fluorophenyl, 2-methylphenyl, 2-trifluoromethyl-4-chlorophenyl, 2-trifluoromethyl-6-chlorophenyl, 2-trifluoromethylphenyl, 3,4-dichlorophenyl, 3-chloro-4-trifluoromethylphenyl or 3-trifluoromethyl-4-chlorophenyl.

In another embodiment, in conjunction with any one of the above and below embodiments, $R^4$ is $R^c$ substituted by 0, 1, 2, 3 or 4 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$ and $R^e$; wherein $R^4$ is not imidazol-5-yl or 4-$C_{1-8}$alkylimidazol-5-yl.

In another embodiment, in conjunction with any one of the above and below embodiments, $R^4$ is an unsaturated 5-, 6- or 7-membered monocyclic or 6-, 7-, 8-, 9-, 10- or 11-membered bicyclic ring containing 1, 2, 3 or 4 atoms selected from N, O and S, wherein the carbon atoms of the ring are substituted by 0, 1 or 2 oxo groups and the rings are substituted by 0, 1, 2, 3 or 4 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^3$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$ and $R^e$; wherein $R^4$ is not imidazol-5-yl or 4-$C_{1-8}$alkylimidazol-5-yl.

In another embodiment, in conjunction with any one of the above and below embodiments, $R^4$ is an unsaturated 6- or 7-membered monocyclic or 6-, 7-, 8-, 9-, 10- or 11-membered bicyclic ring containing 1, 2, 3 or 4 atoms selected from N, O and S, wherein the carbon atoms of the ring are substituted by 0, 1 or 2 oxo groups and the rings are substituted by 0, 1, 2, 3 or 4 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$ and $R^e$.

In another embodiment, in conjunction with any one of the above and below embodiments, $R^4$ is an unsaturated 6-membered monocyclic ring containing 1, 2 or 3 atoms selected from N, O and S, wherein the carbon atoms of the ring are substituted by 0, 1 or 2 oxo groups and the rings are substituted by 0, 1, 2, 3 or 4 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$ and $R^e$.

In another embodiment, in conjunction with any one of the above and below embodiments, $R^4$ is an unsaturated 6-membered monocyclic ring containing 1 or 2 N atoms and the rings are substituted by 1, 2, 3 or 4 substituents selected from $C_{1-8}$alkyl, $C_{1-4}$haloalkyl, halo, —O$R^a$, —N$R^aR^a$.

In another embodiment, in conjunction with any one of the above and below embodiments, $R^4$ is pyridine or pyrimidine, wherein the pyridine or pyrimidine by substituted by 1, 2, 3 or 4 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$ and $R^e$.

In another embodiment, in conjunction with any one of the above and below embodiments, $R^4$ is an unsaturated 5-membered monocyclic ring containing 1, 2 or 3 atoms selected from N, O and S, but no more than one N, wherein the carbon atoms of the ring are substituted by 0, 1 or 2 oxo groups and the rings are substituted by 0, 1, 2, 3 or 4 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$ and $R^e$.

In another embodiment, in conjunction with any one of the above and below embodiments, $R^4$ is a saturated, partially saturated or unsaturated 6-, 7-, 8-, 9-, 10- or 11-membered bicyclic ring containing 1, 2, 3 or 4 atoms selected from N, O and S, wherein the carbon atoms of the ring are substituted by 0, 1 or 2 oxo groups and the rings are substituted by 0, 1, 2, 3 or 4 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)N$R^aR^a$, —N$R^aC_{2-6}$alkylN$R^aR^a$, —N$R^aC_{2-6}$alkylO$R^a$ and $R^e$.

In another embodiment, in conjunction with any one of the above and below embodiments, $R^4$ is a saturated, partially saturated or unsaturated 9- or 10-membered bicyclic ring containing 1, 2, 3 or 4 N atoms, wherein the rings are substituted by 0, 1, 2, 3 or 4 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C (=O)$R^b$, —S(=O)$_2$N($R^a$)C(=O)O$R^b$, —S(=O)$_2$N($R^a$)C(=O)N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a$C$_{2-6}$alkylN$R^a R^a$, —N$R^a$C$_{2-6}$alkylO$R^a$ and $R^e$.

In another embodiment, in conjunction with any one of the above and below embodiments, $R^5$ is independently, at each instance, H, C$_{1-8}$alkyl, C$_{1-4}$haloalkyl, halo, cyano, —C(=O)$R^b$, —C(=N$R^a$)N$R^a R^a$, —O$R^a$, —OC(=O)$R^b$, —OC(=O)N$R^a R^a$, —OC(=O)N($R^a$)S(=O)$_2 R^b$, —OC$_{2-6}$alkylN$R^a R^a$, —OC$_{2-6}$alkylO$R^a$, —S$R^a$, —S(=O)$R^b$, —S(=O)$_2 R^b$, —S(=O)$_2$N$R^a R^a$, —S(=O)$_2$N($R^a$)C(=O)$R^b$, —S(=O)$_2$N($R^a$)C(=O)O$R^b$, —S(=O)$_2$N($R^a$)C(=O)N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a$C$_{2-6}$alkylN$R^a R^a$, —N$R^a$C$_{2-6}$alkylO$R^a$, C$_{1-3}$alkylR$^c$, C$_{1-3}$alkylR$^f$ and $R^e$; or $R^5$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2, 3 or 4 substituents selected from C$_{1-8}$alkyl, C$_{1-4}$haloalkyl, halo, cyano, nitro, —C(=O)$R^b$, —C(=O)O$R^b$, —C(=O)N$R^a R^a$, —C(=N$R^a$)N$R^a R^a$, —O$R^a$, —OC(=O)$R^b$, —OC(=O)N$R^a R^a$, —OC(=O)N($R^a$)S(=O)$_2 R^b$, —OC$_{2-6}$alkylN$R^a R^a$, —OC$_{2-6}$alkylO$R^a$, —S$R^a$, —S(=O)$R^b$, —S(=O)$_2 R^b$, —S(=O)$_2$N$R^a R^a$, —S(=O)$_2$N($R^a$)C(=O)$R^b$, —S(=O)$_2$N($R^a$)C(=O)O$R^b$, —S(=O)$_2$N($R^a$)C(=O)N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a$C$_{2-6}$alkylN$R^a R^a$, —N$R^a$C$_{2-6}$alkylO$R^a$ and $R^e$.

In another embodiment, in conjunction with any one of the above and below embodiments, $R^5$ is, at each instance, H.

In another embodiment, in conjunction with any one of the above and below embodiments, at least one $R^5$ is C$_{1-8}$alkyl, C$_{1-4}$haloalkyl, halo, cyano, —C(=O)$R^b$, —C(=N$R^a$)N$R^a R^a$, —O$R^a$, —OC(=O)$R^b$, —OC(=O)N$R^a R^a$, —OC(=O)N($R^a$)S(=O)$_2 R^b$, —OC$_{2-6}$alkylN$R^a R^a$, —OC$_{2-6}$alkylO$R^a$, —S$R^a$, —S(=O)$R^b$, —S(=O)$_2 R^b$, —S(=O)$_2$N$R^a R^a$, —S(=O)$_2$N($R^a$)C(=O)$R^b$, —S(=O)$_2$N($R^a$)C(=O)O$R^b$, —S(=O)$_2$N($R^a$)C(=O)N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a$C$_{2-6}$alkylN$R^a R^a$, —N$R^a$C$_{2-6}$alkylO$R^a$, C$_{1-3}$alkylR$^b$, C$_{1-3}$alkylR$^f$ and $R^e$.

In another embodiment, in conjunction with any one of the above and below embodiments, at least one $R^5$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2, 3 or 4 substituents selected from C$_{1-8}$alkyl, C$_{1-4}$haloalkyl, halo, cyano, nitro, —C(=O)$R^b$, —C(=O)O$R^b$, —C(=O)N$R^a R^a$, —C(=N$R^a$)N$R^a R^a$, —O$R^a$, —OC(=O)$R^b$, —OC(=O)N$R^a R^a$, —OC(=O)N($R^a$)S(=O)$_2 R^b$, —OC$_{2-6}$alkylN$R^a R^a$, —OC$_{2-6}$alkylO$R^a$, —S$R^a$, —S(=O)$R^b$, —S(=O)$_2 R^b$, —S(=O)$_2$N$R^a R^a$, —S(=O)$_2$N($R^a$)C(=O)$R^b$, —S(=O)$_2$N($R^a$)C(=O)O$R^b$, —S(=O)$_2$N($R^a$)C(=O)N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a$C$_{2-6}$alkylN$R^a R^a$, —N$R^a$C$_{2-6}$alkylO$R^a$ and $R^e$.

In another embodiment, in conjunction with any one of the above and below embodiments, at least one $R^5$ is an unsaturated 5-, 6- or 7-membered monocyclic ring containing 0, 1, 2 or 3 atoms selected from N, O and S, wherein the carbon atoms of the ring are substituted by 0, 1 or 2 oxo groups and the ring is substituted by 0, 1, 2, 3 or 4 substituents selected from C$_{1-8}$alkyl, C$_{1-4}$haloalkyl, halo, cyano, nitro, —C(=O)$R^b$, —C(=O)O$R^b$, —C(=O)N$R^a R^a$, —C(=N$R^a$)N$R^a R^a$, —O$R^a$, —OC(=O)$R^b$, —OC(=O)N$R^a R^a$, —OC(=O)N($R^a$)S(=O)$_2 R^b$, —OC$_{2-6}$alkylN$R^a R^a$, —OC$_{2-6}$alkylO$R^a$, —S$R^a$, —S(=O)$R^b$, —S(=O)$_2 R^b$, —S(=O)$_2$N$R^a R^a$, —S(=O)$_2$N($R^a$)C(=O)$R^b$, —S(=O)$_2$N($R^a$)C(=O)O$R^b$, —S(=O)$_2$N($R^a$)C(=O)N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a$C$_{2-6}$alkylN$R^a R^a$, —N$R^a$C$_{2-6}$alkylO$R^a$ and $R^e$.

In another embodiment, in conjunction with any one of the above and below embodiments, at least one $R^5$ is an unsaturated 6-membered monocyclic ring containing 0, 1 or 2 N atoms, wherein the ring is substituted by 0, 1, 2, 3 or 4 substituents selected from C$_{1-8}$alkyl, C$_{1-4}$haloalkyl, halo, cyano, nitro, —C(=O)$R^b$, —C(=O)O$R^b$, —C(=O)N$R^a R^a$, —C(=N$R^a$)N$R^a R^a$, —O$R^a$, —OC(=O)$R^b$, —OC(=O)N$R^a R^a$, —OC(=O)N($R^a$)S(=O)$_2 R^b$, —OC$_{2-6}$alkylN$R^a R^a$, —OC$_{2-6}$alkylO$R^a$, —S$R^a$, —S(=O)$R^b$, —S(=O)$_2 R^b$, —S(=O)$_2$N$R^a R^a$, —S(=O)$_2$N($R^a$)C(=O)$R^b$, —S(=O)$_2$N($R^a$)C(=O)O$R^b$, —S(=O)$_2$N($R^a$)C(=O)N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a$C$_{2-6}$alkylN$R^a R^a$, —N$R^a$C$_{2-6}$alkylO$R^a$ and $R^e$.

In another embodiment, in conjunction with any one of the above and below embodiments, at least one $R^5$ is a saturated, partially saturated or unsaturated 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2, 3 or 4 substituents selected from C$_{1-8}$alkyl, C$_{1-4}$haloalkyl, halo, cyano, nitro, —C(=O)$R^b$, —C(=O)O$R^b$, —C(=O)N$R^a R^a$, —C(=N$R^a$)N$R^a R^a$, —O$R^a$, —OC(=O)$R^b$, —OC(=O)N$R^a R^a$, —OC(=O)N($R^a$)S(=O)$_2 R^b$, —OC$_{2-6}$alkylN$R^a R^a$, —OC$_{2-6}$alkylO$R^a$, —S$R^a$, —S(=O)$R^b$, —S(=O)$_2 R^b$, —S(=O)$_2$N$R^a R^a$, —S(=O)$_2$N($R^a$)C(=O)$R^b$, —S(=O)$_2$N($R^a$)C(=O)O$R^b$, —S(=O)$_2$N($R^a$)C(=O)N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —($R^a$)S(=O)$_2 R^b$, —N($R^a$)S(=O)$_2$N$R^a R^a$, —N$R^a$C$_{2-6}$alkylN$R^a R^a$, —N$R^a$C$_{2-6}$alkylO$R^a$ and $R^e$.

In another embodiment, in conjunction with any one of the above and below embodiments, $R^6$ is, at each instance, H.

In another embodiment, in conjunction with any one of the above and below embodiments, at least one $R^6$ is selected from C$_{1-8}$alkyl, C$_{1-4}$haloalkyl, halo, cyano, —C(=O)$R^b$, —C(=O)O$R^b$, —C(=O)N$R^a R^a$, —C(=N$R^a$)N$R^a R^a$, —OC(=O)$R^b$, —OC(=O)N$R^a R^a$, —OC(=O)N($R^a$)S(=O)$_2 R^b$, —OC$_{2-6}$alkylN$R^a R^a$, —OC$_{2-6}$alkylO$R^a$, —S$R^a$, —S(=O)$R^b$, —S(=O)$_2 R^b$, —S(=O)$_2$N$R^a R^a$, —S(=O)$_2$N($R^a$)C(=O)$R^b$, —S(=O)$_2$N($R^a$)C(=O)O$R^b$, —S(=O)$_2$N($R^a$)C(=O)N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a$C$_{2-6}$alkylN$R^a R^a$, —N$R^a$C$_{2-6}$alkylO$R^a$ and $R^e$.

In another embodiment, in conjunction with any one of the above and below embodiments, at least one $R^6$ is selected from C$_{1-8}$alkyl, C$_{1-4}$haloalkyl and halo.

In another embodiment, in conjunction with any one of the above and below embodiments, at least one $R^6$ is selected from $C_{1-4}$haloalkyl and halo.

Another aspect of the invention relates to a method of treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound according to any of the above embodiments.

Another aspect of the invention relates to a pharmaceutical composition comprising a compound according to any of the above embodiments and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders.

The compounds of this invention may have in general several asymmetric centers and are typically depicted in the form of racemic mixtures. This invention is intended to encompass racemic mixtures, partially racemic mixtures and separate enantiomers and diasteromers.

Unless otherwise specified, the following definitions apply to terms found in the specification and claims:

"$C_{\alpha-\beta}$alkyl" means an alkyl group comprising a minimum of α and a maximum of β carbon atoms in a branched, cyclical or linear relationship or any combination of the three, wherein α and β represent integers. The alkyl groups described in this section may also contain one or two double or triple bonds. Examples of $C_{1-6}$alkyl include, but are not limited to, the following:

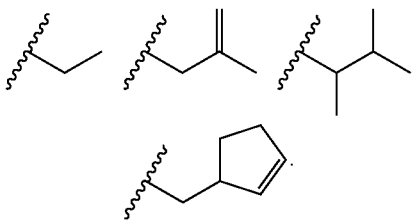

"Benzo group", alone or in combination, means the divalent radical $C_4H_4=$, one representation of which is —CH=CH—CH=CH—, that when vicinally attached to another ring forms a benzene-like ring—for example tetrahydronaphthylene, indole and the like.

"Halo" or "halogen" means a halogen atoms selected from F, Cl, Br and I.

"$C_{v-w}$haloalkyl" means an alkyl group, as described above, wherein any number—at least one—of the hydrogen atoms attached to the alkyl chain are replaced by F, Cl, Br or I.

"Heterocycle" means a ring comprising at least one carbon atom and at least one other atom selected from N, O and S. Examples of heterocycles that may be found in the claims include, but are not limited to, the following:

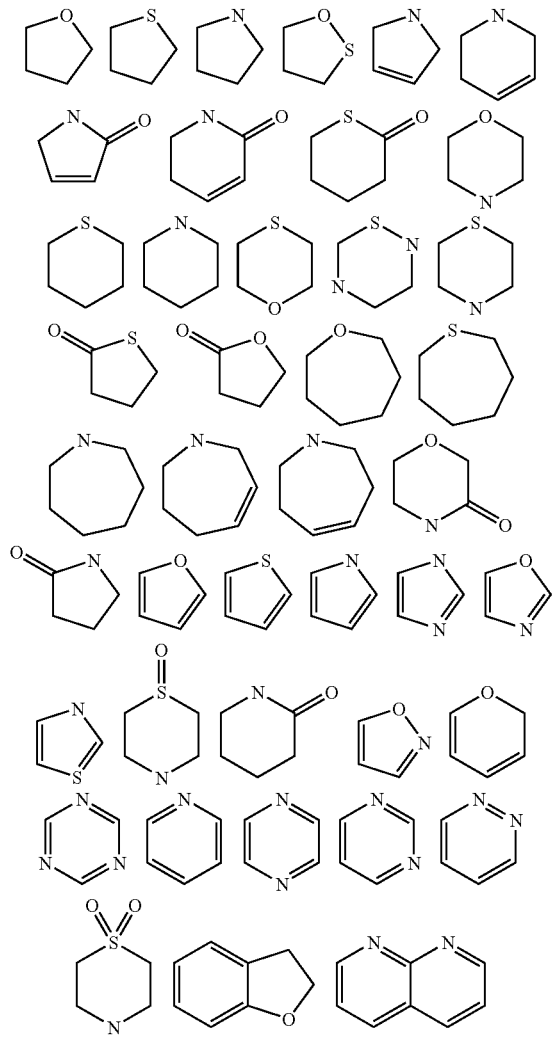

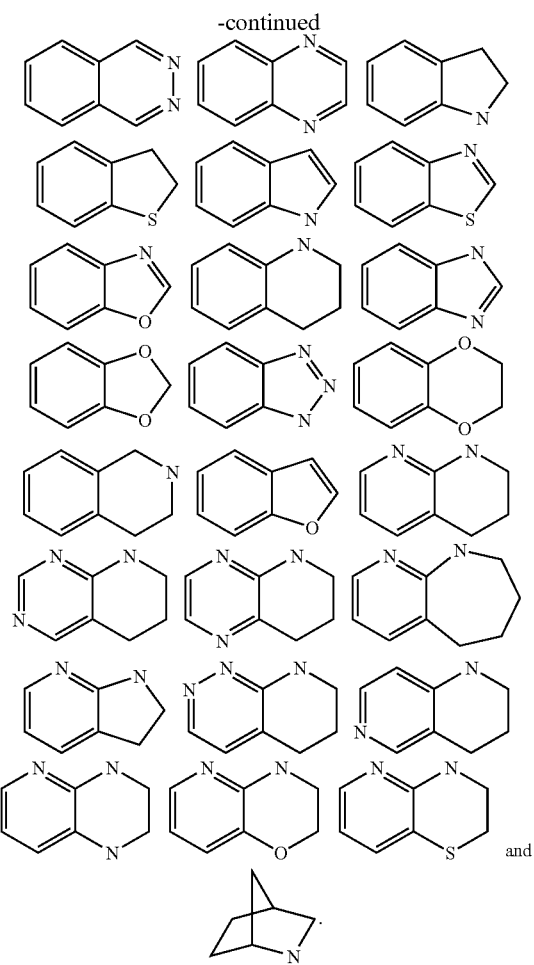

"Available nitrogen atoms" are those nitrogen atoms that are part of a heterocycle and are joined by two single bonds (e.g. piperidine), leaving an external bond available for substitution by, for example, H or $CH_3$.

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate. "Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyldimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, —S, NR), and the like, which are illustrated in the following examples:

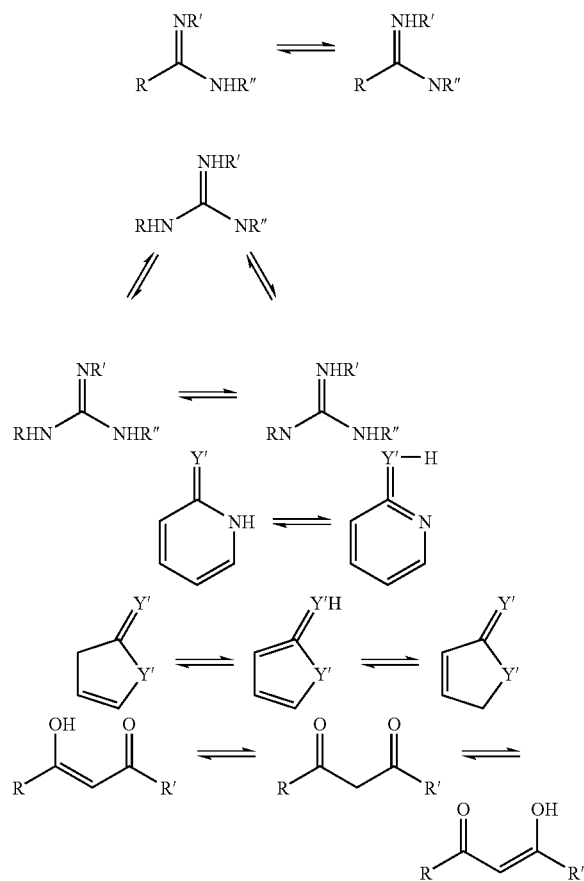

though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

Experimental

Unless otherwise noted, all materials were obtained from commercial suppliers and used without further purification. All parts are by weight and temperatures are in degrees centigrade unless otherwise indicated. All microwave assisted reactions were conducted with a Smith Synthesizer from Personal Chemistry, Uppsala, Sweden. All compounds showed NMR spectra consistent with their assigned structures. Melting points were determined on a Buchi apparatus and are uncorrected. Mass spectral data was determined by electrospray ionization technique. All examples were purified to >90% purity as determined by high-performance liquid chromatography. Unless otherwise stated, reactions were run at room temperature.

The following abbreviations are used:

DMSO—dimethyl sulfoxide

DMF—N,N-dimethylformamide

THF—tetrahydrofuran $Et_2O$—diethyl ether

EtOAc—ethyl acetate

MeOH—methyl alcohol

EtOH—ethyl alcohol

MeCN—acetonitrile

MeI—iodomethane

NMP—1-methyl-2-pyrrolidinone

DCM—dichloromethane

TFA—trifluoroacetic acid

Sat.—saturated h—hour min—minutes

Generic Scheme
Scheme 1
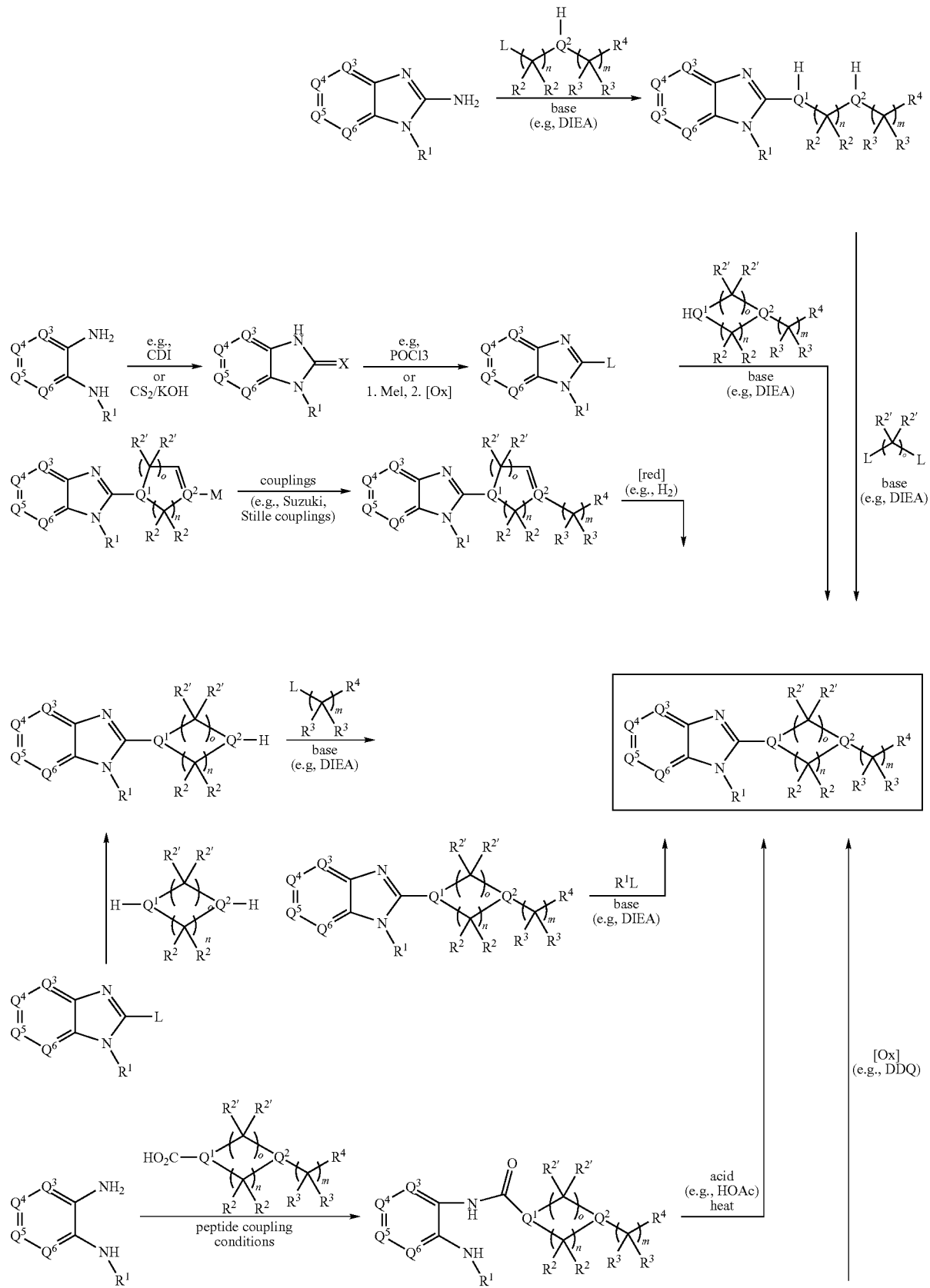

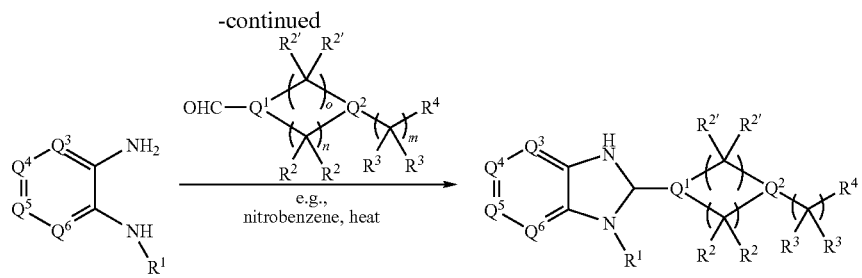

Example 1

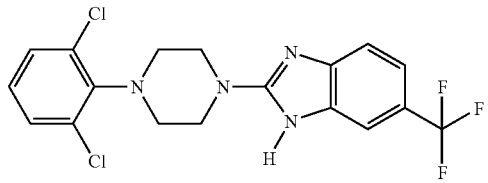

2-[4-(2,6-Dichlorophenyl)piperazin-1-yl]-6-trifluoromethyl-1H-benzoimidazole

(a) 1-(2,6-Dichlorophenyl)piperazine

A mixture of 2,6-dichlorophenylaniline (810 mg, 5 mmol, Aldrich) and bis(2-chloroethyl)amine hydrochloride (823 mg, 5 mmol, Aldrich) was subjected to microwave irradiation at 200° C. for 10 min. The reaction mixture was allowed to cool to room temperature then treated with 5N NaOH (5 mL) and extracted with EtOAc (2×20 mL). The combined organic extracts were washed with brine (5 mL), dried over $Na_2SO_4$ and filtered. The solvent was removed in vacuo and the residue was purified by silica gel chromatography, eluting with 10% $MeOH/CH_2Cl_2$+1% ammonia (30% in water) to give the title compound. MS (ESI, pos. ion) m/z: 231 (M+1).

(b) 5-Trifluoromethyl-1,3-dihydrobenzoimidazol-2-one

A mixture of 4-trifluoromethyl-1,2-phenylenediamine (8.8 g, 50 mmol, Lancaster) and 1,1'-carbonyldiimidazole (9.0 g, 55 mmol, Aldrich) in THF (50 mL) was stirred at room temperature for 16 h. The solvent was removed in vacuo and the residue was purified by silica gel chromatography, eluting with EtOAc to give the title compound. MS (ESI, pos. ion) m/z: 203 (M+1).

(c) 2-Chloro-6-trifluoromethyl-1H-benzoimidazole

A solution of the dihydrobenzoimidazol-2-one from step (b) above (2.02 g, 10 mmol) in $POCl_3$ (30 mL) was heated at 95° C. for 16 h. The reaction mixture was cooled to room temperature, the solvent was removed in vacuo and the resulting oily residue subjected to azeotropic distillation with toluene (3×50 mL) at 50° C. The crude product was dissolved in EtOAc (50 mL), washed with brine (10 mL) then dried over $Na_2SO_4$ and filtered. The solvent was removed in vacuo and the residue was recrystallized from EtOAc/hexane to give the title compound.

(d) 2-[4-(2,6-Dichlorophenyl)piperazin-1-yl]-6-trifluoromethyl-1H-benzoimidazole A mixture of the benzoimidazole from step (c) above (75 mg, 0.34 mmol), the piperazine from step (a) above (90 mg, 0.39 mmol) and N,N-diisopropylethylamine (0.1 mL, 0.58 mmol, Aldrich) in DMSO (2 mL) was stirred at 80° C. for 24 h. The mixture was cooled to room temperature, water (10 mL) was added and the mixture was extracted with EtOAc (2×20 mL). The combined organic phases were washed with water (2×10 mL) and brine (5 mL), dried over $Na_2SO_4$, and filtered. The solvent was removed in vacuo and the residue was purified by silica gel chromatography, eluting with 20% EtOAc/hexane to give the title compound as a white solid. M.p. 263-265° C. MS (ESI, pos. ion) m/z: 415 (M+1).

Example 2

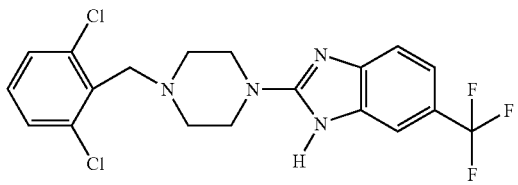

2-[4-(2,6-Dichlorobenzyl)piperazin-1-yl]-6-trifluoromethyl-1H-benzoimidazole

(a) 2-piperazin-1-yl-6-trifluoromethyl-1H-benzoimidazole

A mixture of 2-chloro-6-trifluoromethyl-1H-benzoimidazole (221 mg, 1 mmol, Example 1c), piperazine (172 mg, 2 mmol, Aldrich) and DMSO (2 mL) was stirred at 80° C. for 24 h. The mixture was cooled to room temperature, water (10 mL) was added and the mixture was extracted with EtOAc (2×20 mL). The combined organic phases were washed with water (2×5 mL) and brine (5 mL), dried over $Na_2SO_4$, and filtered. The solvent was removed in vacuo and the residue was purified by silica gel chromatography, eluting with 10% $MeOH/CH_2Cl_2$+1% ammonia (30% in water) to give the title compound. MS (ESI, pos. ion) m/z: 271 (M+1).

(b) 2-[4-(2,6-Dichlorobenzyl)piperazin-1-yl]-6-trifluoromethyl-1H-benzoimidazole A mixture of the benzoimidazole from step (a) above (96 mg, 0.36 mmol), 2,6-dichlorobenzyl bromide (86 mg, 0.36 mmol, Aldrich) and $NaHCO_3$ (151 mg, 1.8 mmol) in DMF (2 mL) was stirred at room temperature for 16 h. Water (10 mL)

was then added and the mixture was extracted with EtOAc (2×20 mL). The combined organic phases were washed with water (5 mL) and brine (5 mL) then dried over $Na_2SO_4$ and filtered. The solvent was removed in vacuo and the residue purified by silica gel chromatography, eluting with 40% EtOAc/hexane. The material was recrystallized from EtOAc/hexanes to give the title compound as a white solid. M.p. 254-256° C. MS (ESI, pos. ion) m/z: 429 (M+1).

Example 3

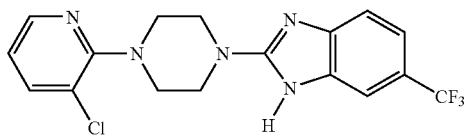

2-[4-(3-Chloropyridin-2-yl)piperazin-1-yl]-6-trifluoromethyl-1H-benzoimidazole (a) 4-(3-Chloropyridin-2-yl)piperazine-1-carboxylic acid tert-butyl Ester A mixture of 2,3-dichloropyridine (10 g, 67.5 mmol, Aldrich), tert-butyl 1-piperazinecarboxylate (12.58 g, 67.5 mmol, Aldrich), copper powder (0.5 g, 7.8 mmol) and $K_2CO_3$ (9.33 g, 67.5 mmol) in DMF (100 mL) was stirred at 120° C. for 16 h. The reaction mixture was cooled to room temperature, concentrated in vacuo and the residue was dissolved in EtOAc (200 mL). The organic solution was washed with saturated aqueous solution of $NaHCO_3$ (50 mL) and brine (50 mL), dried over $Na_2SO_4$, and filtered. The solvent was removed in vacuo and the residue was purified by silica gel column chromatography, eluting with 15% EtOAc/hexane, to give the title compound as an orange oil. MS (ESI, pos. ion) m/z: 298 (M+1).

(b) 1-(3-Chloropyridin-2-yl)piperazine Hydrochloride

To a solution of the ester from step (a) above (2.98 g, 10 mmol) in MeOH (5 mL) was added saturated solution of hydrogen chloride in EtOAc (50 mL) and the mixture was stirred at room temperature for 4 h. The solvent was removed in vacuo, and the residue was washed with EtOAc and dried in the air to provide the title compound as a light-yellow solid. MS (ESI, pos. ion) m/z: 198 (M+1).

(c) 2-[4-(3-Chloropyridin-2-yl)piperazin-1-yl]-6-trifluoromethyl-1H-benzoimidazole A mixture of the hydrochloride salt from step (b) above (0.564 g, 2.4 mmol), 2-chloro-6-trifluoromethyl-1H-benzoimidazole (0.27 g, 1.22 mmol, Example 1c) and N,N-diisopropylethylamine (0.84 mL, 4.8 mmol, Aldrich) in MeCN (1 mL) was subjected to microwave irradiation at 180° C. with stirring for 20 min. The solvent was removed in vacuo and the residue was purified by silica gel chromatography, eluting with 30% EtOAc/hexane, to give the title compound as a white solid. M.p. 208-210° C. MS (ESI, pos. ion) m/z: 382 (M+1).

Example 4

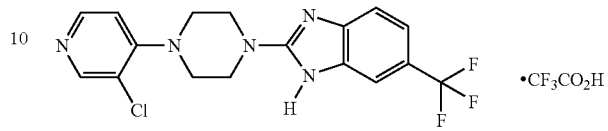

2-[4-(3-Chloropyridin-4-yl)piperazin-1-yl]-6-trifluoromethyl-1H-benzoimidazole, Trifluoroacetic Acid Salt (a) 3,4-Dichloropyridine N,N-Diisopropylethylamine (14 mL, 0.1 mol, Aldrich) was added drop-wise to a solution of n-butyllithium (40 mL, 2.5M in hexane, Aldrich) in a THF/hexane (140 mL/60 mL) mixture with stirring at −78° C. 3-Chloropyridine (9.4 mL, 0.1 mol, Aldrich) was added, the reaction mixture was stirred at −78° C. for 2 h and then treated with 1,1,2-trichlorotrifluoroethane (12 mL, 0.1 mol, Aldrich) at −78° C. The reaction was quenched with a saturated aqueous solution of $NaHCO_3$ (100 mL) and extracted with EtOAc (2×100 mL). The combined organic extracts were dried over $Na_2SO_4$, filtered and concentrated in vacuo. The residue was purified by silica gel column chromatography (10% EtOAc/hexane) to afford the title compound as an orange oil. MS (ESI, pos. ion) m/z: 150 (M+1).

(b) 1-(3-Chloropyridin-4-yl)piperazine-4-carboxylic Acid tert-butyl Ester

The pyridine from step (a) above (5 g, 3.38 mmol) and tert-butylpiperazinecarboxylate (6.29 g, 3.38 mmol, Aldrich) reacted under the conditions of Example 3a to give the title compound as an orange oil. MS (ESI, pos. ion) m/z: 298 (M+1).

(c) 1-(3-Chloropyridin-4-yl)piperazine, Trifluoroacetic Acid Salt

A solution of the ester from step (b) above (5 g, 16.79 mmol) in a 1:1 mixture of $CF_3COOH/CH_2Cl_2$ (50 mL) was stirred for 2 h at room temperature. The solvent was removed in vacuo to give the title compound as an orange oil, which was used in the next step without purification. MS (ESI, pos. ion) m/z: 198 (M+1).

(d) 2-[4-(3-Chloropyridin-4-yl)piperazin-1-yl]-6-trifluoromethyl-1H-benzoimidazole, Trifluoroacetic Acid Salt The piperazine from step (c) above (0.9 g, 1.67 mmol), 2-chloro-6-trifluoromethyl-1H-benzoimidazole (0.370 g, 1.67 mmol, Example 1c) and N,N-diisopropylethylamine (1.16 mL, 6.68 mmol, Aldrich) reacted under the conditions of Example 3c and the product was purified by preparative HPLC (gradient 0.1% trifluoroacetic acid in acetonitrile) to give the title compound. M.p. 159-161° C. MS (ESI, pos. ion) m/z: 382 (M+1).

Example 5

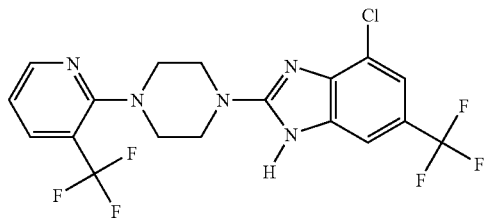

4-Chloro-6-trifluoromethyl-2-[4-(3-trifluoromethylpyridin-2-yl)piperazin-1-yl]-1H-benzoimidazole (a) 4-Chloro-6-trifluoromethyl-1,3-dihydrobenzoimidazol-2-one 3-Chloro-4,5-diaminobenzotrifluoride (10 g, 47.48 mmol, Lancaster) reacted under the conditions of Example 1b to give the title compound. MS (ESI, pos. ion) m/z: 237 (M+1).

(b) 2,4-Dichloro-6-trifluoromethyl-1H-benzoimidazole

The benzoimidazol-2-one from step (a) above (10.2 g, 43.1 mmol) reacted under the conditions of Example 1c to give the title compound as a white solid. MS (ESI, pos. ion) m/z: 255 (M+1).

(c) 4-Chloro-6-trifluoromethyl-2-[4-(3-trifluoromethylpyridin-2-yl)piperazin-1-yl]-1H-benzoimidazole The benzoimidazole from step (b) above (69.3 mg, 0.3 mmol) reacted with 1-(3-trifluoromethylpyridin-2-yl)piperazine (128 mg, 0.5 mmol, Fluorochem) under the conditions of Example 1d to give the title compound as a white solid. M.p. 204° C. MS (ESI, pos. ion) m/z: 450 (M+1).

Example 6

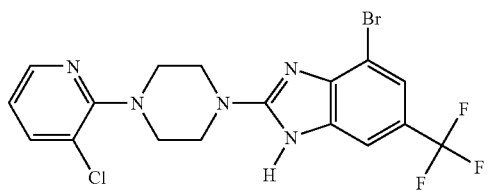

4-Bromo-2-[4-(3-chloropyridin-2-yl)piperazin-1-yl]-6-trifluoromethyl-1H-benzoimidazole (a) 4-Bromo-6-trifluoromethyl-1,3-dihydrobenzoimidazol-2-one 3-Bromo-4,5-diaminobenzotrifluoride (9.9 g, 38.8 mmol, Apollo) reacted under the conditions of Example 1b to give the title compound. MS (ESI, pos. ion) m/z: 281 (M+1).

(b) 4-Bromo-2-chloro-6-trifluoromethyl-1H-benzoimidazole

The benzoimidazol-2-one from step (a) above (7.42 g, 26.4 mmol) reacted under the conditions of Example 1c to give the title compound as a white solid. MS (ESI, pos. ion) m/z: 299 (M+1).

(c) 4-Bromo-2-[4-(3-chloropyridin-2-yl)piperazin-1-yl]-6-trifluoromethyl-1H-benzoimidazole The benzoimidazole from step (b) above (210 mg, 0.7 mmol), 1-(3-chloropyridin-2-yl)piperazine hydrochloride (187 mg, 0.8 mmol, Example 3b) and N,N-diisopropylethylamine (0.28 mL, 1.6 mmol, Aldrich) were reacted under the conditions of Example 3c to give the title compound as a white amorphous solid. MS (ESI, pos. ion) m/z: 461 (M+1).

Example 7

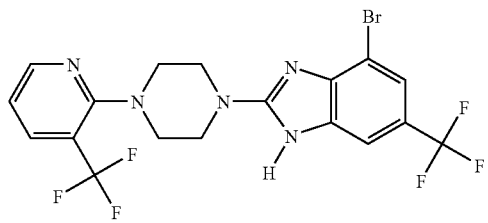

4-Bromo-6-trifluoromethyl-2-[4-(3-trifluoromethylpyridin-2-yl)piperazin-1-yl]-1H-benzoimidazole The reaction of 1-(3-trifluoromethylpyridin-2-yl)piperazine (128 mg, 0.5 mmol, Fluorochem) and 4-bromo-2-chloro-6-trifluoromethyl-1H-benzoimidazole (210 mg, 0.7 mmol, Example 6b) under the conditions of Example 3c afforded the title compound as a white solid. M.p. 196° C. MS (ESI, pos. ion) m/z: 494 (M+1).

Example 8

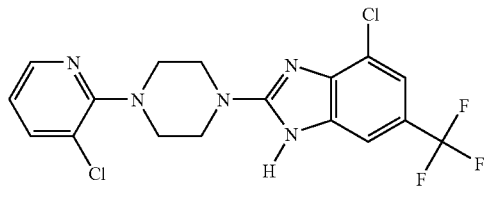

4-Chloro-2-[4-(3-chloropyridin-2-yl)piperazin-1-yl]-6-trifluoromethyl-1H-benzoimidazole The reaction of 1-(3-chloropyridin-2-yl)piperazine hydrochloride (99 mg, 0.5 mmol, Example 3b) and 2,4-dichloro-6-trifluoromethyl-1H-benzoimidazole (76 mg, 0.3 mmol, Example 5b) and N,N-diisopropylethylamine (0.17 mL, 1 mmol, Aldrich) under the conditions of Example 3c afforded the title compound as a white amorphous solid. MS (ESI, pos. ion) m/z: 416 (M+1).

Example 9

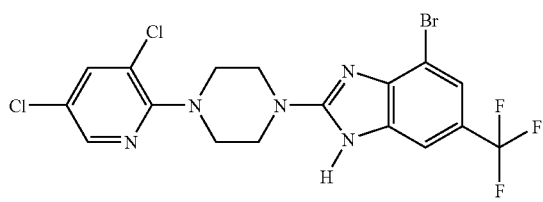

4-Bromo-2-[4-(3,5-dichloropyridin-2-yl)piperazin-1-yl]-6-trifluoromethyl-1H-benzoimidazole (a) 1-(3,5-Dichloropyridin-2-yl)piperazine Piperazine (256 mg, 3.0 mmol, Aldrich) and 2,3,5-trichloropyridine (364 mg, 20 mmol, Aldrich) were reacted under the conditions of Example 3a to give the title compound as a light-yellow solid. MS (ESI, pos. ion) m/z: 232 (M+1).

(b) 4-Bromo-2-[4-(3,5-dichloropyridin-2-yl)piperazin-1-yl]-6-trifluoromethyl-1H-benzoimidazole The piperazine from step (a) above (162 mg, 0.7 mmol) and 4-bromo-2-chloro-6-trifluoromethyl-1H-benzoimidazole (168 mg, 0.56 mmol, Example 6b) reacted under the conditions of Example 3c to give the title compound as a white solid. M.p. 176-179° C. MS (ESI, pos. ion) m/z: 495 (M+1).

Example 10

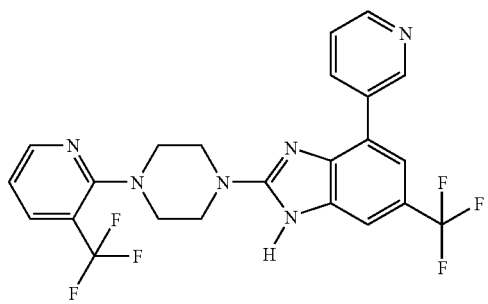

4-Pyridin-3-yl-6-trifluoromethyl-2-[4-(3-trifluoromethylpyridin-2-yl)piperazin-1-yl]-1H-benzoimidazole A mixture of 4-bromo-6-trifluoromethyl-2-[4-(3-trifluoromethylpyridin-2-yl)piperazin-1-yl]-1H-benzoimidazole (99 mg, 0.2 mmol, Example 7), diethyl(3-pyridyl)borane (37 mg, 0.25 mmol, Aldrich), Pd(PPh$_3$)$_4$ (23 mg, 0.02 mmol, Aldrich), Na$_2$CO$_3$ (32 mg, 0.3 mmol) and dimethoxyethane (1 mL) was subjected to microwave irradiation at 200° C. with stirring for 40 min. The solvent was removed in vacuo and the residue was purified by silica gel chromatography, eluting with 60% EtOAc/hexane, to give the title compound as a yellow amorphous solid. MS (ESI, pos. ion) m/z: 493 (M+1).

Example 11

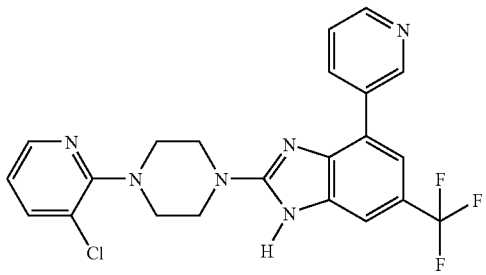

2-[4-(3-Chloropyridin-2-yl)piperazin-1-yl]-4-pyridin-3-yl-6-trifluoromethyl-1H-benzoimidazole The reaction of 4-bromo-2-[4-(3-chloropyridin-2-yl)piperazin-1-yl]-6-trifluoromethyl-1H-benzoimidazole (92 mg, 0.2 mmol, Example 6c) under the conditions of Example 10 gave the title compound as a yellow amorphous solid. MS (ESI, pos. ion) m/z: 459 (M+1).

Example 12

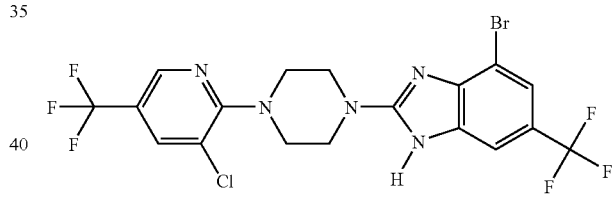

4-Bromo-6-trifluoromethyl-2-[4-(3-chloro-5-trifluoromethylpyridin-2-yl)piperazin-1-yl]-1H-benzoimidazole The reaction of 1-(3-chloro-5-trifluoromethylpyridin-2-yl)piperazine (212 mg, 0.8 mmol, ABCR) and 4-bromo-2-chloro-6-trifluoromethyl-1H-benzoimidazole (210 mg, 0.7 mmol, Example 6b) under the conditions of Example 3c afforded the title compound as a white amorphous solid. MS (ESI, pos. ion) m/z: 530 (M+1).

Example 13

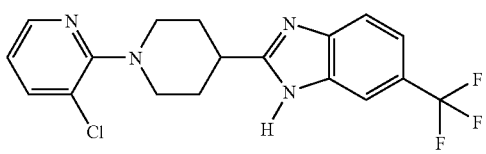

2-[1-(3-Chloropyridin-2-yl)piperidin-4-yl]-6-trifluoromethyl-1H-benzoimidazole (a) 1-(3-Chloropyridin-2-yl)piperidine-4-carboxylic Acid Methyl Ester 2,3-Dichloropyridine (1.48 g, 10 mmol, Aldrich) and piperidine-4-carboxylic acid methyl ester (1.43 g, 10 mmol, Aldrich) were reacted under the conditions of Example 3a to give the title compound as a colorless viscous oil. MS (ESI, pos. ion) m/z: 256 (M+1).

(b) 1-(3-Chloropyridin-2-yl)piperidine-4-carboxylic Acid

A mixture of the ester from step (a) above (1.77 g, 6.9 mmol) and 5N NaOH (4 mL) in THF/MeOH (20 mL/30 mL) mixture was stirred at room temperature for 16 h. The organic solvent was removed in vacuo, the aqueous solution was acidified with 10% HCl to pH 2 and then lyophilized to give the title compound, which was used in the next step without additional purification. MS (ESI, pos. ion) m/z: 241 (M+1).

(c) N-(2-Amino-4-trifluoromethylphenyl)-1-[1-(3-chloropyridin-2-yl)piperidin-4-yl]formamide and N-(2-Amino-5-trifluoromethylphenyl)-1-[1-(3-chloropyridin-2-yl)piperidin-4-yl]formamide To a solution of the acid from step (b) above (0.48 g, 2 mmol) in DMF (20 mL) was added 3,4-diaminobenzotrifluoride (0.354 g, 2 mmol, Lancaster), followed by N,N-diisopropylethylamine (0.516 g, 4 mmol, Aldrich) and O-(7-azabenzotriazol-1-yl)-N,N,N',N'-tetramethyluronium hexafluorophosphate (0.912 g, 2.4 mmol, Aldrich). The reaction mixture was stirred at room temperature for 16 h, and then concentrated in vacuo. The residue was dissolved in EtOAc and the organic solution was washed with saturated NaHCO₃ and brine, dried over MgSO₄, filtered, and concentrated in vacuo. The residue was purified by silica gel chromatography, eluting with hexane/EtOAc (3:7) to give the title compound as a purple solid. MS (ESI, pos. ion) m/z: 399 (M+1).

(d) 2-[1-(3-Chloropyridin-2-yl)piperidin-4-yl]-6-trifluoromethyl-1H-benzoimidazole A solution of the mixture of the amides from step (c) above in AcOH/toluene (30 mL/3 mL) was stirred at 75° C. for 3 h in a 100 mL round-bottomed flask opened to air. The reaction was then cooled to room temperature and the solvent was removed in vacuo. The residue was dissolved in EtOAc and the organic solution was washed with saturated NaHCO₃ and brine, dried over MgSO₄, filtered, and concentrated in vacuo. The residue was purified by silica gel chromatography, eluting with EtOAc/hexane (1:3) to afford the title compound as a brown solid. M.p. 74° C. MS (ESI, pos. ion) m/z: 381 (M+1).

Example 14

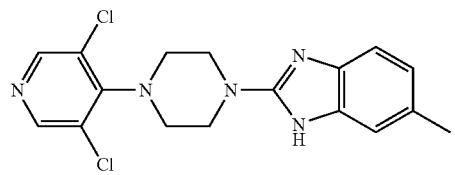

2-[4-(3,5-Dichloropyridin-4-yl)piperazin-1-yl]-6-methyl-1H-benzoimidazole (a) 5-Methyl-1,3-dihydrobenzoimidazol-2-one The reaction of 4-methylbenzene-1,2-diamine (14.36 g, 0.117 mol, Aldrich) under the conditions of Example 1b afforded the title compound as an off-white solid. MS (ESI, pos. ion) m/z: 149 (M+1).

(b) 2-Chloro-6-methyl-1H-benzoimidazole

The benzoimidazol-2-one from step (a) above (4.5 g, 0.03 mol) reacted under the conditions of Example 1c to give the title compound as a pink solid. MS (ESI, pos. ion) m/z: 167 (M+1).

(c) 2-[4-(3,5-Dichloropyridin-4-yl)piperazin-1-yl]-6-methyl-1H-benzoimidazole

The benzoimidazole from step (b) above (0.287 g, 1.73 mmol) and 1-(3,5-dichloropyridin-4-yl)piperazine (0.4 g, 1.73 mmol, Maybridge) reacted under the conditions of Example 1d to give the title compound as a white solid. M.p. 251-254° C. MS (ESI, pos. ion) m/z: 362 (M+1).

Example 15

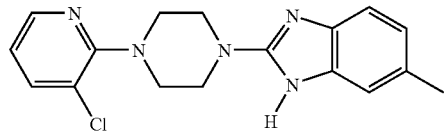

2-[4-(3-Chloropyridin-2-yl)piperazin-1-yl]-6-methyl-1H-benzoimidazole

The reaction of 2-chloro-6-methyl-1H-benzoimidazole (0.202 g, 1.59 mmol, Example 14b), 1-(3-chloropyridin-2-yl)piperazine hydrochloride (0.373 g, 1.22 mmol, Example 3b) and N,N-diisopropylethylamine (0.56 mL, 3.2 mmol, Aldrich) under the conditions of Example 3c afforded the title compound as a white solid. M.p. 258-259° C. MS (ESI, pos. ion) m/z: 328 (M+1).

Example 16

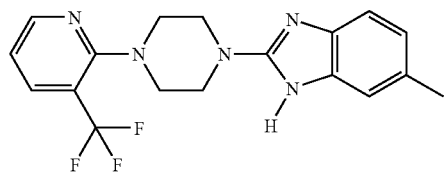

6-Methyl-2-[4-(3-trifluoromethylpyridin-2-yl)piperazin-1-yl]-1H-benzoimidazole

The reaction of 2-chloro-6-methyl-1H-benzoimidazole (0.261 g, 1.57 mmol, Example 14b) with 1-(3-trifluoromethylpyridin-2-yl)piperazine (0.54 g, 1.6 mmol, Maybridge) under the conditions of Example 3c afforded the title compound as a white solid. M.p. 216-217° C. MS (ESI, pos. ion) m/z: 362 (M+1).

Example 17

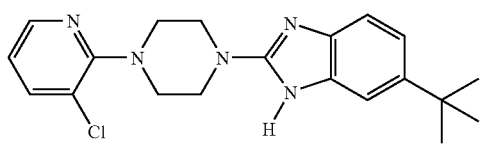

6-tert-Butyl-2-[4-(3-chloropyridin-4-yl)piperazin-1-yl]-1H-benzoimidazole (a) 5-tert-Butyl-1,3-dihydrobenzoimidazol-2-one The reaction of 4-tert-butylbenzene-1,2-diamine (5 g, 30.5 mmol, Maybridge) under the conditions of Example 1b afforded the title compound as a white solid. MS (ESI, pos. ion) m/z: 191 (M+1).

(b) 6-tert-Butyl-2-chloro-1H-benzoimidazole

The benzoimidazol-2-one from step (a) above (5.4 g, 28 mmol) reacted under the conditions of Example 1c to give the title compound as an off-white solid. MS (ESI, pos. ion) m/z: 209 (M+1).

(c) 6-tert-Butyl-2-[4-(3-chloropyridin-4-yl)piperazin-1-yl]-1H-benzoimidazole

The benzoimidazole from step (b) above (0.209 g, 1 mmol), 1-(3-chloropyridin-2-yl)piperazine hydrochloride (0.304 g, 1.3 mmol, Example 3b) and N,N-diisopropylethylamine (0.45 mL, 2.6 mmol, Aldrich) were reacted under the conditions of Example 1d to give the title compound as a yellow amorphous solid. MS (ESI, pos. ion) m/z: 371 (M+1).

Example 18

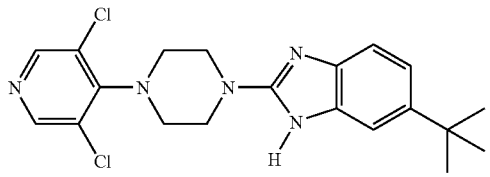

6-tert-Butyl-2-[4-(3,5-dichloropyridin-4-yl)piperazin-1-yl]-1H-benzoimidazole

The 6-tert-butyl-2-chloro-1H-benzoimidazole (209 mg, 1 mmol, Example 17b) and 1-(3,5-dichloropyridin-4-yl)piperazine (464 mg, 2 mmol, Maybridge) reacted under the conditions of Example 1d to give the title compound as a white amorphous solid. MS (ESI, pos. ion) m/z: 404 (M+1).

Example 19

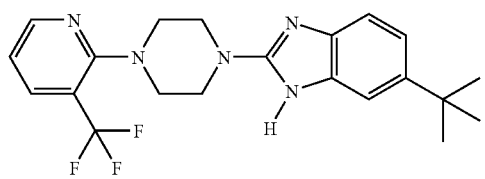

6-tert-Butyl-2-[4-(3-trifluoromethylpyridin-2-yl)piperazin-1-yl]-1H-benzoimidazole The reaction of 6-tert-butyl-2-chloro-1H-benzoimidazole (0.209 g, 1 mmol, Example 17b) with 1-(3-trifluoromethylpyridin-2-yl)piperazine (0.346 g, 1.65 mmol, Maybridge) under the conditions of Example 3c afforded the title compound as a white solid. M.P. 247-249° C. MS (ESI, pos. ion) m/z: 404 (M+1).

Example 20

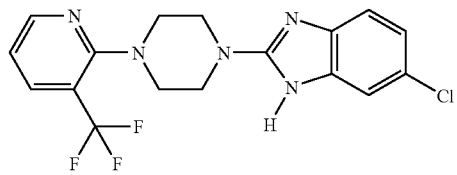

6-Chloro-2-[4-(3-trifluoromethylpyridin-2-yl)piperazin-1-yl]-1H-benzoimidazole (a) 5-Chloro-1,3-dihydrobenzoimidazol-2-one The reaction of 4-chlorobenzene-1,2-diamine (10 g, 0.07 mol, Aldrich) under the conditions of Example 1b afforded the title compound as a red solid. MS (ESI, pos. ion) m/z: 169 (M+1).

(b) 2,5-Dichloro-1H-benzoimidazole

The benzoimidazol-2-one from step (a) above (6.5 g, 38.7 mmol) reacted under the conditions of Example 1c to give the title compound as a brown solid. MS (ESI, pos. ion) m/z: 187 (M+1).

(c) 6-Chloro-2-[4-(3-trifluoromethylpyridin-2-yl)piperazin-1-yl]-1H-benzoimidazole The benzoimidazole from step (b) above (0.186 g, 0.995 mmol) and 1-(3-trifluoromethylpyridin-2-yl)piperazine (0.23 g, 0.995 mmol, Maybridge) reacted under the condi-

Example 21

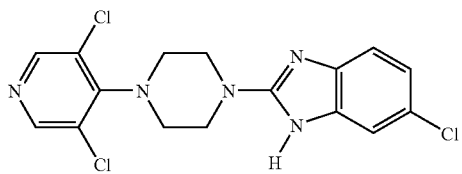

6-Chloro-2-[4-(3,5-dichloropyridin-4-yl)piperazin-1-yl]-1H-benzoimidazole

The 2,5-dichloro-1H-benzoimidazole (0.37 g, 1.98 mmol, Example 20b) and 1-(3,5-dichloropyridin-4-yl)piperazine (0.46 g, 1.98 mmol, Maybridge) reacted under the conditions of Example 3c to give the title compound as a white solid. M.p. 258-260° C. MS (ESI, pos. ion) m/z: 382 (M+1).

Example 22

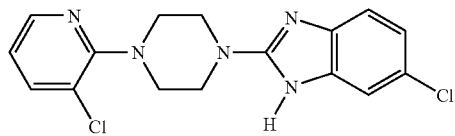

6-Chloro-2-[4-(3-chloropyridin-2-yl)piperazin-1-yl]-1H-benzoimidazole

The 2,5-dichloro-1H-benzoimidazole (0.244 g, 1.3 mmol, Example 20b), 1-(3-chloropyridin-2-yl)piperazine hydrochloride (0.4 g, 1.7 mmol, Example 3b) and N,N-diisopropylethylamine (0.59 mL, 3.4 mmol, Aldrich) were reacted under the conditions of Example 3c to give the title compound as a white solid. M.p. 214-215° C. MS (ESI, pos. ion) m/z: 348 (M+1).

Example 23

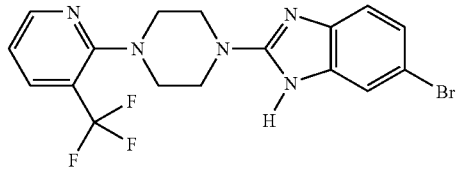

6-Bromo-2-[4-(3-trifluoromethylpyridin-2-yl)piperazin-1-yl]-1H-benzoimidazole (a) 5-Bromo-1,3-dihydrobenzoimidazol-2-one The reaction of 4-bromobenzene-1,2-diamine (10 g, 53.4 mmol, Indofine) under the conditions of Example 1b afforded the title compound as a gray solid. MS (ESI, pos. ion) m/z: 214 (M+1).

(b) 5-Bromo-2-chloro-1H-benzoimidazole

The benzoimidazol-2-one from step (a) above (4.2 g, 20 mmol) reacted under the conditions of Example 1c to give the title compound as a gray solid. MS (ESI, pos. ion) m/z: 232 (M+1).

(c) 6-Bromo-2-[4-(3-trifluoromethylpyridin-2-yl)piperazin-1-yl]-1H-benzoimidazole The benzoimidazole from step (b) above (0.115 g, 0.5 mmol) and 1-(3-trifluoromethylpyridin-2-yl)piperazine (0.231 g, 1 mmol, Maybridge) reacted under the conditions of Example 3c to give the title compound as a white amorphous solid. MS (ESI, pos. ion) m/z: 426 (M+1).

Example 24

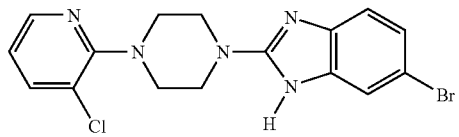

6-Bromo-2-[4-(3-chloropyridin-2-yl)piperazin-1-yl]-1H-benzoimidazole

The 5-bromo-2-chloro-1H-benzoimidazole (0.115 g, 0.5 mmol, Example 23b), 1-(3-chloropyridin-2-yl)piperazine (0.198 g, 1 mmol, Example 3b) and N,N-diisopropylethylamine (0.35 mL, 2 mmol, Aldrich) were reacted under the conditions of Example 3c to give the title compound as a white solid. M.p. 207-208° C. MS (ESI, pos. ion) m/z: 394 (M+1).

Example 25

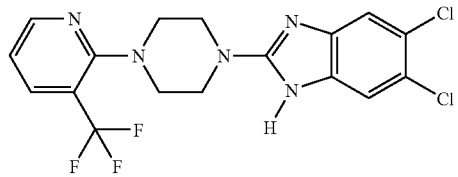

5,6-Dichloro-2-[4-(3-trifluoromethylpyridin-2-yl)piperazin-1-yl]-1H-benzoimidazole (a) 5,6-Dichloro-1,3-dihydrobenzoimidazol-2-one The reaction of 4,5-dichlorobenzene-1,2-diamine (10 g, 56.5 mmol, Aldrich) under the conditions of Example 1b afforded the title compound as an off-white solid. MS (ESI, pos. ion) m/z: 204 (M+1).

(b) 2,5,6-Trichloro-1H-benzoimidazole

The benzoimidazol-2-one from step (a) above (10 g, 49 mmol) reacted under the conditions of Example 1c to give the title compound as an off-white solid.

(c) 5,6-Dichloro-2-[4-(3-trifluoromethylpyridin-2-yl)piperazin-1-yl]-1H-benzoimidazole The benzoimidazole from step (b) above (0.110 g, 0.5 mmol) and 1-(3-trifluoromethylpyridin-2-yl)piperazine (0.231 g, 1 mmol, Maybridge) reacted under the conditions Example 3c to give the title compound as a white amorphous solid. MS (ESI, pos. ion) m/z: 416 (M+1).

Example 26

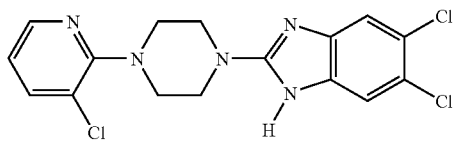

2-[4-(3-Chloropyridin-2-yl)piperazin-1-yl]-5,6-dichloro-1H-benzoimidazole

The 2,5,6-trichloro-1H-benzoimidazole (0.110 g, 0.5 mmol, Example 25b), 1-(3-chloropyridin-2-yl)piperazine hydrochloride (0.234 g, 1 mmol, Example 3b) and N,N-diisopropylethylamine (0.35 mL, 2 mmol, Aldrich) were reacted under the conditions of Example 3c to give the title compound as a white amorphous solid. MS (ESI, pos. ion) m/z: 382 (M+1).

Example 27

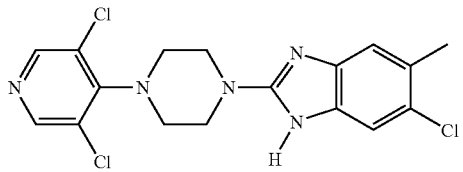

6-Chloro-2-[4-(3,5-dichloropyridin-4-yl)piperazin-1-yl]-5-methyl-1H-benzoimidazole

(a) 5-Chloro-6-methyl-1,3-dihydrobenzoimidazol-2-one

The reaction of 4-chloro-5-methylbenzene-1,2-diamine (10 g, 64 mmol, Aldrich) under the conditions of Example 1b afforded the title compound as a off-white solid. MS (ESI, pos. ion) m/z: 204 (M+1).

(b) 2,5-Dichloro-6-methyl-1H-benzoimidazole

The benzoimidazol-2-one from step (a) above (10.6 g, 58 mmol, Aldrich) reacted under the conditions of Example 1c to give the title compound as a brown solid. MS (ESI, pos. ion) m/z: 201 (M+1).

(c) 6-Chloro-2-[4-(3,5-dichloropyridin-4-yl)piperazin-1-yl]-5-methyl-1H-benzoimidazole The benzoimidazole from step (b) above (0.201 g, 1 mmol) and 1-(3,5-dichloropyridin-4-yl)piperazine (0.462 g, 2 mmol, Maybridge) reacted under the conditions of Example 1d to give the title compound as a white amorphous solid. MS (ESI, pos. ion) m/z: 396 (M+1).

Example 28

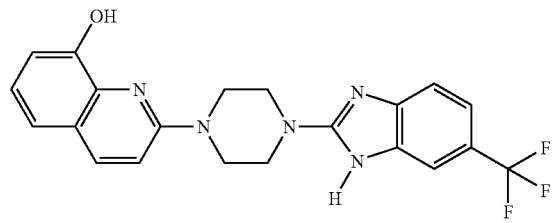

2-[4-(8-Hydroxyquinolin-2-yl)piperazin-1-yl]-6-trifluoromethyl-1H-benzoimidazole

(a) 2-Chloro-8-hydroxyquinoline

A mixture of 2,8-dihydroxyquinoline (4 g, 24.8 mmol, Fluka) and phosphorus oxychloride (20 mL, Aldrich) was stirred at 100° C. for 1 h. The clear solution was cooled to room temperature and poured slowly with stirring into a mixture of NH₄OH (150 mL) and crushed ice (200 g). The white solid that precipitated was filtered, dissolved in concentrated HCl (200 mL) and stirred at 100° C. for 1 h. Neutralization of the cooled to room temperature acid solution with NH₄OH afforded white precipitate, which was filtered, washed with water and dried to give the title compound as a white solid. MS (ESI, pos. ion) m/z: 180 (M+1).

(b) 1-(8-Hydroxyquinolin-2-yl)piperazine

The quinoline from step (a) above (0.18 g, 1 mmol) and piperazine (0.172 g, 2 mmol, Aldrich) reacted under the conditions of Example 3a to give the title compound as a white solid.

(c) 2-[4-(8-Hydroxyquinolin-2-yl)piperazin-1-yl]-6-trifluoromethyl-1H-benzoimidazole The piperazine from step (b) above (0.329 g, 1.67 mmol) and 2-chloro-6-trifluoromethyl-1H-benzoimidazole (0.370 g, 1.67 mmol, Example 1c) reacted under the conditions of Example 3c to give the title compound. M.p. 191-193° C. MS (ESI, pos. ion) m/z: 414 (M+1).

Example 29

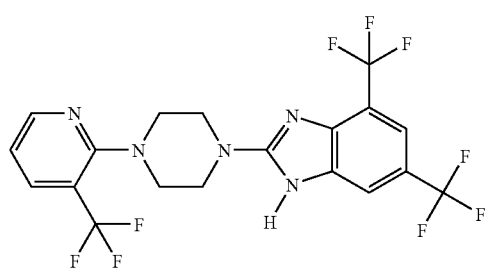

4,6-Bis(trifluoromethyl)-2-[4-(3-trifluoromethylpyridin-2-yl)piperazin-1-yl]-1H-benzoimidazole (a) 1,3-Dihydro-4,6-bis(trifluoromethyl)benzoimidazol-2-one 3,5-bis(trifluoromethyl)-1,2-diaminobenzene (10 g, 41 mmol, ABCR) reacted under the conditions of Example 1b to give the title compound. MS (ESI, pos. ion) m/z: 271 (M+1).

(b) 4,6-Bis(trifluoromethyl)-2-chloro-1H-benzoimidazole

The benzoimidazol-2-one from step (a) above (6 g, 22 mmol) reacted under the conditions of Example 1c to give the title compound as a white solid. MS (ESI, pos. ion) m/z: 289 (M+1).

(c) 4,6-Bis(trifluoromethyl)-2-[4-(3-trifluoromethylpyridin-2-yl)piperazin-1-yl]-1H-benzoimidazole The benzoimidazole from step (b) above (115 mg, 0.4 mmol) and 1-(3-trifluoromethylpyridin-2-yl)piperazine (140 mg, 0.6 mmol, Maybridge) reacted under the conditions of Example 3c to give the title compound as a white solid. M.p. 142° C. MS (ESI, pos. ion) m/z: 484 (M+1).

Example 30

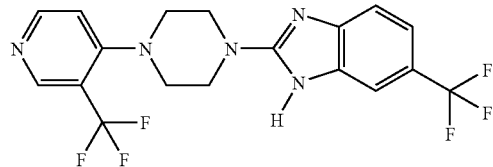

6-Trifluoromethyl-2-[4-(3-trifluoromethylpyridin-4-yl)piperazin-1-yl]-1H-benzoimidazole (a) 4-(3-Trifluoromethylpyridin-4-yl)piperazine-1-carboxylic acid tert-butyl Ester The reaction of 4-chloro-3-trifluoromethylpyridine (2.05 g, 9.4 mmol, Matrix Scientific) and tert-butyl 1-piperazinecarboxylate (2.1 g, 11.3 mmol, Aldrich) under the conditions of Example 3a afforded the crude product, which was purified by silica gel column chromatography (60% EtOAc/hexane) to give the title compound as a white solid. MS (ESI, pos. ion) m/z: 332 (M+1).

(b) 1-(3-Trifluoromethylpyridin-4-yl)piperazine Trihydrochloride

The ester from step (a) above (1.9 g, 5.7 mmol) reacted under the conditions of Example 3b to give the title compound as a white solid. MS (ESI, pos. ion) m/z: 232 (M+1).

(c) 6-Trifluoromethyl-2-[4-(3-trifluoromethylpyridin-4-yl)piperazin-1-yl]-1H-benzoimidazole The piperazine from step (b) above (0.55 g, 1.81 mmol), 2-chloro-6-trifluoromethyl-1H-benzoimidazole (0.4 g, 1.81 mmol, Example 1c) and N,N-diisopropylethylamine (0.63 mL, 3.62 mmol, Aldrich) reacted under the conditions of Example 3c to give the title compound as a light-yellow solid. M.p. 220-224° C. MS (ESI, pos. ion) m/z: 416 (M+1).

Example 31

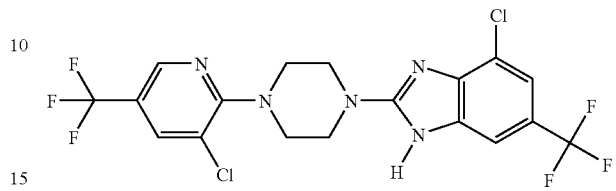

4-Chloro-6-trifluoromethyl-2-[4-(3-chloro-5-trifluoromethylpyridin-2-yl)piperazin-1-yl]-1H-benzoimidazole The reaction of 1-(3-chloro-5-trifluoromethylpyridin-2-yl)piperazine (186 mg, 0.7 mmol, ABCR) and 2,4-dichloro-6-trifluoromethyl-1H-benzoimidazole (127 mg, 0.5 mmol, Example 5b) under the conditions of Example 3c afforded the title compound as a white amorphous solid. MS (ESI, pos. ion) m/z: 484 (M+1).

Example 32

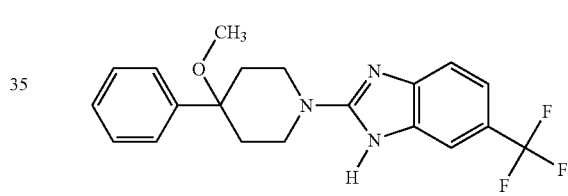

2-(4-Methoxy-4-phenylpiperidin-1-yl)-6-trifluoromethyl-1H-benzoimidazole (a) 4-Hydroxy-4-phenylpiperidine-1-carboxylic Acid tert-butyl Ester A solution of 4-hydroxy-4-phenylpiperidine (5.42 g, 30.5 mmol, Aldrich) and di-tert-butyl dicarbonate (6.67 g, 30.5 mmol, Aldrich) in CH$_2$Cl$_2$ (200 mL) was stirred at room temperature for 16 h. The solvent was removed in vacuo and the residue was suspended in 2% EtOAc/hexane solution (50 mL), filtered and dried in the air to give the title compound as a white solid. MS (ESI, pos. ion) m/z: 278 (M+1).

(b) 4-Methoxy-4-phenylpiperidine-1-carboxylic Acid tert-butyl Ester

To a solution of the ester from step (a) above (4.3 g, 15.5 mol) in DMF (30 mL) was added NaH (60% in mineral oil, 0.93 g, 23.2 mmol) and the mixture was stirred at 0° C. for 1 h. MeI (1.16 mL, 18.6 mmol, Aldrich) was added drop-wise with stirring at 0° C., and the mixture was stirred at room temperature for 18 h. The reaction mixture was diluted with EtOAc (50 mL), washed with saturated solution of NH$_4$Cl (25 mL) and brine (25 mL), dried over Na$_2$SO$_4$ and filtered. The solvent was removed in vacuo and the residue purified by silica gel chromatography, eluting with 10% EtOAc/hexane, to give the title compound as a light-yellow oil, which was used in the next step without additional purification. MS (ESI, pos. ion) m/z: 292 (M+1).

(c) 4-Methoxy-4-phenylpiperidine Hydrochloride

A mixture of the ester from step (b) above (8.6 g) and saturated solution of hydrogen chloride in EtOAc (100 mL) was stirred at room temperature for 1 h. The solvent was removed in vacuo and the residue was washed with EtOAc, and dried in vacuo to give the title compound as a white solid. MS (ESI, pos. ion) m/z: 192 (M+1).

(d) 2-(4-Methoxy-4-phenylpiperidin-1-yl)-6-trifluoromethyl-1H-benzoimidazole The piperidine from step(c) above (0.39 g, 1.72 mmol), 2-chloro-6-trifluoromethyl-1H-benzoimidazole (0.38 g, 1.72 mmol, Example 1c) and N,N-diisopropylethylamine (0.59 mL, 3.4 mmol, Aldrich) reacted under the conditions of Example 1d to give the title compound as an amorphous solid. MS (ESI, pos. ion) m/z: 376 (M+1).

Example 33

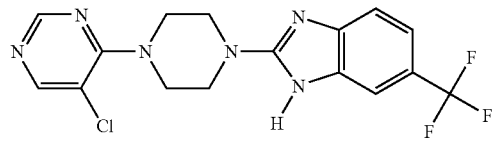

2-[4-(5-Chloropyrimidin-4-yl)piperazin-1-yl]-6-trifluoromethyl-1H-benzoimidazole

(a) 5-Chloro-3H-pyrimidin-4-one

4(3H)-Pyrimidone (2.98 g, 31 mmol, Aldrich) was added to a solution of chlorine (2.2 g, 31 mmol) in AcOH (50 mL) prepared by bubbling of chlorine gas for 10 min at room temperature. The mixture was stirred at room temperature for 5 h and then concentrated to a 30 mL volume by evaporation of the solvent in vacuo. The solid which precipitated was filtered and dried at 40° C. for 24 h to give the title compound as a white solid. MS (ESI, pos. ion) m/z: 131 (M+1).

(b) 4,5-Dichloropyrimidine

A solution of the pyrimidin-4-one from step (a) above (3.5 g, 26.8 mmol) in phosphorus oxychloride (50 mL) was heated under for 3 h. The reaction mixture was cooled to room temperature, the solvent was evaporated in vacuo and the residue was dissolved in EtOAc (100 mL). The organic solution was washed with saturated aqueous solution of NaHCO$_3$ (50 mL) and brine (50 mL), dried over Na$_2$SO$_4$, filtered, and concentrated in vacuo. The residue was purified by silica gel column chromatography, eluting with 10% EtOAc/hexane, to give the title compound as an orange oil. MS (ESI, pos. ion) m/z: 131 (M+1).

(c) 4-(5-Chloro-pyrimidin-4-yl)-piperazine-1-carboxylic Acid tert-butyl Ester The pyrimidine from step (b) above (1.75 g, 1.2 mmol) and tert-butyl 1-piperazinecarboxylate (2.235 g, 0.012 mol, Ald-rich) reacted under the conditions of Example 3a to give the title compound as an orange oil. MS (ESI, pos. ion) m/z: 299 (M+1).

(d) 1-(5-Chloropyrimidin-4-yl)piperazine, Trifluoroacetic Acid Salt

A solution of the ester from step (c) above (1.8 g, 6 mmol) in a 1:1 mixture of CF$_3$CO$_2$H/CH$_2$Cl$_2$ (60 mL) was stirred at room temperature for 1 h. The solvents were removed in vacuo to give the title compound as an orange oil, which was used in the next step without additional purification: MS (ESI, pos. ion) m/z: 199 (M+1).

(e) 2-[4-(5-Chloropyrimidin-4-yl)piperazin-1-yl]-6-trifluoromethyl-1H-benzoimidazole The piperazine from step (d) above (0.62 g, 1.45 mmol), 2-chloro-6-trifluoromethyl-1H-benzoimidazole (0.32 g, 1.45 mmol, Example 1c) and N,N-diisopropylethylamine (0.76 mL, 4.35 mmol, Aldrich) reacted under the conditions of Example 1d to give the title compound as an amorphous solid. MS (ESI, pos. ion) m/z: 383 (M+1).

Example 34

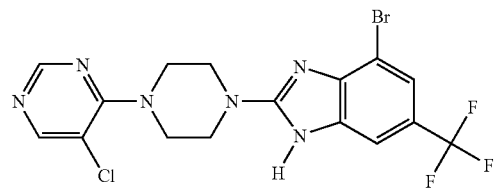

4-Bromo-2-[4-(5-chloropyrimidin-4-yl)piperazin-1-yl]-6-trifluoromethyl-1H-benzoimidazole The reaction of 1-(5-chloropyrimidin-4-yl)piperazine trifluoroacetic acid salt (0.414 g, 0.97 mmol, Example 33d), 4-bromo-2-chloro-6-trifluoromethyl-1H-benzoimidazole (0.29 g, 0.97 mmol, Example 9b) and N,N-diisopropylethylamine (0.5 mL, 2.91 mmol, Aldrich) under the conditions of Example 1d gave the title compound as an amorphous solid. MS (ESI, pos. ion) m/z: 461 (M+1).

Example 35

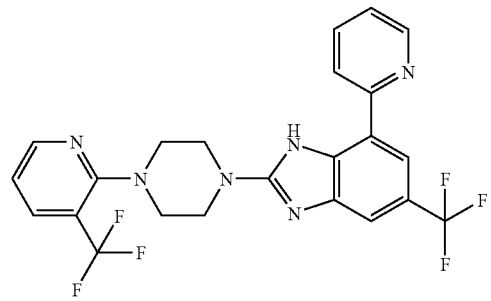

7-Pyridin-2-yl-5-(trifluoromethyl)-2-{4-[3-(trifluoromethyl)pyridin-2-yl]piperazin-1-yl}-1H-benzoimidazole A mixture of 4-bromo-6-trifluoromethyl-2-[4-(3-trifluoromethylpyridin-2-yl)piperazin-1-yl]-1H-benzoimidazole (148 mg, 0.3 mmol, Example 7), 2-tributylstannylpyridine (148 mg, 0.5 mmol, Frontier), Pd(PPh₃)₄ (46 mg, 0.04 mmol, Aldrich) and 1,4-dioxane (1 mL) was subjected to microwave irradiation at 140° C. with stirring for 60 min. The solvent was removed in vacuo and the residue was purified by silica gel chromatography, eluting with 60% EtOAc/hexane, to give the title compound as a yellow amorphous solid. MS (ESI, pos. ion) m/z: 493 (M+1).

Example 36

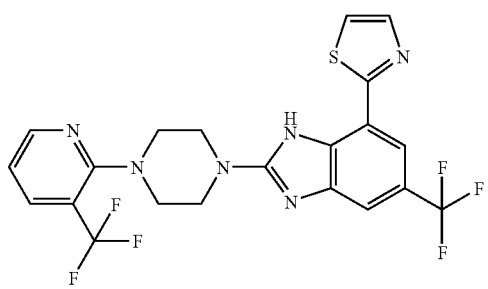

7-Thiazol-2-yl-5-trifluoromethyl-2-[4-(3-trifluoromethyl-pyridin-2-yl)-piperazin-1-yl]-1H-benzoimidazole The reaction of 4-bromo-6-trifluoromethyl-2-[4-(3-trifluoromethylpyridin-2-yl)piperazin-1-yl]-1H-benzoimidazole (148 mg, 0.3 mmol, Example 7) with 2-tributylstannylthiazole (Matrix Scientific) under the conditions of Example 35 gave the title compound as an amorphous solid. MS (ESI, pos. ion) m/z: 499 (M+1).

Example 37

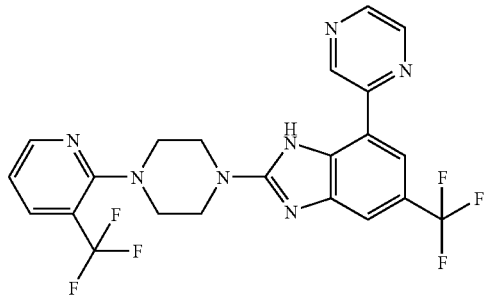

7-Pyrazin-2-yl-5-trifluoromethyl-2-[4-(3-trifluoromethyl-pyridin-2-yl)-piperazin-1-yl]-1H-benzoimidazole The reaction of 4-bromo-6-trifluoromethyl-2-[4-(3-trifluoromethylpyridin-2-yl)piperazin-1-yl]-1H-benzoimidazole (Example 7) with 2-tributylstannylpyrazine (Matrix Scientific) under the conditions of Example 35 gave the title compound as an amorphous solid. MS (ESI, pos. ion) m/z: 494 (M+1).

Example 38

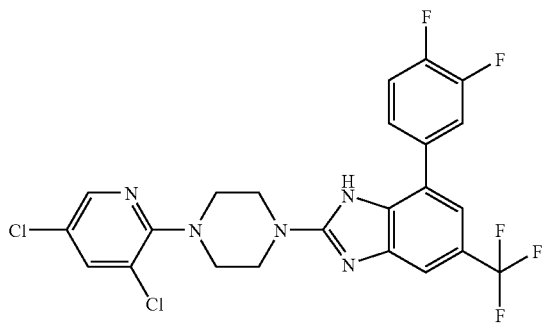

2-[4-(3,5-Dichloropyridin-2-yl)piperazin-1-yl]-7-(3,4-difluorophenyl)-5-(trifluoromethyl)-1H-benzoimidazole The reaction of 4-bromo-2-[4-(3,5-dichloropyridin-2-yl)piperazin-1-yl]-6-trifluoromethyl-1H-benzoimidazole (99 mg, 0.2 mmol, Example 9) and 3,4-difluorophenylboronic acid (40 mg, 0.25 mmol, Aldrich) under the conditions of Example 10 gave the title compound as a light-yellow amorphous solid. MS (ESI, pos. ion) m/z: 528 (M+1).

Example 39

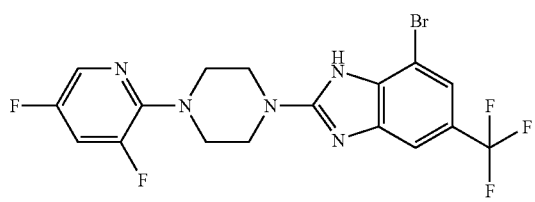

7-Bromo-2-[4-(3,5-difluoropyridin-2-yl)piperazin-1-yl]-5-(trifluoromethyl)-1H-benzoimidazole (a) 4-(3,5,6-Trifluoro-pyridin-2-yl)-piperazine-1-carboxylic Acid tert-butyl Ester A mixture of 2,3,5,6-tetrafluoropyridine (755 mg, 5 mmol, Aldrich), 1-Boc-piperazine (558 mg, 3 mmol, Aldrich) and N,N-diisopropylethylamine (1 mL, 5.8 mmol, Aldrich) in NMP (5 mL) was heated at 150° C. for 16 h. The reaction mixture was cooled to room temperature, water (25 mL) was added, and the mixture was extracted with EtOAc (2×40 mL). The combined organic phases were washed with brine (50 mL), then dried over Na₂SO₄ and filtered. The filtrate was concentrated in vacuo and the residue was purified by silica gel column chromatography, eluting with 20% EtOAc/hexane to give the title compound as a white solid. MS (ESI, pos. ion) m/z: 318 (M+1).

(b) 4-(3,5-Difluoro-pyridin-2-yl)-piperazine-1-carboxylic Acid tert-butyl Ester (Analogous to the procedure of Hee-Gweon Woo; Bo-Hye, Kim and Sun-Jung Song, *Bull. Korean Chem. Soc.* 1999, 20, 865-866). 4-(3,5,6-Trifluoro-pyridin-2-yl)-piperazine-1-carboxylic acid tert-butyl ester from step (a) above (950 mg, 3 mmol) was added to a mixture of bis(cyclopentadienyl)titanium dichloride (37 mg, 0.15 mmol, Aldrich) and Red-Al (1.32 mL, Aldrich) in toluene (3 mL). The reaction mixture was stirred at room temperature for 3 h and quenched by the addition of water (50 mL). The mixture was extracted with EtOAc (2×40 mL) and the combined organic phases were washed with brine (50 mL), dried over $Na_2SO_4$, and filtered. The filtrate was concentrated in vacuo and the residue was purified by silica gel chromatography, eluting with 20% EtOAc/hexane to give the title compound as a light-yellow oil. MS (ESI, pos. ion) m/z: 300 (M+1).

(c) 1-(3,5-Difluoro-pyridin-2-yl)-piperazine

A mixture of 4-(3,5-difluoro-pyridin-2-yl)-piperazine-1-carboxylic acid tert-butyl ester from step (b) above (140 mg, 0.47 mmol) and 4 M solution of HCl in dioxane (1 mL, Aldrich) was stirred at room temperature for 30 h. The solvent was evaporated in vacuo and the residue was dissolved in EtOAc (30 mL). The solution was washed successively with 1 N NaOH (20 mL) and brine (20 mL), dried over $MgSO_4$, filtered, and the solvent was removed in vacuo. The residue was purified by silica gel chromatography, eluting with 10% MeOH in $CH_2Cl_2$ to give the title compound as a white solid. MS (ESI, pos. ion) m/z: 200 (M+1).

(d) 7-Bromo-2-[4-(3,5-difluoropyridin-2-yl)piperazin-1-yl]-5-(trifluoromethyl)-1H-benzoimidazole The piperazine from step (c) above (80 mg, 0.4 mmol) reacted with 2-chloro-6-trifluoromethyl-1H-benzoimidazole (44 mg, 0.2 mmol, Example 1c) under the conditions of Example 3c to give the title compound as a white amorphous solid. MS (ESI, pos. ion) m/z: 462 (M+1).

Example 40

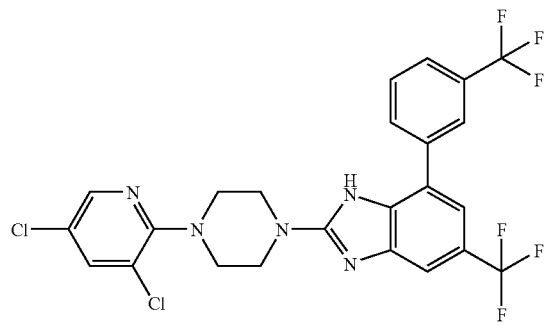

2-[4-(3,5-Dichloropyridin-2-yl)piperazin-1-yl]-5-(trifluoromethyl)-7-[3-(trifluoromethyl)phenyl]-1H-benzoimidazole The reaction of 4-bromo-2-[4-(3,5-dichloropyridin-2-yl)piperazin-1-yl]-6-trifluoromethyl-1H-benzoimidazole (99 mg, 0.2 mmol, Example 9) and 3-trifluoromethylphenylboronic acid (48 mg, 0.25 mmol, Aldrich) under the conditions of Example 10 gave the title compound as a light-yellow amorphous solid. MS (ESI, pos. ion) m/z: 560 (M+1).

Example 41

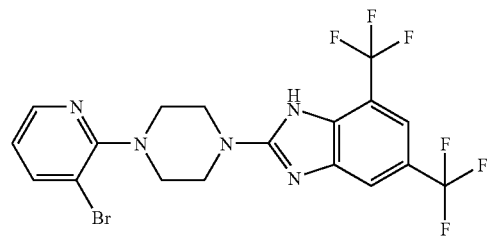

2-[4-(3-Bromopyridin-2-yl)piperazin-1-yl]-5,7-bis(trifluoromethyl)-1H-benzoimidazole

(a) 1-(3-Bromo-pyridin-2-yl)-piperazine

A mixture of 3-bromo-2-chloropyridine (0.96 g, 5 mmol, Aldrich), piperazine (0.86 g, 10 mmol, Aldrich) and N,N-diisopropylethylamine (1 mL, 5.8 mmol, Aldrich) was heated in a microwave synthesizer for 40 min at 200° C. The reaction mixture was concentrated and the residue was purified by column chromatography on silica gel, eluting with 10% MeOH in dichloromethane to give the title compound as a white amorphous solid. MS (ESI, pos. ion) m/z: 242 (M+1).

(b) 2-[4-(3-Bromopyridin-2-yl)piperazin-1-yl]-5,7-bis(trifluoromethyl)-1H-benzoimidazole The piperazine from step (a) above (97 mg, 0.4 mmol) reacted with 6-bis(trifluoromethyl)-2-chloro-1H-benzoimidazole (86 mg, 0.3 mmol, Example 29b) under the conditions of Example 3c to give the title compound as a white amorphous solid. M.p. 166° C. MS (ESI, pos. ion) m/z: 494 (M+1).

Example 42

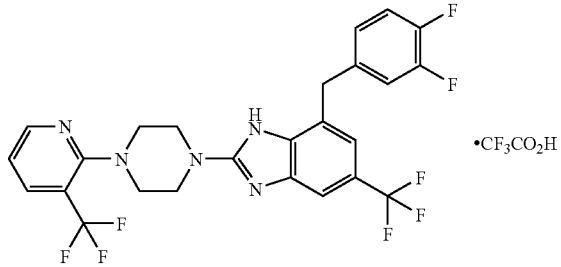

7-(3,4-Difluorobenzyl)-5-(trifluoromethyl)-2-{4-[3-(trifluoromethyl)pyridin-2-yl]piperazin-1-yl}-1H-benzoimidazole, Trifluoroacetic Acid Salt A mixture of 4-bromo-6-trifluoromethyl-2-[4-(3-trifluoromethylpyridin-2-yl)piperazin-1-yl]-1H-benzoimidazole (148 mg, 0.3 mmol, Example 7), 0.5 M solution of 3,4-difluorobenzylzinc bromide in THF (2 mL, 1 mmol, Aldrich)

and Pd(PPh$_3$)$_4$ (35 mg, 0.03 mmol, Aldrich) was heated at reflux for 12 h. The solvent was removed in vacuo and the residue was purified by preparative HPLC (gradient 0.1% trifluoroacetic acid in acetonitrile) to give the title compound as a white amorphous solid. MS (ESI, pos. ion) m/z: 542 (M+1).

Example 43

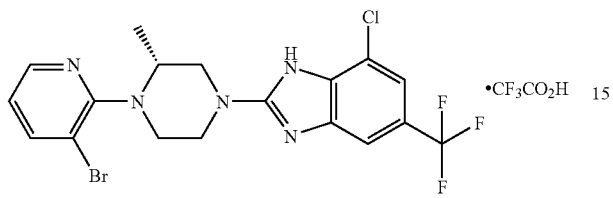

2-[(3R)-4-(2-Bromophenyl)-3-methylpiperazin-1-yl]-7-chloro-5-(trifluoromethyl)-1H-benzoimidazole, Trifluoroacetic Acid Salt (a) (2R)-1-(3-Bromopyridin-2-yl)-2-methylpiperazine and (3R)-1-(3-Bromopyridin-2-yl)-3-methylpiperazine A mixture of 3-bromo-2-chloropyridine (2 g, 9 mmol, Aldrich), (R)-(−)-2-methylpiperazine (1.5 g. 15 mmol) and N,N-diisopropylethylamine (1 mL, 5.8 mmol) in NMP (1 mL) was heated in a microwave synthesizer for 60 min at 240° C. The reaction mixture was concentrated and purified by silica gel chromatography, eluting with 10% MeOH in dichloromethane to give 0.5 g (22%) of (2R)-1-(3-bromopyridin-2-yl)-2-methylpiperazine MS (ESI, pos. ion). MS m/z: 256 (M+1), and 0.75 g (33%) of (3R)-1-(3-bromopyridin-2-yl)-3-methylpiperazine. MS m/z: 256 (M+1).

(b) 2-[(3R)-4-(2-Bromophenyl)-3-methylpiperazin-1-yl]-7-chloro-5-(trifluoromethyl)-1H-benzoimidazole, Trifluoroacetic Acid Salt (2R)-1-(3-Bromopyridin-2-yl)-3-methylpiperazine from step (a) above (77 mg, 0.3 mmol,) reacted with 2,4-dichloro-6-trifluoromethyl-1H-benzoimidazole (51 mg, 0.2 mmol, Example 5b) under the conditions of Example 3c to give the crude product. Purification by preparative HPLC (gradient 0.1% trifluoroacetic acid in acetonitrile) gave the title compound as a white amorphous solid. MS (ESI, pos. ion) m/z: 474 (M+1).

Example 44

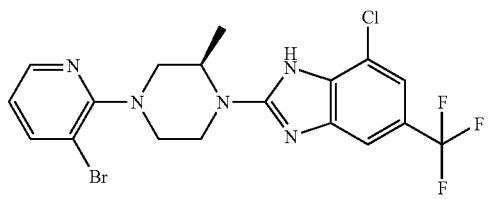

2-[(3R)-4-(3-Bromopyridin-2-yl)-2-methylpiperazin-1-yl]-7-chloro-5-(trifluoromethyl)-1H-benzoimidazole (2R)-1-(3-Bromopyridin-2-yl)-3-methylpiperazine (77 mg, 0.3 mmol, Example 43a) reacted with 2,4-dichloro-6-trifluoromethyl-1H-benzoimidazole (51 mg, 0.2 mmol, Example 5b) under the conditions of Example 3c to give the title compound as a white amorphous solid. MS (ESI, pos. ion) m/z: 474 (M+1).

Example 45

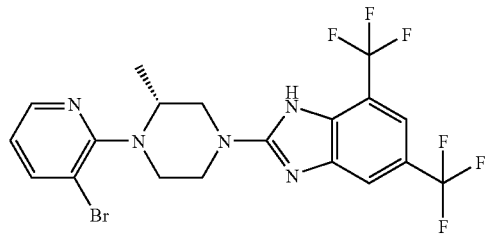

2-[(3R)-4-(3-Bromopyridin-2-yl)-3-methylpiperazin-1-yl]-5,7-bis(trifluoromethyl)-1H-benzoimidazole (2R)-1-(3-Bromopyridin-2-yl)-3-methylpiperazine (77 mg, 0.3 mmol, Example 43a) reacted with 2-chloro-4,6-bis-trifluoromethyl-1H-benzoimidazole (58 mg, 0.2 mmol, Example 29b) under the conditions of Example 3c to give the title compound as a white amorphous solid. MS (ESI, pos. ion) m/z: 508 (M+1).

Example 46

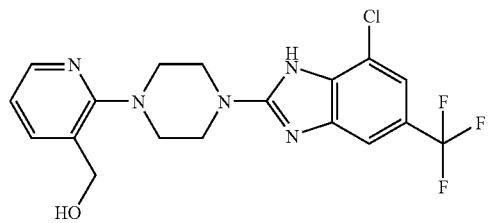

(2-{4-[7-Chloro-5-(trifluoromethyl)-1H-benzimidazol-2-yl]piperazin-1-yl}pyridin-3-yl)methanol (a) (2-piperazin-1-ylpyridin-3-yl)methanol A mixture of (2-fluoro-pyridin-3-yl)methanol (1 g, 8 mmol, Asymchem), piperazine (1.3 g, 15 mmol) and N,N-diisopropylethylamine (1 mL, 5.8 mmol, Aldrich) was reacted under the conditions of Example 43a to give the title compound as a white solid. MS (ESI, pos. ion) m/z: 194 (M+1).

(b) (2-{4-[7-Chloro-5-(trifluoromethyl)-1H-benzimidazol-2-yl]piperazin-1-yl}pyridin-3-yl)methanol The piperazine from step (a) above (97 mg, 0.5 mmol) reacted with 2,4-dichloro-6-trifluoromethyl-1H-benzoimidazole (85 mg, 0.33 mmol, Example 5b) under the conditions of Example 3c to give the title compound as a white solid. M.p. 252° C. MS (ESI, pos. ion) m/z: 412 (M+1).

Example 47

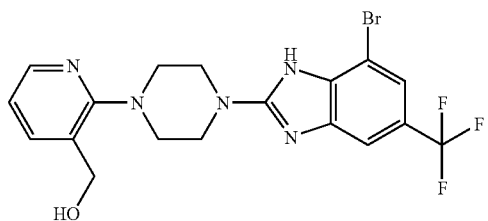

(2-{4-[7-Bromo-5-(trifluoromethyl)-1H-benzimidazol-2-yl]piperazin-1-yl}pyridin-3-yl)methanol (2-piperazin-1-ylpyridin-3-yl)methanol (0.48 g, 2.5 mmol, Example 46a) reacted with 4-bromo-2-chloro-6-trifluoromethyl-1H-benzoimidazole (0.60 g, 2 mmol, Example 6b) under the conditions of Example 3c to give the title compound as a white amorphous solid. MS (ESI, pos. ion) m/z: 456 (M+1).

Example 48

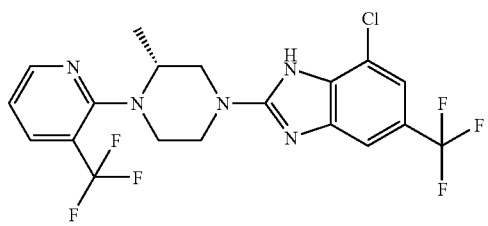

7-Chloro-2-{(3R)-3-methyl-4-[3-(trifluoromethyl)pyridin-2-yl]piperazin-1-yl}-5-(trifluoromethyl)-1H-benzoimidazole (a) 7-Chloro-2-[(3R)-3-methylpiperazin-1-yl]-5-(trifluoromethyl)-1H-benzoimidazole A mixture of 2,4-dichloro-6-trifluoromethyl-1H-benzoimidazole (0.51 g, 2 mmol, Example 5b), (R)-(−)-2-methylpiperazine (0.25 g. 2.5 mmol) and N,N-diisopropylethylamine (0.5 mL, 2.9 mmol) in NMP (5 mL) was heated at 120° C. for 16 h. The reaction mixture was cooled to room temperature, diluted with water (10 mL) and extracted with EtOAc (2×20 mL). The combined organic phases were washed with brine (10 mL), dried over Na₂SO₄ and filtered. The filtrate was concentrated in vacuo and the residue was purified by silica gel chromatography, eluting with 10% MeOH in dichloromethane to give the title compound as a light-yellow solid. MS (ESI, pos. ion) m/z: 319 (M+1).

(b) 7-Chloro-2-{(3R)-3-methyl-4-[3-(trifluoromethyl)pyridin-2-yl]piperazin-1-yl}-5-(trifluoromethyl)-1H-benzoimidazole A mixture of the piperazine from step (a) above (80 mg, 0.25 mmol), 2-chloro-3-trifluoromethyl-pyridine (54 mg, 0.3 mmol, Aldrich) and N,N-diisopropylethylamine (0.5 mL, 2.9 mmol, Aldrich) was heated in a microwave synthesizer for 120 min at 250° C. Water (10 mL) was added and the mixture was extracted with EtOAc (2×20 mL). The combined organic phases were washed with brine (10 mL), dried over Na₂SO₄ and filtered. The filtrate was concentrated in vacuo and the residue was purified by silica gel chromatography, eluting with 35% EtOAc/hexane to give the title compound as a white amorphous solid. MS (ESI, pos. ion) m/z: 464 (M+1).

Example 49

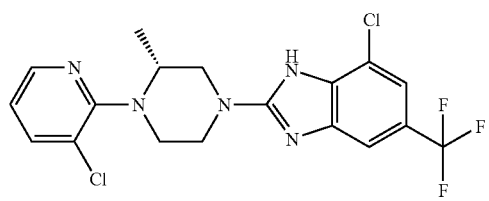

7-Chloro-2-[(3R)-4-(3-chloropyridin-2-yl)-3-methylpiperazin-1-yl]-5-(trifluoromethyl)-1H-benzoimidazole A mixture of 2,3-dichloro-pyridine (44 mg, 0.3 mmol, Aldrich), 7-chloro-2-[(3R)-3-methylpiperazin-1-yl]-5-(trifluoromethyl)-1H-benzoimidazole (80 mg, 0.25 mmol, Example 48a) and N,N-diisopropylethylamine (0.1 mL, 0.58 mmol, Aldrich) reacted under the conditions of Example 48b to give the title compound as a white amorphous solid. MS (ESI, pos. ion) m/z: 430 (M+1).

Example 50

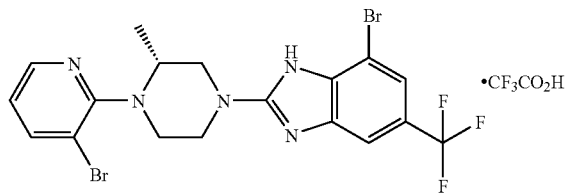

7-Bromo-2-[(3R)-4-(3-bromopyridin-2-yl)-3-methylpiperazin-1-yl]-5-(trifluoromethyl)-1H-benzoimidazole, Trifluoroacetic Acid Salt 4-Bromo-2-chloro-6-trifluoromethyl-1H-benzoimidazole (145 mg, 0.5 mmol, Example 6b) reacted with (2R)-1-(3-bromopyridin-2-yl)-2-methylpiperazine (154 mg, 0.6 mmol, Example 43a) under the conditions of Example 3c, and the crude product was purified by preparative HPLC (gradient 0.1% trifluoroacetic acid in acetonitrile) to give the title compound as a white amorphous solid. MS (ESI, pos. ion) m/z: 518 (M+1).

Example 51

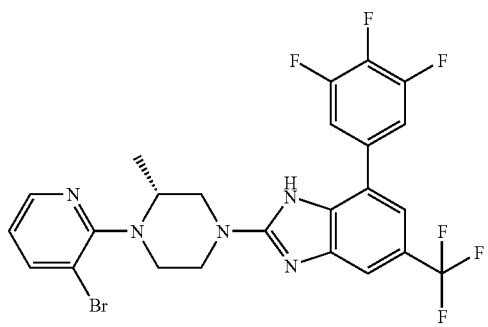

2-[(3R)-4-(3-Bromopyridin-2-yl)-3-methylpiperazin-1-yl]-5-(trifluoromethyl)-7-(3,4,5-trifluorophenyl)-1H-benzoimidazole

(a) 6-(Trifluoromethyl)-4-(3,4,5-trifluorophenyl)-1,3-dihydro-2H-benzimidazol-2-one A mixture of 4-bromo-6-trifluoromethyl-1,3-dihydrobenzoimidazol-2-one (1.12 g, 4 mmol, Example 6a), 3,4,5-trifluorophenylboronic acid (1.1 g, 6 mmol, Lancaster), PdCl$_2$(PPh$_3$)$_2$ (35 mg, 0.05 mmol, Aldrich), Na$_2$CO$_3$.H$_2$O (1 g, 8 mmol), dimethoxyethane (7 mL), H$_2$O (3 mL) and EtOH (2 mL) was subjected to microwave irradiation at 120° C. with stirring for 10 min. Water (10 mL) was added and the mixture was extracted with EtOAc (2×20 mL). The combined organic phases were washed with brine (10 mL), dried over Na$_2$SO$_4$, and filtered. The filtrate was concentrated in vacuo, and the residue was purified by silica gel chromatography, eluting with 35% EtOAc/hexane to give the title compound as a light-brown solid. MS (ESI, pos. ion) m/z: 333 (M+1).

(b) 2-Chloro-6-(trifluoromethyl)-4-(3,4,5-trifluorophenyl)-1H-benzoimidazole The benzoimidazol-2-one from step (a) above (1.1 g, 3.3 mmol) reacted with POCl$_3$ under the conditions of Example 1c to give the title compound as a white solid. MS (ESI, pos. ion) m/z: 350 (M+1).

(c) 2-[(3R)-4-(3-Bromopyridin-2-yl)-3-methylpiperazin-1-yl]-5-(trifluoromethyl)-7-(3,4,5-trifluorophenyl)-1H-benzoimidazole The benzoimidazole from step (b) above (105 mg, 0.3 mmol) reacted with (2R)-1-(3-bromopyridin-2-yl)-2-methylpiperazine (77 mg, 0.3 mmol, Example 43a) under the conditions of Example 3c to give the title compound as a white amorphous solid. MS (ESI, pos. ion) m/z: 570 (M+1).

Example 52

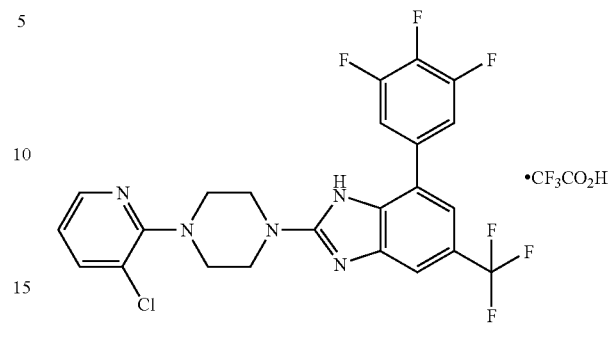

2-[4-(3-Chloropyridin-2-yl)piperazin-1-yl]-5-(trifluoromethyl)-7-(3,4,5-trifluorophenyl)-1H-benzoimidazole, Trifluoroacetic Acid Salt The reaction of 4-bromo-2-[4-(3-chloropyridin-2-yl)piperazin-1-yl]-6-trifluoromethyl-1H-benzoimidazole (92 mg, 0.2 mmol, Example 9) with 3,4,5-trifluorophenylboronic acid (52 mg, 0.3 mmol, Lancaster) under the conditions of Example 10 afforded the crude product, which was purified by preparative HPLC (gradient 0.1% trifluoroacetic acid in acetonitrile) to give the title compound as a white amorphous solid. MS (ESI, pos. ion) m/z: 512 (M+1).

Example 53

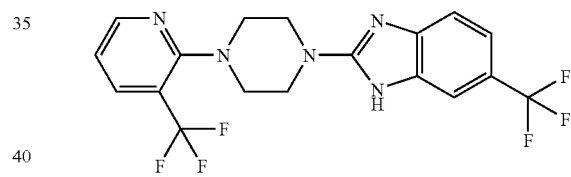

5-(Trifluoromethyl)-2-{4-[3-(trifluoromethyl)(2-pyridyl)]piperazinyl}benzoimidazole The title compound was prepared from 1-(3-trifluoromethylpyridin-2-yl)piperazine (Maybridge) and 2-chloro-6-trifluoromethyl-1H-benzoimidazole (Example 1c) under the conditions of Example 3c. MS (ESI, pos. ion) m/z: 416 (M+1). M.p. 221-224° C.

Example 54

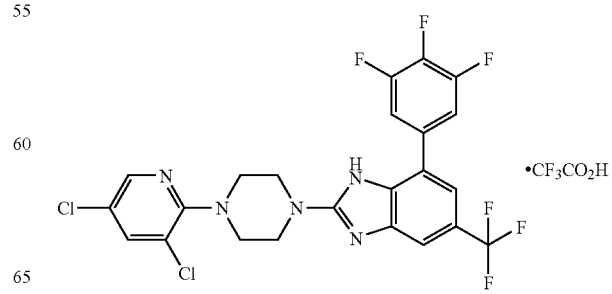

2-[4-(3,5-Dichloropyridin-2-yl)piperazin-1-yl]-5-(trifluoromethyl)-7-(3,4,5-trifluorophenyl)-1H-benzoimidazole, Trifluoroacetic Acid Salt 4-Bromo-2-[4-(3,5-dichloropyridin-2-yl)piperazin-1-yl]-6-trifluoromethyl-1H-benzoimidazole (296 mg, 0.6 mmol, Example 9) reacted with 3,4,5-trifluorophenylboronic acid (161 mg, 0.9 mmol, Lancaster) under the conditions of Example 51a to give the title compound as a white amorphous solid. MS (ESI, pos. ion) m/z: 546 (M+1).

Example 55

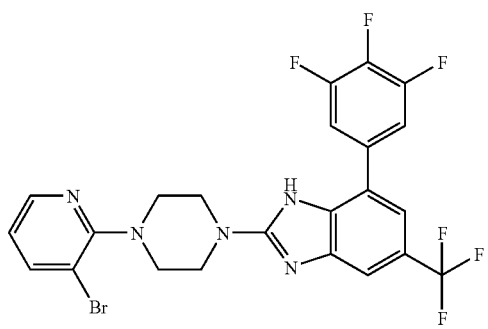

2-[4-(3-Bromopyridin-2-yl)piperazin-1-yl]-5-(trifluoromethyl)-7-(3,4,5-trifluorophenyl)-1H-benzoimidazole 2-Chloro-6-(trifluoromethyl)-4-(3,4,5-trifluorophenyl)-1H-benzoimidazole (140 mg, 0.4 mmol, Example 51b) reacted with 1-(3-bromo-pyridin-2-yl)-piperazine (120 mg, 0.5 mmol, Example 41a) under the conditions of Example 3c to give the title compound as a white amorphous solid. MS (ESI, pos. ion) m/z: 556 (M+1).

Example 56

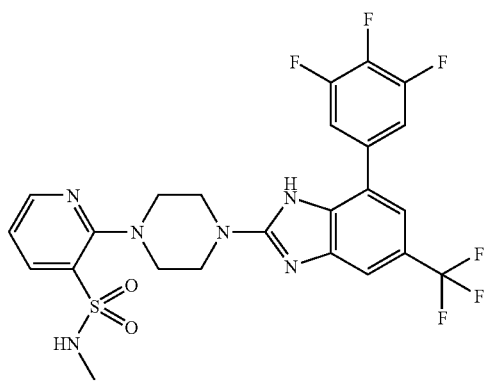

N-Methyl-2-{4-[5-(trifluoromethyl)-7-(3,4,5-trifluorophenyl)-1H-benzimidazol-2-yl]piperazin-1-yl}pyridine-3-sulfonamide (a) 2-piperazin-1-yl-pyridine-3-sulfonic Acid Methylamide A mixture of 2-chloro-N-methyl-3-pyridinesulfonamide (1 g, 4.8 mmol, Specs), piperazine (0.43 g, 5 mmol) and N,N-diisopropylethylamine (1 mL, 5.8 mmol, Aldrich) was reacted under the conditions of Example 41a to give the title compound as a white amorphous solid. MS (ESI, pos. ion) m/z: 257 (M+1).

(b) N-Methyl-2-{4-[5-(trifluoromethyl)-7-(3,4,5-trifluorophenyl)-1H-benzimidazol-2-yl]piperazin-1-yl}pyridine-3-sulfonamide The piperazine from step (a) above (128 mg, 0.5 mmol) reacted with 2-chloro-6-(trifluoromethyl)-4-(3,4,5-trifluorophenyl)-1H-benzoimidazole (140 mg, 0.4 mmol, Example 51b) under the conditions of Example 3c to give the title compound as a white amorphous solid. MS (ESI, pos. ion) m/z: 571 (M+1).

Example 57

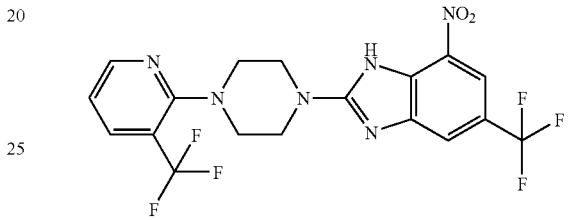

7-Nitro-5-(trifluoromethyl)-2-{4-[3-(trifluoromethyl)pyridin-2-yl]piperazin-1-yl}-1H-benzoimidazole (a) 3-Nitro-5-(trifluoromethyl)benzene-1,2-diamine 4-Amino-3,5-dininitrobenzotrifluoride (25 g, 100 mmol, Aldrich) was added to a suspension of 10% Pd/C (4 g) in EtOH (150 mL) under a hydrogen atmosphere. The reaction mixture was stirred at room temperature for 4 h, filtered through a pad of Celite®, and the filtrate was evaporated under reduced pressure. The residue was purified by silica gel column chromatography, eluting with 45% EtOAc/hexane to give the title compound as a yellow solid. MS (ESI, pos. ion) m/z: 222 (M+1).

(b) 4-Nitro-6-(trifluoromethyl)-1,3-dihydro-2H-benzimidazol-2-one

The reaction of 3-nitro-5-(trifluoromethyl)benzene-1,2-diamine (2.2 g, 10 mmol) with 1,1'-carbonyldiimidazole (1.78 g, 11 mmol, Aldrich) under the conditions of Example 1b afforded the title compound as a yellow solid. MS (ESI, pos. ion) m/z: 248 (M+1).

(c) 2-Chloro-4-nitro-6-(trifluoromethyl)-1H-benzoimidazole

The benzoimidazol-2-one from step (b) above (1.8 g, 7.3 mmol) reacted with POCl₃ under the conditions of Example 1c to give the title compound as a yellow solid. MS (ESI, pos. ion) m/z: 266 (M+1).

(d) 7-Nitro-5-(trifluoromethyl)-2-{4-[3-(trifluoromethyl)pyridin-2-yl]piperazin-1-yl}-1H-benzoimidazole The benzoimidazole from step (c) above (1.5 g, 5.7 mmol) and 1-(3-trifluoromethylpyridin-2-yl)piperazine (1.8 g, 7.8 mmol, Matrix) reacted under the conditions of Example 3c to give the title compound as a orange solid. M.p. 192° C. MS (ESI, pos. ion) m/z: 461 (M+1).

EtOAc/hexane to give the title compound as a white solid. MS (ESI, pos. ion) m/z: 575 (M+1).

Example 58

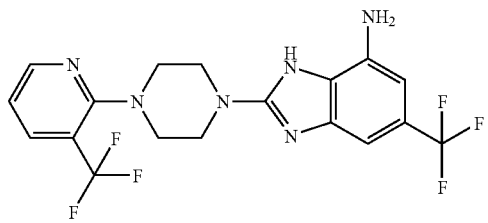

5-(Trifluoromethyl)-2-{4-[3-(trifluoromethyl)pyridin-2-yl]piperazin-1-yl}-1H-benzimidazol-7-amine 7-Nitro-5-(trifluoromethyl)-2-{4-[3-(trifluoromethyl)pyridin-2-yl]piperazin-1-yl}-1H-benzoimidazole (1.8 g, 3.9 mmol, Example 57d) reacted under the conditions of Example 57a to give the title compound as a off-white amorphous solid. MS (ESI, pos. ion) m/z: 431 (M+1).

Example 59

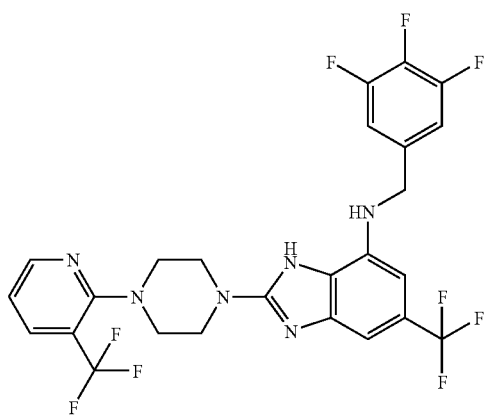

N-(3,4,5-trifluorobenzyl)-5-(trifluoromethyl)-2-{4-[3-(trifluoromethyl)pyridin-2-yl]piperazin-1-yl}-1H-benzimidazol-7-amine NaBH(OAc)₃ (211 mg, 1 mmol, Aldrich) was added to a mixture of 5-(trifluoromethyl)-2-{4-[3-(trifluoromethyl)pyridin-2-yl]piperazin-1-yl}-1H-benzimidazol-7-amine (215 mg, 0.5 mmol, Example 58) and 3,4,5-trifluoro-benzaldehyde (88 mg, 0.55 mmol, Aldrich) in chloroform (2 mL) in one portion. The reaction mixture was stirred at room temperature for 2 h and concentrated in vacuo. The residue was dissolved in EtOAc (30 mL), and washed successively with 1 N NaOH (15 mL) and brine (15 mL), dried over MgSO₄, filtered, and the solvent was evaporated in vacuo. The residue was purified by silica gel chromatography, eluting with 25%

Example 60

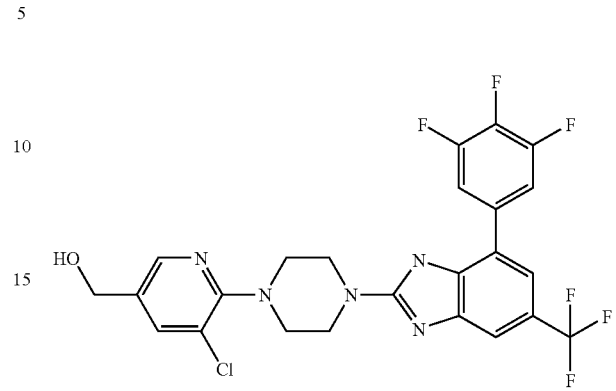

(5-Chloro-6-{4-[5-(trifluoromethyl)-7-(3,4,5-trifluorophenyl)-1H-benzimidazol-2-yl]piperazin-1-yl}pyridin-3-yl)methanol (a) (5-Chloro-6-piperazin-1-yl-pyridin-3-yl)methanol A mixture of 5,6-dichloro-3-pyridinemethanol (0.71 g, 4 mmol, TCI-US), piperazine (0.52 g, 6 mmol) and N,N-diisopropylethylamine (1 mL, 5.8 mmol, Aldrich) was reacted under the conditions of Example 43a to give the title compound as a light-yellow solid. MS (ESI, pos. ion) m/z: 228 (M+1).

(b) (5-Chloro-6-{4-[5-(trifluoromethyl)-7-(3,4,5-trifluorophenyl)-1H-benzimidazol-2-yl]piperazin-1-yl}pyridin-3-yl)methanol The piperazine from step (a) above (114 mg, 0.5 mmol) reacted with 2-chloro-6-(trifluoromethyl)-4-(3,4,5-trifluorophenyl)-1H-benzoimidazole (140 mg, 0.4 mmol, Example 51b) under the conditions of Example 3c to give the title compound as a white amorphous solid. MS (ESI, pos. ion) m/z: 542 (M+1).

Example 61

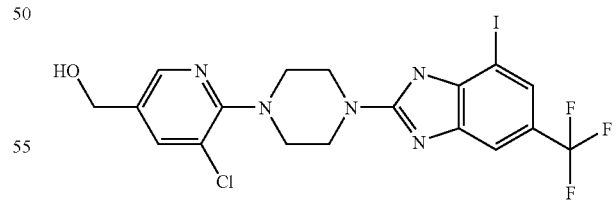

(5-Chloro-6-{4-[7-iodo-5-(trifluoromethyl)-1H-benzimidazol-2-yl]piperazin-1-yl}pyridin-3-yl)methanol (a) 4-Amino-6-(trifluoromethyl)-1,3-dihydro-2H-benzimidazol-2-one 4-Nitro-6-(trifluoromethyl)-1,3-dihydro-2H-benzimidazol-2-one (1.7 g, 7 mmol, Example 57b) reacted under the conditions of Example 57a to give the title compound as a brown solid. MS (ESI, pos. ion) m/z: 218 (M+1).

(b) 4-Iodo-6-(trifluoromethyl)-1,3-dihydro-2H-benzimidazol-2-one (Analogous to the procedure described in *Heterocycles*, 2001, 55, 461-464). To a solution of 4-amino-6-(trifluoromethyl)-1,3-dihydro-2H-benzimidazol-2-one from step (a) above (0.76 g, 3.5 mmol) in 20 mL of DCM was added CsI (0.91 g, 3.5 mmol), $I_2$ (0.44 g, 1.75 mmol), and CuI (0.2 g, 1.06 mmol). To the mixture was added isoamyl nitrite (2.8 mL, Aldrich) and the reaction mixture was heated at 60° C. with stirring for 3 h. The reaction mixture was cooled to room temperature, filtered, and the filtrate was diluted with EcOAc (60 mL). The solution was washed with 25% $NH_4OH$ (2×30 mL), 5% $Na_2S_2O_3$ (20 mL) and brine, dried over $MgSO_4$ and filtered. The filtrate was evaporated and the residue was purified by silica gel column chromatography, eluting with 30% EtOAc/hexane to give the title compound as a brown solid. MS (ESI, pos. ion) m/z: 329 (M+1)

(c) 2-Chloro-4-iodo-6-(trifluoromethyl)-1H-benzoimidazole

4-Iodo-6-(trifluoromethyl)-1,3-dihydro-2H-benzimidazol-2-one (328 mg, 1 mmol) reacted with $POCl_3$ under the conditions of Example 1c to give the title compound as a off-white solid. MS (ESI, pos. ion) m/z: 347 (M+1).

(d) (5-Chloro-6-{4-[7-iodo-5-(trifluoromethyl)-1H-benzimidazol-2-yl]piperazin-1-yl}pyridin-3-yl)methanol The benzoimidazole from step (c) above (69 mg, 0.2 mmol) reacted with (5-chloro-6-piperazin-1-yl-pyridin-3-yl)methanol (68 mg, 0.3 mmol, Example 60c) under the conditions of Example 3c to give the title compound as a yellow amorphous solid. MS (ESI, pos. ion) m/z: 538 (M+1).

Example 62

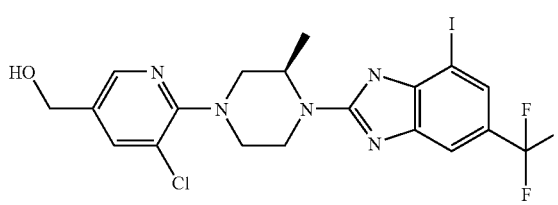

(5-Chloro-6-{(3R)-4-[7-iodo-5-(trifluoromethyl)-1H-benzimidazol-2-yl]-3-methylpiperazin-1-yl}pyridin-3-yl)methanol (a) {5-Chloro-6-[(3R)-3-methylpiperazin-1-yl]pyridin-3-yl}methanol A mixture of 5,6-dichloro-3-pyridinemethanol (0.35 g, 2 mmol, TCI-US) and (R)-(−)-2-methylpiperazine (0.3 g. 3 mmol, Aldrich) reacted under the conditions of Example 43a to give the title compound as a light-brown solid. MS (ESI, pos. ion) m/z: 242 (M+1).

(b) (5-Chloro-6-{(3R)-4-[7-iodo-5-(trifluoromethyl)-1H-benzimidazol-2-yl]-3-methylpiperazin-1-yl}pyridin-3-yl)methanol The piperazine from step (a) above (73 mg, 0.3 mmol) reacted with 2-chloro-4-iodo-6-(trifluoromethyl)-1H-benzoimidazole (69 mg, 0.2 mmol, Example 61c) under the conditions of Example 3c to give the title compound as a yellow amorphous solid. MS (ESI, pos. ion) m/z: 552 (M+1).

Example 63

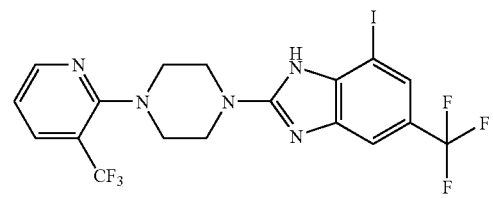

7-Iodo-5-(trifluoromethyl)-2-{4-[3-(trifluoromethyl)pyridin-2-yl]piperazin-1-yl}-1H-benzoimidazole 5-(Trifluoromethyl)-2-{4-[3-(trifluoromethyl)pyridin-2-yl]piperazin-1-yl}-1H-benzimidazol-7-amine (215 mg, 0.5 mmol, Example 58) reacted under the conditions of Example 61b to give the title compound as a light-yellow solid. MS (ESI, pos. ion) m/z: 542 (M+1).

Example 64

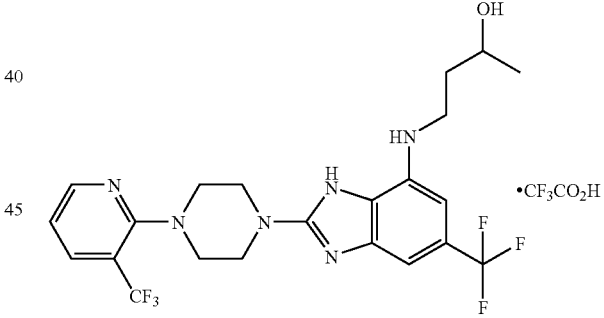

4-[(5-(Trifluoromethyl)-2-{4-[3-(trifluoromethyl)pyridin-2-yl]piperazin-1-yl}-1H-benzimidazol-7-yl)amino]butan-2-ol, Trifluoroacetic Acid Salt To a mixture of 5-(trifluoromethyl)-2-{4-[3-(trifluoromethyl)pyridin-2-yl]piperazin-1-yl}-1H-benzimidazol-7-amine (86 mg, 0.2 mmol, Example 58) and 3-hydroxy-butyraldehyde (26.4, 0.3 mmol, Pfaltz&Bauer) in dichloromethane (2 mL) was added $NaBH(OAc)_3$ (127 mg, 0.6 mmol) and one drop of acetic acid. The reaction mixture was stirred at room temperature for 12 h, diluted with dichloromethane (10 mL), washed with satd aq. $NaHCO_3$ solution (10 mL), dried over $Na_2SO_4$, and filtered. The filtrate was evaporated and the residue was purified by silica gel column chromatography, eluting with 60% EtOAc/hexane to give the crude product. Additional purification by preparative HPLC

Example 65

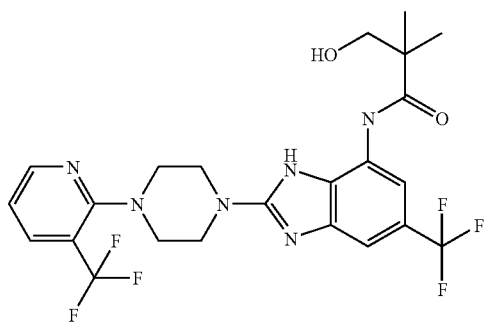

3-Hydroxy-2,2-dimethyl-N-(5-(trifluoromethyl)-2-{4-[3-(trifluoromethyl)pyridin-2-yl]piperazin-1-yl}-1H-benzimidazol-7-yl)propanamide To a 25-mL, round-bottom flask was added 5-(trifluoromethyl)-2-{4-[3-(trifluoromethyl)pyridin-2-yl]piperazin-1-yl}-1H-benzimidazol-7-amine (108 mg, 0.25 mmol, Example 58), 2,2-dimethyl-3-hydroxypropionic acid (47 mg, 0.4 mmol, Aldrich), 1-(3-dimethylaminopropyl)-3-ethylcarbodiimide hydrochloride (76 mg, 0.4 mmol, Aldrich) and dichloromethane (5 mL). The reaction mixture was stirred at room temperature for 36 h, washed with satd aq. NaHCO$_3$ solution (10 mL), dried over Na$_2$SO$_4$, and filtered. The filtrate was evaporated and the residue was purified by silica gel column chromatography, eluting with 50% EtOAc/hexane to give the title compound as a white amorphous solid. MS (ESI, pos. ion) m/z: 531 (M+1)

Example 66

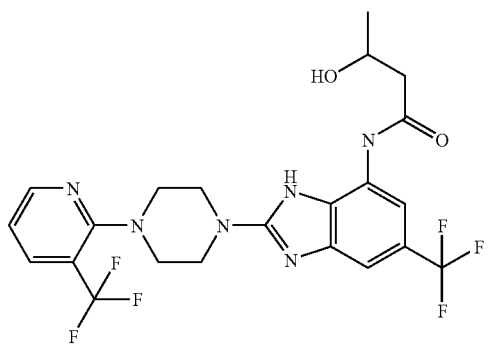

3-Hydroxy-N-(5-(trifluoromethyl)-2-{4-[3-(trifluoromethyl)pyridin-2-yl]piperazin-1-yl}-1H-benzimidazol-7-yl)butanamide, di-trifluoroacetic Acid Salt 5-(Trifluoromethyl)-2-{4-[3-(trifluoromethyl)pyridin-2-yl]piperazin-1-yl}-1H-benzimidazol-7-amine (43 mg, 0.1 mmol, Example 58) was reacted with 3-hydroxy-butyric acid (10 mg, 0.1 mmol, Aldrich) under the conditions of Example 65, and the crude product purified by preparative HPLC (gradient 0.11% trifluoroacetic acid in acetonitrile) afforded the title compound as white amorphous solid. MS (ESI, pos. ion) m/z: 503 (M+1). 65, and the crude product purified by preparative HPLC (gradient 0.1% trifluoroacetic acid in acetonitrile) to give the title compound as a white amorphous solid. MS (ESI, pos. ion) m/z: 517 (M+1).

Example 67

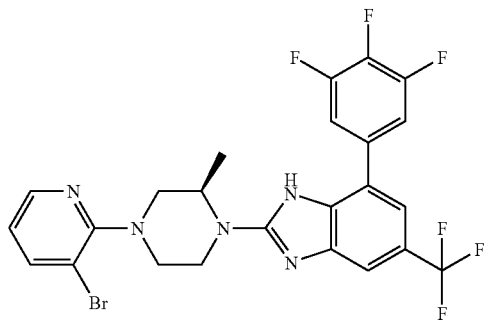

2-[(2R)-4-(3-Bromopyridin-2-yl)-2-methylpiperazin-1-yl]-5-(trifluoromethyl)-7-(3,4,5-trifluorophenyl)-1H-benzoimidazole 2-Chloro-6-(trifluoromethyl)-4-(3,4,5-trifluorophenyl)-1H-benzoimidazole (52 mg, 0.15 mmol, Example 51b) reacted with (3R)-1-(3-bromopyridin-2-yl)-3-methylpiperazine (48 mg, 0.2 mmol, Example 43a) under the conditions of Example 3c to give the title compound as a white amorphous solid. MS (ESI, pos. ion) m/z: 570 (M+1).

Example 68

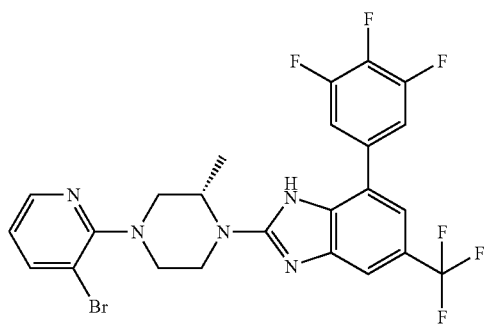

2-[(2S)-4-(3-Bromopyridin-2-yl)-2-methylpiperazin-1-yl]-5-(trifluoromethyl)-7-(3,4,5-trifluorophenyl)-1H-benzoimidazole (a) (3S)-1-(3-Bromopyridin-2-yl)-3-methylpiperazine A mixture of 3-bromo-2-chloropyridine (0.76 g, 4 mmol, Aldrich) and (S)-(+)-2-methylpiperazine (0.6 g, 6 mmol, Aldrich) reacted under the conditions of Example 3c to give the title compound as a light-brown solid. MS (ESI, pos. ion) m/z: 256 (M+1).

(b) 2-[(2S)-4-(3-Bromopyridin-2-yl)-2-methylpiperazin-1-yl]-5-(trifluoromethyl)-7-(3,4,5-trifluorophenyl)-1H-benzoimidazole The piperazine from step (a) above (51 mg, 0.2 mmol) reacted with 2-chloro-6-(trifluoromethyl)-4-(3,4,5-trifluorophenyl)-1H-benzoimidazole (53 mg, 0.15 mmol, Example 51b) under the conditions of Example 3c to give the title compound as a white amorphous solid. MS (ESI, pos. ion) m/z: 570 (M+1).

Example 69

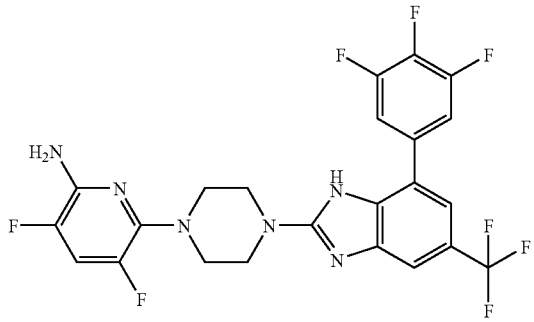

3,5-Difluoro-6-{4-[5-(trifluoromethyl)-7-(3,4,5-trifluorophenyl)-1H-benzimidazol-2-yl]piperazin-1-yl}pyridin-2-amine (a) tert-Butyl 4-(6-amino-3,5-difluoropyridin-2-yl)piperazine-1-carboxylate A mixture of 4-(3,5,6-trifluoro-pyridin-2-yl)-piperazine-1-carboxylic acid tert-butyl ester (1.59 g, 5 mmol, Example 39a), potassium phthalimide (0.93 g, 5 mmol, Aldrich) in DMF (20 mL) was heated at 140° C. with stirring for 16 h. The reaction mixture was cooled to room temperature, diluted with water (60 mL) and extracted with EtOAc (2×70 mL). The combined organic extracts were dried over Na₂SO₄, and filtered. The filtrate was evaporated and the residue was purified by silica gel column chromatography, eluting with 20% EtOAc in hexane to give the title compound as a yellow solid. MS (ESI, pos. ion) m/z: 315 (M+1).

(b) 3,5-Difluoro-6-piperazin-1-ylpyridin-2-amine tert-Butyl 4-(6-amino-3,5-difluoropyridin-2-yl)piperazine-1-carboxylate (133 mg, 0.42 mmol) was reacted under the conditions of Example 39c to give the title compound as a yellow oil. MS (ESI, pos. ion) m/z: 215 (M+1).

(c) 3,5-Difluoro-6-{4-[5-(trifluoromethyl)-7-(3,4,5-trifluorophenyl)-1H-benzimidazol-2-yl]piperazin-1-yl}pyridin-2-amine The piperazine from step (a) above (74 mg, 0.35 mmol) reacted with 2-chloro-6-(trifluoromethyl)-4-(3,4,5-trifluorophenyl)-1H-benzimidazole (87 mg, 0.25 mmol, Example 51b) under the conditions of Example 3c to give the title compound as a white amorphous solid. MS (ESI, pos. ion) m/z: 529 (M+1).

Example 70

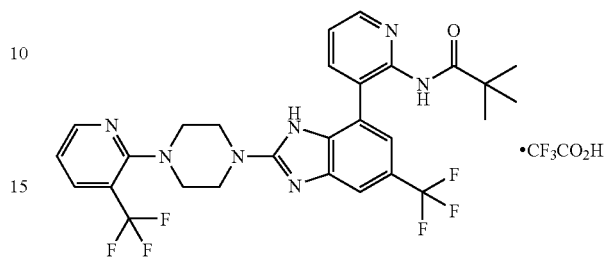

2,2-Dimethyl-N-[3-(5-(trifluoromethyl)-2-{4-[3-(trifluoromethyl)pyridin-2-yl]piperazin-1-yl}-1H-benzimidazol-7-yl)pyridin-2-yl]propanamide, Trifluoroacetic Acid Salt 4-Bromo-6-trifluoromethyl-2-[4-(3-trifluoromethylpyridin-2-yl)piperazin-1-yl]-1H-benzoimidazole (495 mg, 1 mmol, Example 7) and 2,2-dimethyl-N-[3-(4,4,5,5-tetramethyl-1,3,2-dioxaborolan-2-yl)pyridin-2-yl]propanamide (456 mg, 1.5 mmol, CBRD) reacted under the conditions of Example 54, and the crude product was purified by preparative HPLC (gradient 0.1% trifluoroacetic acid in acetonitrile) to give the title compound as a white amorphous solid. MS (ESI, pos. ion) m/z: 592 (M+1).

Example 71

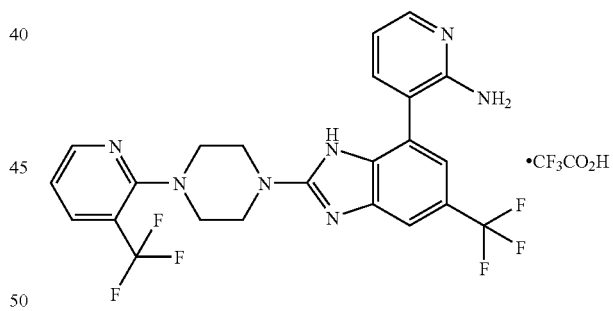

3-(5-(Trifluoromethyl)-2-{4-[3-(trifluoromethyl)pyridin-2-yl]piperazin-1-yl}-1H-benzimidazol-7-yl)pyridin-2-amine, Trifluoroacetic Acid Salt A mixture of 2,2-dimethyl-N-[3-(5-(trifluoromethyl)-2-{4-[3-(trifluoromethyl)pyridin-2-yl]piperazin-1-yl}-1H-benzimidazol-7-yl)pyridin-2-yl]propanamide, trifluoroacetic acid salt (118 mg, 0.2 mmol, Example 70), 4 N HCl in dioxane (4 mL) and H₂O (4 mL) was heated at 80° C. with stirring overnight. The mixture was cooled to room temperature, concentrated in vacuo and the residue dissolved in EtOAc (50 mL). The solution was washed with 2 N NaOH (2×20 mL) and satd NaCl (40 mL), dried over MgSO₄ and filtered. The filtrate was evaporated in vacuo and the residue was purified by preparative HPLC (gradient 0.1% trifluoroacetic acid in acetonitrile) to give the title compound as a white amorphous solid MS (ESI, pos. ion) m/z: 508 (M+1).

Example 72

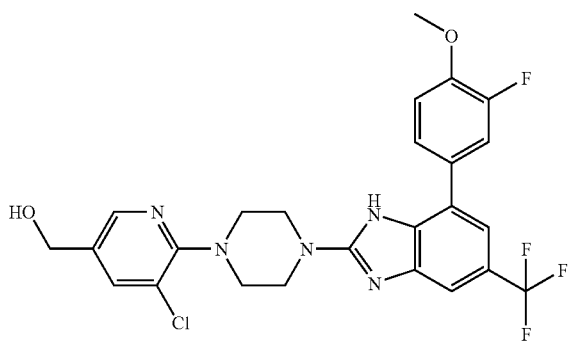

(5-Chloro-6-{4-[7-(3-fluoro-4-methoxyphenyl)-5-(trifluoromethyl)-1H-benzimidazol-2-yl]piperazin-1-yl}pyridin-3-yl)methanol (a) (6-{4-[7-Bromo-5-(trifluoromethyl)-1H-benzimidazol-2-yl]piperazin-1-yl}-5-chloropyridin-3-yl)methanol 4-Bromo-2-chloro-6-trifluoromethyl-1H-benzoimidazole (180 mg, 0.6 mmol, Example 6b) reacted with (5-chloro-6-piperazin-1-yl-pyridin-3-yl)methanol (228 mg, 1 mmol, Example 60a) under the conditions of Example 3c to give the title compound as a white solid. MS (ESI, pos. ion) m/z: 490 (M+1).

(b) (5-Chloro-6-{4-[7-(3-fluoro-4-methoxyphenyl)-5-(trifluoromethyl)-1H-benzimidazol-2-yl]piperazin-1-yl}pyridin-3-yl)methanol (6-{4-[7-Bromo-5-(trifluoromethyl)-1H-benzimidazol-2-yl]piperazin-1-yl}-5-chloropyridin-3-yl)methanol from step (a) above (98 mg, 0.2 mmol) and 3-fluoro-4-methoxyphenyl-boronic acid (43 mg, 0.25 mmol, Aldrich) reacted under the conditions of Example 51 to give the title compound as a white amorphous solid. MS (ESI, pos. ion) m/z: 536 (M+1).

Example 73

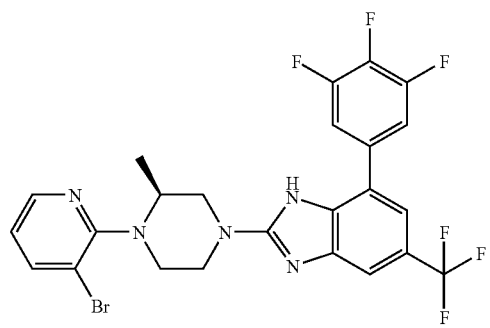

2-[(3S)-4-(3-Bromopyridin-2-yl)-3-methylpiperazin-1-yl]-5-(trifluoromethyl)-7-(3,4,5-trifluorophenyl)-1H-benzoimidazole (a) 2-[(3S)-3-Methylpiperazin-1-yl]-5-(trifluoromethyl)-7-(3,4,5-trifluorophenyl)-1H-benzoimidazole 2-Chloro-6-(trifluoromethyl)-4-(3,4,5-trifluorophenyl)-1H-benzoimidazole (350 mg, 1 mmol, Example 51b) reacted with (S)-(+)-2-methylpiperazine (150 mg. 1.5 mmol, Aldrich) under the conditions of Example 3c to give the title compound as a light-brown solid. MS (ESI, pos. ion) m/z: 415 (M+1).

(b) 2-[(3S)-4-(3-bromopyridin-2-yl)-3-methylpiperazin-1-yl]-5-(trifluoromethyl)-7-(3,4,5-trifluorophenyl)-1H-benzoimidazole The piperazine from step (a) above (41 mg, 0.1 mmol) reacted with 3-bromo-2-chloropyridine (19 mg, 0.1 mmol, Aldrich) under the conditions of Example 48b to give the title compound as a white amorphous solid. MS (ESI, pos. ion) m/z: 570 (M+1).

Example 74

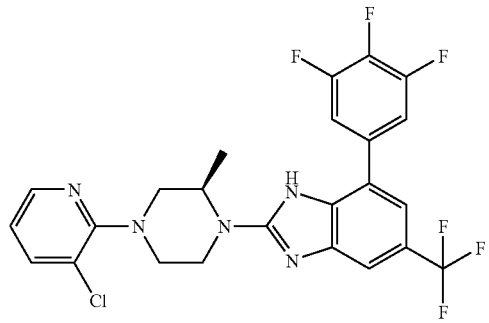

2-[(2R)-4-(3-Chloropyridin-2-yl)-2-methylpiperazin-1-yl]-5-(trifluoromethyl)-7-(3,4,5-trifluorophenyl)-1H-benzoimidazole (a) (3R)-1-(3-Chloropyridin-2-yl)-3-methylpiperazine A mixture of 2,3-dichloropyridine (0.74 g, 5 mmol, Aldrich) and (R)-(−)-2-methylpiperazine (0.6 g. 6 mmol, Aldrich) reacted under the conditions of Example 43a to give the title compound as a off-white solid. MS (ESI, pos. ion) m/z: 212 (M+1).

(b) 2-[(2R)-4-(3-Chloropyridin-2-yl)-2-methylpiperazin-1-yl]-5-(trifluoromethyl)-7-(3,4,5-trifluorophenyl)-1H-benzoimidazole The piperazine from step (a) above (84 mg. 0.4 mmol) reacted with 2-chloro-6-(trifluoromethyl)-4-(3,4,5-trifluorophenyl)-1H-benzoimidazole (105 mg, 0.3 mmol, Example

Example 75

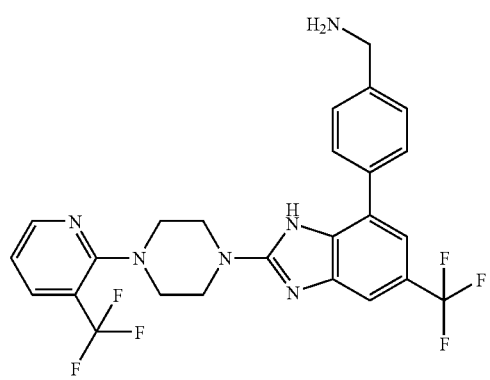

4-{6-Trifluoromethyl-2-[4-(3-trifluoromethyl-pyridin-2-yl)-piperazin-1-yl]-3H-benzoimidazol-4-yl}-benzylamine The title compound was prepared from 4-bromo-6-trifluoromethyl-2-[4-(3-trifluoromethyl-pyridin-2-yl)-piperazin-1-yl]-1H-benzoimidazole (Example 7) and 4-aminomethylphenylboronic acid hydrochloride (Acros) under the conditions of Example 51a and isolated as a white amorphous solid. MS (ESI, pos. ion) m/z: 521 (M+1).

Example 76

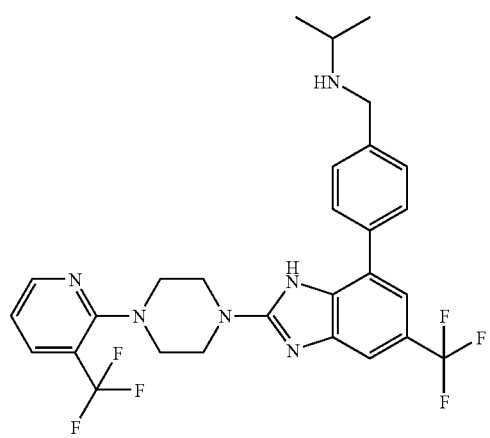

N-Isopropyl-N-[4-(5-(trifluoromethyl)-2-{4-[3-(trifluoromethyl)pyridin-2-yl]piperazin-1-yl}-1H-benzimidazol-7-yl)benzyl]amine To a mixture of 4-(5-(trifluoromethyl)-2-{4-[3-(trifluoromethyl)pyridin-2-yl]piperazin-1-yl}-1H-benzimidazol-7-yl)benzylamine (172 mg, 0.33 mmol, Example 75) and acetone (1 mL) in chloroform (5 mL) were added NaBH(OAc)$_3$ (211 mg, 1 mmol) and one drop of acetic acid. The mixture was stirred at room temperature for 2 h, diluted with dichloromethane (30 mL), washed with satd aq. NaHCO$_3$ solution (25 mL), dried over Na$_2$SO$_4$, and filtered. The filtrate was evaporated and the residue was purified by silica gel column chromatography, eluting with 5% MeOH in dichloromethane to give the title compound as white amorphous solid. MS (ESI, pos. ion) m/z: 563 (M+1), (ESI, neg. ion)

Example 77

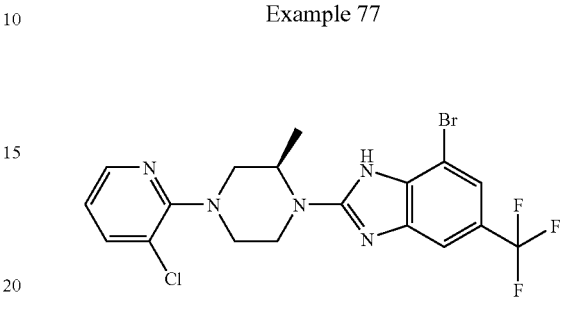

7-Bromo-2-[(2R)-4-(3-chloropyridin-2-yl)-2-methylpiperazin-1-yl]-5-(trifluoromethyl)-1H-benzoimidazole 4-Bromo-2-chloro-6-trifluoromethyl-1H-benzoimidazole (1.2 g, 4 mmol, Example 6b) reacted with (3R)-1-(3-chloropyridin-2-yl)-3-methylpiperazine (0.95 g, 4.5 mmol, Example 74a) under the conditions of Example 3c to give the title compound as a light-yellow solid. MS (ESI, pos. ion) m/z: 474 (M+1).

Example 78

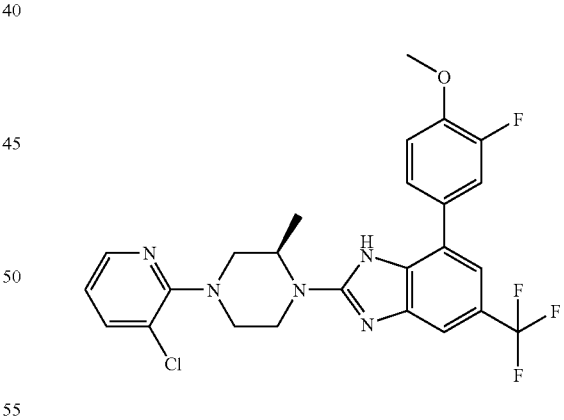

2-[(2R)-4-(3-chloropyridin-2-yl)-2-methylpiperazin-1-yl]-7-(3-fluoro-4-methoxyphenyl)-5-(trifluoromethyl)-1H-benzoimidazole 7-Bromo-2-[(2R)-4-(3-chloropyridin-2-yl)-2-methylpiperazin-1-yl]-5-(trifluoromethyl)-1H-benzoimidazole (95 mg, 0.2 mmol, Example 77) and 3-fluoro-4-methoxyphenylboronic acid (43 mg, 0.25 mmol, Aldrich) reacted under the conditions of Example 51a to give the title compound as a white amorphous solid. MS (ESI, pos. ion) m/z: 520 (M+1).

Example 79

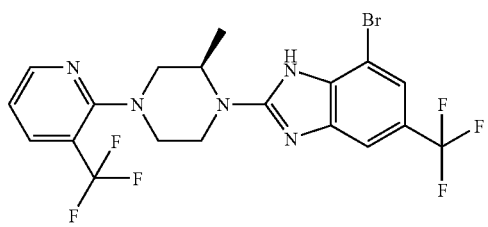

7-Bromo-2-{(2R)-2-methyl-4-[3-(trifluoromethyl) pyridin-2-yl]piperazin-1-yl}-5-(trifluoromethyl)-1H-benzoimidazole (a) (3R)-3-Methyl-1-[3-(trifluoromethyl)pyridin-2-yl]piperazine A mixture of 2-chloro-3-trifluoromethylpyridine (1.45 g, 8 mmol, Aldrich) and (R)-(−)-2-methylpiperazine (1.0 g. 10 mmol, Aldrich) was reacted under the conditions of Example 43a to give the title compound as a off-white solid. MS (ESI, pos. ion) m/z: 246 (M+1).

(b) 7-Bromo-2-{(2R)-2-methyl-4-[3-(trifluoromethyl)pyridin-2-yl]piperazin-1-yl}-5-(trifluoromethyl)-1H-benzoimidazole The piperazine from step (a) above (0.37 g, 1.5 mmol) reacted with 4-bromo-2-chloro-6-trifluoromethyl-1H-benzoimidazole (0.36 g, 1.2 mmol, Example 6b) under the conditions of Example 3c to give the title compound as a white amorphous solid. MS (ESI, pos. ion) m/z: 508 (M+1).

Example 80

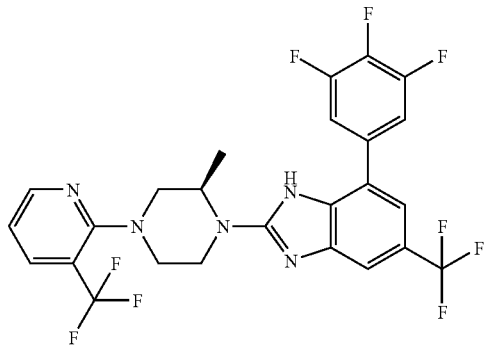

2-{(2R)-2-Methyl-4-[3-(trifluoromethyl)pyridin-2-yl]piperazin-1-yl}-5-(trifluoromethyl)-7-(3,4,5-trifluorophenyl)-1H-benzoimidazole 7-Bromo-2-{(2R)-2-methyl-4-[3-(trifluoromethyl)pyridin-2-yl]piperazin-1-yl}-5-(trifluoromethyl)-1H-benzoimidazole (152 mg, 0.3 mmol, Example 79) and 3,4,5-trifluorophenylboronic acid (88 mg, 0.5 mmol, Lancaster) reacted under the conditions of Example 51a to give the title compound as a white amorphous solid. MS (ESI, pos. ion) m/z: 560 (M+1).

Example 81

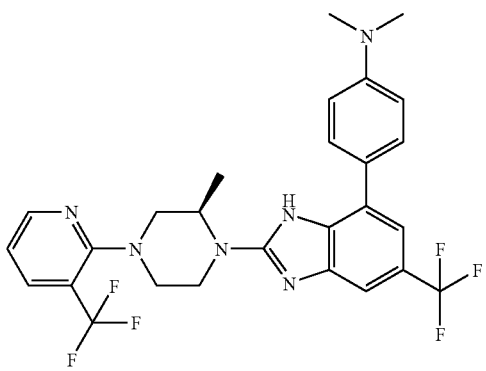

N,N-Dimethyl-4-[2-{(2R)-2-methyl-4-[3-(trifluoromethyl)pyridin-2-yl]piperazin-1-yl}-5-(trifluoromethyl)-1H-benzimidazol-7-yl]aniline 7-Bromo-2-{(2R)-2-methyl-4-[3-(trifluoromethyl)pyridin-2-yl]piperazin-1-yl}-5-(trifluoromethyl)-1H-benzoimidazole (152 mg, 0.3 mmol, Example 79) and 4-dimethylaminophenylboronic acid (83 mg, 0.5 mmol, Aldrich) reacted under the conditions of Example 51a to give the title compound as a white amorphous solid. MS (ESI, pos. ion) m/z: 549 (M+1).

Example 82

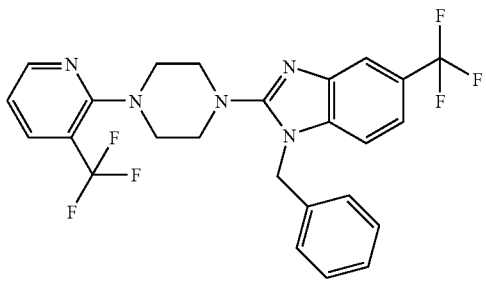

1-Benzyl-5-trifluoromethyl-2-[4-(3-trifluoromethyl-pyridin-2-yl)-piperazin-1-yl]-1H-benzoimidazole To a solution of 5-(trifluoromethyl)-2-{4-[3-(trifluoromethyl)(2-pyridyl)]piperazinyl}benzoimidazole (415 mg, 1.0 mmol, Example 53) in anhydrous DMF (5 mL, Aldrich) was added sodium hydride (72 mg, 50% in mineral oil, 1.5 mmol, Aldrich) at 0° C. The reaction mixture was stirred at room temperature for 0.5 h. After the mixture was cooled to 0° C., it was treated with benzyl bromide (171 mg, 1.0 mmol, Aldrich) and stirred at room temperature for 16 h. The reaction was then quenched with saturated aqueous solution of NaHCO$_3$ (30 mL) and extracted with EtOAc (2×50 mL). The combined organic extracts were dried over MgSO$_4$, filtered and concentrated in vacuo. The residue was purified by silica gel column chromatography (25% EtOAc/hexane) to give the title compound as white solid. MS (ESI, pos. ion) m/z: 506.2 (M+1).

Example 83

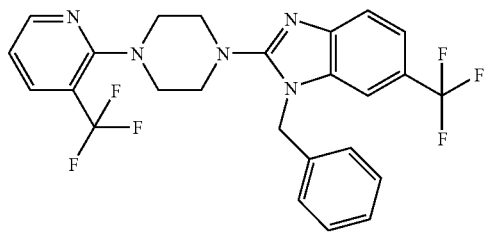

1-Benzyl-6-trifluoromethyl-2-[4-(3-trifluoromethyl-pyridin-2-yl)-piperazin-1-yl]-1H-benzoimidazole The title compound was obtained as a second product of the reaction described in Example 82 and isolated as a white solid. Yield 84.3 mg (16.7%). M.p. 154.3-157.1° C. MS (ESI, pos. ion) m/z: 506.2 (M+1).

Example 84

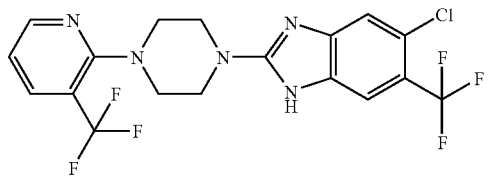

5-Chloro-6-trifluoromethyl-2-[4-(3-trifluoromethyl-pyridin-2-yl)-piperazin-1-yl]-1H-benzoimidazole (a) 5-Chloro-4-(trifluoromethyl)benzene-1,2-diamine To a solution of 5-chloro-2-nitro-4-(trifluoromethyl)phenylamine (2 g, 8.3 mmol, Oakwood) in EtOAc (26 mL) and EtOH (13 mL) was added tin (II) chloride dihydrate (13.1 g, 45 mmol, Aldrich). The reaction mixture was stirred at 70° C. for 1 h. The light-yellow reaction solution was poured to crushed ice (50 mL) and carefully neutralized using saturated aqueous solution of NaHCO$_3$. The resulting suspension was extracted with EtOAc (3×60 mL). The combined organic extracts were dried over MgSO$_4$, filtered and the filtrate evaporatedcon in vacuo to give the title compound as white solid, which was used in the next step without additional purification. MS (ESI, pos. ion) m/z: 211.4 (M+1).

(b) 5-Chloro-6-trifluoromethyl-1,3-dihydro-benzoimidazol-2-one

The benzene-1,2-diamine from step (a) above (1.68 g, 8.0 mmol) reacted under the conditions of Example 1b to give the title compound as a white solid. MS (ESI, pos. ion) m/z: 237.6 (M+1).

(c) 2,5-Dichloro-6-(trifluoromethyl)benzoimidazole

The benzoimidazol-2-one from step (b) above (1.43 g, 6.0 mmol) reacted with POCl$_3$ under the conditions of Example 1c to give the title compound as a white solid. MS (ESI, pos. ion) m/z: 254.9 (M+1).

(d) 5-Chloro-6-trifluoromethyl-2-[4-(3-trifluoromethyl-pyridin-2-yl)-piperazin-1-yl]-1H-benzoimidazole The benzoimidazole from step (c) above (255 mg, 1.0 mmol) reacted with 1-(3-trifluoromethylpyridin-2-yl)piperazine (231 mg, 1.0 mmol, Oakwood) under the conditions of Example 3c to give the title compound as a white solid. M.p. 206.4-208.1° C. MS (ESI, pos. ion) m/z: 450.4 (M+1).

Example 85

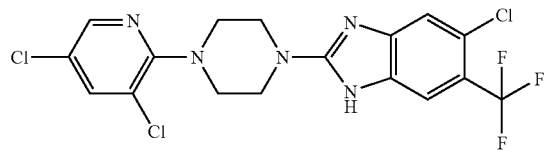

5-Chloro-2-[4-(3,5-dichloro-pyridin-2-yl)-piperazin-1-yl]-6-trifluoromethyl-1H-benzoimidazole 2,5-Dichloro-6-(trifluoromethyl)benzoimidazole (255 mg, 1.0 mmol, Example 84c) reacted with 1-(3,5-dichloro-pyridin-2-yl)piperazine (232 mg, 1.0 mmol, Example 9a) under the conditions of Example 3c to give the title compound as a white solid. M.p. 93.5-196.4° C. MS (ESI, pos. ion) m/z: 452.0, 454.1 (M+1).

Example 86

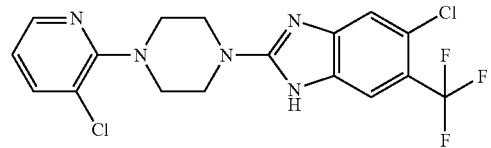

5-Chloro-2-[4-(3-chloro-pyridin-2-yl)-piperazin-1-yl]-6-trifluoromethyl-1H-benzoimidazole 2,5-Dichloro-6-(trifluoromethyl)benzoimidazole (255 mg, 1.0 mmol, Example 84c) reacted with 1-(3-chloropyridin-2-yl)piperazine hydrochloride (233 mg, 1.0 mmol, Example 3b) under the conditions of Example 3c to give the title compound as a white solid. M.p. 208.9-211.0° C. MS (ESI, pos. ion) m/z: 416.3, 420.1 (M+1).

Example 87

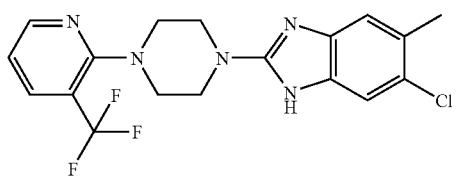

6-Chloro-5-methyl-2-[4-(3-trifluoromethyl-pyridin-2-yl)-piperazin-1-yl]-1H-benzoimidazole (a) 5-Chloro-6-methyl-1,3-dihydro-benzoimidazol-2-one The 5-chloro-4-methylbenzene-1,2-diamine (10 g, 64 mmol, Aldrich) reacted under the conditions of Example 1b to give the title compound as a dark brown solid. MS (ESI, pos. ion) m/z: 183.0 (M+1).

(b) 2,6-Dichloro-5-methylbenzoimidazole

The benzimidazol-2-one from step (a) above (10.6 g, 58 mmol) reacted with POCl₃ under the conditions of Example 1c to give the title compound as a brown solid. MS (ESI, pos. ion) m/z: 201.3 (M+1).

(c) 6-Chloro-5-methyl-2-[4-(3-trifluoromethyl-pyridin-2-yl)-piperazin-1-yl]-1H-benzoimidazole The benzoimidazole from step (b) above (201 mg, 1.0 mmol) reacted with 1-(3-trifluoromethylpyridin-2-yl)piperazine (231 mg, 1.0 mmol, Oakwood) under the conditions of Example 3c to give the title compound as a white solid. MS (ESI, pos. ion) m/z: 396.1 (M+1).

Example 88

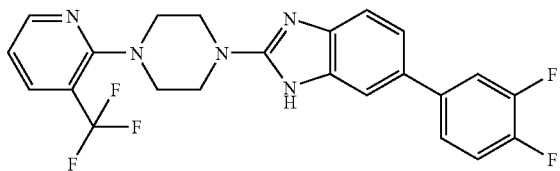

6-(3,4-Difluoro-phenyl)-2-[4-(3-trifluoromethyl-pyridin-2-yl)-piperazin-1-yl]-1H-benzoimidazole To a mixture of 3,4-difluorophenylboronic acid (111 mg, 0.7 mmol, Aldrich) and 6-bromo-2-[4-(3-trifluoromethylpyridin-2-yl)piperazin-1-yl]-1H-benzoimidazole (213 mg, 0.5 mmol, Example 23c) in ethylene glycol dimethyl ether (2 mL) were added lithium chloride (63 mg, 1.5 mmol, Aldrich) and 2M aqueous sodium carbonate (0.75 mL, 1.5 mmol). Nitrogen gas was bubbled through the mixture for 10 min and tetrakis(triphenylphosphine)palladium (58 mg, 0.05 mmol, Aldrich) was added. The reaction mixture was stirred at 80° C. under nitrogen atmosphere for 16 h, cooled to room temperature, diluted with EtOAc (50 mL) and filtered through Celite® pad. The filtrate was washed with water and brine, dried over MgSO₄, filtered and concentrated in vacuo. The residue was purified by silica gel column chromatography (55% EtOAc/hexane) to give the title compound as a white solid. MS (ESI, pos. ion) m/z: 460.2 (M+1).

Example 89

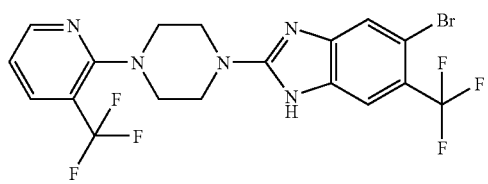

5-Bromo-6-trifluoromethyl-2-[4-(3-trifluoromethyl-pyridin-2-yl)-piperazin-1-yl]-1H-benzoimidazole (a) N-[4-Bromo-3-(trifluoromethyl)phenyl]acetamide A mixture of 4-bromo-3-(trifluoromethyl)phenylamine (7.2 g, 30 mmol, Aldrich) and acetic anhydride (29 mL) was stirred at room temperature for 16 h. The reaction mixture was evaporated in vacuo to give the title product as a white solid which was used in the next step without additional purification. MS (ESI, pos. ion) m/z: 484.0 (M+1).

(b) N-[4-Bromo-2-nitro-5-(trifluoromethyl)phenyl]acetamide

To a solution of the acetamide from step (a) above (8.46 g, 30 mmol) in concentrated sulfuric acid (32.5 mL) was added dropwise concentrated HNO₃ (4.1 mL, 90%. J. T. Baker) with stirring at 0° C. The resulting solution was stirred at room temperature for 3 h and poured into crushed ice (80 mL). The mixture was carefully neutralized with solid NaHCO₃ and extracted with EtOAc (3×200 mL). The combined organic extracts were washed with water and brine, dried over MgSO₄, filtered and concentrated in vacuo. The residue was purified by silica gel column chromatography (25% EtOAc/hexane) to give the title compound as a yellow solid. MS (ESI, neg. ion) m/z: 325.0 (M−1).

(c) 4-Bromo-2-nitro-5-(trifluoromethyl)phenylamine

To a solution of the acetamide from step (b) above (4.5 g, 14 mmol) in MeOH (8 mL) was added aqueous 3N NaOH (50 mL) at room temperature. The reaction mixture was stirred at 90° C. for 2 h, cooled to room temperature and extracted with EtOAc (4×50 mL). The combined organic extracts were washed with 1% aqueous HCl and brine, dried over MgSO₄, filtered and concentrated in vacuo. The residue was purified by silica gel column chromatography (15% EtOAc/hexane) to give the title compound as a yellow solid. MS (ESI, neg. ion) m/z: 282.9 (M−1).

(d) 5-Bromo-4-(trifluoromethyl)benzene-1,2-diamine

The reaction of 4-bromo-2-nitro-5-(trifluoromethyl)phenylamine from step (c) above (3.3 g, 10 mmol) under the conditions of Example 84a afforded the title compound as a brown solid. MS (ESI, pos. ion) m/z: 257.0 (M+1).

(e)
5-Bromo-6-methyl-1,3-dihydro-benzoimidazol-2-one

5-Bromo-4-(trifluoromethyl)benzene-1,2-diamine from step (d) above (1.25 g, 5 mmol) reacted under the conditions of Example 1b to give the title compound as a light-yellow solid. MS (ESI, pos. ion) m/z: 283.0 (M+1).

(f)
5-Bromo-2-chloro-6-(trifluoromethyl)benzoimidazole

5-Bromo-6-methyl-1,3-dihydro-benzoimidazol-2-one from step (e) above (1.36 g, 4.85 mmol) reacted with POCl$_3$ under the conditions of Example 1c to give the title compound as a white solid. MS (ESI, pos. ion) m/z: 300.8, 302.7 (M+1).

(g) 5-Bromo-6-trifluoromethyl-2-[4-(3-trifluoromethyl-pyridin-2-yl)-piperazin-1-yl]-1H-benzoimidazole The benzoimidazole from step (f) above (1.2 g, 4.0 mmol) reacted with 1-(3-trifluoromethylpyridin-2-yl)piperazine (1.4 g, 6.0 mmol, Oakwood) under the conditions of Example 3c to give the title compound as a white solid. MS (ESI, pos. ion) m/z: 496.0 (M+1).

Example 90

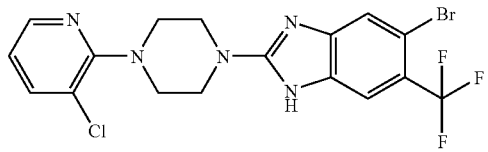

5-Bromo-2-[4-(3-chloro-pyridin-2-yl)-piperazin-1-yl]-6-trifluoromethyl-1H-benzoimidazole The reaction of 5-bromo-2-chloro-6-(trifluoromethyl)benzoimidazole (100 mg, 0.3 mmol, Example 89f) with 1-(3-chloropyridin-2-yl)piperazine hydrochloride (186 mg, 0.61 mmol, Example 3b) under the conditions of Example 3c afforded the title compound as a white solid. MS (ESI, pos. ion) m/z: 461.7, 464.0 (M+1).

Example 91

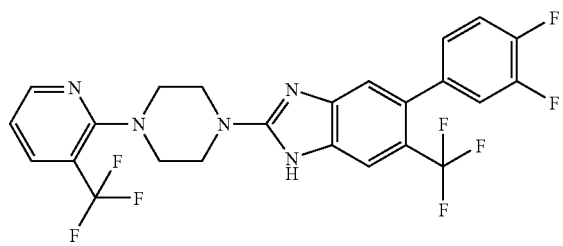

5-(3,4-Difluoro-phenyl)-6-trifluoromethyl-2-[4-(3-trifluoromethyl-pyridin-2-yl)-piperazin-1-yl]-1H-benzoimidazole The reaction of 5-bromo-6-trifluoromethyl-2-[4-(3-trifluoromethyl-pyridin-2-yl)-piperazin-1-yl]-1H-benzoimidazole (250 mg, 0.5 mmol, Example 89 g) with 3,4-difluorophenylboronic acid (95 mg, 0.60 mmol, Aldrich) under the conditions of Example 88 afforded the title compound as a white solid. MS (ESI, pos. ion) m/z: 528.0 (M+1).

Example 92

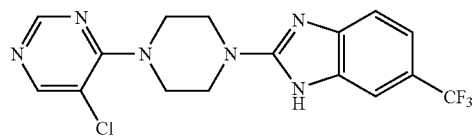

2-[4-(5-Chloro-pyrimidin-4-yl)-piperazin-1-yl]-6-trifluoromethyl-1H-benzoimidazole A solution of 1-(5-chloropyrimidin-4-yl)piperazine, trifluoroacetic acid salt (0.62 g, 1.45 mmol, Example 33d), 2-chloro-6-trifluoromethyl-1H-benzoimidazole (0.32 g, 1.45 mmol, Example 1c) and i-Pr$_2$NEt (0.76 mL, 4.35 mmol) in DMSO (10 mL) was heated to 80° C. for 16 h. The reaction mixture was cooled to room temperature, diluted with EtOAc (50 mL), washed with satd. aq. NaHCO$_3$ (25 mL) and brine (25 mL), dried over Na$_2$SO$_4$, filtered and concentrated in vacuo. The crude product was purified by silica gel column chromatography (50% EtOAc in hexane to EtOAc) to give the title compound as white solid. M.p. 66.6-66.7° C. MS (ESI, pos. ion) m/z: 383 (M+1). Anal. Calcd for C$_{16}$H$_{14}$ClF$_3$N$_6$·0.75H$_2$O: C, 48.43; H, 3.97; N, 20.84. Found: C, 48.30; H, 3.86; N, 20.47.

Example 93

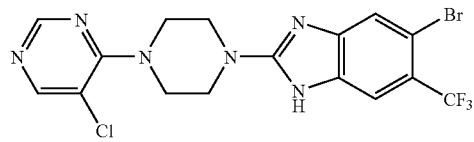

5-Bromo-2-[4-(5-chloro-pyrimidin-4-yl)-piperazin-1-yl]-6-trifluoromethyl-1H-benzoimidazole 5-Chloro-4-piperazin-1-yl-pyrimidine; trifluoroacetic acid salt (0.32 g, 0.75 mmol, Example 33d) and 5-bromo-2-chloro-6-trifluoromethyl-1H-benzoimidazole (0.226 g, 0.75 mmol, Example 89f) reacted under the conditions of Example 3c to give the title compound as a white solid. M.p. 229.7-233.2° C. MS (ESI, pos. ion) m/z: 461.0 (M+1).

Example 94

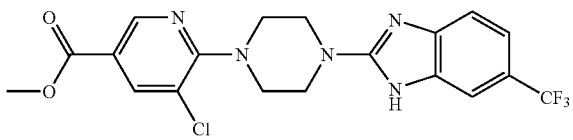

5-Chloro-6-[4-(6-trifluoromethyl-1H-benzoimidazol-2-yl)-piperazin-1-yl]-nicotinic Acid Methyl Ester (a) 4-(5-Carboxy-3-chloro-pyridin-2-yl)-piperazine-1-carboxylic Acid tert-butyl Ester 5,6-Dichloro-nicotinic acid (5.0 g, 0.026 mol, Aldrich) reacted with piperazine-1-carboxylic acid tert-butyl ester (4.87 g, 0.026 mol, Aldrich) under the conditions of Example 3a to give the title compound as yellow semi-solid, which was used in the next step without further purification. MS (ESI, neg. ion) m/z: 340 (M−1).

(b) 4-(3-Chloro-5-methoxycarbonyl-pyridin-2-yl)-piperazine-1-carboxylic Acid tert-butyl Ester To a mixture of 4-(5-carboxy-3-chloro-pyridin-2-yl)-piperazine-1-carboxylic acid tert-butyl ester from step (a) above (1.1 g, 3.22 mmol) and $K_2CO_3$ (0.67 g, 4.83 mmol) in DMF (10 mL) was added dropwise MeI (0.3 mL, 4.83 mmol) with stirring at room temperature. The reaction mixture was stirred at room temperature for 16 h, quenched with 20 mL of satd. aq. solution of $NaHCO_3$ and extracted with EtOAc (50 mL). The organic extract was washed with brine (20 mL), dried over $Na_2SO_4$, filtered and concentrated in vacuo. The residue was purified by column chromatography (gradient 30% to 50% EtOAc in hexane) to give the title compound as white solid.

(c) 5-Chloro-6-piperazin-1-yl-nicotinic Acid Methyl Ester, HCl Salt

A mixture of 4-(3-chloro-5-methoxycarbonyl-pyridin-2-yl)-piperazine-1-carboxylic acid tert-butyl ester from step (b) above and satd. solution of HCl in EtOAc (20 mL) was stirred at room temperature for 2 h. The solution was concentrated in vacuo and the residue was washed with 50% EtOAc in hexane, and dried in vacuo to give the title compound as a white solid. MS (ESI, pos. ion) m/z: 256 (M+1).

(d) 5-Chloro-6-[4-(6-trifluoromethyl-1H-benzoimidazol-2-yl)-piperazin-1-yl]-nicotinic Acid Methyl Ester A solution of 5-chloro-6-piperazin-1-yl-nicotinic acid methyl ester, HCl salt from step (c) above (0.13 g, 0.4 mmol), 2-chloro-6-trifluoromethyl-1H-benzoimidazole (88 mg, 0.4 mmol, Example 1c) and i-$Pr_2NEt$ (0.21 mL, 1.2 mmol) in dioxane (2 mL) was subjected to microwave irradiation at 190° C. for 45 min. The solution was cooled to room temperature, diluted with EtOAc (100 mL), washed with saturated aqueous solution of $NaHCO_3$ (50 mL) and brine (50 mL), dried over $Na_2SO_4$, filtered and concentrated in vacuo. The residue was purified by silica gel column chromatography (30% EtOAc in hexane) to give the title compound as a white solid. M.p. 152.8-159.3° C. MS (ESI, pos. ion) m/z: 440 (M+1). Anal. Calcd for $C_{19}H_{17}ClF_3N_5O_2$: C, 51.89; H, 3.90; N, 15.92; Cl, 8.06. Found: C, 51.72; H, 3.86; N, 15.92, Cl, 8.16.

Example 95

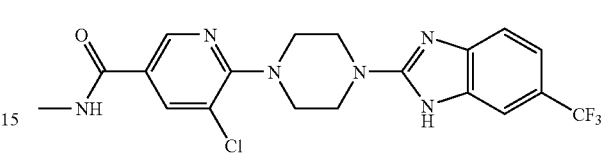

5-Chloro-N-methyl-6-[4-(6-trifluoromethyl-1H-benzoimidazol-2-yl)-piperazin-1-yl]-nicotinamide (a) 4-(3-Chloro-5-pentafluorophenyloxycarbonyl-pyridin-2-yl)-piperazine-1-carboxylic Acid tert-butyl Ester To a solution of 4-(5-carboxy-3-chloro-pyridin-2-yl)-piperazine-1-carboxylic acid tert-butyl ester (0.6 g, 1.7 mmol, Example 94a) and 2,3,4,5,6-pentafluorophenol (0.33 g, 1.76 mmol, Aldrich) in EtOAc (15 mL) was added 1,3-dicyclohexylcarbodiimide (0.351 g 1.7 mmol) at 0° C. The reaction mixture was stirred for 16 h at room temperature, diluted with EtOAc (50 mL) and filtered through a Celite® pad. The filtrate was washed with satd. solution of $NaHCO_3$ (25 mL) and brine (25 mL), dried over $Na_2SO_4$, filtered and evaporated in vacuo to give the title compound as a yellow wax. MS (ESI, pos. ion) m/z: 508 (M+1).

(b) 4-(3-Chloro-5-methylcarbamoyl-pyridin-2-yl)-piperazine-1-carboxylic Acid tert-butyl Ester A mixture of 4-(3-chloro-5-pentafluorophenyloxycarbonyl-pyridin-2-yl)-piperazine-1-carboxylic acid tert-butyl ester from step (a) above (0.9 g, 1.77 mmol) and 2M $MeNH_2$ in THF (9 mL, 18 mmol, Aldrich) was stirred at room temperature for 6 h. The solution was concentrated in vacuo and the residue was purified by silica gel column chromatography (gradient 30% to 50% EtOAc in hexane) to give the title compound as colorless oil. MS (ESI, pos. ion) m/z: 355 (M+1).

(c) 5-Chloro-N-methyl-6-piperazin-1-yl-nicotinamide, HCl Salt

A mixture of 4-(3-chloro-5-methylcarbamoyl-pyridin-2-yl)-piperazine-1-carboxylic acid tert-butyl ester from step (b) above (0.31 g, 0.87 mmol) and satd. HCl in EtOAc (10 mL) was stirred at room temperature for 3 h. The solution was concentrated in vacuo and the residue was washed with 50% EtOAc in hexane, and dried in vacuo to give the title compound as white solid. MS (ESI, pos. ion) m/z: 256 (M+1).

(d) 5-Chloro-N-methyl-6-[4-(6-trifluoromethyl-1H-benzoimidazol-2-yl)-piperazin-1-yl]-nicotinamide 5-Chloro-N-methyl-6-piperazin-1-yl-nicotinamide, HCl salt from step (c) above (0.12 g, 0.37 mmol) and 2-chloro-6- trifluoromethyl-1H-benzoimidazole (82 mg, 0.37 mmol, Example 1c) reacted under the conditions of Example 94d to give the title compound as a white amorphous solid. MS (ESI, pos. ion) m/z: 439 (M+1).

Example 96

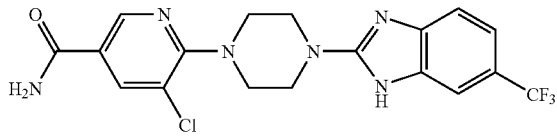

5-Chloro-6-[4-(6-trifluoromethyl-1H-benzoimidazol-2-yl)-piperazin-1-yl]-nicotinamide (a) 5,6-Dichloro-nicotinoyl Chloride A mixture of 5,6-dichloro-nicotinic acid (7.0 g, 0.036 mol, Aldrich), (COCl)$_2$ (50 mL, Aldrich) and DMF (2 drops) was stirred at room temperature for 4 h. The solution was evaporated in vacuo to give the title compound as an orange solid.

(b) 5,6-Dichloro-nicotinamide

A solution of 5,6-dichloro-nicotinoyl chloride from step (a) above (1.73 g, 8.22 mmol)) in CH$_2$Cl$_2$ (50 mL) was added to a mixture of 28% aq. NH$_4$OH (20 mL), water (20 mL) and CH$_2$Cl$_2$ (50 mL), and vigorously stirred at room temperature for 2 h. The organic phase was separated, washed with brine (50 mL), dried over Na$_2$SO$_4$, filtered and concentrated in vacuo to give the title compound as a white solid. MS (ESI, pos. ion) m/z: 191 (M+1).

(c) 4-(5-Carbamoyl-3-chloro-pyridin-2-yl)-piperazine-1-carboxylic Acid tert-butyl Ester The nicotinamide from step (b) above (1.3 g, 6.8 mmol) and piperazine-1-carboxylic acid tert-butyl ester (1.27 g, 6.8 mmol, Aldrich) reacted under the conditions Example 3a to give the title compound as a light-yellow solid. MS (ESI, pos. ion) m/z: 341 (M+1).

(d) 5-Chloro-6-piperazin-1-yl-nicotinamide, Trifluoroacetic Acid Salt

The 4-(5-carbamoyl-3-chloro-pyridin-2-yl)-piperazine-1-carboxylic acid tert-butyl ester from step (c) above (0.8 g, 2.35 mmol) reacted under the conditions of Example 4c to give the title compound as an orange oil.

(e) 5-Chloro-6-[4-(6-trifluoromethyl-1H-benzoimidazol-2-yl)-piperazin-1-yl]-nicotinamide 5-Chloro-6-piperazin-1-yl-nicotinamide, trifluoroacetic acid salt from step (d) above (0.3 g, 0.64 mmol) reacted with 2-chloro-6-trifluoromethyl-1H-benzoimidazole (0.141 g, 0.64 mmol, Example 1c) under the conditions of Example 94d to give the title compound as a white amorphous solid. MS (ESI, pos. ion) m/z: 424 (M+1).

Example 97

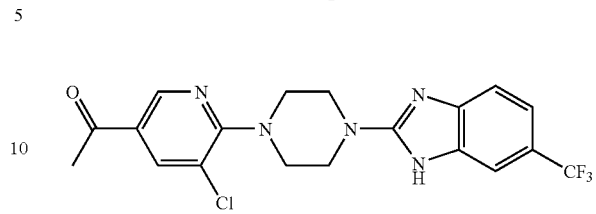

1-{5-Chloro-6-[4-(6-trifluoromethyl-1H-benzoimidazol-2-yl)-piperazin-1-yl]-pyridin-3-yl}-ethanone (a) 5,6-Dichloro-N-methoxy-N-methyl-nicotinamide A solution of 5,6-dichloro-nicotinoyl chloride (3.24 g, 0.0154 mol, Example 96a) in CH$_2$Cl$_2$ (20 mL) was added dropwise to a mixture of O,N-dimethyl-hydroxylamine, HCl salt (1.5 g, 15.4 mmol, Aldrich), 10% aq. K$_2$CO$_3$ (20 mL) and CH$_2$Cl$_2$ (50 mL) and vigorously stirred at room temperature for 3 h. The organic phase was separated, washed with brine (50 mL), dried over Na$_2$SO$_4$, filtered and concentrated in vacuo. The residue was purified by silica gel column chromatography (EtOAc) to give the title compound as a white solid. MS (ESI, pos. ion) m/z: 257 (M+Na$^+$).

(b) 4-[3-Chloro-5-(methoxy-methyl-carbamoyl)-pyridin-2-yl]-piperazine-1-carboxylic Acid tert-butyl Ester 5,6-Dichloro-N-methoxy-N-methyl-nicotinamide from step (a) above (3.2 g, 1.36 mmol) reacted with piperazine-1-carboxylic acid tert-butyl ester (2.53 g, 1.36 mmol, Aldrich) under the conditions of Example 3a to give the title compound as a white solid. MS (ESI, pos. ion) m/z: 385 (M+1).

(c) 4-(5-Acetyl-3-chloro-pyridin-2-yl)-piperazine-1-carboxylic Acid tert-butyl Ester To a solution of 4-[3-chloro-5-(methoxy-methyl-carbamoyl)-pyridin-2-yl]-piperazine-1-carboxylic acid tert-butyl ester from step (b) above (1.0 g, 2.6 mmol) in anhydrous THF (20 mL) was added MeMgBr (2.6 mL, 3M solution in Et$_2$O, 7.8 mmol, Aldrich) with stirring at 0° C. The reaction mixture was stirred at room temperature for 4 h and poured into satd. aq. NaHCO$_3$ solution (20 mL). After the addition of EtOAc (50 mL), the mixture was washed with brine (20 mL), dried over Na$_2$SO$_4$, filtered, and concentrated in vacuo. The residue was purified by silica gel column chromatography (70% EtOAc in hexane) to give the title compound as a white solid. MS (ESI, pos. ion) m/z: 340 (M+1).

(d) 1-(5-Chloro-6-piperazin-1-yl-pyridin-3-yl)-ethanone, Hydrochloride

A mixture of 4-(5-acetyl-3-chloro-pyridin-2-yl)-piperazine-1-carboxylic acid tert-butyl ester from step (c) above (0.65 g, 1.92 mmol) and satd. solution of HCl in EtOAc (50 mL) was stirred at room temperature for 4 h. The solution was evaporated in vacuo to give the title compound as a white solid. MS (ESI, pos. ion) m/z: 240 (M+1).

(e) 1-{5-Chloro-6-[4-(6-trifluoromethyl-1H-benzoimidazol-2-yl)-piperazin-1-yl]-pyridin-3-yl}-ethanone 1-(5-Chloro-6-piperazin-1-yl-pyridin-3-yl)-ethanone, hydrochloride from step (d) above (0.6 g, 1.92 mmol) reacted with 2-chloro-6-trifluoromethyl-1H-benzoimidazole (0.423 g, 1.92 mmol, Example 1c) under the conditions of Example 94d to give the title compound as a white amorphous solid. MS (ESI, pos. ion) m/z: 424 (M+1).

Example 98

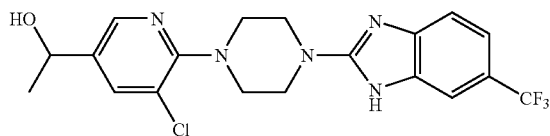

1-{5-Chloro-6-[4-(6-trifluoromethyl-1H-benzoimidazol-2-yl)-piperazin-1-yl]-pyridin-3-yl}-ethanol To a solution of 1-{5-chloro-6-[4-(6-trifluoromethyl-1H-benzoimidazol-2-yl)-piperazin-1-yl]-pyridin-3-yl}-ethanone (0.3 g, 0.71 mmol, Example 97e) in MeOH (20 mL) was added portionwise NaBH$_4$ (0.037 g, 1.0 mmol, Aldrich) with stirring at 0° C. The reaction mixture was stirred at 0° C. for 30 min, quenched with 20 mL of satd. aq. NaHCO$_3$, and diluted with EtOAc (50 mL). The organic phase was separated, washed with brine (20 mL), dried over Na$_2$SO$_4$, filtered and concentrated in vacuo. The residue was recrystallized from 1:1 EtOAc/hexane mixture to give the title compound as a white foam. MS (ESI, pos. ion) m/z: 426 (M+1).

Example 99

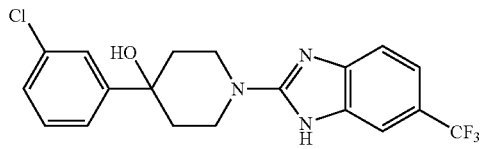

4-(3-Chloro-phenyl)-1-(6-trifluoromethyl-1H-benzoimidazol-2-yl)-piperidin-4-ol 4-(3-Chloro-phenyl)-piperidin-4-ol (0.25 g, 1.18 mmol, Aldrich) reacted with 2-chloro-6-trifluoromethyl-1H-benzoimidazole (0.26 g, 1.18 mmol, Example 1c) under the conditions of Example 94d to give the title compound as a white solid. M.p. 246.7-247.4° C. MS (ESI, pos. ion) m/z: 424 (M+1).

Example 100

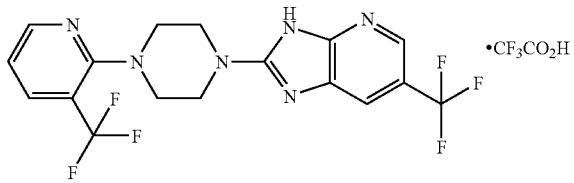

6-Trifluoromethyl-2-[4-(3-trifluoromethyl-pyridin-2-yl)-piperazin-1-yl]-3H-imidazo[4,5-b]pyridine, Trifluoroacetic Acid Salt

(a) 3-Nitro-5-trifluoromethyl-pyridin-2-ylamine

To a 250-mL, round-bottomed flask was added 5-trifluoromethyl-pyridin-2-ylamine (8.3 g, 51.2 mmol, Matrix Scientific) and H$_2$SO$_4$ (49 mL). The resulting mixture was cooled to 0° C., and HNO$_3$ (8.2 mL) was added dropwise. The mixture was heated to 80° C. for 48 h, cooled to room temperature and added dropwise into a vigorously stirred ice-water (500 mL). After the addition, the mixture was basified to pH 9 with 10N NaOH and extracted with EtOAc (2×500 mL). The combined organic extracts were dried over MgSO$_4$ and filtered. The solvent was removed in vacuo and the residue was purified by silica gel column chromatography, eluting with EtOAc/hexane (1:2) to give the title compound as a yellow solid. MS (ESI, positive ion) m/z: 208 (M+1).

(b) 5-Trifluoromethyl-pyridine-2,3-diamine

A mixture of 3-nitro-5-trifluoromethyl-pyridin-2-ylamine from step (a) above (1.2 g, 5.59 mmol), tin (TI) chloride dihydrate (3.9 g, 17.3 mmol, Aldrich), and DMF (19 mL) was heated to 60° C. for 4 h. The reaction mixture was cooled to room temperature and NaHCO$_3$ (150 mL) was added. The mixture was stirred for 0.5 h, diluted with EtOAc (300 mL), stirred for 0.5 h and filtered. The organic layer was separated and the aqueous layer was extracted with EtOAc (2×300 mL). The combined organic extracts were dried over MgSO$_4$ and filtered. The solvent was removed in vacuo to give the title compound, which was used in the next step without additional purification. MS (ESI, positive ion) m/z: 178 (M+1).

(c) 6-Trifluoromethyl-1,3-dihydro-imidazo[4,5-b]pyridin-2-one, Trifluoroacetic Acid Salt A mixture of 5-trifluoromethyl-pyridine-2,3-diamine from step (b) above and N,N-carbonyldiimidazole (938 mg, 579 mmol, Aldrich) in THF (10 mL) was stirred at room temperature for 16 h. The reaction mixture was diluted with H$_2$O (20 mL) and extracted with EtOAc (2×30 mL). The combined organic extracts were concentrated in vacuo and the residue was purified by preparative HPLC (gradient 0.1% trifluoroacetic acid in acetonitrile) to give the title compound. MS (ESI positive ion) m/z: 204 (M+1).

(d) 2-Chloro-6-trifluoromethyl-1H-imidazo[4,5-b]pyridine

A solution of 6-trifluoromethyl-1,3-dihydro-imidazo[4,5-b]pyridin-2-one from step (c) above (161 mg, 0.789 mmol) in POCl$_3$ (5 mL) was heated at 95° C. for 16 h. The reaction mixture was cooled to room temperature, the solvent was removed in vacuo and the resulting oily residue was purified by silica gel column chromatography, eluting with EtOAc/hexane (1:3) to give the title compound as a light-yellow solid. MS (ESI positive ion) m/z: 222 (M+1).

(e) 6-Trifluoromethyl-2-[4-(3-trifluoromethyl-pyridin-2-yl)-piperazin-1-yl]-3H-imidazo[4,5-b]pyridine A mixture of 2-chloro-6-trifluoromethyl-1H-imidazo[4,5-b]pyridine from step (d) above (45 mg, 0.203 mmol), 1-(3-trifluoromethyl-pyridin-2-yl)-piperazine (47 mg, 0.203 mmol, Fluorochem), triethylamine (59 µL, 0.406 mmol, Aldrich) and copper(I) iodide (1 mg, 0.005 mmol, Aldrich) in 3-methyl-butan-1-ol (0.5 mL, Aldrich) was subjected to microwave irradiation at 220° C. for 0.5 h. The reaction mixture was cooled to room temperature and was filtered. The filtrate was purified by preparative HPLC (gradient 0.1% trifluoroacetic acid in acetonitrile) to give the title compound as a colorless solid. MS (ESI, positive ion) m/z: 417 (M+1).

Example 101

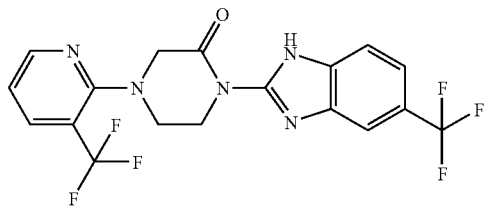

1-(5-Trifluoromethyl-1H-benzoimidazol-2-yl)-4-(3-trifluoromethyl-pyridin-2-yl)-piperazin-2-one (a) 2-Chloro-5-trifluoromethyl-1-(2-trimethylsilanyl-ethoxymethyl)-1H-benzoimidazole A mixture of 2-chloro-5-trifluoromethyl-1H-benzoimidazole (1 g, 4.52 mmol, Example 1c), triethylamine (1.3 mL, 9.04 mmol, Aldrich) and (2-chloromethoxy-ethyl)-trimethylsilane (881 µL, 4.98 mmol, Aldrich) in dichloromethane (30 mL) was stirred at room temperature for 16 h. Water (150 mL) was added, and the mixture was extracted with dichloromethane (2×150 mL). The combined organic extracts were dried over MgSO$_4$ and filtered. The solvent was removed in vacuo and the residue was purified by silica gel column chromatography, eluting with hexane/EtOAc (10:1) to give the title compound as an orange solid. MS (ESI, positive ion) m/z: 351 (M+1).

(b) 4-(3-Trifluoromethyl-pyridin-2-yl)-piperazin-2-one

A mixture of piperazin-2-one (4.85 g, 48.47 mmol, Avocado Research), 2-chloro-3-trifluoromethyl-pyridine (8.8 g, 48.47 mmol, TCI America) and diisopropylethylamine (111 mL, 58.16 mmol, Aldrich) in DMSO (160 mL) was heated at 120° C. for 16 h. The mixture was cooled to room temperature, diluted with H$_2$O (500 mL) and extracted with EtOAc (2×500 mL). The combined organic extracts were dried over MgSO$_4$ and filtered. The solvent was removed in vacuo and the residue was purified by silica gel column chromatography, eluting with dichloromethane/MeOH (15:1) to give the title compound as a yellow solid. MS (ESI, positive ion) m/z: 206 (M+1).

(c) 4-(3-Trifluoromethyl-pyridin-2-yl)-1-[5-trifluoromethyl-1-(2-trimethylsilanyl-ethoxymethyl)-1H-benzoimidazol-2-yl]-piperazin-2-one A mixture of 2-chloro-5-trifluoromethyl-1-(2-trimethylsilanyl-ethoxymethyl)-1H-benzoimidazole from step (a) above (716 mg, 2 mmol), 4-(3-trifluoromethyl-pyridin-2-yl)-piperazin-2-one from step (b) above (500 mg, 2 mmol), tris(dibenzylideneacetone) dipalladium (0) chloroform adduct (207 mg, 0.2 mmol, Strem Chemicals), 4,5-bis(diphenylphosphino)-9,9-dimethylxanthene (213 mg, 0.4 mmol, Aldrich) and cesium carbonate (978 mg, 3 mmol, Aldrich) in 1,4-dioxane (2 mL) was subjected to microwave irradiation at 160° C. for 1.5 h. The mixture was cooled to room temperature, filtered, and the filtrate was purified by preparative HPLC (gradient 0.1% trifluoroacetic acid in acetonitrile) to give the title compound as a brown oil. MS (ESI, positive ion) m/z: 560 (M+1).

(d) 1-(5-Trifluoromethyl-1H-benzoimidazol-2-yl)-4-(3-trifluoromethyl-pyridin-2-yl)-piperazin-2-one A solution of 4-(3-trifluoromethyl-pyridin-2-yl)-1-[5-trifluoromethyl-1-(2-trimethylsilanyl-ethoxymethyl)-1H-benzoimidazol-2-yl]-piperazin-2-one from step (c) above (114 mg, 0.2 mmol) in 30% TFA in dichloromethane (3 mL) was stirred at room temperature for 5 h. The solvent was removed in vacuo and the residue was purified by silica gel column chromatography, eluting with EtOAc/hexane (1:3) to give the title compound as a yellow solid. MS (ESI, positive ion) m/z: 430 (M+1).

Example 102

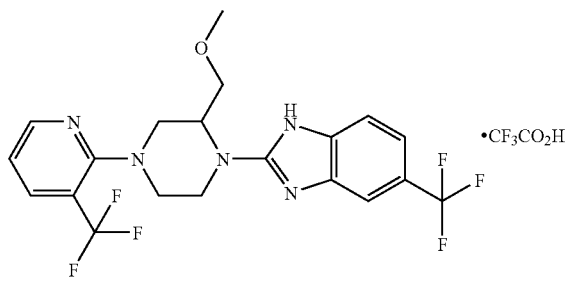

2-[2-Methoxymethyl-4-(3-trifluoromethyl-pyridin-2-yl)-piperazin-1-yl]-5-trifluoromethyl-1H-benzoimidazole, Trifluoroacetic Acid Salt (a) 3-Methoxymethyl-piperazine-1-carboxylic Acid Benzyl Ester, Trifluoroacetic Acid Salt A mixture of iodomethane (356 µL, 5.71 mmol, Aldrich) and sodium hydride (137 mg, 5.71 mmol, Aldrich) in DMF (19 mL) was stirred at room temperature for 10 min. A solution of 2-hydroxymethyl-piperazine-1,4-dicarboxylic acid 4-benzyl ester 1-tert-butyl ester (2 g, 5.71 mmol, Monomerchem Inc.) in DMF (19 mL) was added dropwise, and the mixture was stirred at room temperature for 0.5 h. The reaction mixture was diluted with H$_2$O (300 mL) and extracted with EtOAc (2×400 mL). The combined organic extracts were concentrated in vacuo and the residue was dissolved in 30% TFA in dichloromethane (40 mL). The solution was stirred at room temperature for 0.5 h and the solvent was removed in vacuo. Methanol (10 mL) was added to the residue and the mixture was filtered. The filtrate was purified by preparative HPLC (gradient 0.1% trifluoroacetic acid in acetonitrile) to give the title compound as a colorless oil. MS (ESI, positive ion) m/z: 265 (M+1).

(b) 3-Methoxymethyl-4-(5-trifluoromethyl-1H-benzoimidazol-2-yl)-piperazine-1-carboxylic Acid Benzyl Ester, Trifluoroacetic Acid Salt 2-Chloro-5-trifluoromethyl-1H-benzoimidazole (703 mg, 3.18 mmol, Example 1c) and 3-methoxymethyl-piperazine-1-carboxylic acid benzyl ester, trifluoroacetic acid salt from step (a) above (840 mg, 3.18 mmol) reacted under the conditions of Example 10e to give the title compound as a yellow oil. MS (ESI, positive ion) m/z: 449 (M+1).

(c) 2-(2-Methoxymethyl-piperazin-1-yl)-5-trifluoromethyl-1H-benzoimidazole, Rifluoroacetic Acid Salt To a solution of 3-methoxymethyl-4-(5-trifluoromethyl-1H-benzoimidazol-2-yl)-piperazine-1-carboxylic acid benzyl ester, trifluoroacetic acid salt from step (b) above (216 mg, 0.482 mmol) in methanol (3.2 mL, Aldrich) was added palladium, 10 wt % on activated carbon (30 mg, Aldrich). The mixture was stirred under hydrogen for 16 h and filtered through a Celite® pad. The filtrate was concentrated in vacuo to give the title compound as a yellow oil, which was used in next step without purification. MS (ESI, positive ion) m/z: 315 (M+1).

(d) 2-[2-Methoxymethyl-4-(3-trifluoromethyl-pyridin-2-yl)-piperazin-1-yl]-5-trifluoromethyl-1H-benzoimidazole Trifluoroacetic Acid Salt 2-(2-Methoxymethyl-piperazin-1-yl)-5-trifluoromethyl-1H-benzoimidazole, trifluoroacetic acid salt from step (c) above and 2-chloro-3-trifluoromethyl-pyridine (100 mg, 0.55 mmol, TCI America) reacted under the condition of Example 10e to give the title compound as a light-yellow oil. MS (ESI, positive ion) m/z: 460 (M+1).

Example 103

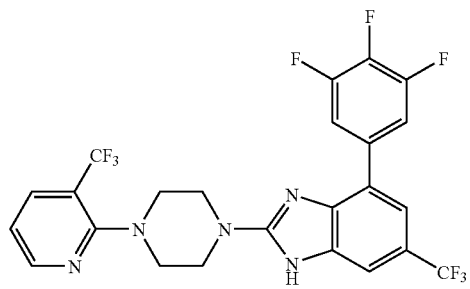

6-Trifluoromethyl-2-[4-(3-trifluoromethyl-pyridin-2-yl)-piperazin-1-yl]-4-(3,4,5-trifluoro-phenyl)-1H-benzoimidazole 4-Bromo-6-trifluoromethyl-2-[4-(3-trifluoromethylpyridin-2-yl)piperazin-1-yl]-1H-benzoimidazole (1.99 g, 4 mmol, Example 7) reacted with 3,4,5-trifluorophenylboronic acid (1.1 g, 6 mmol, Lancaster) under the conditions of Example 51a to give the title compound as a white amorphous solid. MS (ESI, pos. ion) m/z: 546 (M+1).

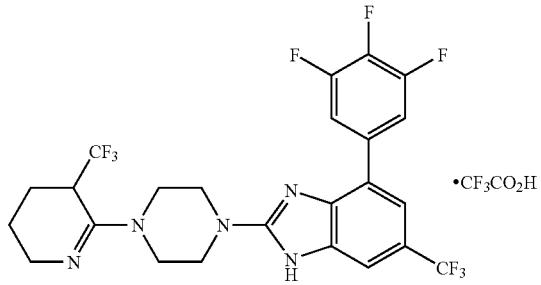

6-Trifluoromethyl-2-[4-(3-trifluoromethyl-3,4,5,6-tetrahydro-pyridin-2-yl)-piperazin-1-yl]-4-(3,4,5-trifluoro-phenyl)-1H-benzoimidazole, Trifluoroacetic Acid Salt A solution of 6-trifluoromethyl-2-[4-(3-trifluoromethyl-pyridin-2-yl)-piperazin-1-yl]-4-(3,4,5-trifluoro-phenyl)-1H-benzoimidazole (42 mg, 0.08 mmol) in MeOH (4.5 mL) and anhydrous HCl (0.175 mL, 0.70 mmol, 4M in dioxane, Aldrich) was stirred with 10% Pd/C (20 mg, Aldrich) under hydrogen at atmospheric pressure and at room temperature for 18 h. The palladium catalyst was removed by filtration over a Celite® pad. The filtrates were concentrated in vacuo and the residue was dissolved in MeOH (0.75 mL), and purified by preparative HPLC (gradient 0.1% trifluoroacetic acid in acetonitrile) to give the title compound as a white amorphous solid. MS (ESI, pos. ion) m/z: 550 (M+1).

Example 104

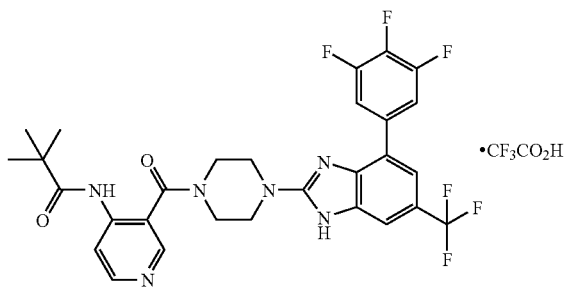

2,2-Dimethyl-N-(3-{4-[6-trifluoromethyl-4-(3,4,5-trifluoro-phenyl)-1H-benzoimidazol-2-yl]-piperazine-1-carbonyl}-pyridin-4-yl)-propionamide, Trifluoro Acetic Acid Salt (a) 2-piperazin-1-yl-6-trifluoromethyl-4-(3,4,5-trifluoro-phenyl)-1H-benzoimidazole 2-piperazine (429 mg, 4.99 mmol, Aldrich) and 2-chloro-5-trifluoromethyl-7-(3,4,5-trifluoro-phenyl)-1H-benzoimidazole (582 mg, 1.66 mmol, Example 51b) reacted under the conditions of Example 100e to give the title compound as a yellow solid. MS (ESI, positive ion) m/z: 401 (M+1).

(b) 2,2-Dimethyl-N-(2-{4-[6-trifluoromethyl-4-(3,4,5-trifluoro-phenyl)-1H-benzoimidazol-2-yl]-piperazine-1-carbonyl}-pyridin-3-yl)-propionamide, Trifluoro Acetic Acid Salt A mixture of 2-piperazin-1-yl-6-trifluoromethyl-4-(3,4,5-trifluoro-phenyl)-1H-benzoimidazole from step (a) above (50 mg, 0.13 mmol), 3-(2,2-dimethyl-propionylamino)-pyridine-2-carboxylic acid (42 mg, 0.19 mmol, Maybridge), PS-carbodiimide (146 mg, 0.187 mmol, Argonaut Technologies Inc.) and HOAt (8.5 mg, 0.062 mmol, Perseptive Biosystems)

in a 1:1 solution of DMF/dichloromethane (0.9 mL) was stirred at room temperature for 16 h. The mixture was filtered and the resin was washed with a solution of MeOH/dichloromethane (1:1) (2×2 mL). The filtrate was concentrated in vacuo and the residue was purified by preparative HPLC (gradient 0.1% trifluoroacetic acid in acetonitrile) to give the title compound as a colorless solid. MS (ESI, positive ion) m/z: 605 (M+1).

Example 105

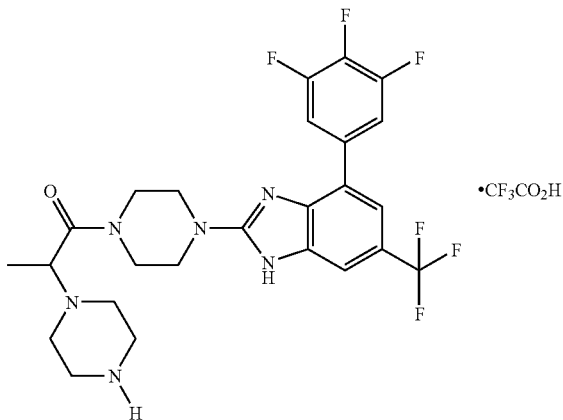

2-piperazin-1-yl-1-{4-[6-trifluoromethyl-4-(3,4,5-trifluoro-phenyl)-1H-benzoimidazol-2-yl]-piperazin-1-yl}-propan-1-one, Trifluoroacetic Acid Salt A mixture of 2-piperazin-1-yl-6-trifluoromethyl-4-(3,4,5-trifluoro-phenyl)-1H-benzoimidazole (100 mg, 0.25 mmol, Example 104a), 2-(1-tert-butoxycarbonylpiperazin-4-yl)propionic acid hydrochloride (110 mg, 0.38 mmol, Chess), PS-carbodiimide (292 mg, 0.38 mmol, Argonaut Technologies Inc.), diisopropylethylamine (65 µL, 0.38 mmol, Aldrich) and HOAt (26 mg, 0.19 mmol, Perseptive Biosystems) in a solution of 1:1 DMF/dichloromethane (1.8 mL) reacted under the condition of Example 104b to give a colorless solid. MS (ESI, positive ion) m/z: 641 (M+1). The solid was dissolved in 30% TFA in dichloromethane (1 mL) and the solution was stirred at room temperature for 0.5 h. The solvent was removed in vacuo and the residue was purified by preparative HPLC (gradient 0.1% trifluoroacetic acid in acetonitrile) to give the title compound as a colorless solid. MS (ESI, positive ion) m/z: 541 (M+1).

Example 106

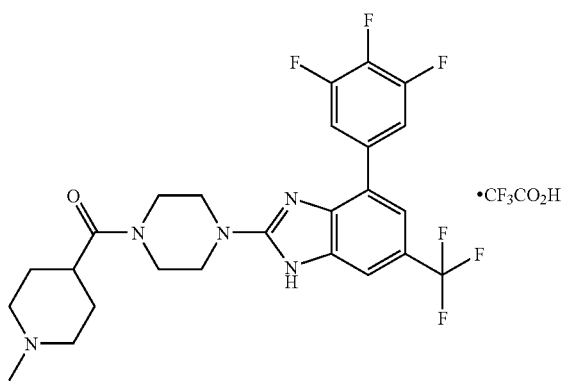

(1-Methyl-piperidin-4-yl)-{4-[6-trifluoromethyl-4-(3,4,5-trifluoro-phenyl)-1H-benzoimidazol-2-yl]-piperazin-1-yl}-methanone, Trifluoroacetic Acid Salt 2-piperazin-1-yl-6-trifluoromethyl-4-(3,4,5-trifluoro-phenyl)-1H-benzoimidazole (100 mg, 0.25 mmol, Example 104a) and 1-methyl-piperidine-4-carboxylic acid hydrochloride (67.5 mg, 0.38 mmol, Chess) reacted under the condition of Example 104b to give the title compound as a colorless solid. MS (ESI, positive ion) m/z: 526 (M+1).

Example 107

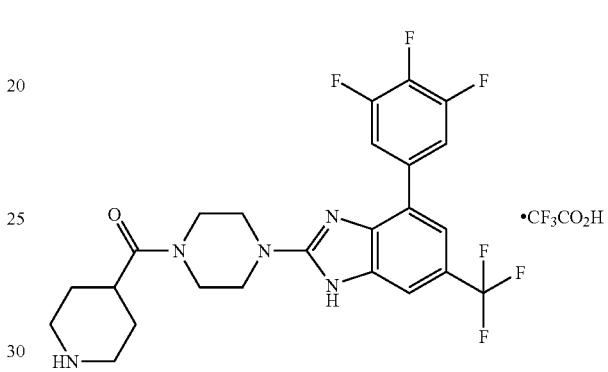

Piperidin-4-yl-{4-[6-trifluoromethyl-4-(3,4,5-trifluoro-phenyl)-1H-benzoimidazol-2-yl]-piperazin-1-yl}-methanone, Trifluoroacetic Acid Salt 2-piperazin-1-yl-6-trifluoromethyl-4-(3,4,5-trifluoro-phenyl)-1H-benzoimidazole (100 mg, 0.25 mmol, Example 104a) and piperidine-1,4-dicarboxylic acid mono-tert-butyl ester (86 mg, 0.38 mmol, Carbogen) reacted under the condition of Example 104b to give the title compound as a colorless solid. MS (ESI, positive ion) m/z: 512 (M+1).

Example 108

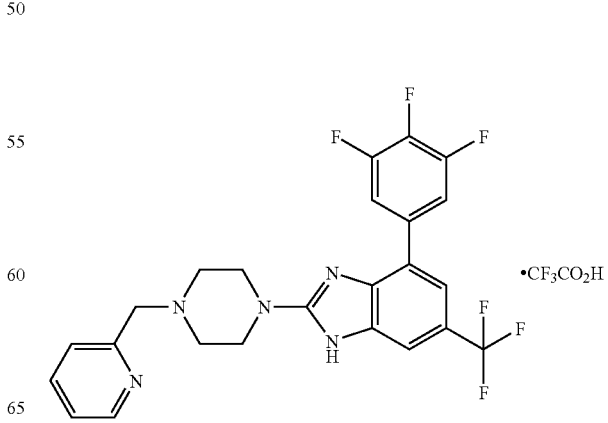

2-(4-Pyridin-2-ylmethyl-piperazin-1-yl)-6-trifluoromethyl-4-(3,4,5-trifluoro-phenyl)-1H-benzoimidazole, Trifluoroacetic Acid Salt A mixture of 2-piperazin-1-yl-6-trifluoromethyl-4-(3,4,5-trifluoro-phenyl)-1H-benzoimidazole (160 mg, 0.4 mmol, Example 104a), 2-(chloromethyl)pyridine hydrochloride (66 mg, 0.4 mmol, Aldrich) and $K_2CO_3$ (61 mg, 0.44 mmol) in DMF (2.7 mL) was stirred at room temperature for 16 h. The solvent was removed in vacuo and MeOH (1 mL) was added to the residue. The mixture was filtered and the filtrate was purified by preparative HPLC (gradient 0.1% trifluoroacetic acid in acetonitrile) to give the title compound as a white solid. MS (ESI, positive ion) m/z: 492 (M+1).

Example 109

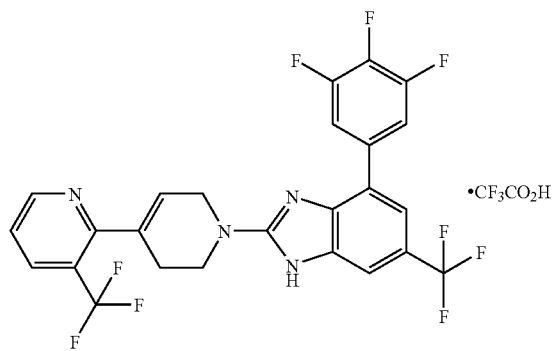

3-Trifluoromethyl-1'-[6-trifluoromethyl-4-(3,4,5-trifluoro-phenyl)-1H-benzoimidazol-2-yl]-1',2',3',6'-tetrahydro-[2,4]bipyridinyl, Trifluoroacetic Acid Salt (a) 4-Trifluoromethanesulfonyloxy-3,6-dihydro-2H-pyridine-1-carboxylic Acid tert-butyl Ester To a 500-mL, round-bottomed flask was added THF (42 mL) and diisopropylamine (4 mL, 27.6 mmol, Aldrich). The resulting mixture was cooled to −78° C. and n-butyllithium (1.6 M in hexane, 17 mL, Aldrich) was added dropwise over 20 min under nitrogen. After stirring at −78° C. for 45 min, a solution of N-Boc-4-piperidone (5 g, 25 mmol, Aldrich) in THF (42 mL) was added dropwise over 25 min. After stirring for 20 min at −78° C., a solution of N-phenyltrifluoromethanesulfonimide (9.8 g, 27.6 mmol, Aldrich) in THF (42 mL) was added and the mixture was stirred at 0° C. for 3.5 h. Then, a solution of THF/$H_2O$ (1:1) (100 mL) was added dropwise and the mixture was stirred at room temperature for 16 h. The solvent was removed in vacuo and the residue was purified by silica gel chromatography, eluting with hexane/EtOAc (7:1) to give the title compound as a yellow oil.

(b) 4-(4,4,5,5-Tetramethyl-[1,3,2]dioxaborolan-2-yl)-3,6-dihydro-2H-pyridine-1-carboxylic Acid tert-butyl Ester A mixture of 4-trifluoromethanesulfonyloxy-3,6-dihydro-2H-pyridine-1-carboxylic acid tert-butyl ester from step (a) above (2 g, 6 mmol), bis(pinacolato)diboron (1.7 g, 6.6 mmol, Lancaster), potassium acetate (1.76 g, 18 mmol, Aldrich), [1,1-bis(diphenylphosphino)ferrocene]dichloro-palladium (II), complex with dichloromethane (147 mg, 0.18 mmol, Aldrich) and 1,1-bis(diphenylphosphino)ferrocene (100 mg, 0.18 mmol, Strem chemicals) in 1,4-dioxane (36 mL) was heated at 80° C. for 16 h. The mixture was cooled to room temperature and was filtered. The filtrate was concentrated in vacuo and the residue was purified by silica gel chromatography, eluting with EtOAc/hexane (1:15) to give the title compound as a white solid. MS (ESI, positive ion) m/z: 310 (M+1).

(c) 3-Trifluoromethyl-1',2',3',6'-tetrahydro-[2,4']bipyridinyl, Trifluoroacetic Acid Salt A mixture of 2-chloro-3-trifluoromethyl-pyridine (400 mg, 1.3 mmol, TCI America), 4-(4,4,5,5-tetramethyl-[1,3,2]dioxaborolan-2-yl)-3,6-dihydro-2H-pyridine-1-carboxylic acid tert-butyl ester from step (b) above (234 mg, 1.3 mmol), dichloro-bis(triphenylphosphine) palladium (TI) (180 mg, 0.258 mmol, Strem Chemicals), $Na_2CO_3$ (544 mg, 5.18 mmol) in a 7:3:2 solution of dimethoxyethane/$H_2O$/EtOH (8 mL) was subjected to microwave irradiation at 140° C. for 0.5 h. The mixture was cooled to room temperature, filtered and washed with dichloromethane (2×100 mL). The filtrate was concentrated in vacuo and the residue was purified by silica gel column chromatography, eluting with EtOAc/hexane (1:3) to give a solid intermediate. MS (ESI, positive ion) m/z: 329 (M+1). The solid was dissolved in 30% TFA in dichloromethane (10 mL) and the mixture was stirred at room temperature for 0.75 h. The solvent was removed in vacuo to give the title compound, which was used in the next step without additional purification. MS (ESI, positive ion) m/z: 229 (M+1).

(d) 3-Trifluoromethyl-1'-[6-trifluoromethyl-4-(3,4,5-trifluoro-phenyl)-1H-benzoimidazol-2-yl]-1',2',3',6'-tetrahydro-[2,4']bipyridinyl, Trifluoroacetic Acid Salt 3-Trifluoromethyl-1',2',3',6'-tetrahydro-[2,4]bipyridinyl, trifluoroacetic acid salt from step (c) above and 2-chloro-5-trifluoromethyl-7-(3,4,5-trifluoro-phenyl)-1H-benzoimidazole (400 mg, 1.14 mmol, Example 51b) reacted under the conditions of Example 100e to give the title compound as a yellow solid. MS (ESI, positive ion) m/z: 543 (M+1).

Example 110

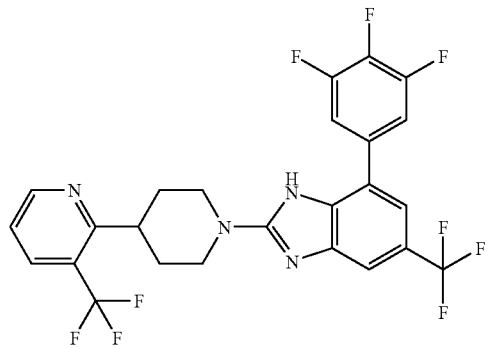

3-Trifluoromethyl-1'-[5-trifluoromethyl-7-(3,4,5-trifluoro-phenyl)-1H-benzoimidazol-2-yl]-1',2',3',4',5',6'-hexahydro-[2,4']bipyridinyl A mixture of 3-trifluoromethyl-1'-[6-trifluoromethyl-4-(3,4,5-trifluoro-phenyl)-1H-benzoimidazol-2-yl]-1',2',3',6'-tetrahydro-[2,4']bipyridinyl, trifluoroacetic acid salt (192 mg, 0.354 mmol, Example 109d) and palladium, 10 wt % on activated carbon (20 mg, Aldrich) in methanol (2 mL) was stirred at room temperature under hydrogen for 32 h. The mixture was filtered through Celite®, the filtrate was concentrated in vacuo and the residue was purified by silica gel column chromatography, eluting with EtOAc/hexane (1:1) to give the title compound as a white solid. MS (ESI, positive ion) m/z: 545 (M+1).

Example 111

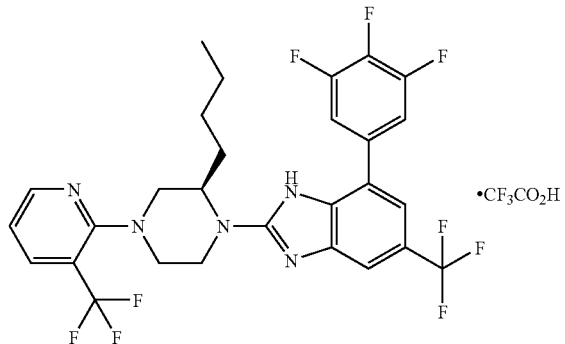

2-[(2R)-2-Butyl-4-(3-trifluoromethyl-pyridin-2-yl)-piperazin-1-yl]-5-trifluoromethyl-7-(3,4,5-trifluoro-phenyl)-1H-benzoimidazole, Trifluoroacetic Acid Salt (a) Methyl N-{[(9H-fluoren-9-ylmethyl)oxy]carbonyl}-D-norleucylglycinate A mixture of fmoc-D-Nle-OH (10 g, 28.3 mmol, Novabiochem) and PS-carbodiimide (33 g, 42.45 mmol, 1.28 mmol/g, Argonaut Technologies Inc.) in dichloromethane (250 mL) was stirred at room temperature for 0.5 h. Then, glycine methyl ester hydrochloride (5.3 g, 42.45 mmol, Aldrich), HOAt (3.8 g, 28.3 mmol, Perseptive Biosystems) and diisopropylethylamine (16 mL, 84.9 mmol, Aldrich) were added and the mixture was stirred at room temperature for 16 h. The mixture was filtered and the resin was washed with dichloromethane (2×70 mL). The filtrate was concentrated in vacuo and the residue was purified by column chromatography, eluting with EtOAc/hexane (1:2) to give the title compound as a yellow solid. MS (ESI, positive ion) m/z: 425 (M+1).

(b) (3R)-3-Butyl-2,5-piperazinedione

A solution of methyl N-{[(9H-fluoren-9-ylmethyl)oxy]carbonyl}-D-norleucylglycinate from step (a) above (2 g, 4.7 mmol) in a 7:3 mixture of dichloromethane/piperidine (30 mL) was stirred at room temperature for 0.75 h. The reaction mixture was diluted with dichloromethane (200 mL) and solid which precipitated was filtered, washed with cold DCM (2×50 mL) and dried in vacuo to give the title compound as a white solid. MS (ESI, positive ion) m/z: 171 (M+1).

(c) (2R)-2-Butylpiperazine

To a cooled to −78° C. solution of (3R)-3-butyl-2,5-piperazinedione from step (b) above (600 mg, 2.52 mmol) in THF (10 mL) was added dropwise lithium aluminum hydride (21 mL, 21.1 mmol, 1M in THF, Aldrich). The mixture was stirred at room temperature for 1 h, and then heated at reflux for 16 h. The mixture was cooled to 0° C. and quenched with sodium sulfate decahydrate until the gas evolution ceased. The mixture was stirred at room temperature for 3 h, filtered and the filter cake was washed with THF (2×10 mL). The filtrate was concentrated in vacuo to give the title compound as a yellow solid. MS (ESI, positive ion) m/z: 143 (M+1).

(d) (3R)-3-Butyl-1-(3-(trifluoromethyl)-2-pyridinyl)piperazine, Trifluoroacetic Acid Salt A mixture of (2R)-2-butylpiperazine from step (c) above (381 mg, 2.68 mmol), 2-chloro-3-trifluoromethyl-pyridine (486 mg, 2.68 mmol, TCI America) triethylamine (425 μL, 2.9 mmol, Aldrich) in 3-methyl-butan-1-ol (5 mL) was subjected to microwave irradiation at 180° C. for 1 h. The mixture was cooled to room temperature and filtered. The filtrate was purified by preparative HPLC (gradient 0.1% trifluoroacetic acid in acetonitrile) to give the title compound as a yellow oil. MS (ESI, positive ion) m/z: 288 (M+1).

(e) 2-[(2R)-2-Butyl-4-(3-trifluoromethyl-pyridin-2-yl)-piperazin-1-yl]-5-trifluoromethyl-7-(3,4,5-trifluoro-phenyl)-1H-benzoimidazole, Trifluoroacetic Acid Salt (3R)-3-Butyl-1-(3-(trifluoromethyl)-2-pyridinyl)piperazine, trifluoroacetic acid salt from step (d) above (220 mg, 0.76 mmol) and 2-chloro-5-trifluoromethyl-7-(3,4,5-trifluoro-phenyl)-1H-benzoimidazole (100 mg, 0.285 mmol, Example 51b) reacted under the conditions of Example 100e to give the title compound as a light-yellow oil. MS (ESI, positive ion) m/z: 602 (M+1).

Example 112

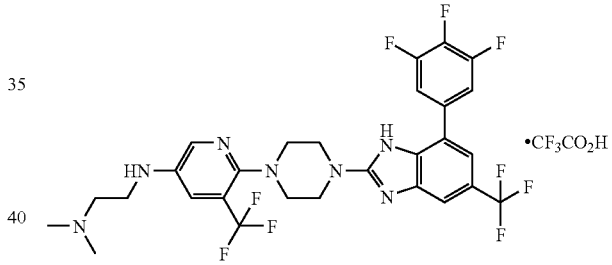

N,N-Dimethyl-N'-(5-trifluoromethyl-6-{4-[5-trifluoromethyl-7-(3,4,5-trifluoro-phenyl)-1H-benzoimidazol-2-yl]-piperazin-1-yl}-pyridin-3-yl)-ethane-1,2-diamine, Trifluoroacetic Acid Salt (a) 1-(5-Bromo-3-trifluoromethyl-pyridin-2-yl)-piperazine To a solution of 1-(3-trifluoromethyl-pyridin-2-yl)-piperazine (8 g, 34.6 mmol, Oakwood) in dichloromethane (230 mL) was added dropwise bromine (3.92 mL, 76.12 mmol, Aldrich) with stirring at room temperature. The resulting mixture was stirred at room temperature for 16 h and the precipitate was filtered, washed with EtOAc (2×100 mL) and dried in vacuo to give the title compound as a yellow solid, which was used in the next step without additional purification. MS (ESI, positive ion) m/z: 310 (M+1).

(b) 4-(5-Bromo-3-trifluoromethyl-pyridin-2-yl)-piperazine-1-carboxylic Acid tert-butyl Ester A solution of bis(1,1-dimethylethyl) dicarbonate (8.2 g, 38.06 mmol, Aldrich) in dichloromethane (100 mL) was added dropwise to a mixture of 1-(5-bromo-3-trifluoromethyl-pyridin-2-yl)-piperazine from step (a) above and diisopropylethylamine (9.6 mL, 51.9 mmol, Aldrich) in dichloromethane (130 mL) with stirring at 0° C. The reaction mixture was stirred at 0° C. for 3 h, the solvent was removed in vacuo and the residue was purified by silica gel column chromatography (gradient EtOAc in dichloromethane) to give the title compound as a light-yellow solid. MS (ESI, positive ion) m/z: 410 (M+1).

(c) 4-[5-(2-Dimethylamino-ethylamino)-3-trifluoromethyl-pyridin-2-yl]-piperazine-1-carboxylic Acid tert-butyl Ester A mixture of 4-(5-bromo-3-trifluoromethyl-pyridin-2-yl)-piperazine-1-carboxylic acid tert-butyl ester from step (b) above (174 mg, 0.42 mmol), N-(2-aminoethyl)-N,N-dimethylamine (56 µL, 0.51 mmol, Aldrich), tris (dibenzylideneacetone) dipalladium (0) chloroform adduct (22 mg, 0.021 mmol, Strem Chemicals), biphenyl-2-yl-di-tert-butyl-phosphane (13 mg, 0.042 mmol, Strem Chemicals), sodium t-butoxide (65 mg, 0.63 mmol, Aldrich) in toluene (2 mL) was subjected to microwave irradiation at 150° C. for 0.5 h. The mixture was cooled to room temperature and was filtered. The filtrate was purified by silica gel column chromatography, eluting with 5%-100% (2M NH$_3$ in MeOH) in dichloromethane, to give the title product as a brown solid. MS (ESI, positive ion) m/z: 418 (M+1).

(d) N,N-Dimethyl-N'-(6-piperazin-1-yl-5-trifluoromethyl-pyridin-3-yl)-ethane-1,2-diamine, Trifluoroacetic Acid Salt A solution of 4-[5-(2-dimethylamino-ethylamino)-3-trifluoromethyl-pyridin-2-yl]-piperazine-1-carboxylic acid tert-butyl ester from step (c) above in 30% TFA in dichloromethane (10 mL) was stirred at room temperature for 0.5 h. The solvent was removed in vacuo to give the title compound, which was used in the next step without additional purification. MS (ESI, positive ion) m/z: 318 (M+1).

(e) N,N-Dimethyl-N'-(5-trifluoromethyl-6-{4-[5-trifluoromethyl-7-(3,4,5-trifluoro-phenyl)-1H-benzoimidazol-2-yl]-piperazin-1-yl}-pyridin-3-yl)-ethane-1,2-diamine, Trifluoroacetic Acid Salt N,N-Dimethyl-N'-(6-piperazin-1-yl-5-trifluoromethyl-pyridin-3-yl)-ethane-1,2-diamine trifluoro acetic acid from step (d) above and 2-chloro-5-trifluoromethyl-7-(3,4,5-trifluoro-phenyl)-1H-benzoimidazole (46 mg, 0.131 mmol, Example 51b) reacted under the condition of Example 100e to give the title compound as a light-yellow oil. MS (ESI, positive ion) m/z: 632 (M+1).

Example 113

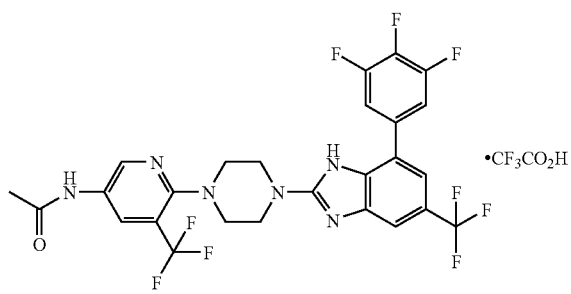

N-(5-Trifluoromethyl-6-{4-[5-trifluoromethyl-7-(3,4,5-trifluoro-phenyl)-1H-benzoimidazol-2-yl]-piperazin-1-yl}-pyridin-3-yl)-acetamide, Trifluoroacetic Acid Salt (a) 4-(5-Bromo-3-trifluoromethyl-pyridin-2-yl)-piperazine-1-carboxylic Acid Benzyl Ester Benzyl chloroformate (806 µL, 5.7 mmol, Aldrich) was added dropwise to a mixture of 1-(5-bromo-3-trifluoromethyl-pyridin-2-yl)-piperazine (1.6 g, 5.2 mmol, Example 112a) and diisopropylethylamine (1.1 mL, 6.24 mmol, Aldrich) in dichloromethane (35 mL) with stirring at 0° C. The mixture was stirred at room temperature for 16 h. The solvent was removed in vacuo and the residue was purified by silica gel column chromatography (2%-100% EtOAc/hexane) to give the title compound as an orange oil. MS (ESI, positive ion) m/z: 444 (M+1).

(b) 4-(5-Acetylamino-3-trifluoromethyl-pyridin-2-yl)-piperazine-1-carboxylic Acid Benzyl Ester A mixture of 4-(5-bromo-3-trifluoromethyl-pyridin-2-yl)-piperazine-1-carboxylic acid benzyl ester from step (a) above (300 mg, 0.677 mmol), acetamide (60 mg, 1 mmol, Aldrich), tris(dibenzylideneacetone) dipalladium (0) chloroform adduct (70 mg, 0.068 mmol, Strem Chemicals), 4,5-bis(diphenylphosphino)-9,9-dimethylxanthene (78 mg, 0.135 mmol, Aldrich) and cesium carbonate (331 mg, 1.01 mmol, Aldrich) in 1,4-dioxane (4 mL) was subjected to microwave irradiation at 170° C. for 0.5 h. The mixture was cooled to room temperature and was filtered. The filtrate was purified by silica gel column chromatography (2%-100% EtOAc/hexane) to give the title compound as a light-brown solid. MS (ESI, positive ion) m/z: 423 (M+1).

(c) N-(6-piperazin-1-yl-5-trifluoromethyl-pyridin-3-yl)-acetamide 4-(5-Acetylamino-3-trifluoromethyl-pyridin-2-yl)-piperazine-1-carboxylic acid benzyl ester from step (b) above reacted under the conditions of Example 110 to give the title compound. MS (ESI, positive ion) m/z: 289 (M+1).

(d) N-(5-Trifluoromethyl-6-{4-[5-trifluoromethyl-7-(3,4,5-trifluoro-phenyl)-1H-benzoimidazol-2-yl]-piperazin-1-yl}-pyridin-3-yl)-acetamide, Trifluoroacetic Acid Salt N-(6-piperazin-1-yl-5-trifluoromethyl-pyridin-3-yl)-acetamide from step (c) above and 2-chloro-5-trifluoromethyl-7-(3,4,5-trifluoro-phenyl)-1H-benzoimidazole (134 mg, 0.382 mmol, Example 51b) reacted under the conditions of Example 100e to give the title compound as a white solid. MS (ESI, positive ion) m/z: 603 (M+1).

Example 114

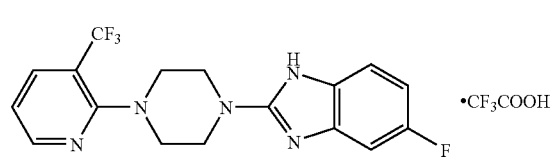

5-Fluoro-2-[4-(3-trifluoromethyl-pyridin-2-yl)-piperazin-1-yl]-1H-benzoimidazole, Trifluoroacetic Acid Salt

(a) 5-Fluoro-1,3-dihydro-benimidazol-2-one 3,4-Diamino-1-fluorobenzene (1.205 g, 9.6 mmol, Lancaster) and 1,1'-carbonyldiimidazole (1.549 g, 9.6 mmol, Aldrich) reacted under the conditions of Example 1b to give the title compound as an amorphous solid. MS (ESI, pos. ion) m/z: 153 (M+1).

(b) 2-Chloro-5-fluoro-1H-benzimidazole

The dihydrobenzimidazol-2-one from step (a) above (572 mg, 3.8 mmol) and $POCl_3$ (6 mL) reacted under the conditions of Example 1c to give the title compound as an amorphous solid. MS (ESI, pos. ion) m/z: 171 (M+1).

(c) 5-Fluoro-2-[4-(3-trifluoromethyl-pyridin-2-yl)-piperazin-1-yl]-1H-benzoimidazole, Trifluoroacetic Acid Salt A mixture of the chlorobenzimidazole from step (b) above (170 mg, 1.0 mmol), 1-(3-trifluoromethylpyridin-2-yl)piperazine (347 mg, 1.5 mmol) and sodium bicarbonate (250 mg, 2.9 mmol) in isoamyl alcohol (2 mL) was heated at 150° C. in a microwave synthesizer for 10 min. The reaction mixture was the cooled to room temperature, diluted with MeOH (3 mL), filtered and the filtrate was purified by preparative HPLC (gradient 0.1% trifluoroacetic acid in acetonitrile) to give the title compound as an amorphous solid. MS (ESI, pos. ion) m/z: 366 (M+1).

Example 115

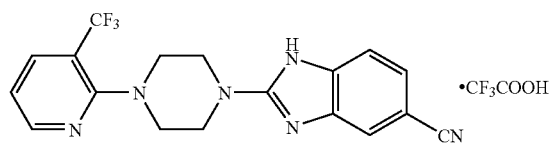

2-[4-(3-Trifluoromethyl-pyridin-2-yl)-piperazin-1-yl]-1H-benzoimidazole-5-carbonitrile, Trifluoroacetic Acid Salt

(a) 2-Oxo-2,3-dihydro-1H-benzoimidazole-5-carbonitrile 3,4-Diaminobenzonitrile (3.171 g, 23.8 mmol, Oakwood) was reacted with 1,1'-carbonyldiimidazole (3.862 g, 23.8 mmol, Aldrich) under the conditions of Example 1b to give the title compound as an amorphous solid. MS (ESI, pos. ion) m/z: 160 (M+1).

(b) 2-Chloro-1H-benzoimidazole-5-carbonitrile

A solution of the dihydrobenzimidazol-2-one from step (a) above (854 mg, 5.4 mmol) was reacted under the conditions of Example 1c to give the title compound as an amorphous solid. MS (ESI, pos. ion) m/z: 178 (M+1).

(c) 2-[4-(3-Trifluoromethyl-pyridin-2-yl)-piperazin-1-yl]-1H-benzoimidazole-5-carbonitrile, Trifluoroacetic Acid Salt A mixture of the chlorobenzimidazole from step (b) above (310 mg, 1.7 mmol), 1-(3-trifluoromethylpyridin-2-yl)piperazine (405 mg, 1.8 mmol) and sodium bicarbonate (370 mg, 4.4 mmol) in isoamyl alcohol (2.5 mL) was reacted under the conditions of Example 114c to give the title compound as an amorphous solid. MS (ESI, pos. ion) m/z: 373 (M+1).

Example 116

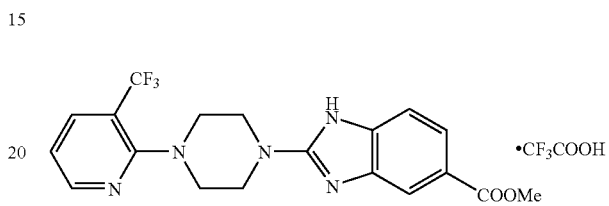

2-[4-(3-Trifluoromethyl-pyridin-2-yl)-piperazin-1-yl]-1H-benzoimidazole-5-carboxylic Acid Methyl Ester, Trifluoroacetic Acid Salt

(a) 2-Oxo-2,3-dihydro-1H-benzoimidazole-5-carboxylic Acid Methyl Ester

Methyl-3,4-diaminobenzoate (1.251 g, 7.5 mmol, Lancaster) was reacted with 1,1'-carbonyldiimidazole (2.128 g, 13.1 mmol, Aldrich) under the conditions of Example 1b to give the title compound as an amorphous solid. MS (ESI, pos. ion) m/z: 193 (M+1).

(b) 2-Chloro-1H-benzoimidazole-5-carboxylic Acid Methyl Ester

A solution of the dihydrobenzimidazol-2-one from step (a) above (263 mg, 1.4 mmol) was reacted under the conditions of Example 1c to give the title compound as an amorphous solid. MS (ESI, pos. ion) m/z: 211 (M+1).

(c) 2-[4-(3-Trifluoromethyl-pyridin-2-yl)-piperazin-1-yl]-1H-benzoimidazole-5-carboxylic Acid Methyl Ester, Trifluoroacetic Acid Salt A mixture of the chlorobenzimidazole from step (b) above (218 mg, 1.04 mmol), 1-(3-trifluoromethylpyridin-2-yl)piperazine (360 mg, 1.6 mmol, Fluorochem) and sodium bicarbonate (135 mg, 1.6 mmol) in isoamyl alcohol (2.2 mL) was reacted under the conditions of Example 114c to give the title compound as an amorphous solid. MS (ESI, pos. ion) m/z: 406 (M+1).

Example 117

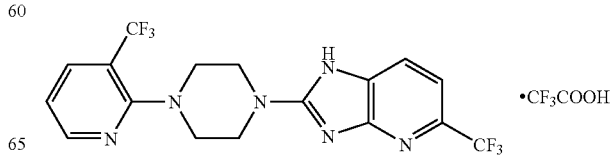

5-Trifluoromethyl-2-[4-(3-trifluoromethyl-pyridin-2-yl)-piperazin-1-yl]-1H-imidazo[4,5-b]pyridine, Trifluoroacetic Acid Salt (a) N²-(4-Methoxy-benzyl)-6-trifluoromethyl-pyridine-2,3-diamine A mixture of the 3-amino-2-chloro-6-(trifluoromethyl)pyridine (416 mg, 2.1 mmol, Matrix), 4-methoxy-benzylamine (294 mg, 2.1 mmol, Aldrich) and sodium bicarbonate (265 mg, 3.2 mmol) in isoamyl alcohol (0.6 mL) was heated at 220° C. in a microwave synthesizer for 30 min. The reaction mixture was then cooled to room temperature, diluted with MeOH (5 mL), filtered and the filtrate was evaporated in vacuo. The residue was purified by preparative HPLC (gradient 0.1% trifluoroacetic acid in acetonitrile) to give the title compound as a yellow oil. MS (ESI, pos. ion) m/z: 298 (M+1)

(b) 6-Trifluoromethyl-pyridine-2,3-diamine

A solution of N²-(4-methoxy-benzyl)-6-trifluoromethyl-pyridine-2,3-diamine from step (a) above (220 mg, 0.7 mmol) in 1:1 TFA/DCM (4 mL) was stirred at room temperature for 90 min. The reaction mixture was concentrated to yield a gummy residue, which was dissolved in MeOH (2 mL) and purified by preparative HPLC (gradient 0.1% trifluoroacetic acid in acetonitrile) to give the title compound as an amorphous solid. MS (ESI, pos. ion) m/z: 178 (M+1)

(c) 5-Trifluoromethyl-1,3-dihydro-imidazo[4,5-b]pyridin-2-one

A mixture of the pyridine-2,3-diamine (160 mg, 0.9 mmol) from step (b) above and N,N'-disuccinimidyl carbonate (250 mg, 0.9 mmol, Aldrich) in MeCN (5 mL) was stirred at room temperature for 13 h. Another batch of N,N'-disuccinimidyl carbonate (125 mg, 0.5 mmol, Aldrich) was added and the reaction mixture was heated at 75° C. for 90 min. The reaction mixture was cooled to room temperature and dichloromethane (20 mL) was added. The precipitate was filtered and dried under vacuo to give the title compound, which was used in the next step without additional purification. MS (ESI, pos. ion) m/z: 204 (M+1).

(d) 2-Chloro-5-trifluoromethyl-1H-imidazo[4,5-b]pyridine

The product from above step (c) above reacted with POCl₃ (1.5 mL) under the conditions of Example 1c to give the title compound as an amorphous solid. MS (ESI, pos. ion) m/z: 222 (M+1).

(e) 5-Trifluoromethyl-2-[4-(3-trifluoromethyl-pyridin-2-yl)-piperazin-1-yl]-1H-imidazo[4,5-b]pyridine, Trifluoroacetic Acid Salt A mixture of the chlorobenzimidazole from step (d) above (165 mg, 0.7 mmol), 1-(3-trifluoromethylpyridin-2-yl)piperazine (260 mg, 1.1 mmol, Fluorochem) and sodium bicarbonate (160 mg, 1.9 mmol) in isoamyl alcohol (2.3 mL) reacted under the conditions of Example 114c to give the title compound as an amorphous solid. MS (ESI, pos. ion) m/z: 417 (M+1).

Example 118

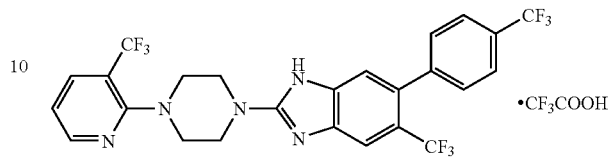

5-Trifluoromethyl-6-(4-trifluoromethyl-phenyl)-2-[4-(3-trifluoromethyl-pyridin-2-yl)-piperazin-1-yl]-1H-benzoimidazole, Trifluoroacetic Acid Salt A mixture of 6-bromo-5-trifluoromethyl-2-[4-(3-trifluoromethyl-pyridin-2-yl)-piperazin-1-yl]-1H-benzoimidazole (120 mg, 0.24 mmol, Example 89 g), 4-(trifluoromethyl)phenylboronic acid (60 mg, 0.32 mmol, Aldrich), tetrakis(triphenylphosphine)palladium(0) (28 mg, 0.02 mmol, Aldrich), sodium carbonate (0.25 mL, 2 M solution in water) in dioxane (1.75 mL) was heated to 170° C. in a microwave synthesizer for 20 min. The reaction mixture was cooled to room temperature, diluted with EtOAc (10 mL), filtered through a Varian Chem-Elut® (3 mL) diatomaceous earth cartridge and the filtrate was evaporated in vacuo. The residue was purified by preparative HPLC (gradient 0.1% trifluoroacetic acid in acetonitrile) to give the title compound as an amorphous solid. MS (ESI, pos. ion) m/z: 560 (M+1)

Example 119

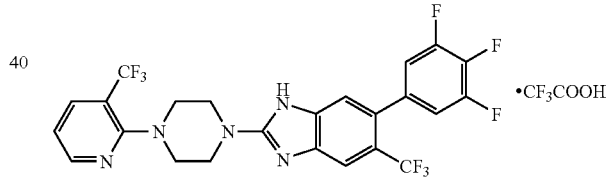

5-Trifluoromethyl-2-[4-(3-trifluoromethyl-pyridin-2-yl)-piperazin-1-yl]-6-(3,4,5-trifluoro-phenyl)-1H-benzoimidazole, Trifluoroacetic Acid Salt A mixture of 6-bromo-5-trifluoromethyl-2-[4-(3-trifluoromethyl-pyridin-2-yl)-piperazin-1-yl]-1H-benzoimidazole (150 mg, 0.3 mmol, Example 89 g), 3,4,5-trifluorophenylboronic acid (65 mg, 0.37 mmol, Aldrich) reacted under the conditions of Example 118 to give the title compound as an amorphous solid. MS (ESI, pos. ion) m/z: 546 (M+1).

Example 120

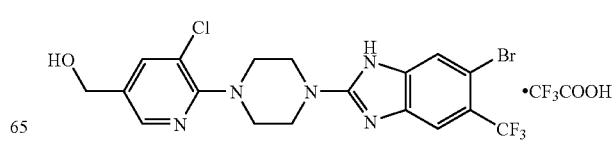

{6-[4-(6-Bromo-5-trifluoromethyl-1H-benzoimidazol-2-yl)-piperazin-1-yl]-5-chloro-pyridin-3-yl}-methanol, Trifluoroacetic Acid Salt A mixture of the 6-bromo-2-chloro-5-trifluoromethyl-1H-benzoimidazole (396 mg, 1.32 mmol, Example 89f), (5-chloro-6-piperazin-1-yl-pyridin-3-yl)-methanol (288 mg, 1.3 mmol, Example 60a) and sodium bicarbonate (249 mg, 2.96 mmol) in isoamyl alcohol (2.25 mL) was heated at 190° C. in a microwave synthesizer for 33 min. The reaction mixture was cooled to room temperature, diluted with MeOH (4 mL) and filtered. The filtrate was purified by preparative HPLC (gradient 0.1% trifluoroacetic acid in acetonitrile) to give the title compound as an amorphous solid. MS (ESI, pos. ion) m/z: 490 (M+1).

Example 121

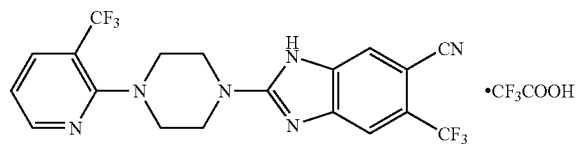

5-Trifluoromethyl-2-[4-(3-trifluoromethyl-pyridin-2-yl)-piperazin-1-yl]-1H-benzoimidazole-6-carbonitrile, Trifluoroacetic Acid Salt A mixture of 6-bromo-5-trifluoromethyl-2-[4-(3-trifluoromethyl-pyridin-2-yl)-piperazin-1-yl]-1H-benzoimidazole (123 mg, 0.25 mmol, Example 89 g) and cuprous cyanide (205 mg, 2.29 mmol), Aldrich) in N-methylpyrrolidinone (2 mL) was heated at 220° C. in a microwave synthesizer for 10 min. The reaction mixture was allowed to cool to room temperature, diluted with MeOH (5 mL) and filtered. The filtrate was purified by preparative HPLC (gradient 0.1% trifluoroacetic acid in acetonitrile) to give the title compound as an amorphous solid. MS (ESI, pos. ion) m/z: 441 (M+1)

Example 122

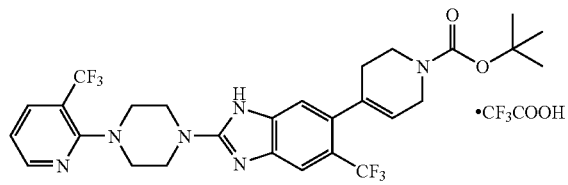

4-{5-Trifluoromethyl-2-[4-(3-trifluoromethyl-pyridin-2-yl)-piperazin-1-yl]-1H-benzoimidazol-6-yl}-3,6-dihydro-2H-pyridine-1-carboxylic Acid tert-butyl Ester, Trifluoroacetic Acid Salt 6-Bromo-5-trifluoromethyl-2-[4-(3-trifluoromethyl-pyridin-2-yl)-piperazin-1-yl]-1H-benzoimidazole (136 mg, 0.28 mmol, Example 89 g) and 4-(4,4,5,5-tetramethyl-[1,3,2]dioxaborolan-2-yl)-3,6-dihydro-2H-pyridine-1-carboxylic acid tert-butyl ester (99 mg, 0.32 mmol, Chemshop) reacted under the conditions of Example 118 to give the title compound as an amorphous solid. MS (ESI, pos. ion) m/z: 597 (M+1).

Example 123

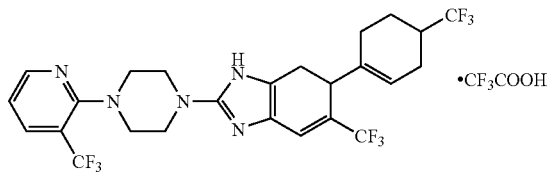

5-Trifluoromethyl-6-(4-trifluoromethyl-cyclohex-1-enyl)-2-[4-(3-trifluoromethyl-pyridin-2-yl)-piperazin-1-yl]-1H-benzoimidazole, Trifluoroacetic Acid Salt 6-Bromo-5-trifluoromethyl-2-[4-(3-trifluoromethyl-pyridin-2-yl)-piperazin-1-yl]-1H-benzoimidazole (91 mg, 0.18 mmol, Example 89 g) and 4,4,5,5-tetramethyl-2-(4-trifluoromethyl-cyclohex-1-enyl)-[1,3,2]dioxaborolane (73 mg, 0.26 mmol, Chemshop) reacted under the conditions of Example 118 to give the title compound as an amorphous solid. MS (ESI, pos. ion) m/z: 564 (M+1)

Example 124

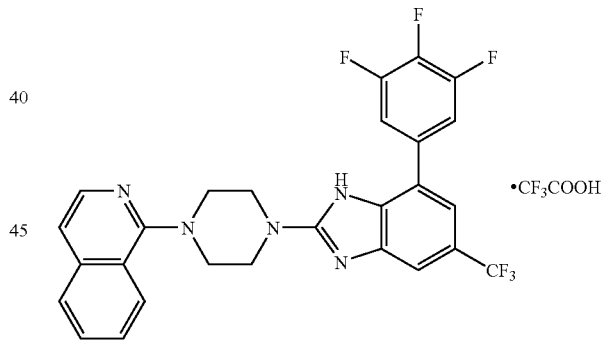

1-{4-[5-Trifluoromethyl-7-(3,4,5-trifluoro-phenyl)-1H-benzoimidazol-2-yl]-piperazin-1-yl}-isoquinoline, Trifluoroacetic Acid Salt A mixture of the 2-piperazin-1-yl-5-trifluoromethyl-7-(3,4,5-trifluoro-phenyl)-1H-benzoimidazole (79 mg, 0.20 mmol, Example 104a), 1-chloroisoquinoline (67 mg, 0.41 mmol, Lancaster) and sodium bicarbonate (25 mg, 0.30 mmol) in isoamyl alcohol (1.0 mL) was heated at 185° C. in a microwave synthesizer for 26 min. The reaction mixture was cooled to room temperature, diluted with MeOH (2 mL), filtered and the filtrate was purified by preparative HPLC (gradient 0.1% trifluoroacetic acid in acetonitrile) to give the title compound as an amorphous solid. MS (ESI, pos. ion) m/z: 528 (M+1).

Example 125

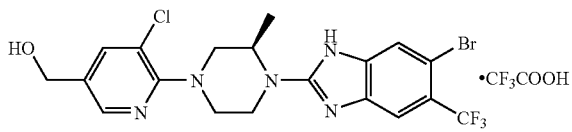

{6-[4-(6-Bromo-5-trifluoromethyl-1H-benzoimidazol-2-yl)-(3R)-3-methyl-piperazin-1-yl]-5-chloropyridin-3-yl}-methanol, Trifluoroacetic Acid Salt A mixture of 6-bromo-2-chloro-5-trifluoromethyl-1H-benzoimidazole (99 mg, 0.33 mmol, Example 89f), {5-chloro-6-[(3R)-3-methylpiperazin-1-yl)pyridin-3-yl}methanol (76 mg, 0.31 mmol, Example 62a) and N,N-diisopropylethylamine (67 mg, 0.52 mmol) in EtOH (0.8 mL) was heated at 180° C. in a microwave synthesizer for 30 min. The reaction mixture was cooled to room temperature, diluted with MeOH (2 mL) and purified by preparative HPLC (gradient 0.1% trifluoroacetic acid in acetonitrile) to give the title compound as an amorphous solid. MS (ESI, pos. ion) m/z: 504 (M+1)

Example 126

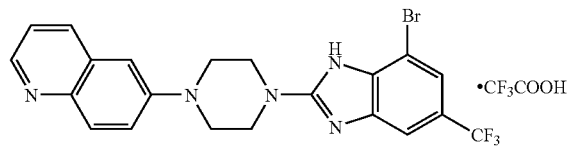

6-[4-(7-Bromo-5-trifluoromethyl-1H-benzoimidazol-2-yl)-piperazin-1-yl]-quinoline, Trifluoroacetic Acid Salt (a) 4-Quinolin-6-yl-piperazine-1-carboxylic Acid tert-butyl Ester A mixture of the 6-bromoquinoline (328 mg, 1.6 mmol, TCI America), 1-BOC-piperazine (340 mg, 1.8 mmol, Aldrich), tris(dibenzylideneacetone)dipalladium(0) (75 mg, 0.1 mmol, Strem), rac-2,2'-bis(diphenylphosphino)-1,1'-binaphthyl (91 mg, 0.15 mmol, Strem) and sodium-tert-butoxide (252 mg, 2.7 mmol, Aldrich) in toluene (4 mL) was heated at 150° C. in a microwave synthesizer for 13 min. The reaction mixture was cooled to room temperature, diluted with EtOAc (5 mL) and filtered through a Celite® pad. The filtrate was concentrated in vacuo and the residue was dissolved in MeOH (4 mL) and purified by preparative HPLC (gradient 0.1% trifluoroacetic acid in acetonitrile) to give the title compound as pale-yellow oil. MS (ESI, pos. ion) m/z: 314 (M+1).

(b) 6-piperazin-1-yl-quinoline, Trifluoroacetic Acid Salt

The product from the above step (a) above was treated with 1:1 TFA/DCM (15 mL) and stirred at room temperature for 12 h. The reaction mixture was concentrated to yield a gummy residue, which was dissolved in MeOH (4 mL) and purified by preparative HPLC (gradient 0.1% trifluoroacetic acid in acetonitrile) to give the title compound as an amorphous solid. MS (ESI, pos. ion) m/z: 214 (M+1).

(c) 6-[4-(7-Bromo-5-trifluoromethyl-1H-benzoimidazol-2-yl)-piperazin-1-yl]-quinoline, Trifluoroacetic Acid Salt A mixture of the 6-piperazin-1-yl-quinoline, trifluoroacetic acid salt from step (b) above (125 mg, 0.59 mmol), 7-bromo-2-chloro-5-trifluoromethyl-1H-benzoimidazole (225 mg, 0.75 mmol, Example 6b) and sodium bicarbonate (225 mg, 2.68 mmol) in isoamyl alcohol (2.5 mL) was heated at 180° C. in a microwave synthesizer for 30 min. The reaction mixture was cooled to room temperature, diluted with MeOH (2 mL) and filtered. The filtrate was purified by preparative HPLC (gradient 0.1% trifluoroacetic acid in acetonitrile) to give the title compound as an amorphous solid. MS (ESI, pos. ion) m/z: 476 (M+1).

Example 127

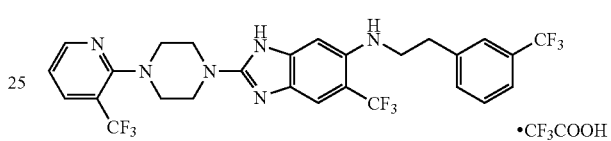

[2-(3-Trifluoromethyl-phenyl)-ethyl]-{6-trifluoromethyl-2-[4-(3-trifluoromethyl-pyridin-2-yl)-piperazin-1-yl]-3H-benzoimidazol-5-yl}-amine, Trifluoroacetic Acid Salt (a) 5-Bromo-6-trifluoromethyl-2-[4-(3-trifluoromethyl-pyridin-2-yl)-piperazin-1-yl]-1-(2-trimethylsilanyl-ethoxymethyl)-1H-benzoimidazole To a solution of 6-bromo-5-trifluoromethyl-2-[4-(3-trifluoromethyl-pyridin-2-yl)-piperazin-1-yl]-1H-benzoimidazole (203 mg, 0.41 mmol, Example 89 g) in dichloromethane (6 mL) was added N,N-diisopropylethylamine (148 mg, 1.15 mmol) followed by 2-(trimethylsilyl)ethoxymethyl chloride (94 mg, 0.57 mmol, Aldrich). The reaction mixture was stirred at room temperature for 16 h. The solvent was removed in vacuo and the residue was purified by silica gel column chromatography, eluting with EtOAc/hexane (1:3) to afford the title compound as an amorphous solid. MS (ESI, pos. ion) m/z: 624 (M+1).

(b) [2-(3-Trifluoromethyl-phenyl)-ethyl]-[6-trifluoromethyl-2-[4-(3-trifluoromethyl-pyridin-2-yl)-piperazin-1-yl]-1-(2-trimethylsilanyl-ethoxymethyl)-1H-benzoimidazol-5-yl]-amine A mixture of the product from step (a) above (88 mg, 0.14 mmol), 2-(3-trifluoromethylphenyl)ethylamine (45 mg, 0.24 mmol, Trans World Chemicals), tris(dibenzylideneacetone)dipalladium(0) (8 mg, 0.01 mmol, Strem), 2-(di-t-butylphosphino)biphenyl (8 mg, 0.03 mmol, Strem) and sodium-tert-butoxide (31 mg, 0.33 mmol, Aldrich) in toluene (2 mL) was heated at 150° C. in a microwave synthesizer for 14 min. The reaction mixture was cooled to room temperature, diluted with EtOAc (5 mL) and filtered through a Celite® pad. The filtrate was concentrated in vacuo and the residue dissolved in MeOH (4 mL), and purified by preparative HPLC (gradient 0.1% trifluoroacetic acid in acetonitrile) to give the title compound as pale-yellow oil. MS (ESI, pos. ion) m/z: 733 (M+1).

117

(c) [2-(3-Trifluoromethyl-phenyl)-ethyl]-{6-trifluoromethyl-2-[4-(3-trifluoromethyl-pyridin-2-yl)-piperazin-1-yl]-3H-benzoimidazol-5-yl}-amine, Trifluoroacetic Acid Salt The product from the above step (b) above was treated with 1:1 TFA/dichloromethane (3 mL) and stirred at room temperature for 12 h. The reaction mixture was concentrated to yield a gummy residue, which was dissolved in MeOH (4 mL) and purified by preparative HPLC (gradient 0.1% trifluoroacetic acid in acetonitrile) to give the title compound as a yellow amorphous solid. MS (ESI, pos. ion) m/z: 603 (M+1).

Example 128

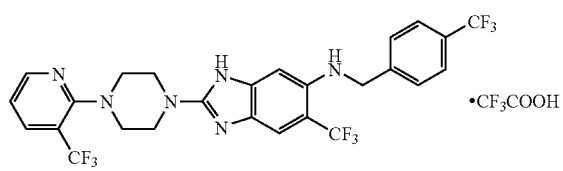

(4-Trifluoromethyl-benzyl)-{6-trifluoromethyl-2-[4-(3-trifluoromethyl-pyridin-2-yl)-piperazin-1-yl]-3H-benzoimidazol-5-yl}-amine, Trifluoroacetic Acid Salt (a) (4-Trifluoromethyl-benzyl)-[6-trifluoromethyl-2-[4-(3-trifluoromethyl-pyridin-2-yl)-piperazin-1-yl]-1-(2-trimethylsilanyl-ethoxymethyl)-1H-benzoimidazol-5-yl]-amine, Trifluoroacetic Acid Salt 5-Bromo-6-trifluoromethyl-2-[4-(3-trifluoromethyl-pyridin-2-yl)-piperazin-1-yl]-1-(2-trimethylsilanyl-ethoxymethyl)-1H-benzoimidazole (88 mg, 0.14 mmol, Example 127a) and 4-(trifluoromethyl)benzylamine (37 mg, 0.21 mmol, Aldrich) reacted under the conditions of Example 127b to give the title compound as pale-yellow oil. MS (ESI, pos. ion) m/z: 719 (M+1).

(b) (4-Trifluoromethyl-benzyl)-{6-trifluoromethyl-2-[4-(3-trifluoromethyl-pyridin-2-yl)-piperazin-1-yl]-3H-benzoimidazol-5-yl}-amine, Trifluoroacetic Acid Salt The product from step (a) above was treated with TFA/DCM (1:1) (3 mL) and stirred at room temperature for 12 h. The reaction mixture was concentrated to yield a gummy residue, which was dissolved in MeOH (4 mL) purified by preparative HPLC (gradient 0.1% trifluoroacetic acid in acetonitrile) to give the title compound as a yellow amorphous solid. MS (ESI, pos. ion) m/z: 589 (M+1).

Example 129

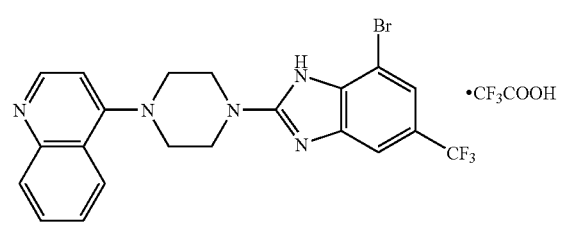

4-[4-(7-Bromo-5-trifluoromethyl-1H-benzoimidazol-2-yl)-piperazin-1-yl]-quinoline, Trifluoroacetic Acid Salt (a) 4-Quinolin-4-yl-piperazine-1-carboxylic Acid tert-butyl Ester, Trifluoroacetic Acid Salt A solution of 4-hydroxyquinoline (300 mg, 2.07 mmol, Aldrich) in DMF (3 mL) was treated with sodium hydride (69 mg, 2.88 mmol, Aldrich) and the resulting slurry was stirred at 45° C. for 30 min. The reaction mixture was cooled to room temperature, N-phenyltrifluoromethanesulfonimide (885 mg, 2.48 mmol, Aldrich) was added and the mixture was stirred for 48 h. 1-BOC-piperazine (775 mg, 4.16 mmol, Aldrich) was added to the mixture and the stirring was continued for another 24 h. The solvent was removed in vacuo and the residue was dissolved in MeOH (4 mL) and purified by preparative HPLC (gradient 0.1% trifluoroacetic acid in acetonitrile) to give the title compound as pale-yellow oil, which was used for the next step. MS (ESI, pos. ion) m/z: 314 (M+1).

(b) 4-piperazin-1-yl-quinoline, Trifluoroacetic Acid Salt

The product from the above step (a) was treated with 1:1 TFA/DCM (10 mL) and stirred at room temperature for 12 h. The reaction mixture was concentrated to yield a gummy residue, which was dissolved in MeOH (4 mL) and purified by preparative HPLC (gradient 0.1% trifluoroacetic acid in acetonitrile) to give the title compound as an amorphous solid. MS (ESI, pos. ion) m/z: 214 (M+1).

(c) 4-[4-(7-Bromo-5-trifluoromethyl-1H-benzoimidazol-2-yl)-piperazin-1-yl]-quinoline, Trifluoroacetic Acid Salt A mixture of the 4-piperazin-1-yl-quinoline from step (b) above (110 mg, 0.52 mmol), 7-bromo-2-chloro-5-trifluoromethyl-1H-benzoimidazole (178 mg, 0.59 mmol, Example 89f) and sodium bicarbonate (172 mg, 2.05 mmol) in isoamyl alcohol (2 mL) was heated at 180° C. in a microwave synthesizer for 30 min. The reaction mixture was cooled to room temperature, diluted with MeOH (3.5 mL), filtered and the filtrate was purified by preparative HPLC (gradient 0.1% trifluoroacetic acid in acetonitrile) to give the title compound as yellow oil. MS (ESI, pos. ion) m/z: 476 (M+1).

Example 130

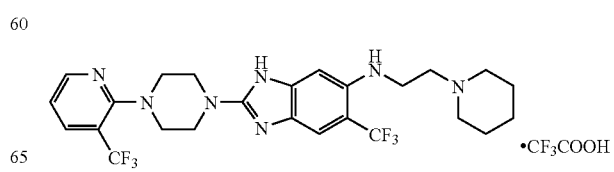

(2-Piperidin-1-yl-ethyl)-{6-trifluoromethyl-2-[4-(3-
trifluoromethyl-pyridin-2-yl)-piperazin-1-yl]-3H-
benzoimidazol-5-yl}-amine, Trifluoroacetic Acid
Salt (a) (2-Piperidin-1-yl-ethyl)-[6-trifluoromethyl-2-[4-
(3-trifluoromethyl-pyridin-2-yl)-piperazin-1-yl]-1-
(2-trimethylsilanyl-ethoxymethyl)-1H-benzoimida-
zol-5-yl]-amine, Trifluoroacetic Acid Salt 5-Bromo-6-trifluoromethyl-2-[4-(3-trifluoromethyl-pyridin-2-yl)-piperazin-1-yl]-1-(2-trimethylsilanyl-ethoxymethyl)-1H-benzoimidazole (99 mg, 0.16 mmol, Example 127a) reacted with 1-(2-aminoethyl)piperidine (36 mg, 0.28 mmol, Aldrich) under the conditions of Example 127b to give the title compound as pale-yellow oil, which was used for the next step. MS (ESI, pos. ion) m/z: 672 (M+1).

(b) (2-Piperidin-1-yl-ethyl)-{6-trifluoromethyl-2-[4-
(3-trifluoromethyl-pyridin-2-yl)-piperazin-1-yl]-3H-
benzoimidazol-5-yl}-amine, Trifluoroacetic Acid
Salt The product from step (a) above was treated with 1:1 TFA/dichloromethane (3 mL) and stirred at room temperature for 12 h. The reaction mixture was concentrated to yield a gummy residue, which was dissolved in MeOH (4 mL) and purified by preparative HPLC (gradient 0.1% trifluoroacetic acid in acetonitrile) to give the title compound as yellow oil. MS (ESI, pos. ion) m/z: 542 (M+1).

Example 131

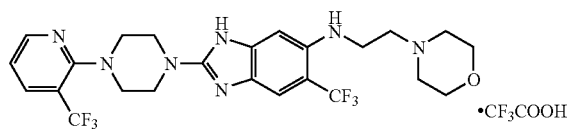

(2-Morpholin-4-yl-ethyl)-{6-trifluoromethyl-2-[4-(3-
trifluoromethyl-pyridin-2-yl)-piperazin-1-yl]-3H-
benzoimidazol-5-yl}-amine, Trifluoroacetic Acid
Salt (a) (2-Morpholin-4-yl-ethyl)-[6-trifluoromethyl-2-
[4-(3-trifluoromethyl-pyridin-2-yl)-piperazin-1-yl]-
1-(2-trimethylsilanyl-ethoxymethyl)-1H-benzoimi-
dazol-5-yl]-amine, Trifluoroacetic Acid Salt 5-Bromo-6-trifluoromethyl-2-[4-(3-trifluoromethyl-pyridin-2-yl)-piperazin-1-yl]-1-(2-trimethylsilanyl-ethoxymethyl)-1H-benzoimidazole (99 mg, 0.15 mmol, Example 127a) and 4-(2-aminoethyl) morpholine (60 mg, 0.46 mmol, Aldrich) reacted under the conditions of Example 127b to give the title compound as pale-yellow oil, which was used for the next step. MS (ESI, pos. ion) m/z: 674 (M+1).

(b) (2-Morpholin-4-yl-ethyl)-{6-trifluoromethyl-2-
[4-(3-trifluoromethyl-pyridin-2-yl)-piperazin-1-yl]-
3H-benzoimidazol-5-yl}-amine, Trifluoroacetic Acid
Salt The product from step (a) above was treated with TFA/DCM (1:1) (3 mL) and stirred at room temperature for 12 h. The reaction mixture was concentrated to yield a gummy residue, which was dissolved in MeOH (4 mL) and purified by preparative HPLC (gradient 0.1% trifluoroacetic acid in acetonitrile) to give the title compound as yellow oil. MS (ESI, pos. ion) m/z: 544 (M+1).

Example 132

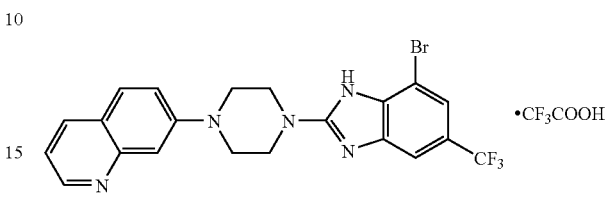

7-[4-(7-Bromo-5-trifluoromethyl-1H-benzoimidazol-
2-yl)-piperazin-1-yl]-quinoline, Trifluoroacetic Acid
Salt (a) Trifluoromethanesulfonic acid quinolin-7-yl ester,
Trifluoroacetic Acid Salt A solution of 7-hydroxyquinoline (324 mg, 2.23 mmol, Acros) in DMF (5 mL) was treated with sodium hydride (75 mg, 3.13 mmol, Aldrich) and the resulting slurry was stirred at 45° C. for 30 min. The reaction mixture was cooled to room temperature, N-phenyltrifluoromethanesulfonimide (955 mg, 2.67 mmol, Aldrich) was added, and the stirring was continued for 20 h. The reaction mixture quenched with MeOH (5 mL) and the solvent was removed in vacuo. The resulting gummy residue was dissolved in MeOH (3 mL) and purified by preparative HPLC (gradient 0.1% trifluoroacetic acid in acetonitrile) to give the title compound as yellow amorphous solid. MS (ESI, pos. ion) m/z: 278 (M+1).

(b) 4-Quinolin-7-yl-piperazine-1-carboxylic acid
tert-butyl Ester, Trifluoroacetic Acid Salt A mixture of the product from step (a) above (155 mg, 0.56 mmol), 1-BOC-piperazine (176 mg, 0.95 mmol, Aldrich), tris(dibenzylideneacetone)dipalladium(0) (34 mg, 0.04 mmol, Strem), 2-(di-t-butylphosphino)biphenyl (31 mg, 0.1 mmol, Strem) and sodium-tert-butoxide (77 mg, 0.8 mmol, Aldrich) in toluene (2 mL) was heated at 150° C. in a microwave synthesizer for 14 min. The reaction mixture was then cooled to room temperature, diluted with dichloromethane (5 mL) and filtered through a Celite®pad. The filtrate was concentrated in vacuo and the residue was dissolved in MeOH (4 mL), and purified by preparative HPLC (gradient 0.1% trifluoroacetic acid in acetonitrile) to give the title compound as yellow amorphous solid, which was used for the next step. MS (ESI, pos. ion) m/z: 314 (M+1).

(c) 7-piperazin-1-yl-quinoline, Trifluoroacetic Acid
Salt

The product from step (b) above was treated with 1:1 TFA/dichloromethane (5 mL) and stirred at room temperature for 12 h. The reaction mixture was concentrated to yield a gummy residue, which was dissolved in MeOH (4 mL) and purified by preparative HPLC (gradient 0.1% trifluoroacetic acid in acetonitrile) to give the title compound as an amorphous solid. MS (ESI, pos. ion) m/z: 214 (M+1).

(d) 7-[4-(7-Bromo-5-trifluoromethyl-1H-benzoimi-dazol-2-yl)-piperazin-1-yl]-quinoline, Trifluoroacetic Acid Salt A mixture of the 7-piperazin-1-yl-quinoline from step (c) above (75 mg, 0.35 mmol), 7-bromo-2-chloro-5-trifluoromethyl-1H-benzoimidazole (130 mg, 0.43 mmol, Example 6b) and sodium bicarbonate (141 mg, 1.7 mmol) in isoamyl alcohol (2 mL) was heated at 180° C. in a microwave synthesizer for 30 min. The reaction mixture was cooled to room temperature, diluted with MeOH (3.5 mL), filtered and the filtrate was purified by preparative HPLC (gradient 0.1% trifluoroacetic acid in acetonitrile) to give the title compound as yellow oil. MS (ESI, pos. ion) m/z: 476 (M+1).

Example 133

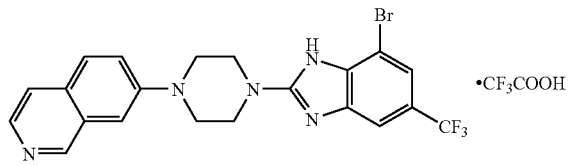

7-[4-(7-Bromo-5-trifluoromethyl-1H-benzoimidazol-2-yl)-piperazin-1-yl]-isoquinoline, Trifluoroacetic Acid Salt (a) Trifluoro-methanesulfonic acid isoquinolin-7-yl Ester 7-Hydroxyisoquinoline (331 mg, 2.28 mmol, Lancaster) was treated with sodium hydride (75 mg, 3.13 mmol, Aldrich) and N-phenyltrifluoromethanesulfonimide (960 mg, 2.69 mmol, Aldrich) under the conditions of Example 132a to give the title compound as an amorphous solid. MS (ESI, pos. ion) m/z: 278 (M+1).

(b) 4-Isoquinolin-7-yl-piperazine-1-carboxylic Acid tert-butyl Ester

The product from step (a) above (300 mg, 1.1 mmol) and 1-BOC-piperazine (307 mg, 1.6 mmol, Aldrich) was reacted under the conditions of Example 132b to give the title compound as yellow amorphous solid, which was used for the next step. MS (ESI, pos. ion) m/z: 314 (M+1).

(c) 7-piperazin-1-yl-isoquinoline, Trifluoroacetic Acid Salt

The product from step (b) above was treated with 1:1 TFA/dichloromethane (5 mL) and stirred at room temperature for 12 h. The reaction mixture was concentrated to yield a gummy residue, which was dissolved in MeOH (4 mL) and purified by preparative HPLC (gradient 0.1% trifluoroacetic acid in acetonitrile) to give the title compound as an amorphous solid. MS (ESI, pos. ion) m/z: 214 (M+1).

(d) 7-[4-(7-Bromo-5-trifluoromethyl-1H-benzoimi-dazol-2-yl)-piperazin-1-yl]-isoquinoline, Trifluoroacetic Acid Salt A mixture of the 7-piperazin-1-yl-isoquinoline from step (c) above (45 mg, 0.21 mmol) and 7-bromo-2-chloro-5-trifluoromethyl-1H-benzoimidazole (87 mg, 0.29 mmol, Example 6b) was reacted under the conditions of Example 132d to give the title compound as yellow oil. MS (ESI, pos. ion) m/z: 476 (M+1).

Example 134

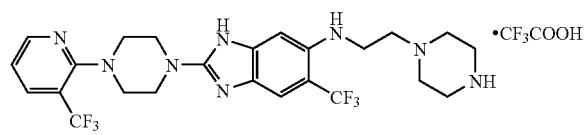

(2-piperazin-1-yl-ethyl)-{6-trifluoromethyl-2-[4-(3-trifluoromethyl-pyridin-2-yl)-piperazin-1-yl]-3H-benzoimidazol-5-yl}-amine, Trifluoroacetic Acid Salt (a) 4-{2-[6-Trifluoromethyl-2-[4-(3-trifluoromethyl-pyridin-2-yl)-piperazin-1-yl]-1-(2-trimethylsilanyl-ethoxymethyl)-1H-benzoimidazol-5-ylamino]-ethyl}-piperazine-1-carboxylic Acid tert-butyl Ester, Trifluoroacetic Acid Salt 5-Bromo-6-trifluoromethyl-2-[4-(3-trifluoromethyl-pyridin-2-yl)-piperazin-1-yl]-1-(2-trimethylsilanyl-ethoxymethyl)-1H-benzoimidazole (105 mg, 0.17 mmol, Example 127a) and 4-N-(2-aminoethyl)-1-N—BOC-piperazine (70 mg, 0.31 mmol, Aldrich) reacted under the conditions of Example 127b to give the title compound as pale-yellow oil, which was used for the next step. MS (ESI, pos. ion) m/z: 773 (M+1).

(b) (2-piperazin-1-yl-ethyl)-{6-trifluoromethyl-2-[4-(3-trifluoromethyl-pyridin-2-yl)-piperazin-1-yl]-3H-benzoimidazol-5-yl}-amine, Trifluoroacetic Acid Salt The product from step (a) above was treated with TFA/DCM (1:1) (3 mL) and stirred at room temperature for 12 h. The reaction mixture was concentrated to yield a gummy residue, which was dissolved in MeOH (4 mL) and purified by preparative HPLC (gradient 0.1% trifluoroacetic acid in acetonitrile) to give the title compound as an amorphous solid. MS (ESI, pos. ion) m/z: 543 (M+1).

Example 135

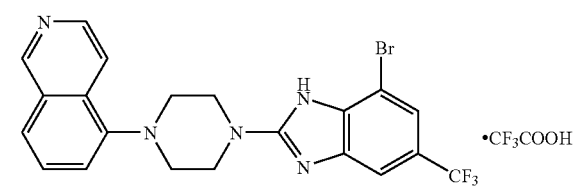

5-[4-(7-Bromo-5-trifluoromethyl-1H-benzoimidazol-2-yl)-piperazin-1-yl]-isoquinoline, Trifluoroacetic Acid Salt (a) Trifluoromethanesulfonic acid isoquinolin-5-yl Ester 5-Hydroxyisoquinoline (278 mg, 1.92 mmol, Aldrich) was treated with sodium hydride (60 mg, 2.5 mmol, Aldrich) and N-phenyltrifluoromethanesulfonimide (765 mg, 2.14 mmol, Aldrich) under the conditions of Example 132a to give the title compound as an amorphous solid. MS (ESI, pos. ion) m/z: 278 (M+1).

(b) 4-Isoquinolin-5-yl-piperazine-1-carboxylic Acid tert-butyl Ester

The product from step (a) above (209 mg, 0.75 mmol) and 1-BOC-piperazine (210 mg, 1.1 mmol, Aldrich) was reacted under the conditions of Example 132b to give the title compound as yellow amorphous solid, which was used for the next step. MS (ESI, pos. ion) m/z: 314 (M+1)

(c) 5-piperazin-1-yl-isoquinoline, Trifluoroacetic Acid Salt

The product from step (b) above was treated with 1:1 TFA/dichloromethane (5 mL) and stirred at room temperature for 12 h. The reaction mixture was concentrated to yield a gummy residue, which was dissolved in MeOH (2 mL) and purified by preparative HPLC (gradient 0.1% trifluoroacetic acid in acetonitrile) to give the title compound as an amorphous solid. MS (ESI, pos. ion) m/z: 214 (M+1).

(d) 5-[4-(7-Bromo-5-trifluoromethyl-1H-benzoimidazol-2-yl)-piperazin-1-yl]-isoquinoline, Trifluoroacetic Acid Salt A mixture of the 5-piperazin-1-yl-isoquinoline from step (c) above (23 mg, 0.1 mmol) and 7-bromo-2-chloro-5-trifluoromethyl-1H-benzoimidazole (36 mg, 0.12 mmol, Example 6b) was reacted under the conditions of Example 132d to give the title compound as yellow amorphous solid. MS (ESI, pos. ion) m/z: 476 (M+1).

Example 136

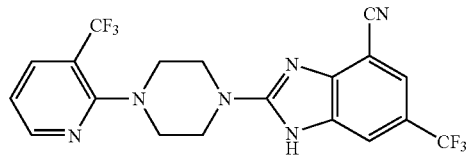

6-Trifluoromethyl-2-[4-(3-trifluoromethyl-pyridin-2-yl)-piperazin-1-yl]-1H-benzoimidazole-4-carbonitrile A mixture of 4-bromo-6-trifluoromethyl-2-[4-(3-trifluoromethyl-pyridin-2-yl)-piperazin-1-yl]-1H-benzoimidazole (100 mg, 0.2 mmol, Example 7) and cuprous cyanide (48 mg, 0.5 mmol), Aldrich) in N-methylpyrrolidinone (2 mL) was heated at 200° C. in a microwave synthesizer for 10 min. The reaction mixture was allowed to cool to room temperature, diluted with MeOH (5 mL) and filtered. The solvent was removed in vacuo, and the residue purified by silica gel column chromatography with 20% ethyl acetate/hexane as eluant to give the title compound as a brown oil. MS (ESI, pos. ion) m/z: 441.3 (M+1).

Example 137

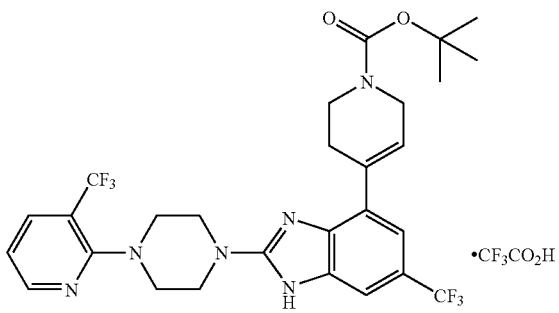

4-{6-Trifluoromethyl-2-[4-(3-trifluoromethyl-pyridin-2-yl)-piperazin-1-yl]-1H-benzoimidazol-4-yl}-3,6-dihydro-2H-pyridine-1-carboxylic Acid tert-butyl Ester, Trifluoroacetic Acid Salt 4-Bromo-6-trifluoromethyl-2-[4-(3-trifluoromethyl-pyridin-2-yl)-piperazin-1-yl]-1H-benzoimidazole (50 mg, 0.1 mmol) and 4-(4,4,5,5-tetramethyl-[1,3,2]dioxaborolan-2-yl)-3,6-dihydro-2H-pyridine-1-carboxylic acid tert-butyl ester (100 mg, 0.32 mmol, ChemShop) reacted under the conditions of Example 10 to provide the title compound. MS (ESI, pos. ion) m/z: 597 (M+1). M.p. 228.3-238.9° C. (decomp.).

Example 138

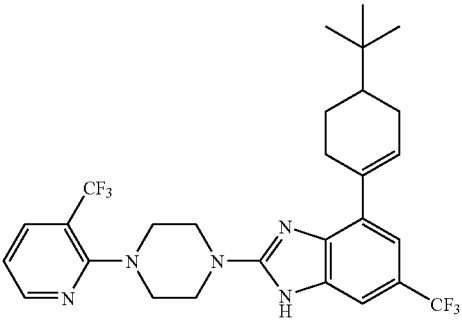

4-(4-tert-Butyl-cyclohex-1-enyl)-6-trifluoromethyl-2-[4-(3-trifluoromethyl-pyridin-2-yl)-piperazin-1-yl]-1H-benzoimidazole (a) Trifluoro-methanesulfonic acid 4-tert-butyl-cyclohex-1-enyl Ester To 4-tert-butylcyclohexanone (6.24 mmol, 40 mmol, Aldrich) in THF (100 mL) was added lithiumbistrimethylsilyl amide (40 mL, 1M solution in THF, Aldrich) over a period of 30 min with stirring at −78° C. After stirring for 1 hr at −78° C., a solution of N-phenyltrifluoromethanesulfonimide (14.28 g, 40 mmol, Aldrich) in THF (100 mL) was added over a period of 30 min. The reaction mixture was stirred at −78° C. for 2 h and slowly warmed to room temperature over a period of 6 h. The reaction mixture was extracted with EtOAc, the combined organic extracts were washed with water, dried over Na₂SO₄ and filtered. The filtrate was evaporated and the residue was purified by silica gel column chromatography (10% ethyl acetate/hexane) to give the title compound as an oil.

(b) 2-(4-tert-Butyl-cyclohex-1-enyl)-4,4,5,5-tetramethyl-[1,3,2]dioxaborolane

To a solution of the triflate from step (a) above in dioxane (100 mL) was added bisboronpinacolate (5.6 g, 22 mmol, Aldrich), potassium acetate (6 g, 61 mmol), PdCl₂(dppf) (315 mg, 0.6 mmol, Strem), dppf (332 mg, 0.6 mmol, Strem) and the contents were flushed with nitrogen. The reaction mixture was heated at 80° C. overnight. The solvents were removed in vacuo and the residue was extracted with EtOAc, and washed with water. The organic layer was separated, dried over Na₂SO₄ and filtered. The filtrate was evaporated and the residue was purified by silica gel column chromatography (10% ethyl acetate/hexane) to give the title compound as a white amorphous solid. MS (ESI, pos. ion) m/z: 265.2 (M+1).

(c) 4-(4-tert-Butyl-cyclohex-1-enyl)-6-trifluoromethyl-2-[4-(3-trifluoromethyl-pyridin-2-yl)-piperazin-1-yl]-1H-benzoimidazole 4-Bromo-6-trifluoromethyl-2-[4-(3-trifluoromethyl-pyridin-2-yl)-piperazin-1-yl]-1H-benzoimidazole (250 mg, 0.5 mmol, Example 7) and 2-(4-tert-butyl-cyclohex-1-enyl)-4,4,5,5-tetramethyl-[1,3,2]dioxaborolane from step (b) above (200 mg, 0.76 mmol) reacted under the conditions of Example 10 to give the title compound as a white solid. MS (ESI, pos. ion) m/z: 552 (M+1). M.p. 96-97.7° C.

Example 139

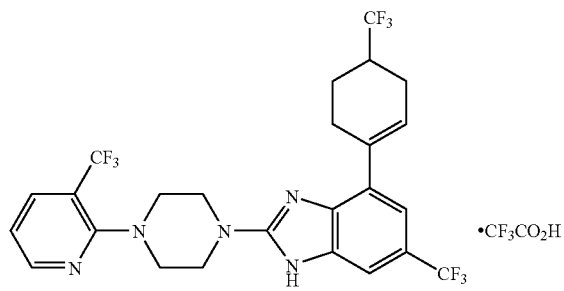

6-Trifluoromethyl-4-(4-trifluoromethyl-cyclohex-1-enyl)-2-[4-(3-trifluoromethyl-pyridin-2-yl)-piperazin-1-yl]-1H-benzoimidazole, Trifluoroacetic Acid Salt (a) 4,4,5,5-Tetramethyl-2-(4-trifluoromethyl-cyclohex-1-enyl)-[1,3,2]dioxaborolane 4-Trifluoromethylcyclohexanone (Matrix) reacted under the conditions of Example 138a to give the title compound. MS (ESI, pos. ion) m/z: 277.2 (M+1).

(b) 6-Trifluoromethyl-4-(4-trifluoromethyl-cyclohex-1-enyl)-2-[4-(3-trifluoromethyl-pyridin-2-yl)-piperazin-1-yl]-1H-benzoimidazole, Trifluoroacetic Acid Salt 4-Bromo-6-trifluoromethyl-2-[4-(3-trifluoromethyl-pyridin-2-yl)-piperazin-1-yl]-1H-benzoimidazole (100 mg, 0.5 mmol, Example 7) reacted with 4,4,5,5-tetramethyl-2-(4-trifluoromethyl-cyclohex-1-enyl)-[1,3,2]dioxaborolane from step (a) above (200 mg, 0.72 mmol) under the conditions of Example 10 to give the title compound as a white solid. MS (ESI, pos. ion) m/z: 564.4 (M+1). M.p. 213.4-217.3° C.

Example 140

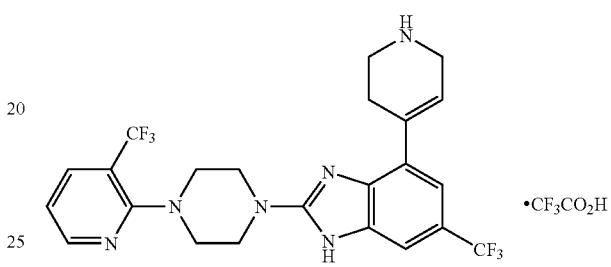

4-(1,2,3,6-Tetrahydro-pyridin-4-yl)-6-trifluoromethyl-2-[4-(3-trifluoromethyl-pyridin-2-yl)-piperazin-1-yl]-1H-benzoimidazole, Trifluoroacetic Acid Salt To 4-{6-trifluoromethyl-2-[4-(3-trifluoromethyl-pyridin-2-yl)-piperazin-1-yl]-1H-benzoimidazol-4-yl}-3,6-dihydro-2H-pyridine-1-carboxylic acid tert-butyl ester, trifluoroacetic acid salt (15 mg, Example 137) was added 1:1 mixture of TFA/dichloromethane (1 mL). The reaction mixture was allowed to stand at 25° C. for 4 h. The solvent was removed in vacuo and the residue was purified by preparative HPLC (gradient 0.1% trifluoroacetic acid in acetonitrile) to give the title compound as an oil. MS (ESI, pos. ion) m/z: 564.4 (M+1).

Example 141

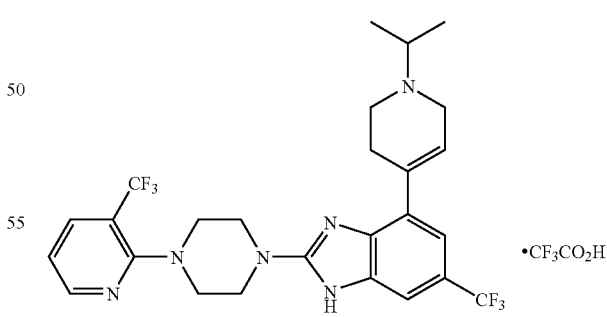

4-(1-Isopropyl-1,2,3,6-tetrahydro-pyridin-4-yl)-6-trifluoromethyl-2-[4-(3-trifluoromethyl-pyridin-2-yl)-piperazin-1-yl]-1H-benzoimidazole, Trifluoroacetic Acid Salt A mixture of 4-(1,2,3,6-tetrahydro-pyridin-4-yl)-6-trifluoromethyl-2-[4-(3-trifluoromethyl-pyridin-2-yl)-piperazin-1- yl]-1H-benzoimidazole, trifluoroacetic acid salt (400 mg, 0.8 mmol, Example 140), acetone (0.5 mL, 6.7 mmol) and 2 drops of glacial acetic acid in DMF (2 mL) was heated at 100° C. in a microwave synthesizer for 5 min. The reaction mixture was cooled to room temperature, triacetoxyborohydride (460 mg, 2.17 mmol, Aldrich) was added and the mixture was heated at 100° C. in a microwave synthesizer for 10 min. The reaction mixture was cooled to room temperature, diluted with EtOAc (100 mL) and washed with water. The organic layer was separated, dried over $Na_2SO_4$ and filtered. The filtrate was evaporated and the residue was purified by preparative HPLC (gradient 0.1% trifluoroacetic acid in acetonitrile) to give the title compound. MS (ESI, pos. ion) m/z: 539 (M+1).

Example 142

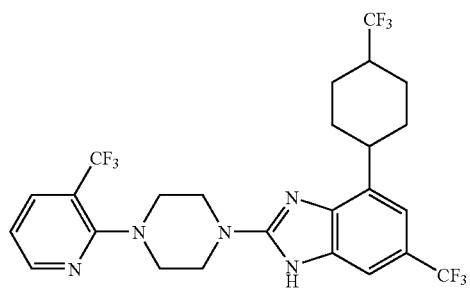

6-Trifluoromethyl-4-(4-trifluoromethyl-cyclohexyl)-2-[4-(3-trifluoromethyl-pyridin-2-yl)-piperazin-1-yl]-1H-benzoimidazole 6-Trifluoromethyl-4-(4-trifluoromethyl-cyclohex-1-enyl)-2-[4-(3-trifluoromethyl-pyridin-2-yl)-piperazin-1-yl]-1H-benzoimidazole (10 mg, Example 139b) was subjected to catalytic hydrogenation in ethanol (1 mL) using 10% Pd/C (10 mg, Aldrich) as catalyst. The reaction was conducted at room temperature under 1 atmosphere hydrogen for 2 days. The catalyst was filtered through a Celite®pad, the filter cake was washed with methanol and the filtrate was evaporated in vacuo to give the title compound as a film. MS (ESI, pos. ion) m/z: 565 (M+1).

Example 143

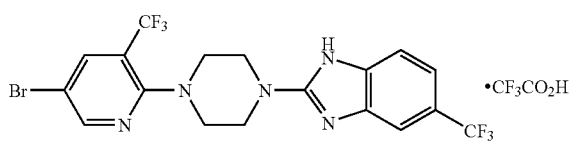

2-[4-(5-Bromo-3-trifluoromethyl-pyridin-2-yl)-piperazin-1-yl]-5-trifluoromethyl-1H-benzoimidazole, Trifluoroacetic Acid Salt (a) 1-(5-Bromo-3-trifluoromethyl-pyridin-2-yl)-piperazine To a suspension of 1-(3-trifluoromethyl-pyridin-2-yl)-piperazine (230 mg, 1 mmol, Oakwood Products) in dichloromethane (5 mL) was added a solution of bromine in dichloromethane (1.5 mL, 1 M, 1.5 mmol). The reaction mixture was stirred at 25° C. for 2 h. The precipitated yellow solid was filtered, washed with small amount of methanol and dried in vacuo to give the title compound as a yellow amorphous solid. MS (ESI, pos. ion) m/z: 311 (M+1).

(b) 2-[4-(5-Bromo-3-trifluoromethyl-pyridin-2-yl)-piperazin-1-yl]-5-trifluoromethyl-1H-benzoimidazole, Trifluoroacetic Acid Salt To a solution of 1-(5-bromo-3-trifluoromethyl-pyridin-2-yl)-piperazine from step (a) above (155 mg, 0.5 mmol) in isoamyl alcohol (2 mL) was added 7-bromo-2-chloro-5-trifluoromethyl-1H-benzoimidazole (100 mg, 0.43 mmol, ChemShop). The reaction mixture was heated at 180° C. in a microwave synthesizer for 5 min. The reaction mixture was cooled to room temperature and filtered. The filtrate was evaporated in vacuo and the residue was purified by preparative HPLC (gradient 0.1% trifluoroacetic acid in acetonitrile) to give the title compound as an oil. MS (ESI, pos. ion) m/z: 494 (M+1)

Example 144

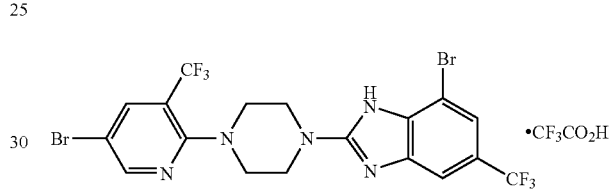

7-Bromo-2-[4-(5-bromo-3-trifluoromethyl-pyridin-2-yl)-piperazin-1-yl]-5-trifluoromethyl-1H-benzoimidazole, Trifluoroacetic Acid Salt 1-(5-Bromo-3-trifluoromethyl-pyridin-2-yl)-piperazine (78 mg, 0.25 mmol, Example 143a) and 4-bromo-2-chloro-6-trifluoromethyl-1H-benzoimidazole (75 mg, 0.25 mmol, Example 6b) reacted under the conditions of Example 143b to give the title compound as a white solid. MS (ESI, pos. ion) m/z: 574 (M+1). M.p. 174.2-175.1° C.

Example 145

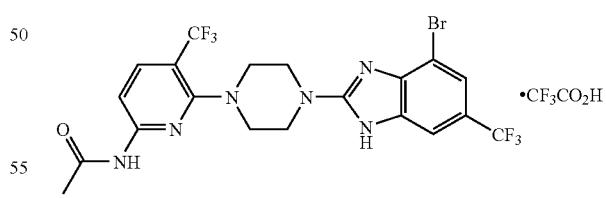

N-{6-[4-(4-Bromo-6-trifluoromethyl-1H-benzoimidazol-2-yl)-piperazin-1-yl]-5-trifluoromethyl-pyridin-2-yl}-acetamide, Trifluoroacetic Acid Salt (a) (6-Chloro-5-trifluoromethyl-pyridin-2-yl)-(4-methoxy-benzyl)-amine, Trifluoroacetic Acid Salt A suspension of 2,6-dichloro-3-trifluoromethylpyridine (1.08 gm, 5 mmol, Lancaster), 4-methoxybenzyl amine (700 mg, 5 mmol, Aldrich) and sodium bicarbonate (430 mg, 5 mmol) in isoamyl alcohol (5 mL) was heated at 150° C. in a microwave synthesizer for 15 min. The reaction mixture was allowed to cool to room temperature, diluted with MeOH (10 mL) and filtered. The filtrate was evaporated in vacuo and the residue was purified by preparative HPLC (gradient 0.1% trifluoroacetic acid in acetonitrile) to provide the title compound as a colorless oil. MS (ESI, pos. ion) m/z: 317 (M+1).

(b) N-(6-Chloro-5-trifluoromethyl-pyridin-2-yl)-N-(4-methoxy-benzyl)-acetamide, Trifluoroacetic Acid Salt To the 4-methoxybenzylamine from step (a) above (200 mg, 0.63 mmol) was added acetic anhydride (2 mL). The reaction mixture was heated at 200° C. in a microwave synthesizer for 30 min. The reaction mixture was cooled to room temperature and evaporated in vacuo. The residue was purified by preparative HPLC (gradient 0.1% trifluoroacetic acid in acetonitrile) to provide the title compound as a colorless solid. MS (ESI, pos. ion) m/z: 359 (M+1).

(c) N-(4-Methoxy-benzyl)-N-(6-piperazin-1-yl-5-trifluoromethyl-pyridin-2-yl)-acetamide, Trifluoroacetic Acid Salt To a solution of N-(6-chloro-5-trifluoromethyl-pyridin-2-yl)-N-(4-methoxy-benzyl)-acetamide from step (b) above (145 mg, 0.40 mmol) in N-methylpyrrolidinone (2 mL) was added piperazine (130 mg, 1.5 mmol). The reaction mixture was heated at 220° C. in a microwave synthesizer for 30 min. The reaction mixture was cooled to room temperature, filtered, and the filtrate evaporated in vacuo. The residue was purified by preparative HPLC (gradient 0.1% trifluoroacetic acid in acetonitrile) to provide the title compound as a white amorphous solid. MS (ESI, pos. ion) m/z: 409 (M+1).

(d) N-{6-[4-(4-Bromo-6-trifluoromethyl-1H-benzoimidazol-2-yl)-piperazin-1-yl]-5-trifluoromethyl-pyridin-2-yl}-N-(4-methoxy-benzyl)-acetamide, Trifluoroacetic Acid Salt A mixture of N-(4-methoxy-benzyl)-N-(6-piperazin-1-yl-5-trifluoromethyl-pyridin-2-yl)-acetamide from step (c) above (50 mg, 0.12 mmol) and 4-bromo-2-chloro-6-trifluoromethyl-1H-benzoimidazole (60 mg, 0.19 mmol, Example 6b) in isoamyl alcohol (0.5 mL) was heated at 180° C. in a microwave synthesizer for 20 min. The reaction mixture was cooled to room temperature and filtered. The filtrate was evaporated in vacuo and the residue was purified by preparative HPLC (gradient 0.1% trifluoroacetic acid in acetonitrile) to give the title compound as a colorless solid. MS (ESI, pos. ion) m/z: 671 (M+1).

(e) N-{6-[4-(4-Bromo-6-trifluoromethyl-1H-benzoimidazol-2-yl)-piperazin-1-yl]-5-trifluoromethyl-pyridin-2-yl}-acetamide, Trifluoroacetic Acid Salt N-{6-[4-(4-Bromo-6-trifluoromethyl-1H-benzoimidazol-2-yl)-piperazin-1-yl]-5-trifluoromethyl-pyridin-2-yl}-N-(4-methoxy-benzyl)-acetamide from step (d) above (20 mg, 0.03 mmol) was treated with trifluoroacetic acid (0.5 mL) at room temperature overnight. The reaction mixture was evaporated in vacuo and the residue was purified by preparative HPLC (gradient 0.1% trifluoroacetic acid in acetonitrile) to give the title compound as a colorless film. MS (ESI, pos. ion) m/z: 551 (M+1).

Example 146

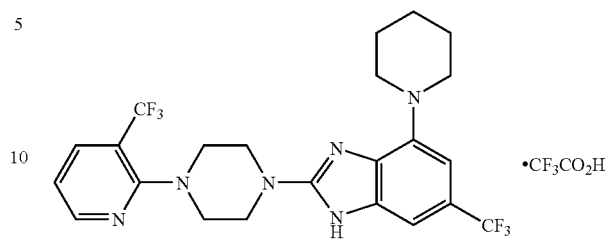

4-Piperidin-1-yl-6-trifluoromethyl-2-[4-(3-trifluoromethyl-pyridin-2-yl)-piperazin-1-yl]-1H-benzoimidazole, Trifluoroacetic Acid Salt (a) 4-Bromo-6-trifluoromethyl-2-[4-(3-trifluoromethyl-pyridin-2-yl)-piperazin-1-yl]-1-(2-trimethylsilanyl-ethoxymethyl)-1H-benzoimidazole 4-Bromo-6-trifluoromethyl-2-[4-(3-trifluoromethyl-pyridin-2-yl)-piperazin-1-yl]-1H-benzoimidazole (2 g, 4 mmol, Example 7) in $CH_2Cl_2$ (20 mL) reacted with 2-(trimethylsilyl)ethoxymethyl chloride (660 mg, 4 mmol, Aldrich) under the conditions of Example 127a to give the title compound as a light-brown oil. MS (ESI, pos. ion) m/z: 564.4 (M+1).

(b) 4-Piperidin-1-yl-6-trifluoromethyl-2-[4-(3-trifluoromethyl-pyridin-2-yl)-piperazin-1-yl]-1-(2-trimethylsilanyl-ethoxymethyl)-1H-benzoimidazole 4-Bromo-6-trifluoromethyl-2-[4-(3-trifluoromethyl-pyridin-2-yl)-piperazin-1-yl]-1-(2-trimethylsilanyl-ethoxymethyl)-1H-benzoimidazole from step (a) above (160 mg, 0.26 mmol) and piperidine (84 mg, 1 mmol) reacted under the conditions of Example 127b to give the title compound as an oil. MS (ESI, pos. ion) m/z: 629 (M+1).

(c) 4-Piperidin-1-yl-6-trifluoromethyl-2-[4-(3-trifluoromethyl-pyridin-2-yl)-piperazin-1-yl]-1H-benzoimidazole, Trifluoroacetic Acid Salt To a solution of 4-piperidin-1-yl-6-trifluoromethyl-2-[4-(3-trifluoromethyl-pyridin-2-yl)-piperazin-1-yl]-1-(2-trimethylsilanyl-ethoxymethyl)-1H-benzoimidazole from step (b) above (30 mg, 0.047 mmol)) in $CH_2Cl_2$ (1 mL) was added trifluoroacetic acid (0.5 mL). The reaction mixture was allowed to stand at room temperature for 8 h. The solvent was removed in vacuo and the residue was purified by preparative HPLC (gradient 0.1% trifluoroacetic acid in acetonitrile) to provide the title compound as a colorless film. MS (ESI, pos. ion) m/z: 499 (M+1).

Example 147

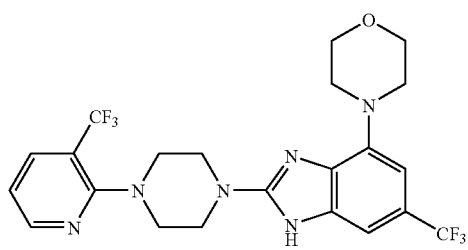

4-Morpholin-4-yl-6-trifluoromethyl-2-[4-(3-trifluoromethyl-pyridin-2-yl)-piperazin-1-yl]-1H-benzoimidazole (a) 4-Morpholin-1-yl-6-trifluoromethyl-2-[4-(3-trifluoromethyl-pyridin-2-yl)-piperazin-1-yl]-1-(2-trimethylsilanyl-ethoxymethyl)-1H-benzoimidazole 4-Bromo-6-trifluoromethyl-2-[4-(3-trifluoromethyl-pyridin-2-yl)-piperazin-1-yl]-1-(2-trimethylsilanyl-ethoxymethyl)-1H-benzoimidazole from Example 146a reacted with morpholine under the conditions of Example 127b to give the title compound.

(b) 4-Morpholin-4-yl-6-trifluoromethyl-2-[4-(3-trifluoromethyl-pyridin-2-yl)-piperazin-1-yl]-1H-benzoimidazole 4-Morpholin-1-yl-6-trifluoromethyl-2-[4-(3-trifluoromethyl-pyridin-2-yl)-piperazin-1-yl]-1-(2-trimethylsilanyl-ethoxymethyl)-1H-benzoimidazole from step (a) above reacted with trifluoroacetic acid under the conditions of Example 146c to give the title compound. MS (ESI, pos. ion) m/z: 501 (M+1).

Example 148

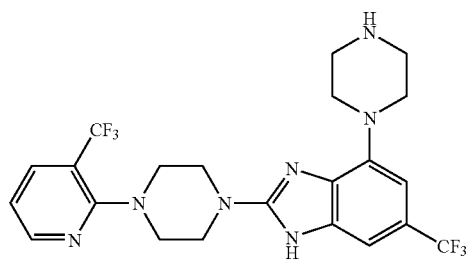

4-piperazin-1-yl-6-trifluoromethyl-2-[4-(3-trifluoromethyl-pyridin-2-yl)-piperazin-1-yl]-1H-benzoimidazole (a) 4-{6-Trifluoromethyl-2-[4-(3-trifluoromethyl-pyridin-2-yl)-piperazin-1-yl]-1H-benzoimidazol-4-yl}-piperazine-1-carboxylic Acid tert-butyl Ester 4-Bromo-6-trifluoromethyl-2-[4-(3-trifluoromethyl-pyridin-2-yl)-piperazin-1-yl]-1-(2-trimethylsilanyl-ethoxymethyl)-1H-benzoimidazole from Example 146a reacted with piperazine-1-carboxylic acid tert-butyl ester under the conditions of Example 127b to give the title compound.

(b) 4-piperazin-1-yl-6-trifluoromethyl-2-[4-(3-trifluoromethyl-pyridin-2-yl)-piperazin-1-yl]-1H-benzoimidazole 4-{6-Trifluoromethyl-2-[4-(3-trifluoromethyl-pyridin-2-yl)-piperazin-1-yl]-1H-benzoimidazol-4-yl}-piperazine-1-carboxylic acid tert-butyl ester from step (a) above reacted with trifluoroacetic acid under the conditions of Example 146c to give the title compound. MS (ESI, pos. ion) m/z: 500 (M+1).

Example 149

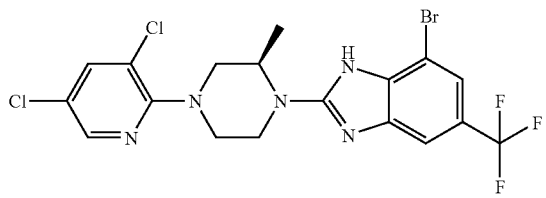

4-Bromo-2-[(2R)-4-(3,5-dichloro-pyridin-2-yl)-2-methyl-piperazin-1-yl]-6-trifluoromethyl-1H-benzoimidazole (a) (3R)-1-(3,5-Dichloro-pyridin-2-yl)-3-methyl-piperazine 2,3,5-Trichloro-pyridine (910 mg, 5.0 mmol, Aldrich) and (R)-(−)-2-methyl-piperazine (700 mg, 7.0 mmol, Aldrich) reacted under the conditions of Example 3a to give the title compound as a light-yellow solid. MS (ESI, pos. ion) m/z: 247 (M+1).

(b) 4-Bromo-2-[(2R)-4-(3,5-dichloro-pyridin-2-yl)-2-methyl-piperazin-1-yl]-6 trifluoromethyl-1H-benzoimidazole A mixture of the piperazine from step (a) above (148 mg, 0.6 mmol) and 7-bromo-2-chloro-5-trifluoromethyl-1H-benzoimidazole (150 mg, 0.5 mmol, Example 6b) in dioxane (2 mL) reacted under the conditions of Example 3c to give the title compound. Mp: 135-137° C. MS (ESI, pos. ion) m/z: 510 (M+1)

Example 150

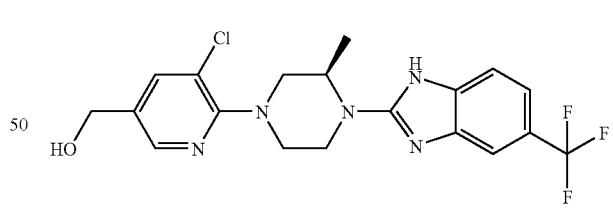

{5-Chloro-6-[(3R)-3-methyl-4-(5-trifluoromethyl-1H-benzoimidazol-2-yl)-piperazin-1-yl]-pyridin-3-yl}-methanol (a) {5-Chloro-6-[(3R)-3-methyl-piperazin-1-yl]-pyridin-3-yl}-methanol A mixture of (5,6-dichloro-pyridin-3-yl)-methanol (356 mg, 2.0 mmol, Aldrich) and (R)-(−)-2-methyl-piperazine (240 mg, 2.4 mmol, Aldrich reacted under the conditions of Example 3a to give the title compound. MS (ESI, pos. ion) m/z: 242 (M+1).

(b) {5-Chloro-6-[(3R)-3-methyl-4-(5-trifluoromethyl-1H-benzoimidazol-2-yl)-piperazin-1-yl]-pyridin-3-yl}-methanol A mixture of {5-chloro-6-[(3R)-3-methyl-piperazin-1-yl]-pyridin-3-yl}-methanol from step (a) above (96 mg, 0.4 mmol) and 2-chloro-6-trifluoromethyl-1H-benzoimidazole (71 mg, 0.32 mmol, Example 1c) in dioxane (2 mL) reacted under the conditions of Example 3c to give the title compound. MS (ESI, pos. ion) m/z: 426 (M+1).

Example 151

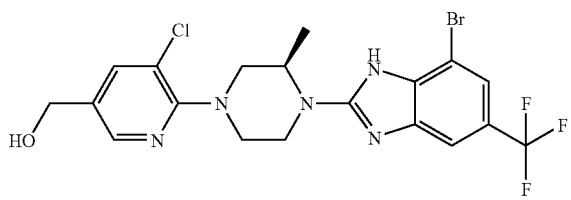

{6-[(3R)-4-(7-Bromo-5-trifluoromethyl-1H-benzoimidazol-2-yl)-3-methyl-piperazin-1-yl]-5-chloro-pyridin-3-yl}-methanol A mixture of 7-bromo-2-chloro-5-trifluoromethyl-1H-benzoimidazole (96 mg, 0.32 mmol, Example 6b) and {5-chloro-6-[(3R)-3-methyl-piperazin-1-yl]-pyridin-3-yl}-methanol (96 mg, 0.4 mmol, Example 150a) in dioxane (2 mL) reacted under the conditions of Example 3c to give the title compound. MS (ESI, pos. ion) m/z: 506 (M+1).

Example 152

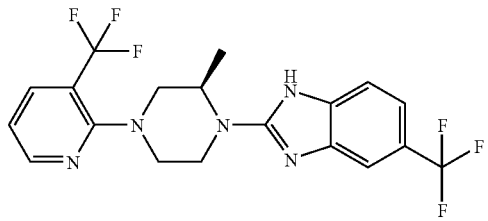

2-[(2R)-2-Methyl-4-(3-trifluoromethyl-pyridin-2-yl)-piperazin-1-yl]-5-trifluoromethyl-1H-benzoimidazole A mixture of 2-chloro-6-trifluoromethyl-1H-benzoimidazole (176 mg, 0.8 mmol, Example 1c) and (3R)-3-methyl-1-(3-trifluoromethyl-pyridin-2-yl)-piperazine (245 mg, 1.0 mmol, Example 79a) in dioxane (2 mL) reacted under the conditions of Example 3c to give the title compound. MS (ESI, pos. ion) m/z: 430 (M+1).

Example 153

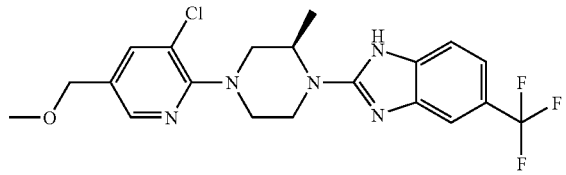

2-[(2R)-4-(3-Chloro-5-methoxymethyl-pyridin-2-yl)-2-methyl-piperazin-1-yl]-5-trifluoromethyl-1H-benzoimidazole

(a) 2,3-Dichloro-5-methoxymethyl-pyridine

To a solution of (5,6-dichloro-pyridin-3-yl)-methanol (356 mg, 2.0 mmol, Aldrich) and iodomethane (0.25 mL, 4.0 mmol, Aldrich) in DMF (3.0 mL) was added NaH (120 mg, 3.0 mmol, Aldrich, 60% dispersion in mineral oil) portionwise with stirring at room temperature. The mixture was stirred for 30 min at room temperature, saturated aqueous solution of NH$_4$Cl (10 mL) was added, and the mixture was extracted with EtOAc (2×30 mL). The combined organic phases were washed with water (5 mL) and brine (5 mL), dried over Na$_2$SO$_4$, and filtered. The solvent was removed in vacuo and the residue was purified by silica gel column chromatography, eluting with 20% EtOAc/hexane to give the title compound. MS (ESI, pos. ion) m/z: 192 (M+1).

(b) (3R)-1-(3-Chloro-5-methoxymethyl-pyridin-2-yl)-3-methyl-piperazine

A mixture of 2,3-dichloro-5-methoxymethyl-pyridine from step (a) above (370 mg, 1.93 mmol) and (R)-(−)-2-methyl-piperazine (231 mg, 2.3 mmol, Aldrich) reacted under the condition of Example 3a to give the title compound. MS (ESI, pos. ion) m/z: 256 (M+1).

(c) 2-[(2R)-4-(3-Chloro-5-methoxymethyl-pyridin-2-yl)-2-methyl-piperazin-1-yl]-5-trifluoromethyl-1H-benzoimidazole A mixture of (3R)-1-(3-chloro-5-methoxymethyl-pyridin-2-yl)-3-methyl-piperazine from step (b) above (153 mg, 0.6 mmol) and 2-chloro-6-trifluoromethyl-1H-benzoimidazole (153 mg, 0.48 mmol, Example 1c) in dioxane (2 mL) reacted under the conditions of Example 3c to give the title compound. MS (ESI, pos. ion) m/z: 440 (M+1).

Example 154

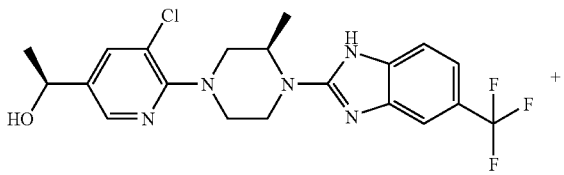

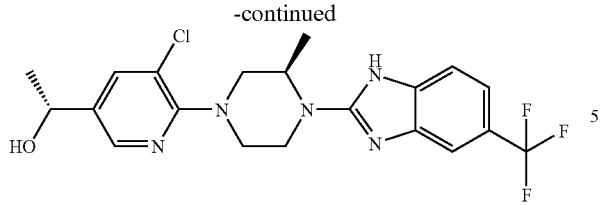

(1S)-1-{5-Chloro-6-[(3R)-3-methyl-4-(5-trifluoromethyl-1H-benzoimidazol-2-yl)-piperazin-1-yl]-pyridin-3-yl}-ethanol and (1R)-1-{5-Chloro-6-[(3R)-3-methyl-4-(5-trifluoromethyl-1H-benzoimidazol-2-yl)-piperazin-1-yl]-pyridin-3-yl}-ethanol (a) 5,6-Dichloro-pyridine-3-carbaldehyde A mixture of (5,6-dichloro-pyridin-3-yl)-methanol (1.78 g, 10 mmol, TCI-US) and $MnO_2$ (17.39 g, 200 mmol, Aldrich) in 1:1 $CH_2Cl_2$/hexane (10 mL) was stirred at room temperature for 1 h. The catalyst was filtered and washed with 50% EtOAc/hexane. The filtrate was evaporated and the residue dried in vacuo to give the title compound product, which was used in the next step without additional purification. MS (ESI, pos. ion) m/z: 176 (M+1).

(b) (1S,1R)-1-(5,6-Dichloro-pyridin-3-yl)-ethanol

MeMgBr (2.5 mL, 7.5 mmol, 3.0 M in ether, Aldrich) was added dropwise to a solution of 5,6-dichloro-pyridine-3-carbaldehyde from step (a) above (880 mg, 5.0 mmol) in THF (20 mL, Aldrich) with stirring at 0° C. The mixture was stirred at 0° C. for 30 min, saturated aqueous solution of $NH_4Cl$ (20 mL) was added, and the mixture was extracted with EtOAc (2×40 mL). The combined organic extracts were washed with brine (20 mL), dried over $Na_2SO_4$ and filtered. The filtrate was concentrated in vacuo and the residue was purified by silica gel column chromatography, eluting with 40% EtOAc/hexane to give the title compound. MS (ESI, pos. ion) m/z: 192 (M+1).

(c) (1S)-1-[5-Chloro-6-[(3R)-3-methyl-piperazin-1-yl]-pyridin-3-yl]-ethanol and (1R)-1-[5-Chloro-6-[(3R)-3-methyl-piperazin-1-yl]-pyridin-3-yl]-ethanol 1-(5,6-Dichloro-pyridin-3-yl)-ethanol from step (b) above (192 mg, 1.0 mmol) and (R)-(−)-2-methyl-piperazine (110 mg, 1.1 mmol, Aldrich) reacted under the conditions of Example 3a to give the title compound as a mixture of diastereoisomers. MS (ESI, pos. ion) m/z: 256 (M+1).

(d) (1S)-1-{5-Chloro-6-[(3R)-3-methyl-4-(5-trifluoromethyl-1H-benzoimidazol-2-yl)-piperazin-1-yl]-pyridin-3-yl}-ethanol and (1R)-1-{5-Chloro-6-[(3R)-3-methyl-4-(5-trifluoromethyl-1H-benzoimidazol-2-yl)-piperazin-1-yl]-pyridin-3-yl}-ethanol The diastereoisomeric mixture from step (c) above (128 mg, 0.5 mmol) and 2-chloro-6-trifluoromethyl-1H-benzoimidazole (88 mg, 0.4 mmol, Example 1c) in ethanol (2 mL) reacted under the conditions of Example 3c to give the title compound as a mixture of diastereoisomers. MS (ESI, pos. ion) m/z: 440 (M+1).

Example 155

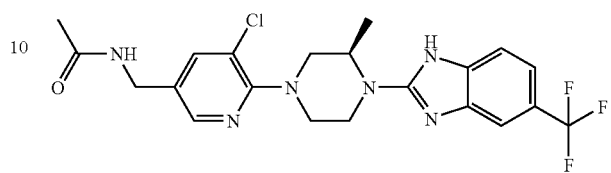

N-{5-Chloro-6-[(3R)-3-methyl-4-(5-trifluoromethyl-1H-benzoimidazol-2-yl)-piperazin-1-yl]-pyridin-3-ylmethyl}-acetamide (a) 5-Bromomethyl-2,3-dichloro-pyridine $CBr_4$ (497 mg, 1.5 mmol, Aldrich) was added portionwise to a solution of (5,6-dichloro-pyridin-3-yl)-methanol (178 mg, 1.0 mmol, TCI-US) and $PPh_3$ (393 mg, 1.5 mmol, Aldrich) in $CH_3CN$ (3 mL) with stirring at room temperature. The mixture was stirred at room temperature for 30 min, the solvent was removed in vacuo and the residue was purified by silica gel column chromatography, eluting with 10% EtOAc/hexane to give the title compound. MS (ESI, pos. ion) m/z: 242 (M+1).

(b) 2-(5,6-Dichloro-pyridin-3-ylmethyl)-isoindole-1,3-dione

A mixture of 5-bromomethyl-2,3-dichloro-pyridine from step (a) above (121 mg, 0.5 mmol) and potassium phthalimide (139 mg, 0.75 mmol, Aldrich) in DMF (1 mL) was stirred at room temperature for 30 min. Water (5 mL) was added and the mixture was extracted with EtOAc (2×20 mL). The combined organic extracts were washed with water (5 mL) and brine (5 mL), dried over $Na_2SO_4$, and filtered. The filtrate was evaporated in vacuo and the residue was suspended in 20% EtOAc/hexane, and filtered. The solid was washed with 20% EtOAc/hexane and dried in vacuo to give the title compound. MS (ESI, pos. ion) m/z: 307 (M+1).

(c) (5,6-Dichloro-pyridin-3-ylmethyl)methylamine

A mixture of 2-(5,6-dichloro-pyridin-3-ylmethyl)-isoindole-1,3-dione from step (b) above (307 mg, 1.0 mmol) and methylamine (1.0 mL, 2.0 mmoL, 2.0 M in THF, Aldrich) in EtOH (10 mL) was stirred at room temperature for 4 days. The solvent was removed in vacuo to give the title compound, which was used in the next step without additional purification.

(d) N-(5,6-Dichloro-pyridin-3-ylmethyl)-acetamide

To a mixture of the amine from step (c) above (1.77 g, 10 mmol) and $Et_3N$ (2.78 mL, 20 mmol, Aldrich) was added $Ac_2O$ dropwise with stirring at room temperature. The mixture was stirred for 30 min at room temperature, diluted with EtOAc (30 mL), washed with water (20 mL) and brine (20 mL), dried over $Na_2SO_4$, and filtered. The filtrate was evaporated in vacuo and the residue was purified by silica gel column chromatography, eluting with 80% EtOAc/hexane to give the title compound. MS (ESI, pos. ion) m/z: 219 (M+1).

(e) N-{5-Chloro-6-[(3R)-3-methyl-piperazin-1-yl]-pyridin-3-ylmethyl}-acetamide

A mixture of N-(5,6-dichloro-pyridin-3-ylmethyl)-acetamide from step (d) above (250 mg, 1.14 mmol) and (R)-(−)-2-methyl-piperazine (126 mg, 1.26 mmol, Aldrich) reacted under the conditions of Example 3a to give the title compound. MS (ESI, pos. ion) m/z: 283 (M+1).

(f) N-{5-Chloro-6-[3-methyl-4-(5-trifluoromethyl-1H-benzoimidazol-2-yl)-piperazin-1-yl]-pyridin-3-ylmethyl}-acetamide A mixture of 2-chloro-6-trifluoromethyl-1H-benzoimidazole (88 mg, 0.4 mmol, Example 1c) and N-{5-chloro-6-[(3R)-3-methyl-piperazin-1-yl]-pyridin-3-ylmethyl}-acetamide from step (e) above (141 mg, 0.5 mmol) in ethanol (2 mL) reacted under the conditions of Example 3c to give the title compound. MS (ESI, pos. ion) m/z: 467 (M+1).

Example 156

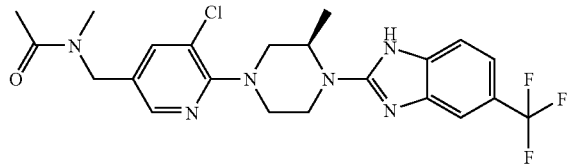

N-{5-Chloro-6-[(3R)-3-methyl-4-(5-trifluoromethyl-1H-benzoimidazol-2-yl)-piperazin-1-yl]-pyridin-3-ylmethyl}-N-methyl-acetamide (a) N-(5,6-Dichloro-pyridin-3-ylmethyl)-N-methyl-acetamide NaH (41 mg, 1.0 mmol, Aldrich, 60% dispersion in mineral oil) was added portionwise to a solution of N-(5,6-dichloro-pyridin-3-ylmethyl)-acetamide (150 mg, 0.68 mmol, Example 155d) and iodomethane (0.063 mL, 1.0 mmol, Aldrich) in DMF (3.0 mL) with stirring at room temperature. The mixture was stirred for 30 min at room temperature, diluted with EtOAc (30 mL), washed with water (20 mL) and brine (20 mL), dried over Na₂SO₄, and filtered. The filtrate was evaporated in vacuo and the residue was purified by silica gel column chromatography, eluting with 80% EtOAc/hexane to give the title compound. MS (ESI, pos. ion) m/z: 233 (M+1).

(b) N-[5-Chloro-6-[(3R)-3-methyl-piperazin-1-yl]-pyridin-3-ylmethyl]-N-methyl-acetamide A mixture of N-(5,6-dichloro-pyridin-3-ylmethyl)-N-methyl-acetamide from step (a) above (233 mg, 1.0 mmol) and (R)-(−)-2-methyl-piperazine (110 mg, 1.1 mmol, Aldrich) reacted under the conditions of Example 3a to give the title compound. MS (ESI, pos. ion) m/z: 297 (M+1).

(c) N-{5-Chloro-6-[(3R)-3-methyl-4-(5-trifluoromethyl-1H-benzoimidazol-2-yl)-piperazin-1-yl]-pyridin-3-ylmethyl}-N-methyl-acetamide A mixture of 2-chloro-6-trifluoromethyl-1H-benzoimidazole (88 mg, 0.4 mmol, Example 1c) and N-[5-chloro-6-[(3R)-3-methyl-piperazin-1-yl]-pyridin-3-ylmethyl]-N-methyl-acetamide from step (b) above (148 mg, 0.5 mmol) in ethanol (2 mL) reacted under the conditions Example 3c to give the title compound. MS (ESI, pos. ion) m/z: 481 (M+1).

Example 157

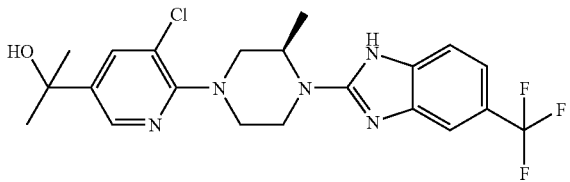

2-{5-Chloro-6-[(3R)-3-methyl-4-(5-trifluoromethyl-1H-benzoimidazol-2-yl)-piperazin-1-yl]-pyridin-3-yl}-propan-2-ol (a) 1-(5,6-Dichloro-pyridin-3-yl)-ethanone A mixture of (1S,1R)-1-(5,6-dichloro-pyridin-3-yl)-ethanol (384 mg, 2.0 mmol, Example 154b) and MnO₂ (3.48 g, 40 mmol, Aldrich) reacted under the conditions of Example 154a to give the title compound. MS (ESI, pos. ion) m/z: 190 (M+1).

(b) 2-(5,6-Dichloro-pyridin-3-yl)-propan-2-ol 1-(5,6-Dichloro-pyridin-3-yl)-ethanone from step (a) above (300 mg, 1.58 mmol) reacted with MeMgBr (0.79 mL, 2.4 mmol, 3.0 M in ether, Aldrich) under the conditions of Example 154b to give the title compound. MS (ESI, pos. ion) m/z: 206 (M+1).

(c) 2-[5-Chloro-6-[(3R)-3-methyl-piperazin-1-yl]-pyridin-3-yl]-propan-2-ol

A mixture of 2-(5,6-dichloro-pyridin-3-yl)-propan-2-ol from step (b) above (140 mg, 0.68 mmol) and (R)-(−)-2-methyl-piperazine (75 mg, 0.75 mmol, Aldrich) reacted under the conditions of Example 3a to give the title compound. MS (ESI, pos. ion) m/z: 270 (M+1).

(d) 2-{5-Chloro-6-[(3R)-3-methyl-4-(5-trifluoromethyl-1H-benzoimidazol-2-yl)-piperazin-1-yl]-pyridin-3-yl}-propan-2-ol A mixture of 2-chloro-6-trifluoromethyl-1H-benzoimidazole (58 mg, 0.26 mmol, Example 1c) and 2-[5-chloro-6-[(3R)-3-methyl-piperazin-1-yl]-pyridin-3-yl]-propan-2-ol from step (c) above (90 mg, 0.33 mmol) in ethanol (1 mL)

reacted under the conditions of Example 3c to give the title compound. MS (ESI, pos. ion) m/z: 454 (M+1).

Example 158

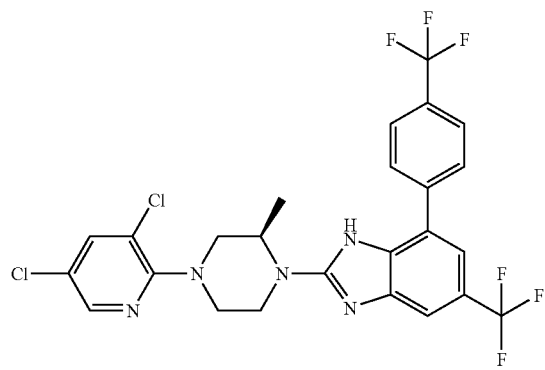

2-[(2R)-4-(3,5-Dichloro-pyridin-2-yl)-2-methyl-piperazin-1-yl]-5-trifluoromethyl-7-(4-trifluoromethyl-phenyl)-1H-benzoimidazole A mixture of 4-bromo-2-[(2R)-4-(3,5-dichloro-pyridin-2-yl)-2-methyl-piperazin-1-yl]-6-trifluoromethyl-1H-benzoimidazole (204 mg, 0.4 mmol, Example 149b), 4-trifluoromethylphenylboronic acid (152 mg, 0.8 mmol, Aldrich), Pd(PPh$_3$)$_4$ (46 mg, 0.04 mmol, Aldrich) and Na$_2$CO$_3$ (2 mL, 0.8 mmol, 0.4 M in H$_2$O) in MeCN (4 mL) was heated at 90° C. with stirring for 16 h. Water (10 mL) was added and the mixture was extracted with EtOAc (2×30 mL). The combined organic extracts were washed with brine (5 mL), dried over Na$_2$SO$_4$ and filtered. The filtrate was evaporated in vacuo and the residue was purified by silica gel column chromatography, eluting with 10% EtOAc/hexane to give the title compound. MS (ESI, pos. ion) m/z: 574 (M+1).

Example 159

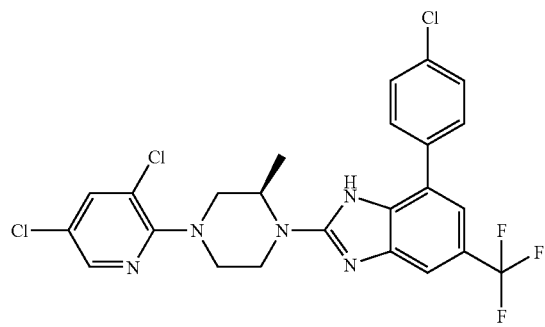

7-(4-Chloro-phenyl)-2-[(2R)-4-(3,5-dichloro-pyridin-2-yl)-2-methyl-piperazin-1-yl]-5-trifluoromethyl-1H-benzoimidazole 4-Bromo-2-[(2R)-4-(3,5-dichloro-pyridin-2-yl)-2-methyl-piperazin-1-yl]-6-trifluoromethyl-1H-benzoimidazole (204 mg, 0.4 mmol, Example 149b) and 4-chlorophenylboronic acid (124 mg, 0.8 mmol, Aldrich) reacted under the conditions of Example 158 to give the title compound. MS (ESI, pos. ion) m/z: 504 (M+1).

Example 160

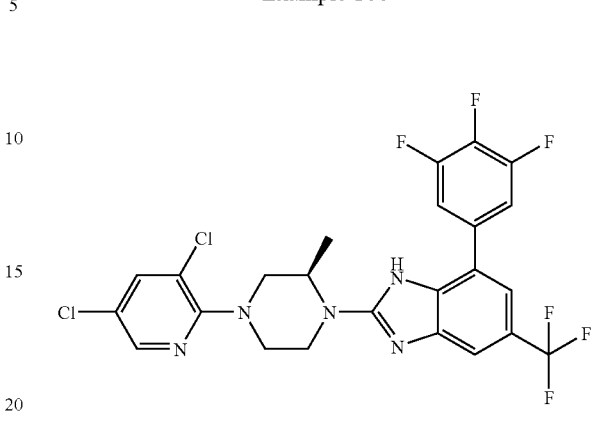

2-[(2R)-4-(3,5-Dichloro-pyridin-2-yl)-2-methyl-piperazin-1-yl]-5-trifluoromethyl-7-(3,4,5-trifluoro-phenyl)-1H-benzoimidazole 4-Bromo-2-[(2R)-4-(3,5-dichloro-pyridin-2-yl)-2-methyl-piperazin-1-yl]-6-trifluoromethyl-1H-benzoimidazole (204 mg, 0.4 mmol, Example 149b) and 4,5,6-trifluorophenylboronic acid (141 mg, 0.8 mmol, Aldrich) reacted under the conditions of Example 158 to give the title compound. MS (ESI, pos. ion) m/z: 504 (M+1).

Example 161

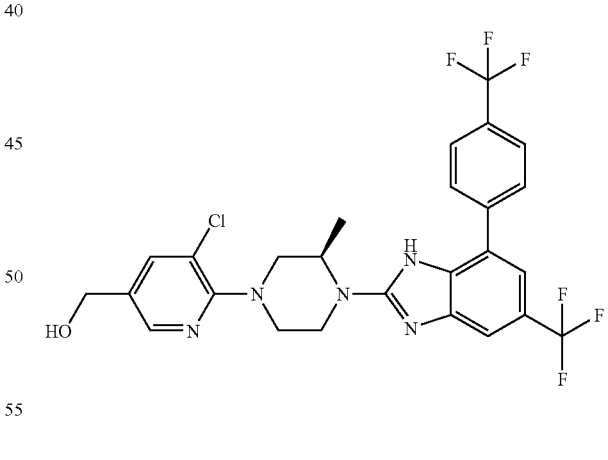

(5-Chloro-6-{(3R)-3-methyl-4-[5-trifluoromethyl-7-(4-trifluoromethyl-phenyl)-1H-benzoimidazol-2-yl]-piperazin-1-yl}-pyridin-3-yl)-methanol {6-[(3R)-4-(7-Bromo-5-trifluoromethyl-1H-benzoimidazol-2-yl)-3-methyl-piperazin-1-yl]-5-chloro-pyridin-3-yl}-methanol (152 mg, 0.3 mmol, Example 151) and 4-trifluoromethylphenylboronic acid (114 mg, 0.6 mmol, Aldrich)

reacted under the conditions of Example 158 to give the title compound. MS (ESI, pos. ion) m/z: 570 (M+1).

Example 162

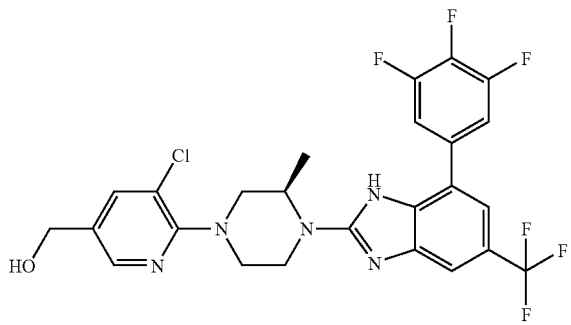

(5-Chloro-6-{(3R)-3-methyl-4-[5-trifluoromethyl-7-(3,4,5-trifluoro-phenyl)-1H-benzoimidazol-2-yl]-piperazin-1-yl}-pyridin-3-yl)-methanol {6-[(3R)-4-(7-Bromo-5-trifluoromethyl-1H-benzoimidazol-2-yl)-3-methyl-piperazin-1-yl]-5-chloro-pyridin-3-yl}-methanol (152 mg, 0.3 mmol, Example 151) and 4,5,6-trifluorophenylboronic acid (106 mg, 0.6 mmol, Aldrich) reacted under the conditions of Example 158 to give the title compound. MS (ESI, pos. ion) m/z: 556 (M+1).

Example 163

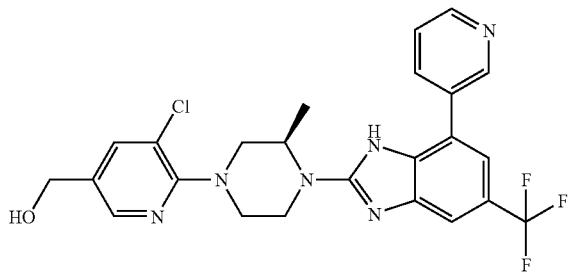

{5-Chloro-6-[(3R)-3-methyl-4-(7-pyridin-3-yl-5-trifluoromethyl-1H-benzoimidazol-2-yl)-piperazin-1-yl]-pyridin-3-yl}-methanol {6-[(3R)-4-(7-Bromo-5-trifluoromethyl-1H-benzoimidazol-2-yl)-3-methyl-piperazin-1-yl]-5-chloro-pyridin-3-yl}-methanol (152 mg, 0.3 mmol, Example 151) and 3-diethylboranyl-pyridine (118 mg, 0.6 mmol, Aldrich) reacted under the conditions of Example 158 to give the title compound. MS (ESI, pos. ion) m/z: 503 (M+1).

Example 164

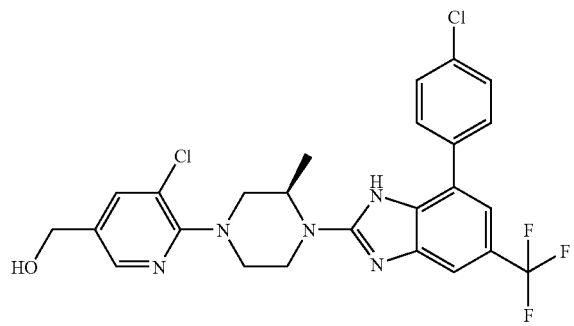

(5-Chloro-6-{(3R)-4-[7-(4-chloro-phenyl)-5-trifluoromethyl-1H-benzoimidazol-2-yl]-3-methyl-piperazin-1-yl}-pyridin-3-yl)-methanol {6-[(3R)-4-(7-Bromo-5-trifluoromethyl-1H-benzoimidazol-2-yl)-3-methyl-piperazin-1-yl]-5-chloro-pyridin-3-yl}-methanol (152 mg, 0.3 mmol, Example 151) and 4-chlorolphenylboronic acid (94 mg, 0.6 mmol, Aldrich) reacted under the conditions of Example 158 to give the title compound. MS (ESI, pos. ion) m/z: 536 (M+1).

Example 165

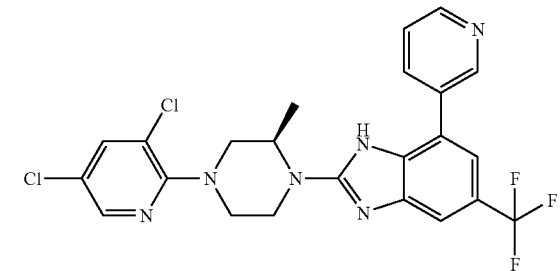

2-[(2R)-4-(3,5-Dichloro-pyridin-2-yl)-2-methyl-piperazin-1-yl]-7-pyridin-3-yl-5-trifluoromethyl-1H-benzoimidazole 4-Bromo-2-[(2R)-4-(3,5-dichloro-pyridin-2-yl)-2-methyl-piperazin-1-yl]-6-trifluoromethyl-1H-benzoimidazole (204 mg, 0.4 mmol, Example 149b) and 3-diethylboranylpyridine (118 mg, 0.8 mmol, Aldrich) reacted under the conditions of Example 158 to give the title compound. MS (ESI, pos. ion) m/z: 510 (M+1).

Example 166

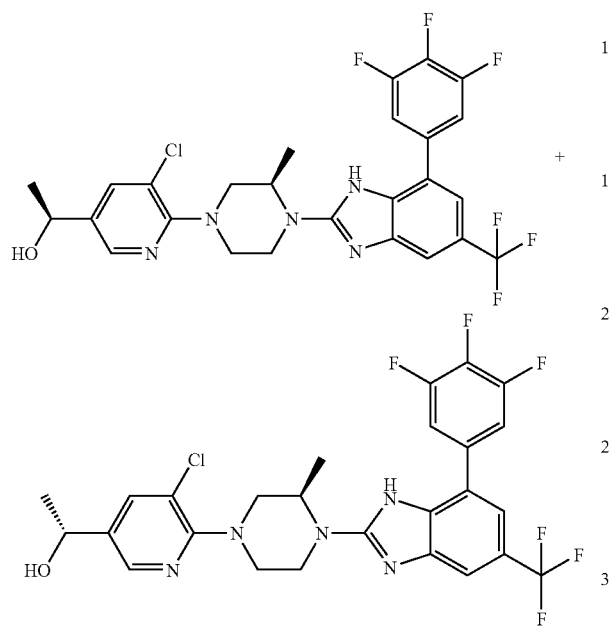

(1S)-1-(5-Chloro-6-{(3R)-3-methyl-4-[5-trifluoromethyl-7-(3,4,5-trifluoro-phenyl)-1H-benzoimidazol-2-yl]-piperazin-1-yl}-pyridin-3-yl)-ethanol and (1R)-1-(5-Chloro-6-{(3R)-3-methyl-4-[5-trifluoromethyl-7-(3,4,5-trifluoro-phenyl)-1H-benzoimidazol-2-yl]-piperazin-1-yl}-pyridin-3-yl)-ethanol (a) (1S)-1-{6-[(3R)-4-(7-Bromo-5-trifluoromethyl-1H-benzoimidazol-2-yl)-3-methyl-piperazin-1-yl]-5-chloro-pyridin-3-yl}-ethanol and (1R)-1-{6-[(3R)-4-(7-Bromo-5-trifluoromethyl-1H-benzoimidazol-2-yl)-3-methyl-piperazin-1-yl]-5-chloro-pyridin-3-yl}-ethanol 7-Bromo-2-chloro-5-trifluoromethyl-1H-benzoimidazole (902 mg, 3.0 mmol, Example 6b) reacted with the diastereomeric mixture of (1S)-1-[5-chloro-6-[(3R)-3-methyl-piperazin-1-yl]-pyridin-3-yl]-ethanol and (1R)-1-[5-chloro-6-[(3R)-3-methyl-piperazin-1-yl]-pyridin-3-yl]-ethanol (766 mg, 3.0 mmol, Example 154c) in ethanol (2 mL) under the conditions of Example 3c to give the title compound as a mixture of diastereoisomers. MS (ESI, pos. ion) m/z: 518 (M+1).

(b) (1S)-1-(5-Chloro-6-{(3R)-3-methyl-4-[5-trifluoromethyl-7-(3,4,5-trifluoro-phenyl)-1H-benzoimidazol-2-yl]-piperazin-1-yl}-pyridin-3-yl)-ethanol and (1R)-1-(5-Chloro-6-{(3R)-3-methyl-4-[5-trifluoromethyl-7-(3,4,5-trifluoro-phenyl)-1H-benzoimidazol-2-yl]-piperazin-1-yl}-pyridin-3-yl)-ethanol.

The diastereoisomeric mixture from step (a) above (104 mg, 0.2 mmol) and 4,5,6-trifluorophenylboronic acid (70 mg, 0.4 mmol, Aldrich) reacted under the conditions of Example 158 to give the title compound as a mixture of diastereoisomers. MS (ESI, pos. ion) m/z: 570 (M+1).

Example 167

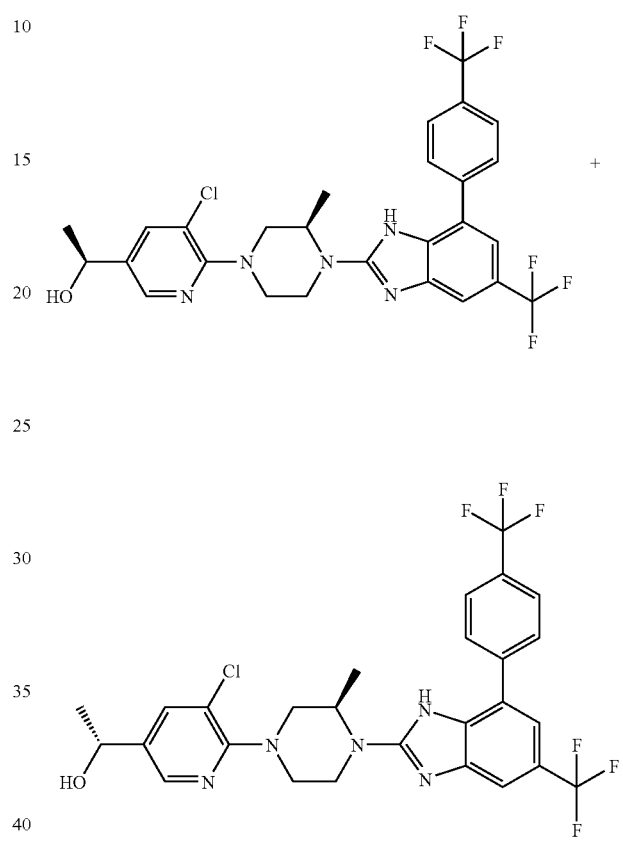

(1S)-1-(5-Chloro-6-{(3R)-3-methyl-4-[5-trifluoromethyl-7-(4-trifluoromethyl-phenyl)-1H-benzoimidazol-2-yl]-piperazin-1-yl}-pyridin-3-yl)-ethanol and (1R)-1-(5-Chloro-6-{(3R)-3-methyl-4-[5-trifluoromethyl-7-(4-trifluoromethyl-phenyl)-1H-benzoimidazol-2-yl]-piperazin-1-yl}-pyridin-3-yl)-ethanol The diastereoisomeric mixture of (1S)-1-{6-[(3R)-4-(7-bromo-5-trifluoromethyl-1H-benzoimidazol-2-yl)-3-methyl-piperazin-1-yl]-5-chloro-pyridin-3-yl}-ethanol and (1R)-1-{6-[(3R)-4-(7-bromo-5-trifluoromethyl-1H-benzoimidazol-2-yl)-3-methyl-piperazin-1-yl]-5-chloro-pyridin-3-yl}-ethanol (104 mg, 0.2 mmol, Example 166a) reacted with 4-trifluoromethylphenylboronic acid (76 mg, 0.4 mmol, Aldrich) under the conditions of Example 158 to give the title compound as a mixture of diastereoisomers. MS: (ESI, pos. ion) m/z: 584 (M+1).

Example 168

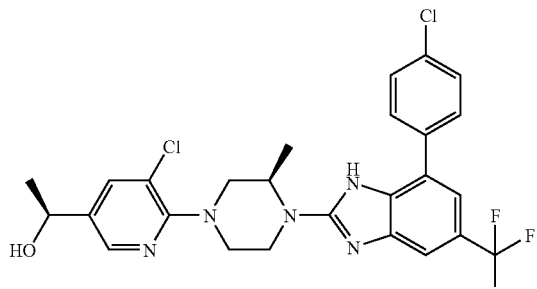

(1S)-1-(5-Chloro-6-{(3R)-4-[7-(4-chloro-phenyl)-5-trifluoromethyl-1H-benzoimidazol-2-yl]-3-methyl-piperazin-1-yl}-pyridin-3-yl)-ethanol and (1R)-1-(5-Chloro-6-{(3R)-4-[7-(4-chloro-phenyl)-5-trifluoromethyl-1H-benzoimidazol-2-yl]-3-methyl-piperazin-1-yl}-pyridin-3-yl)-ethanol The diastereoisomeric mixture of (1S)-1-{6-[(3R)-4-(7-bromo-5-trifluoromethyl-1H-benzoimidazol-2-yl)-3-methyl-piperazin-1-yl]-5-chloro-pyridin-3-yl}-ethanol and (1R)-1-{6-[(3R)-4-(7-bromo-5-trifluoromethyl-1H-benzoimidazol-2-yl)-3-methyl-piperazin-1-yl]-5-chloro-pyridin-3-yl}-ethanol (104 mg, 0.2 mmol, Example 166a) reacted with 4-chlorophenylboronic acid (63 mg, 0.4 mmol, Aldrich) under the conditions of Example 158 to give the title compound as a mixture of diastereoisomers. MS (ESI, pos. ion) m/z: 550 (M+1).

Example 169

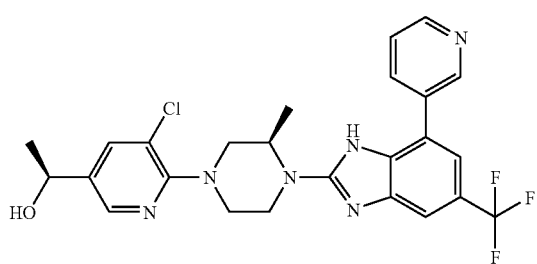

+

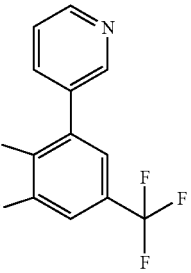

(1S)-1-{5-Chloro-6-[(3R)-3-methyl-4-(7-pyridin-3-yl-5-trifluoromethyl-1H-benzoimidazol-2-yl)-piperazin-1-yl]-pyridin-3-yl}-ethanol and (1R)-1-{5-Chloro-6-[(3R)-3-methyl-4-(7-pyridin-3-yl-5-trifluoromethyl-1H-benzoimidazol-2-yl)-piperazin-1-yl]-pyridin-3-yl}-ethanol The diastereoisomeric mixture of (1S)-1-{6-[(3R)-4-(7-bromo-5-trifluoromethyl-1H-benzoimidazol-2-yl)-3-methyl-piperazin-1-yl]-5-chloro-pyridin-3-yl}-ethanol and (1R)-1-{6-[(3R)-4-(7-bromo-5-trifluoromethyl-1H-benzoimidazol-2-yl)-3-methyl-piperazin-1-yl]-5-chloro-pyridin-3-yl}-ethanol (104 mg, 0.2 mmol, Example 166a) reacted with 3-diethylboranyl-pyridine (59 mg, 0.4 mmol, Aldrich) under the conditions of Example 158 to give 32 mg (31%) of product as a mixture of diastereoisomers. MS (ESI, pos. ion) m/z: 517 (M+1).

Example 170

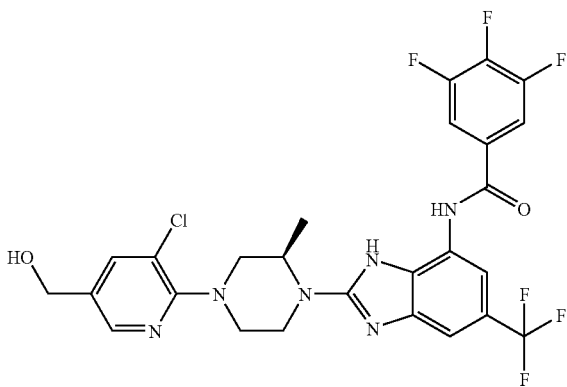

N-{2-[(2R)-4-(3-Chloro-5-hydroxymethyl-pyridin-2-yl)-2-methyl-piperazin-1-yl]-6-trifluoromethyl-3H-benzoimidazol-4-yl}-3,4,5-trifluoro-benzamide (a) 3,4,5-Trifluoro-N-(2-oxo-6-trifluoromethyl-2,3-dihydro-1H-benzoimidazol-4-yl)-benzamide 4-Amino-6-trifluoromethyl-1,3-dihydro-benzoimidazol-2-one (2.17 g, 10 mmol, Example 61a) and 3,4,5-trifluoro-benzoic acid (1.94 g, 11 mmol, Aldrich) reacted under the conditions of Example 65 to give the title compound as a white solid. MS (ESI, pos. ion) m/e: 376 (M+1), (ESI, neg. ion) m/z: 374 (M−1)

(b) N-(2-Chloro-6-trifluoromethyl-3H-benzoimidazol-4-yl)-3,4,5-trifluoro-benzamide 3,4,5-Trifluoro-N-(2-oxo-6-trifluoromethyl-2,3-dihydro-1H-benzoimidazol-4-yl)-benzamide from step (c) above (1.12 g, 3.0 mmol) reacted with POCl$_3$ (5 mL, Aldrich) under the conditions of Example 1c to give the title compound as a white solid. MS (ESI, pos. ion) m/e: 393.7 (M+1), (ESI, neg. ion) m/z: 392 (M−1).

(c) N-{2-[(2R)-4-(3-Chloro-5-hydroxymethyl-pyridin-2-yl)-2-methyl-piperazin-1-yl]-6-trifluoromethyl-3H-benzoimidazol-4-yl}-3,4,5-trifluoro-benzamide A mixture of {5-chloro-6-[(3R)-3-methyl-piperazin-1-yl]-pyridin-3-yl}-methanol (530 mg, 2.2 mmol, Example 150a) and N-(2-chloro-6-trifluoromethyl-3H-benzoimidazol-4-yl)-3,4,5-trifluoro-benzamide from step (d) above (787 mg, 2.0 mmol) in EtOH (2 mL, Aldrich) reacted under the conditions of Example 3c to give the title compound as a white solid. MS (ESI, pos. ion) m/e: 599 (M+1).

Example 171

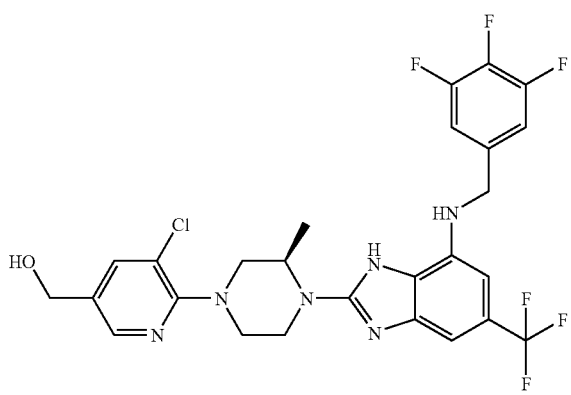

(5-Chloro-6-{(3R)-3-methyl-4-[7-(3,4,5-trifluoro-benzylamino)-5-trifluoromethyl-1H-benzoimidazol-2-yl]-piperazin-1-yl}-pyridin-3-yl)-methanol To a solution of N-{2-[(2R)-4-(3-chloro-5-hydroxymethyl-pyridin-2-yl)-2-methyl-piperazin-1-yl]-6-trifluoromethyl-3H-benzoimidazol-4-yl}-3,4,5-trifluoro-benzamide (120 mg, 0.2 mmol, Example 170c) in THF (1 mL) was added BH$_3$·THF (0.6 mL, 0.6 mmol, Aldrich) dropwise with stirring at 0° C. The mixture was heated at reflux for 5 h, cooled to room temperature and diluted with 1:1 mixture of MeOH and 1N NaOH (2 mL). The mixture was stirred at room temperature for 30 min and extracted with EtOAc (2×20 mL). The combined organic extracts were washed with brine (10 mL), dried over Na$_2$SO$_4$ and filtered. The filtrate was evaporated in vacuo and the residue was purified by silica gel column chromatography, eluting with 5% MeOH/CH$_2$Cl$_2$ to give the title compound as a white solid. MS (ESI, pos. ion) m/e: 586 (M+1).

Example 172

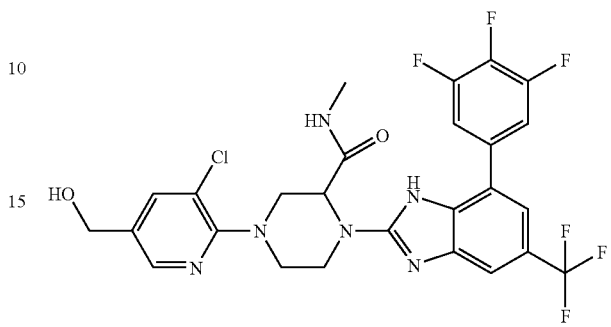

4-(3-Chloro-5-hydroxymethyl-pyridin-2-yl)-1-[5-trifluoromethyl-7-(3,4,5-trifluoro-phenyl)-1H-benzoimidazol-2-yl]-piperazine-2-carboxylic Acid Methylamide

(a) piperazine-1,2,4-tricarboxylic acid 1,4-dibenzyl Ester

Benzyl chloroformate (3.1 mL, 22 mmol, Aldrich) was added dropwise over a period of 5 min to a mixture of piperazine-2-carboxylic acid dihydrochloride (2.03 g, 10 mmol, Aldrich) and Na$_2$CO$_3$ (4.24 g, 40 mmol) in water (10 mL) with stirring at 0° C. The mixture was stirred at 0° C. for 1 h, 2N HCl (10 mL) was added and the mixture was extracted with EtOAc (3×40 mL). The combined organic extracts were washed with water (10 mL) and brine (20 mL), dried over Na$_2$SO$_4$, and filtered. The filtrate was evaporated in vacuo to give the title compound as a gum, which was used for the next step without additional purification. MS (ESI, pos. ion) m/e: 399 (M+1).

(b) 2-Methylcarbamoyl-piperazine-1,4-dicarboxylic acid dibenzyl Ester

Piperazine-1,2,4-tricarboxylic acid 1,4-dibenzyl ester from step (a) above and methylamine (5.5 mL, 11 mmol, Aldrich) reacted under the conditions of Example 61a to give the title compound as a gum. MS (ESI, pos. ion) m/e: 412 (M+1).

(c) piperazine-2-carboxylic Acid Methylamide

A suspension of 2-methylcarbamoyl-piperazine-1,4-dicarboxylic acid dibenzyl ester from step (b) above (1.64 g, 4.0 mmol) and 10% Pd/C (42 mg, 0.04 mmol, Aldrich) in ethanol (10 mL) was vigorously stirred under hydrogen atmosphere for 4 h at room temperature. The catalyst was filtered through Celite® pad and the filter cake was washed with EtOH. The filtrate was evaporated in vacuo to give the title compound, which was used in the next step without additional purification. MS (ESI, pos. ion) m/e: 144 (M+1).

(d) 4-(3-Chloro-5-hydroxymethyl-pyridin-2-yl)-piperazine-2-carboxylic Acid Methylamide piperazine-2-carboxylic acid methylamide from step (c) above (570 mg, 4.0 mmol) and (5,6-dichloro-pyridin-3-yl)-methanol (710 mg, 4.0 mmol, TCI-US) reacted under the conditions of Example 3a to give the title compound as a light-yellow gum. MS ESI, pos. ion) m/e: 285 (M+1).

(e) 4-(3-Chloro-5-hydroxymethyl-pyridin-2-yl)-1-[5-trifluoromethyl-7-(3,4,5-trifluoro-phenyl)-1H-benzoimidazol-2-yl]-piperazine-2-carboxylic Acid Methylamide A mixture of 4-(3-chloro-5-hydroxymethyl-pyridin-2-yl)-piperazine-2-carboxylic acid methylamide from step (d) above (114 mg, 0.4 mmol) and 2-chloro-6-trifluoromethyl-4-(3,4,5-trifluoro-phenyl)-1H-benzoimidazole (140 mg, 0.4 mmol, Example 51b) in EtOH (1 mL) reacted under the conditions of Example 3c to give the title compound as a white solid. MS ESI, pos. ion) m/e: 599 (M+1).

Example 173

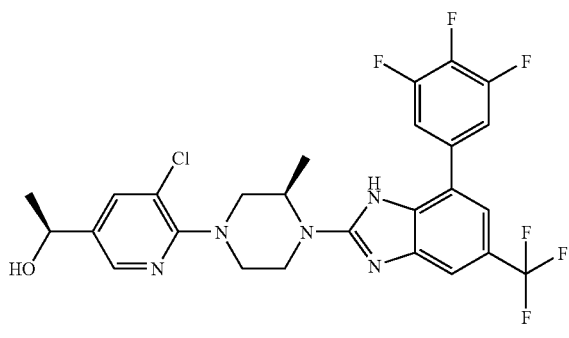

(1S)-1-(5-Chloro-6-{(3R)-3-methyl-4-[5-trifluoromethyl-7-(3,4,5-trifluoro-phenyl)-1H-benzoimidazol-2-yl]-piperazin-1-yl}-pyridin-3-yl)-ethanol The diastereoisomeric mixture of (1S)-1-{6-[(3R)-4-(4-bromo-6-trifluoromethyl-1H-benzoimidazol-2-yl)-3-methyl-piperazin-1-yl]-5-chloro-pyridin-3-yl}-ethanol and (1R)-1-{6-[(3R)-4-(4-bromo-6-trifluoromethyl-1H-benzoimidazol-2-yl)-3-methyl-piperazin-1-yl]-5-chloro-pyridin-3-yl}-ethanol (416 mg, 0.8 mmol, Example 166a) reacted with 3,4,5-trifluorophenylboronic acid (282 mg, 1.6 mmol, Lancaster) under the conditions of Example 158 to give the title compound as a mixture of diastereoisomers. Separation of the mixture by preparative HPLC on a Chiralcel OD column, eluting with 9:1 hexane/EtOH afforded the fast running title compound. The configuration (1S) was assigned at random. (ESI, neg. ion) m/z: 570 (M−1).

Example 174

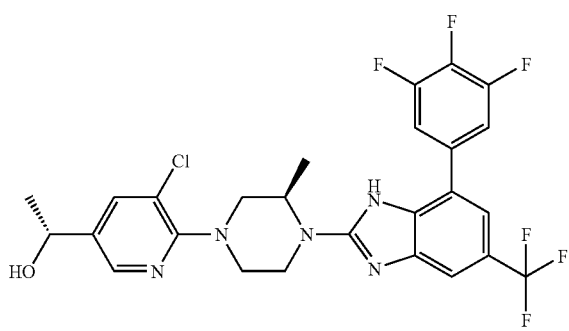

(1R)-1-(5-Chloro-6-{(3R)-3-methyl-4-[5-trifluoromethyl-7-(3,4,5-trifluoro-phenyl)-1H-benzoimidazol-2-yl]-piperazin-1-yl}-pyridin-3-yl)-ethanol The title compound was isolated by preparative HPLC separation of the diastereoisomeric mixture of products of Example 173. The (1R) configuration assignment was based on the randomly assigned (1S) configuration of the diastereoisomer described in Example 173. (ESI, neg. ion) m/z: 570 (M−1).

Example 175

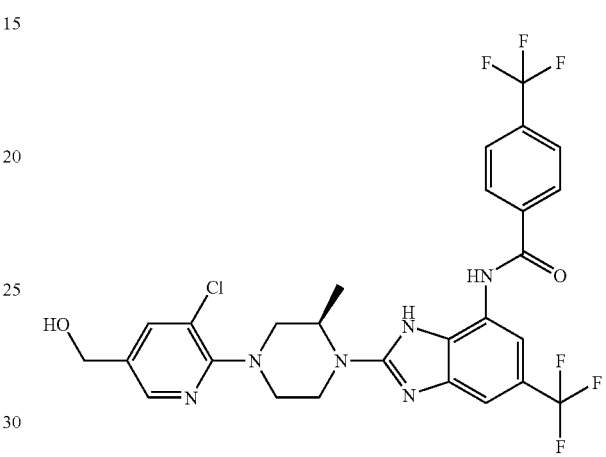

N-{2-[(2R)-4-(3-Chloro-5-hydroxymethyl-pyridin-2-yl)-2-methyl-piperazin-1-yl]-6-trifluoromethyl-3H-benzoimidazol-4-yl}-4-trifluoromethyl-benzamide (a) {5-Chloro-6-[(3R)-3-methyl-4-(7-nitro-5-trifluoromethyl-1H-benzoimidazol-2-yl)-piperazin-1-yl]-pyridin-3-yl}-methanol A mixture of {5-chloro-6-[(3R)-3-methyl-piperazin-1-yl]-pyridin-3-yl}-methanol (1.21 g, 5.0 mmol, Example 150a) and 2-chloro-7-nitro-5-trifluoromethyl-1H-benzoimidazole (1.33 g, 5.0 mmol, Example 57c) in EtOH (4 mL) reacted under the conditions of Example 3c to give the title compound as a yellow solid. MS (ESI, pos. ion) m/e: 471 (M+1).

(b) {6-[(3R)-4-(7-Amino-5-trifluoromethyl-1H-benzoimidazol-2-yl)-3-methyl-piperazin-1-yl]-5-chloro-pyridin-3-yl}-methanol {5-Chloro-6-[(3R)-3-methyl-4-(7-nitro-5-trifluoromethyl-1H-benzoimidazol-2-yl)-piperazin-1-yl]-pyridin-3-yl}-methanol from step (a) above (942 mg, 2.0 mmol) was hydrogenated under the conditions of Example 57a to give 847 mg (96%) the title compound as a yellow gum. MS (ESI, pos. ion) m/e: 441 (M+1).

(c) N-{2-[(2R)-4-(3-Chloro-5-hydroxymethyl-pyridin-2-yl)-2-methyl-piperazin-1-yl]-6-trifluoromethyl-3H-benzoimidazol-4-yl}-4-trifluoromethyl-benzamide {6-[(3R)-4-(7-Amino-5-trifluoromethyl-1H-benzoimidazol-2-yl)-3-methyl-piperazin-1-yl]-5-chloro-pyridin-3-yl}-methanol from step (b) above (221 mg, 0.5 mmol) and 4-trifluoromethyl-benzoic acid (105 mg, 0.55 mmol, Aldrich) reacted under the conditions of Example 65 to give the title compound as a white solid. MS (ESI, pos. ion) m/e: 613 (M+1).

Example 176

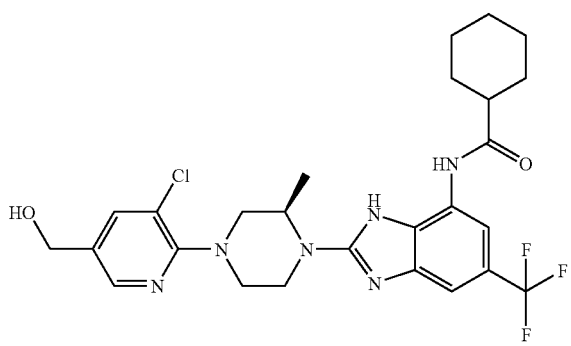

Cyclohexanecarboxylic acid {2-[(2R)-4-(3-chloro-5-hydroxymethyl-pyridin-2-yl)-2-methyl-piperazin-1-yl]-6-trifluoromethyl-3H-benzoimidazol-4-yl}-amide {6-[(3R)-4-(7-Amino-5-trifluoromethyl-1H-benzoimidazol-2-yl)-3-methyl-piperazin-1-yl]-5-chloro-pyridin-3-yl}-methanol from (221 mg, 0.5 mmol, Example 175b) and cyclohexanecarboxylic acid (71 mg, 0.55 mmol, Aldrich) reacted under the conditions of Example 65 to give the title compound as a white solid. MS (ESI, pos. ion) m/e: 551 (M+1).

Example 177

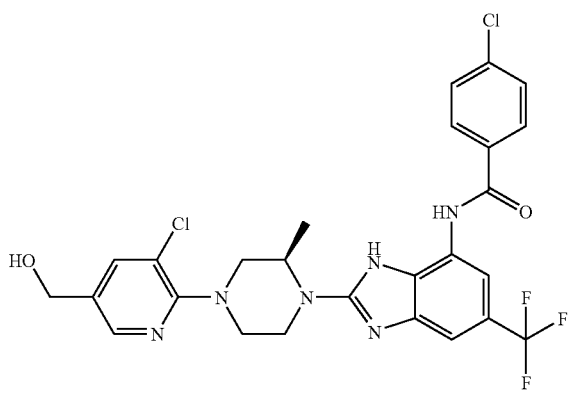

4-Chloro-N-{2-[(2R)-4-(3-chloro-5-hydroxymethyl-pyridin-2-yl)-2-methyl-piperazin-1-yl]-6-trifluoromethyl-3H-benzoimidazol-4-yl}-benzamide {6-[(3R)-4-(7-Amino-5-trifluoromethyl-1H-benzoimidazol-2-yl)-3-methyl-piperazin-1-yl]-5-chloro-pyridin-3-yl}-methanol (221 mg, 0.5 mmol, Example 175b) and 4-chloro-benzoic acid (86 mg, 0.55 mmol, Aldrich) reacted under the conditions of Example 65 to give the title compound as a white solid. MS (ESI, pos. ion) m/e: 579 (M+1).

Example 178

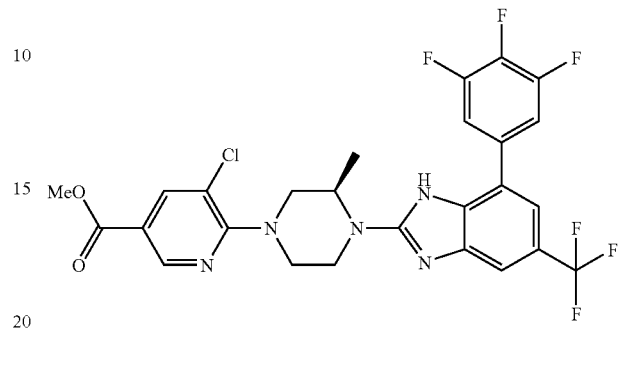

5-Chloro-6-{(3R)-3-methyl-4-[5-trifluoromethyl-7-(3,4,5-trifluoro-phenyl)-1H-benzoimidazol-2-yl]-piperazin-1-yl}-nicotinic Acid Methyl Ester (a) 5,6-Dichloro-nicotinic Acid Methyl Ester A solution of 5,6-dichloro-nicotinic acid (1.92 g, 10 mmol, Aldrich) and p-toluenesulfonic acid monohydrate (190 mg, 1.0 mmol, Aldrich) in methanol (5 mL, Aldrich) was heated at reflux for 25 h. The reaction mixture was cooled to room temperature, the solvent was removed in vacuo and the residue was dissolved in EtOAc (50 mL). The solution was washed with satd. NaHCO$_3$ (20 mL) and brine (20 mL), dried over Na$_2$SO$_4$, and filtered. The filtrate was evaporated in vacuo and the residue was purified by silica gel column chromatography, eluting with 30% EtOAc/hexane to give the title compound as a white solid. MS ESI, pos. ion) m/e: 205 (M+1).

(b) 5-Chloro-6-[(3R)-3-methyl-piperazin-1-yl]-nicotinic Acid Methyl Ester 5,6-Dichloro-nicotinic acid methyl ester from step (a) above (1.23 g, 6.0 mmol) and (R)-(−)-2-methyl-piperazine (667 mg, 6.6 mmol, Aldrich) reacted under the conditions of Example 3a to give the title compound as a white solid. MS ESI, pos. ion) m/e: 270 (M+1).

(c) 5-Chloro-6-{(3R)-3-methyl-4-[5-trifluoromethyl-7-(3,4,5-trifluoro-phenyl)-1H-benzoimidazol-2-yl]-piperazin-1-yl}-nicotinic Acid Methyl Ester 5-Chloro-6-[(3R)-3-methyl-piperazin-1-yl]-nicotinic acid methyl ester from step (b) above (271 mg, 1.0 mmol) and 2-chloro-6-trifluoromethyl-4-(3,4,5-trifluoro-phenyl)-1H-benzoimidazole (350 mg, 1.0 mmol, Example 51b) reacted under the conditions of Example 3c to give the title compound as a white solid. MS (ESI, pos. ion) m/e: 584 (M+1).

Example 179

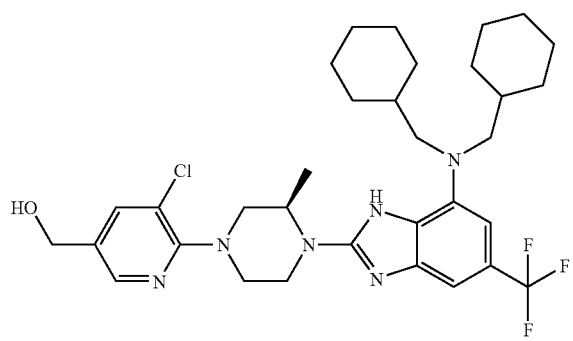

(6-{(3R)-4-[7-(Bis-cyclohexylmethyl-amino)-5-trifluoromethyl-1H-benzoimidazol-2-yl]-3-methyl-piperazin-1-yl}-5-chloro-pyridin-3-yl)-methanol {6-[(3R)-4-(7-Amino-5-trifluoromethyl-1H-benzoimidazol-2-yl)-3-methyl-piperazin-1-yl]-5-chloro-pyridin-3-yl}-methanol (221 mg, 0.5 mmol, Example 175b) and cyclohexanecarbaldehyde (62 mg, 0.55 mmol, Aldrich) reacted under the conditions of Example 59 to give the title compound as a light-yellow solid. MS (ESI, pos. ion) m/e: 633 (M+1).

Example 180

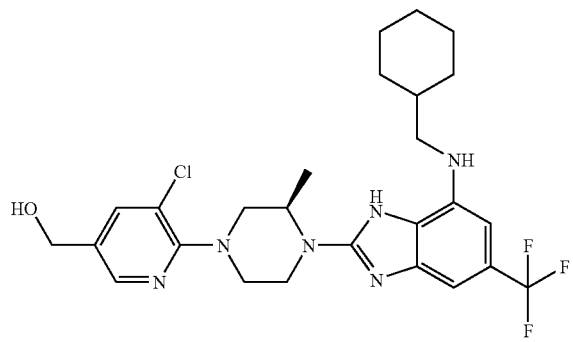

(5-Chloro-6-{(3R)-4-[7-(cyclohexylmethyl-amino)-5-trifluoromethyl-1H-benzoimidazol-2-yl]-3-methyl-piperazin-1-yl}-pyridin-3-yl)-methanol The title compound was formed as a second product of the reaction described in Example 179 and isolated as a light-yellow solid. Yield 112 mg (42%). MS (ESI, pos. ion) m/e: 537 (M+1).

Example 181

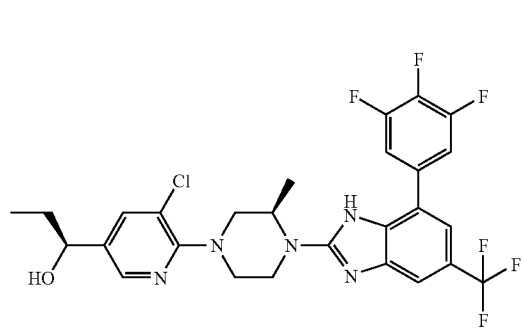

+

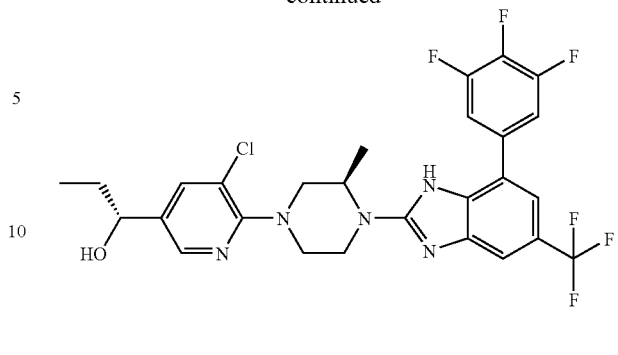

(1S)-1-(5-Chloro-6-{(3R)-3-methyl-4-[5-trifluoromethyl-7-(3,4,5-trifluoro-phenyl)-1H-benzoimidazol-2-yl]-piperazin-1-yl}-pyridin-3-yl)-propan-1-ol and (1R)-1-(5-Chloro-6-{(3R)-3-methyl-4-[5-trifluoromethyl-7-(3,4,5-trifluoro-phenyl)-1H-benzoimidazol-2-yl]-piperazin-1-yl}-pyridin-3-yl)-propan-1-ol (a) 5-Chloro-6-{(3R)-3-methyl-4-[5-trifluoromethyl-7-(3,4,5-trifluoro-phenyl)-1H-benzoimidazol-2-yl]-piperazin-1-yl}-pyridine-3-carbaldehyde (5-Chloro-6-{(3R)-3-methyl-4-[6-trifluoromethyl-4-(3,4,5-trifluoro-phenyl)-1H-benzoimidazol-2-yl]-piperazin-1-yl}-pyridin-3-yl)-methanol (110 mg, 0.2 mmol, Example 162) reacted with $MnO_2$ (348 mg, 4.0 mmol, Aldrich) under the conditions of Example 154a to give the title compound as a gum, which is was used in the next step without additional purification. MS ESI, pos. ion) m/e: 554 (M+1).

(b) (1S)-1-(5-Chloro-6-{(3R)-3-methyl-4-[5-trifluoromethyl-7-(3,4,5-trifluoro-phenyl)-1H-benzoimidazol-2-yl]-piperazin-1-yl}-pyridin-3-yl)-propan-1-ol and (1R)-1-(5-Chloro-6-{(3R)-3-methyl-4-[5-trifluoromethyl-7-(3,4,5-trifluoro-phenyl)-1H-benzoimidazol-2-yl]-piperazin-1-yl}-pyridin-3-yl)-propan-1-ol 5-Chloro-6-{(3R)-3-methyl-4-[6-trifluoromethyl-4-(3,4,5-trifluoro-phenyl)-1H-benzoimidazol-2-yl]-piperazin-1-yl}-pyridine-3-carbaldehyde from step (a) above (88 mg, 0.16 mmol) in THF (2 mL) reacted with $C_2H_5MgBr$ under the conditions of Example 154b to give the title compound as a mixture of diastereoisomers. MS (ESI, pos. ion) m/e: 584 (M+1).

Example 182

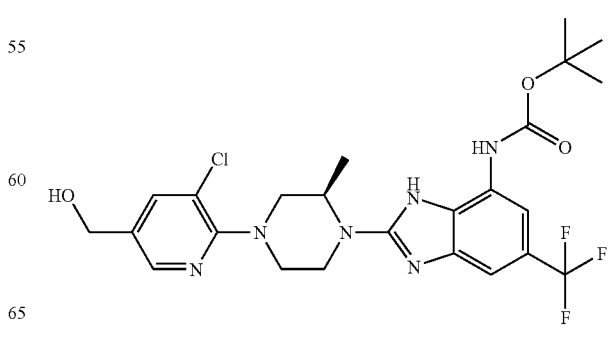

{2-[(2R)-4-(3-Chloro-5-hydroxymethyl-pyridin-2-yl)-2-methyl-piperazin-1-yl]-6-trifluoromethyl-3H-benzoimidazol-4-yl}-carbamic Acid tert-butyl Ester To a mixture of {6-[(3R)-4-(7-amino-5-trifluoromethyl-1H-benzoimidazol-2-yl)-3-methyl-piperazin-1-yl]-5-chloro-pyridin-3-yl}-methanol (221 mg, 1.0 mmol, Example 175b) and 1 N NaOH (1 mL) in THF (5 mL) was added di-tert-butyl dicarbonate (131 mg, 0.6 mmol, Aldrich) in one portion with stirring at room temperature. The mixture was stirred at room temperature for 30 min, diluted with water (20 mL) and extracted with EtOAc (2×40 mL). The combined organic extracts were washed with brine (20 mL), dried over Na$_2$SO$_4$ and filtered. The filtrate was evaporated in vacuo and the residue was purified by silica gel column chromatography, eluting with 60% EtOAc/hexane to give the title compound as a light-yellow solid. MS (ESI, pos. ion) m/e: 541 (M+1).

Example 183

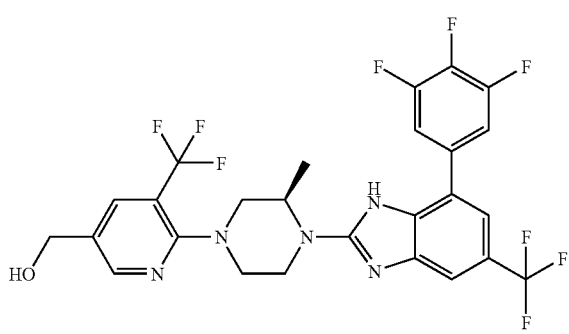

(6-{(3R)-3-Methyl-4-[5-trifluoromethyl-7-(3,4,5-trifluoro-phenyl)-1H-benzoimidazol-2-yl]-piperazin-1-yl}-5-trifluoromethyl-pyridin-3-yl)-methanol (a) (3R)-3-Methyl-1-(3-trifluoromethyl-pyridin-2-yl)-piperazine 2-Chloro-3-trifluoromethyl-pyridine (7.26, 40 mmol, TCI-US) and (R)-(−)-2-methyl-piperazine (4.45 g, 44 mmol, Aldrich) reacted under the conditions of Example 3a to give the title compound as a gum. MS (ESI, pos. ion) m/e: 246 (M+1).

(b) (2R)-2-Methyl-4-(3-trifluoromethyl-pyridin-2-yl)-piperazine-1-carboxylic Acid tert-butyl Ester (3R)-3-Methyl-1-(3-trifluoromethyl-pyridin-2-yl)-piperazine from step (a) above (7.38 g, 30 mmol) reacted with di-tert-butyl dicarbonate under the conditions of Example 182 to give the title compound as a gum. MS (ESI, pos. ion) m/e: 346 (M+1).

(c) (2R)-4-(5-Bromo-3-trifluoromethyl-pyridin-2-yl)-2-methyl-piperazine-1-carboxylic Acid tert-butyl Ester Bromine (1.52 mL, 29.7 mmol, Aldrich) was added dropwise over a period of 5 min to a solution (2R)-2-methyl-4-(3-trifluoromethyl-pyridin-2-yl)-piperazine-1-carboxylic acid tert-butyl ester from step (b) above (9.34 g, 27 mmol) in dichloromethane (100 mL) with stirring at room temperature. The mixture was stirred at room temperature for 30 min, the solvent was removed in vacuo and the residue was dissolved in EtOAc (200 mL). The solution was washed with sat. NaHCO$_3$ (50 mL) and brine (50 mL), dried over Na$_2$SO$_4$, and filtered. The filtrate was evaporated in vacuo and the residue was purified by silica gel column chromatography, eluting with 10% EtOAc/hexane to give the title compound as a gum. MS (ESI, pos. ion) m/e: 426 (M+1).

(d) (2R)-4-[5-(2-Methoxycarbonyl-vinyl)-3-trifluoromethyl-pyridin-2-yl]-2-methyl-piperazine-1-carboxylic Acid tert-butyl Ester A mixture of (2R)-4-(5-bromo-3-trifluoromethyl-pyridin-2-yl)-2-methyl-piperazine-1-carboxylic acid tert-butyl ester from step (c) above (8.48 g, 20 mmol), methyl acrylate (1.9 g, 22 mmol, Aldrich), palladium acetate (49 mg, 2.0 mmol, Aldrich) and benzyltriethyl ammonium chloride (456 mg, 2.0 mmol, Aldrich) in DMF (20 mL) was stirred at 40° C. for 18 h. The reaction mixture was cooled to room temperature, diluted with water (50 mL) and extracted with EtOAc (2×80 mL). The combined organic extracts were washed with brine (40 mL), dried over Na$_2$SO$_4$ and filtered. The filtrate was evaporated in vacuo and the residue was purified by silica gel column chromatography, eluting with 20% EtOAc/hexane to give the title compound as a white solid. MS (ESI, pos. ion) m/e: 430 (M+1).

(e) (2R)-4-(5-Formyl-3-trifluoromethyl-pyridin-2-yl)-2-methyl-piperazine-1-carboxylic Acid tert-butyl Ester A mixture of (2R)-4-[5-(2-methoxycarbonyl-vinyl)-3-trifluoromethyl-pyridin-2-yl]-2-methyl-piperazine-1-carboxylic acid tert-butyl ester from step (d) above (6.02 g, 14 mmol), OsO$_4$ (4.43 mL, 0.7 mmol, 4% in H$_2$O, Aldrich) and N-methylmorpholine N-oxide (1.96 g, 16.8 mmol, Aldrich) in acetone (16 mL) was stirred at room temperature for 5 h. To the mixture was added saturated aqueous solution of NaHSO$_3$ (910 mL) and the mixture was extracted with EtOAc (2×40 mL). The combined organic extracts were washed with brine (20 mL), dried over Na$_2$SO$_4$ and filtered. The filtrate was evaporated in vacuo and the residue was dissolved in dichloromethane (20 mL). To the solution was added Pb(OAc)$_4$ (7.44 g, 16.8 mmol, Aldrich) in one portion and the mixture was stirred at 0° C. for 30 min. The mixture was diluted with hexane (10 mL), filtered through a Celite® pad and the filter cake was washed with 50% EtOAc/hexane. The filtrate was evaporated in vacuo and the residue was purified by silica gel column chromatography, eluting with 30% EtOAc/hexane to give the title compound as a gum. MS (ESI, pos. ion) m/e: 374 (M+1).

(f) (2R)-4-(5-Hydroxymethyl-3-trifluoromethyl-pyridin-2-yl)-2-methyl-piperazine-1-carboxylic Acid tert-butyl Ester To a solution of (2R)-4-(5-formyl-3-trifluoromethyl-pyridin-2-yl)-2-methyl-piperazine-1-carboxylic acid tert-butyl ester from step (e) above (4.48 g, 12 mmol) in methanol (30 mL) was added portionwise NaBH$_4$ (542 mg, 14.4 mmol, Aldrich) with stirring at 0° C. The mixture was stirred at 0° C. for 30 min and the solvent was removed in vacuo. The residue was dissolved in EtOAc (60 mL) and washed with water (20 mL) and brine (20 mL), dried over Na$_2$SO$_4$, and filtered. The solvent was removed in vacuo and the residue was purified by silica gel column chromatography, eluting with 50% EtOAc/hexane to give the title compound as a gum. MS (ESI, pos. ion) m/e: 376 (M+1).

(g) {5-Chloro-6-[(3R)-3-methyl-piperazin-1-yl]-pyridin-3-yl}-methanol

To a stirred solution of 4-(5-hydroxymethyl-3-trifluoromethyl-pyridin-2-yl)-2-methyl-piperazine-1-carboxylic acid tert-butyl ester from step (f) above (3.75 g, 10 mmol) in dichloromethane (10 mL) was added trifluoroacetic acid (10 mL, Aldrich) dropwise at 0° C. over a period of 10 min. The mixture was stirred at room temperature for 16 h and diluted with toluene (20 mL). The solvents were removed in vacuo and the residue was dissolved in EtOAc (100 mL), washed with saturated aqueous solution of $NaHCO_3$ (2×30 mL) and brine (20 mL), dried over $Na_2SO_4$, and filtered. The solvent was evaporated in vacuo and the residue was purified by silica gel column chromatography, eluting with 90:10:1 mixture of $MeOH/CH_2Cl_2$/ammonium hydroxide to give the title compound as a white solid. MS (ESI, pos. ion) m/e: 276 (M+1).

(h) (6-{(3R)-3-Methyl-4-[5-trifluoromethyl-7-(3,4,5-trifluoro-phenyl)-1H-benzoimidazol-2-yl]-piperazin-1-yl}-5-trifluoromethyl-pyridin-3-yl)-methanol A mixture of {5-chloro-6-[(3R)-3-methyl-piperazin-1-yl]-pyridin-3-yl}-methanol from step (g) above (825 mg, 3.0 mmol) and 2-chloro-6-trifluoromethyl-4-(3,4,5-trifluoro-phenyl)-1H-benzoimidazole (1.05 g, 3.0 mmol, Example 51b) in EtOH (5 mL) reacted under the conditions of Example 3c to give the title compound as a white solid. MS (ESI, pos. ion) m/e: 590 (M+1).

Example 184

(1S)-1-(6-{(3R)-3-Methyl-4-[5-trifluoromethyl-7-(3,4,5-trifluoro-phenyl)-1H-benzoimidazol-2-yl]-piperazin-1-yl}-5-trifluoromethyl-pyridin-3-yl)-propan-1-ol and (1R)-1-(6-{(3R)-3-Methyl-4-[5-trifluoromethyl-7-(3,4,5-trifluoro-phenyl)-1H-benzoimidazol-2-yl]-piperazin-1-yl}-5-trifluoromethyl-pyridin-3-yl)-propan-1-ol

(a) 6-{(3R)-3-Methyl-4-[5-trifluoromethyl-7-(3,4,5-trifluoro-phenyl)-1H-benzoimidazol-2-yl]-piperazin-1-yl}-5-trifluoromethyl-pyridine-3-carbaldehyde (6-{(3R)-3-Methyl-4-[6-trifluoromethyl-4-(3,4,5-trifluoro-phenyl)-1H-benzoimidazol-2-yl]-piperazin-1-yl}-5-trifluoromethyl-pyridin-3-yl)-methanol (1.18 g, 2.0 mmol, Example 183 h) reacted with $MnO_2$ (3.48, 40 mmol, Aldrich) under the conditions of Example 154a to give the title compound as a white solid, which was used in the next step without additional purification. MS (ESI, pos. ion) m/e: 588 (M+1).

(b) (1S)-1-(6-{(3R)-3-Methyl-4-[5-trifluoromethyl-7-(3,4,5-trifluoro-phenyl)-1H-benzoimidazol-2-yl]-piperazin-1-yl}-5-trifluoromethyl-pyridin-3-yl)-propan-1-ol and (1R)-1-(6-{(3R)-3-Methyl-4-[5-trifluoromethyl-7-(3,4,5-trifluoro-phenyl)-1H-benzoimidazol-2-yl]-piperazin-1-yl}-5-trifluoromethyl-pyridin-3-yl)-propan-1-ol 6-{(3R)-3-Methyl-4-[6-trifluoromethyl-4-(3,4,5-trifluoro-phenyl)-1H-benzoimidazol-2-yl]-piperazin-1-yl}-5-trifluoromethyl-pyridine-3-carbaldehyde from step (a) above (88 mg, 0.15 mmol) reacted with $C_2H_5MgBr$ under the conditions of Example 154b to give the title compound as a mixture of diastereoisomers. MS (ESI, pos. ion) m/e: 618 (M+1).

Example 185

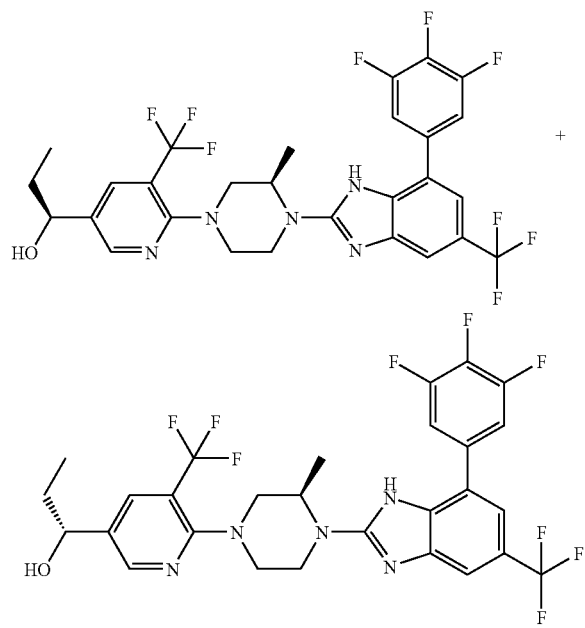

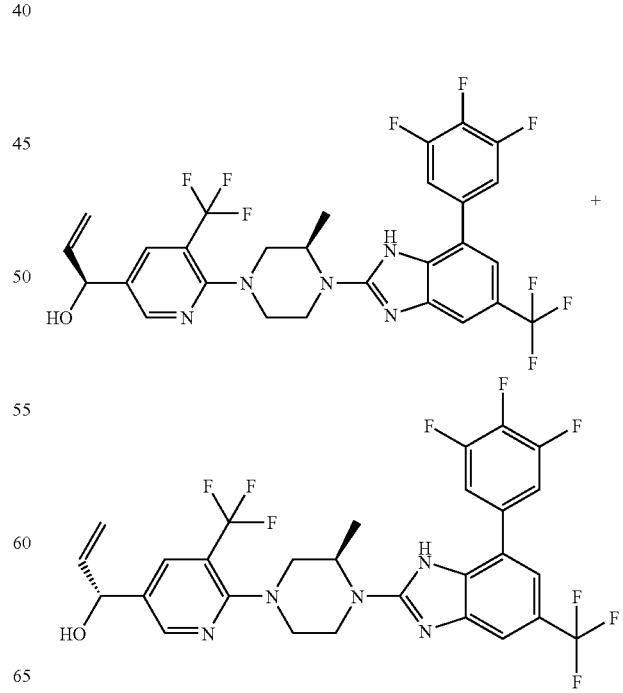

(1S)-1-(6-{(3R)-3-Methyl-4-[5-trifluoromethyl-7-(3,4,5-trifluoro-phenyl)-1H-benzoimidazol-2-yl]-piperazin-1-yl}-5-trifluoromethyl-pyridin-3-yl)-prop-2-en-1-ol and (1R)-1-(6-{(3R)-3-Methyl-4-[5-trifluoromethyl-7-(3,4,5-trifluoro-phenyl)-1H-benzoimidazol-2-yl]-piperazin-1-yl}-5-trifluoromethyl-pyridin-3-yl)-prop-2-en-1-ol 6-{(3R)-3-Methyl-4-[6-trifluoromethyl-4-(3,4,5-trifluoro-phenyl)-1H-benzoimidazol-2-yl]-piperazin-1-yl}-5-trifluoromethyl-pyridine-3-carbaldehyde (88 mg, 0.15 mmol, Example 184a) in THF (2 mL) reacted with C₂H₃MgBr (0.19 mL, 0.19 mmol, Aldrich) under the conditions of Example 154b to give the title compound as a mixture of diastereoisomers. MS (pos. ion) m/e: 616 (M+1).

Example 186

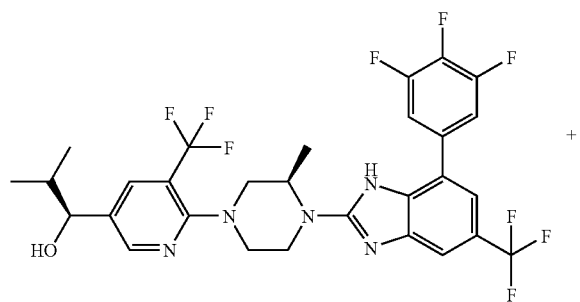

+

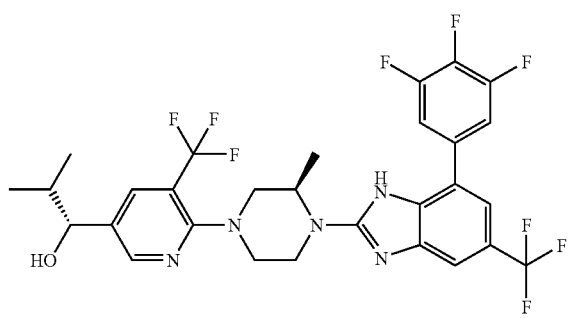

(1S)-2-Methyl-1-(6-{(3R)-3-methyl-4-[5-trifluoromethyl-7-(3,4,5-trifluoro-phenyl)-1H-benzoimidazol-2-yl]-piperazin-1-yl}-5-trifluoromethyl-pyridin-3-yl)-propan-1-ol and (1R)-2-Methyl-1-(6-{(3R)-3-methyl-4-[5-trifluoromethyl-7-(3,4,5-trifluoro-phenyl)-1H-benzoimidazol-2-yl]-piperazin-1-yl}-5-trifluoromethyl-pyridin-3-yl)-propan-1-ol 6-{(3R)-3-Methyl-4-[6-trifluoromethyl-4-(3,4,5-trifluoro-phenyl)-1H-benzoimidazol-2-yl]-piperazin-1-yl}-5-trifluoromethyl-pyridine-3-carbaldehyde (88 mg, 0.15 mmol, Example 184a) reacted with C₃H₇MgBr (0.09 mL, 0.18 mmol, Aldrich) under the conditions of Example 154b to give the title compound as a mixture of diastereoisomers. MS (ESI, pos. ion) m/e: 632 (M+1).

Example 187

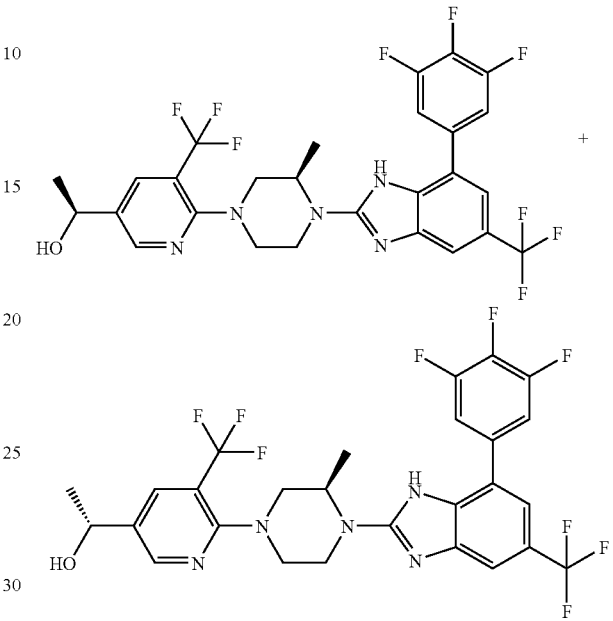

(1S)-1-(6-{(3R)-Methyl-4-[5-trifluoromethyl-7-(3,4,5-trifluoro-phenyl)-1H-benzoimidazol-2-yl]-piperazin-1-yl}-5-trifluoromethyl-pyridin-3-yl)-ethanol and (1R)-1-(6-{(3R)-3-Methyl-4-[5-trifluoromethyl-7-(3,4,5-trifluoro-phenyl)-1H-benzoimidazol-2-yl]-piperazin-1-yl}-5-trifluoromethyl-pyridin-3-yl)-ethanol 6-{(3R)-3-Methyl-4-[6-trifluoromethyl-4-(3,4,5-trifluoro-phenyl)-1H-benzoimidazol-2-yl]-piperazin-1-yl}-5-trifluoromethyl-pyridine-3-carbaldehyde (88 mg, 0.15 mmol, Example 184a) in THF (2 mL, Aldrich) reacted with CH₃MgBr (0.06 mL, 0.19 mmol, Aldrich) under the conditions of Example 154b to give the title compound as a mixture of diastereoisomers. MS ESI, pos. ion) m/e: 604 (M+1).

Example 188

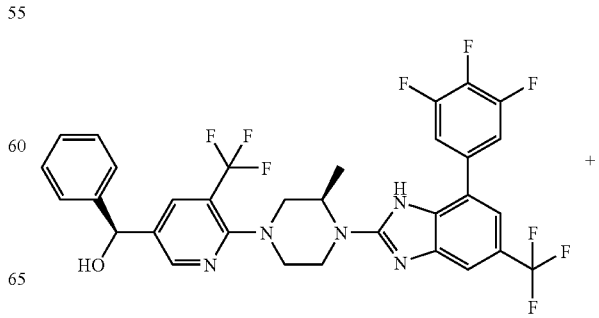

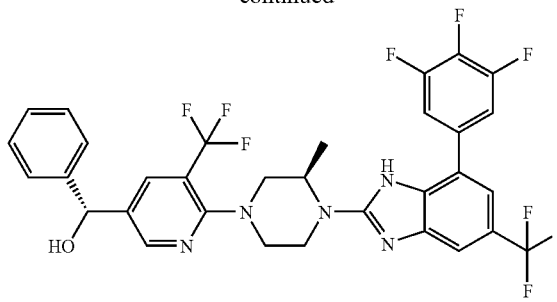

(1S)-1-(6-{(3R)-3-Methyl-4-[5-trifluoromethyl-7-(3,4,5-trifluoro-phenyl)-1H-benzoimidazol-2-yl]-piperazin-1-yl}-5-trifluoromethyl-pyridin-3-yl)-1-phenyl-methanol and (1R)-1-(6-{(3R)-3-Methyl-4-[5-trifluoromethyl-7-(3,4,5-trifluoro-phenyl)-1H-benzoimidazol-2-yl]-piperazin-1-yl}-5-trifluoromethyl-pyridin-3-yl)-1-phenyl-methanol.

6-{(3R)-3-Methyl-4-[6-trifluoromethyl-4-(3,4,5-trifluoro-phenyl)-1H-benzoimidazol-2-yl]-piperazin-1-yl}-5-trifluoromethyl-pyridine-3-carbaldehyde (88 mg, 0.15 mmol, Example 184a) reacted with C$_6$H$_5$MgBr (0.19 mL, 0.19 mmol, Aldrich) under the conditions of Example 154b to give the title compound as a mixture of diastereoisomers. MS ESI, pos. ion) m/e: 666 (M+1).

Example 189

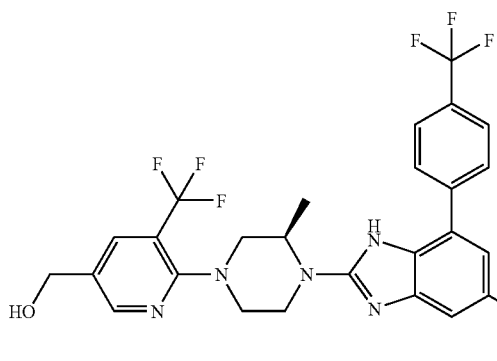

(6-{(3R)-3-Methyl-4-[5-trifluoromethyl-7-(4-trifluoromethyl-phenyl)-1H-benzoimidazol-2-yl]-piperazin-1-yl}-5-trifluoromethyl-pyridin-3-yl)-methanol (a) 6-trifluoromethyl-4-(4-trifluoromethyl-phenyl)-1,3-dihydro-benzoimidazol-2-one 4-Bromo-6-trifluoromethyl-1,3-dihydro-benzoimidazol-2-one 562 mg, 2.0 mmol, Example 6a) reacted with 4-trifluoromethylphenylboronic acid (760 mg, 4.0 mmol, Aldrich) under the conditions of Example 10 to give the title compound as a white solid. MS (ESI, neg. ion) m/z: 345 (M−1).

(b) 2-Chloro-6-trifluoromethyl-4-(3,4,5-trifluoro-phenyl)-1H-benzoimidazole

6-Trifluoromethyl-4-(4-trifluoromethyl-phenyl)-1,3-dihydro-benzoimidazol-2-one from step (a) above (8.6 g, 25 mmol) reacted with POCl$_3$ (50 mL, Aldrich) under the conditions of Example 1c to give the title compound as a white solid. MS (ESI, pos. ion) m/e: 364 (M+1).

(c) (6-{(3R)-3-Methyl-4-[5-trifluoromethyl-7-(4-trifluoromethyl-phenyl)-1H-benzoimidazol-2-yl]-piperazin-1-yl}-5-trifluoromethyl-pyridin-3-yl)-methanol 2-Chloro-6-trifluoromethyl-4-(3,4,5-trifluoro-phenyl)-1H-benzoimidazole from step (b) above (1.09 g, 3.0 mmol) reacted with {5-chloro-6-[(3R)-3-methyl-piperazin-1-yl]-pyridin-3-yl}-methanol (723 mg, 3.0 mmol, Example 183 g) under the conditions of Example 3c to give the title compound as a white solid. MS ESI, pos. ion) m/e: 570 (M+1).

Example 190

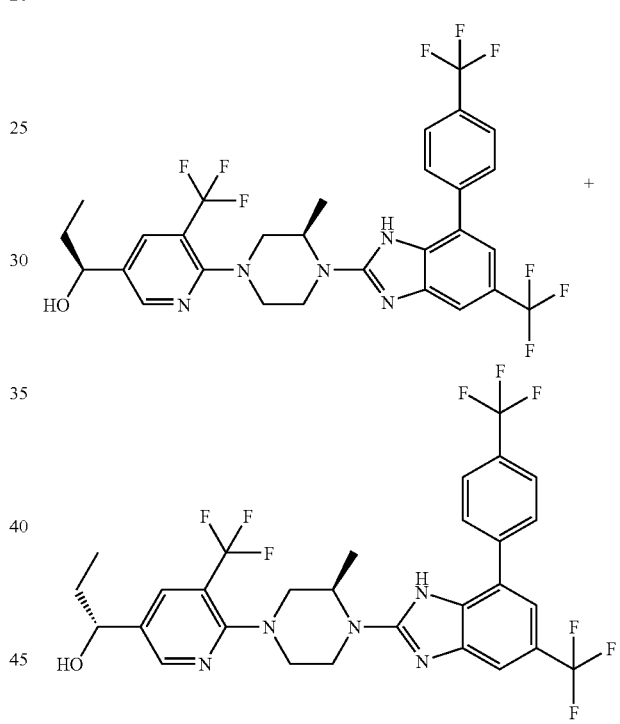

(1S)-1-(6-{(3R)-3-Methyl-4-[5-trifluoromethyl-7-(4-trifluoromethyl-phenyl)-1H-benzoimidazol-2-yl]-piperazin-1-yl}-5-trifluoromethyl-pyridin-3-yl)-propan-1-ol and (1R)-1-(6-{(3R)-3-Methyl-4-[5-trifluoromethyl-7-(4-trifluoromethyl-phenyl)-1H-benzoimidazol-2-yl]-piperazin-1-yl}-5-trifluoromethyl-pyridin-3-yl)-propan-1-ol.

(a) 6-{3-Methyl-4-[5-trifluoromethyl-7-(4-trifluoromethyl-phenyl)-1H-benzoimidazol-2-yl]-piperazin-1-yl}-5-trifluoromethyl-pyridine-3-carbaldehyde (6-{(3R)-3-Methyl-4-[6-trifluoromethyl-4-(4-trifluoromethyl-phenyl)-1H-benzoimidazol-2-yl]-piperazin-1-yl}-5-trifluoromethyl-pyridin-3-yl)-methanol (422 mg, 0.7 mmol, Example 189c) reacted with MnO$_2$ (1.22 g, 14 mmol, Aldrich) under the conditions of Example 154a to give the title compound as a white solid. MS ESI, pos. ion m/e: 602 (M+1).

(b) (1S)-1-(6-{(3R)-3-Methyl-4-[5-trifluoromethyl-7-(4-trifluoromethyl-phenyl)-1H-benzoimidazol-2-yl]-piperazin-1-yl}-5-trifluoromethyl-pyridin-3-yl)-propan-1-ol and (1R)-1-(6-{(3R)-3-Methyl-4-[5-trifluoromethyl-7-(4-trifluoromethyl-phenyl)-1H-benzoimidazol-2-yl]-piperazin-1-yl}-5-trifluoromethyl-pyridin-3-yl)-propan-1-ol 6-{(3R)-3-Methyl-4-[6-trifluoromethyl-4-(4-trifluoromethyl-phenyl)-1H-benzoimidazol-2-yl]-piperazin-1-yl}-5-trifluoromethyl-pyridine-3-carbaldehyde from step (a) above (90 mg, 0.15 mmol) reacted with $C_2H_5MgBr$ (0.19 mL, 0.19 mmol, Aldrich) under the conditions of Example 154b to give the title compound as a mixture of diastereoisomers. MS (ESI, pos. ion) m/e: 632 (M+1).

Example 191

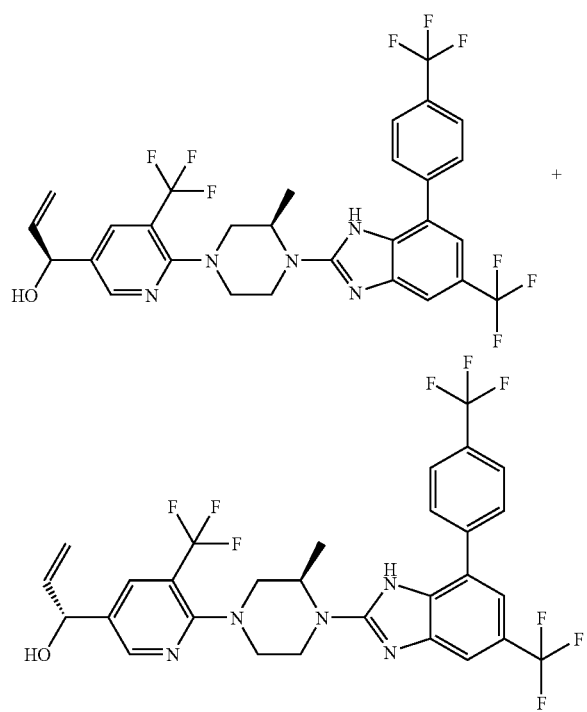

(1S)-1-(6-{(3R)-3-Methyl-4-[5-trifluoromethyl-7-(4-trifluoromethyl-phenyl)-1H-benzoimidazol-2-yl]-piperazin-1-yl}-5-trifluoromethyl-pyridin-3-yl)-prop-2-en-1-ol and (1R)-1-(6-{(3R)-3-Methyl-4-[5-trifluoromethyl-7-(4-trifluoromethyl-phenyl)-1H-benzoimidazol-2-yl]-piperazin-1-yl}-5-trifluoromethyl-pyridin-3-yl)-prop-2-en-1-ol 6-{(3R)-3-Methyl-4-[6-trifluoromethyl-4-(4-trifluoromethyl-phenyl)-1H-benzoimidazol-2-yl]-piperazin-1-yl}-5-trifluoromethyl-pyridine-3-carbaldehyde (90 mg, 0.15 mmol, Example 190a) reacted with $C_2H_3MgBr$ (0.19 mL, 0.19 mmol, Aldrich) under the conditions of Example 154b to give the title compound as a mixture of diastereoisomers. MS (ESI, pos. ion) m/e: 630 (M+1).

Example 192

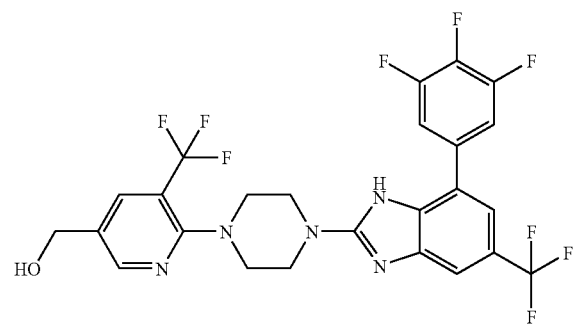

(5-Trifluoromethyl-6-{4-[5-trifluoromethyl-7-(3,4,5-trifluoro-phenyl)-1H-benzoimidazol-2-yl]-piperazin-1-yl}-pyridin-3-yl)-methanol (a) 4-(5-Bromo-3-trifluoromethyl-pyridin-2-yl)-piperazine-1-carboxylic Acid tert-butyl Ester 1-(5-Bromo-3-trifluoromethyl-pyridin-2-yl)-piperazine (3.4 g, 11 mmol, Example 143a) reacted with di-tert-butyl dicarbonate under the conditions of Example 182 to give the title compound as a white solid. MS (ESI, pos. ion) m/e: 310 (M-Bu+1).

(b) 4-[5-(2-Methoxycarbonyl-vinyl)-3-trifluoromethyl-pyridin-2-yl]-piperazine-1-carboxylic Acid tert-butyl Ester 4-(5-Bromo-3-trifluoromethyl-pyridin-2-yl)-piperazine-1-carboxylic acid tert-butyl ester from step (a) above (3.7 g, 9.0 mmol) reacted with methyl acrylate under the conditions of Example 183d to give the title compound as a white solid. MS (ESI, pos. ion) m/e: 316 (M−Bu+1).

(c) 4-(5-Formyl-3-trifluoromethyl-pyridin-2-yl)-piperazine-1-carboxylic Acid tert-butyl Ester 4-[5-(2-Methoxycarbonyl-vinyl)-3-trifluoromethyl-pyridin-2-yl]-piperazine-1-carboxylic acid tert-butyl ester from step (b) above (2.5 g, 6.0 mmol) reacted with $OsO_4$ (1.9 mL, 0.3 mmol, Aldrich) to give a diol intermediate, which was treated with $Pb(OAc)_4$ (3.19 g, 7.2 mmol, Aldrich) under the conditions of Example 183e to give the title compound as a gum. MS (ESI, pos. ion) m/e: 260 (M−Bu+1).

(d) 4-(5-Hydroxymethyl-3-trifluoromethyl-pyridin-2-yl)-piperazine-1-carboxylic Acid tert-butyl Ester 4-(5-Formyl-3-trifluoromethyl-pyridin-2-yl)-piperazine-1-carboxylic acid tert-butyl ester from step (c) above (1.44 g, 4.0 mmol) reacted with $NaBH_4$ (180 mg, 4.8 mmol, Aldrich) under the conditions of Example 183f to give the title compound as a gum. MS (ESI, pos. ion) m/e: 262 (M−Bu+1).

(e) (6-piperazin-1-yl-5-trifluoromethyl-pyridin-3-yl)-methanol 4-(5-Hydroxymethyl-3-trifluoromethyl-pyridin-2-yl)-piperazine-1-carboxylic acid tert-butyl ester from step (d)

above (1.08 g, 3.0 mmol) reacted with TFA (10 mL, Aldrich) under the conditions of Example 183 g to give the title compound as a white solid. MS (ESI, pos. ion) m/e: 262 (M+1).

(f) (5-Trifluoromethyl-6-{4-[5-trifluoromethyl-7-(3,4,5-trifluoro-phenyl)-1H-benzoimidazol-2-yl]-piperazin-1-yl}-pyridin-3-yl)-methanol A mixture of (6-piperazin-1-yl-5-trifluoromethyl-pyridin-3-yl)-methanol from step (e) above (131 mg, 0.5 mmol) and 2-chloro-6-trifluoromethyl-4-(3,4,5-trifluoro-phenyl)-1H-benzoimidazole (175 mg, 0.5 mmol, Example 51b) in EtOH (2 mL) reacted under the conditions of Example 3c to give the title compound as a white solid. MS (ESI, pos. ion) m/e: 576 (M+1).

Example 193

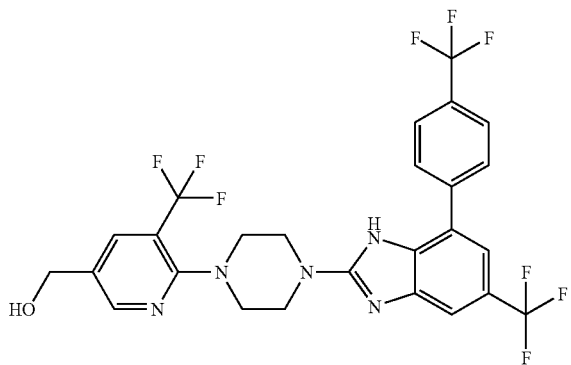

(5-Trifluoromethyl-6-{4-[5-trifluoromethyl-7-(4-trifluoromethyl-phenyl)-1H-benzoimidazol-2-yl]-piperazin-1-yl}-pyridin-3-yl)-methanol A mixture of (6-piperazin-1-yl-5-trifluoromethyl-pyridin-3-yl)-methanol (131 mg, 0.5 mmol, Example 192e) and 2-chloro-6-trifluoromethyl-4-(3,4,5-trifluoro-phenyl)-1H-benzoimidazole (181 mg, 0.5 mmol, Example 189b) in EtOH (2 mL) reacted under the conditions of Example 3c to give the title compound as a white solid. MS (ESI, pos. ion) m/e: 590 (M+1), (ESI, neg. ion) m/z: 588 (M−1).

Example 194

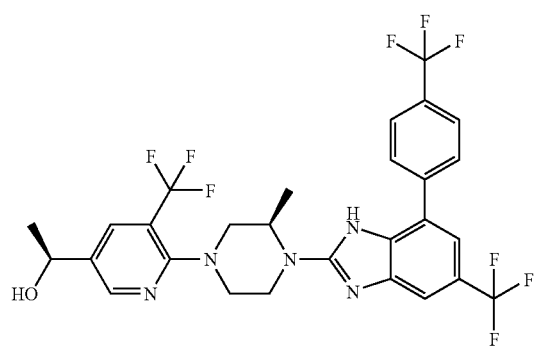

+

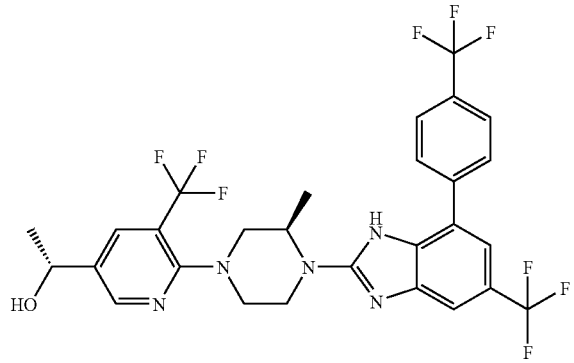

(1S)-1-(6-{(3R)-3-Methyl-4-[5-trifluoromethyl-7-(4-trifluoromethyl-phenyl)-1H-benzoimidazol-2-yl]-piperazin-1-yl}-5-trifluoromethyl-pyridin-3-yl)-ethanol and (1R)-1-(6-{(3R)-3-Methyl-4-[5-trifluoromethyl-7-(4-trifluoromethyl-phenyl)-1H-benzoimidazol-2-yl]-piperazin-1-yl}-5-trifluoromethyl-pyridin-3-yl)-ethanol.

6-{(3R)-3-Methyl-4-[6-trifluoromethyl-4-(4-trifluoromethyl-phenyl)-1H-benzoimidazol-2-yl]-piperazin-1-yl}-5-trifluoromethyl-pyridine-3-carbaldehyde (90 mg, 0.15 mmol, Example 190a) reacted with CH₃MgBr (0.07 mL, 0.19 mmol, Aldrich) under the conditions of Example 154b to give the title compound as a mixture of diastereoisomers. MS (ESI, pos. ion) m/e: 618 (M+1).

Example 195

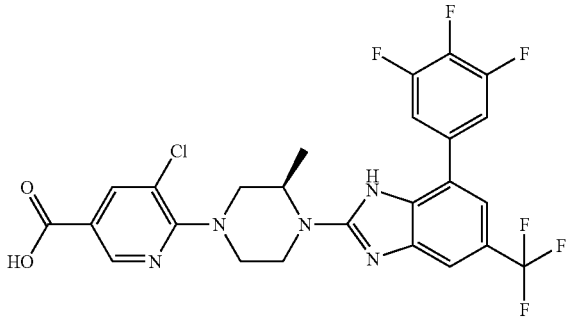

5-Chloro-6-{(3R)-3-methyl-4-[5-trifluoromethyl-7-(3,4,5-trifluoro-phenyl)-1H-benzoimidazol-2-yl]-piperazin-1-yl}-nicotinic Acid A mixture of 5-chloro-6-{(3R)-3-methyl-4-[6-trifluoromethyl-4-(3,4,5-trifluoro-phenyl)-1H-benzoimidazol-2-yl]-piperazin-1-yl}-nicotinic acid methyl ester (58 mg, 0.1 mmol, Example 178c) and 1N NaOH (0.11 mL) in THF (1 mL) was stirred at 50° C. for 16 h. 1N HCl (0.11 mL) was added and the mixture was extracted with EtOAc (2×20 mL). The combined organic extracts were washed with brine (5 mL), dried over Na₂SO₄ and filtered. The filtrate was evaporated in vacuo and the residue was purified by silica gel column chromatography, eluting with 10% MeOH/EtOAc to give the title compound as a white amorphous solid. MS (ESI, pos. ion) m/e: 570 (M+1).

Example 196

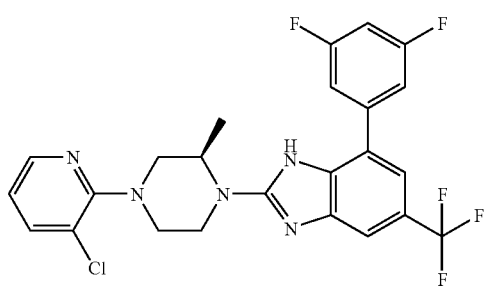

2-[(2R)-4-(3-Chloro-pyridin-2-yl)-2-methyl-piper-
azin-1-yl]-7-(3,5-difluoro-phenyl)-5-trifluoromethyl-
1H-benzoimidazole 7-Bromo-2-[(2R)-4-(3-chloropyridin-2-yl)-2-methylpiperazin-1-yl]-5-(trifluoromethyl)-1H-benzoimidazole (95 mg, 0.2 mmol, Example 77) and 3,5-difluoro-phenylboronic acid (39 mg, 0.25 mmol, Aldrich) reacted under the conditions of Example 51a to give the title compound as a white amorphous solid. MS (ESI, pos. ion) m/z: 508 (M+1).

Example 197

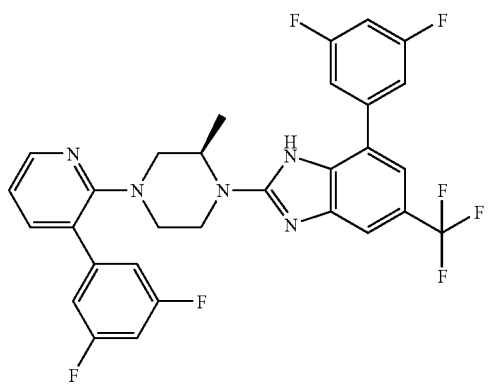

7-(3,5-Difluoro-phenyl)-2-{(2R)-4-[3-(3,5-difluoro-phenyl)-pyridin-2-yl]-2-methyl-piperazin-1-yl}-5-trifluoromethyl-1H-benzoimidazole The title compound was isolated as a side product of the reaction described in Example 196. MS (ESI, pos. ion) m/z: 586 (M+1).

Example 198

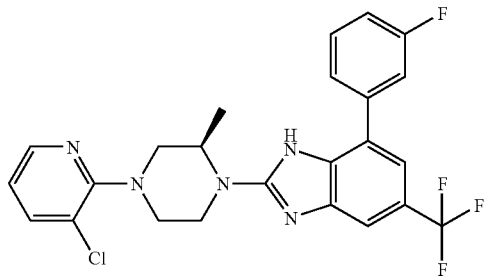

2-[(2R)-4-(3-Chloro-pyridin-2-yl)-2-methyl-piperazin-1-yl]-7-(3-fluoro-phenyl)-5-trifluoromethyl-1H-benzoimidazole 7-Bromo-2-[(2R)-4-(3-chloropyridin-2-yl)-2-methylpiperazin-1-yl]-5-(trifluoromethyl)-1H-benzoimidazole (95 mg, 0.2 mmol, Example 77) and 3-fluoro-phenylboronic acid (35 mg, 0.25 mmol, Aldrich) reacted under the conditions of Example 51a to give the title compound as a white amorphous solid. MS (ESI, pos. ion) m/z: 490 (M+1).

Example 199

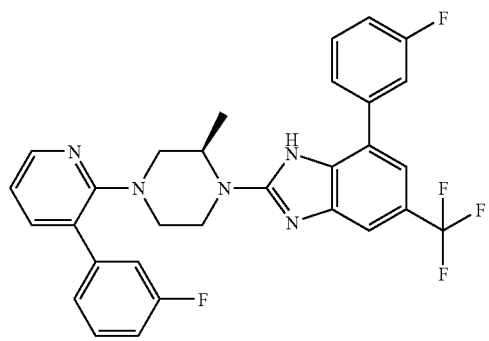

7-(3-Fluoro-phenyl)-2-{(2R)-4-[3-(3-fluoro-phenyl)-pyridin-2-yl]-2-methyl-piperazin-1-yl}-5-trifluoromethyl-1H-benzoimidazole The title compound was isolated as a side product of the reaction described in Example 198. MS (ESI, pos. ion) m/z: 550 (M+1).

Example 200

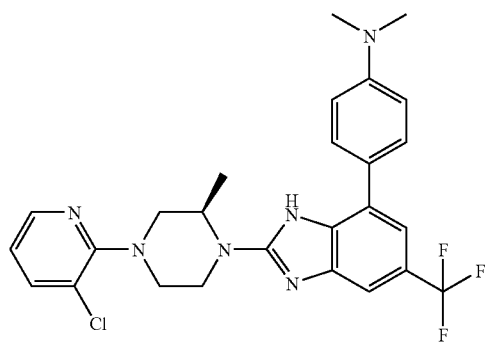

(4-{2-[(2R)-4-(3-Chloro-pyridin-2-yl)-2-methyl-piperazin-1-yl]-6-trifluoromethyl-3H-benzoimidazol-4-yl}-phenyl)-dimethyl-amine 7-Bromo-2-[(2R)-4-(3-chloropyridin-2-yl)-2-methylpiperazin-1-yl]-5-(trifluoromethyl)-1H-benzoimidazole (95 mg, 0.2 mmol, Example 77) and 4-(N,N-dimethylamino)phenylboronic acid (41 mg, 0.25 mmol, Aldrich) reacted under the conditions of Example 51a to give the title compound as a white amorphous solid. MS (ESI, pos. ion) m/z: 515 (M+1).

Example 201

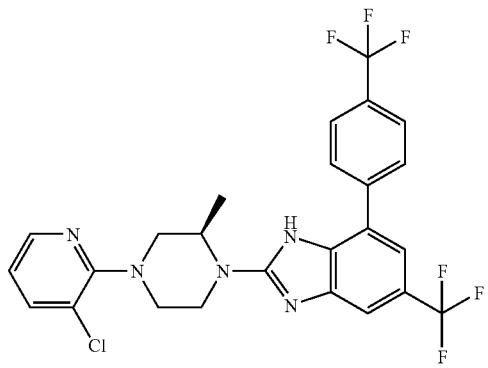

2-[(2R)-4-(3-Chloro-pyridin-2-yl)-2-methyl-piperazin-1-yl]-5-trifluoromethyl-7-(4-trifluoromethylphenyl)-1H-benzoimidazole 7-Bromo-2-[(2R)-4-(3-chloropyridin-2-yl)-2-methylpiperazin-1-yl]-5-(trifluoromethyl)-1H-benzoimidazole (95 mg, 0.2 mmol, Example 77) and 4-(trifluoromethyl)phenylboronic acid (47 mg, 0.25 mmol, Aldrich) reacted under the conditions of Example 51a to give the title compound as a white amorphous solid. MS (ESI, pos. ion) m/z: 515 (M+1).

Example 202

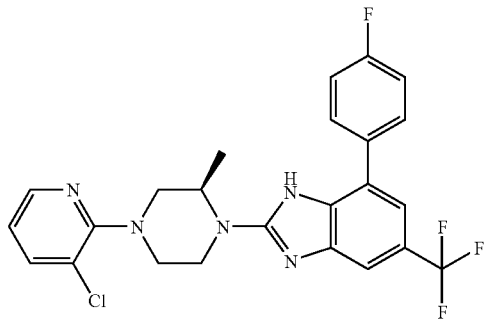

2-[(2R)-4-(3-Chloro-pyridin-2-yl)-2-methyl-piperazin-1-yl]-7-(4-fluoro-phenyl)-5-trifluoromethyl-1H-benzoimidazole 7-Bromo-2-[(2R)-4-(3-chloropyridin-2-yl)-2-methylpiperazin-1-yl]-5-(trifluoromethyl)-1H-benzoimidazole (95 mg, 0.2 mmol, Example 77) and 4-fluoro-phenylboronic acid (35 mg, 0.25 mmol, Aldrich) reacted under the conditions of Example 51a to give the title compound as a white amorphous solid. MS (ESI, pos. ion) m/z: 490 (M+1).

Example 203

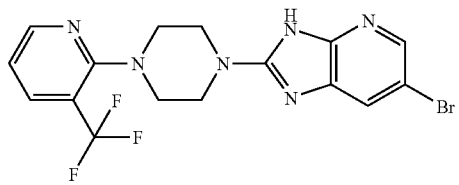

5-Bromo-2-{4-[3-(trifluoromethyl)pyridin-2-yl]piperazin-1-yl}-1H-imidazo[4,5-b]pyridine (a) 6-Bromo-1,3-dihydro-2H-imidazo[4,5-b]pyridin-2-one A mixture of 2,3-diamino-5-bromopyridine (0.94 g, 5 mmol, Aldrich) and disuccinimido carbonate (1.28 g, 5 mmol, Aldrich) in chloroform (50 mL) was heated at reflux for 12 h. The solvent was removed in vacuo and the residue was purified by recrystallization from 40% EtOAc/hexane to give the title compound as a brown solid. MS (ESI, pos. ion) m/z: 214 (M+1).

(b) 6-Bromo-2-chloro-3H-imidazo[4,5-b]pyridine

The pyridin-2-one from step (a) above (1 g, 4.7 mmol) reacted with POCl$_3$ under the conditions of Example 1c to give the title compound as a brown solid. MS (ESI, pos. ion) m/z: 232 (M+1).

(c) 5-Bromo-2-{4-[3-(trifluoromethyl)pyridin-2-yl]piperazin-1-yl}-1H-imidazo[4,5-b]pyridine The imidazo[4,5-b]pyridine from step (b) above (46 mg, 0.2 mmol) reacted with 1-(3-trifluoromethylpyridin-2-yl)piperazine (69 mg, 0.3 mmol, Maybridge) under the conditions of Example 3c to give the title compound as a white amorphous solid. MS (ESI, pos. ion) m/z: 427 (M+1).

Example 204

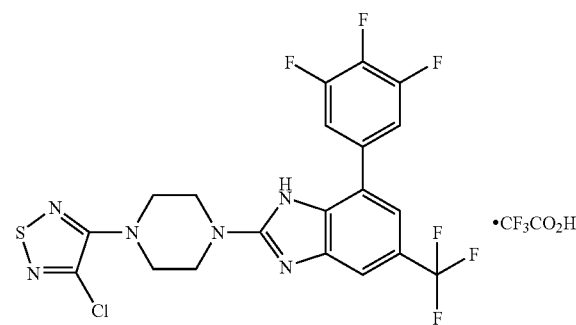

2-[4-(4-Chloro-[1,2,5]thiadiazol-3-yl)-piperazin-1-yl]-5-trifluoromethyl-7-(3,4,5-trifluoro-phenyl)-1H-benzoimidazole, Trifluoroacetic Acid Salt A mixture of 3,4-dichloro-[1,2,5]thiadiazole (30 μL, 0.32 mmol, Aldrich), 2-piperazin-1-yl-5-trifluoromethyl-7-(3,4,5-trifluoro-phenyl)-1H-benzoimidazole (65 mg, 0.16 mmol, Example 104a) and N,N-diisopropylethylamine (0.1 mL, 0.58 mmol) in 4:1 dioxane/DMSO (2.5 mL) was subjected to microwave irradiation at 190° C. for 15 min. The mixture was cooled to room temperature and filtered. The filtrate was evaporated in vacuo and the residue was purified by preparative HPLC (gradient 0.1% trifluoroacetic acid in acetonitrile) to give the title compound as an amorphous solid. MS (ESI, positive ion) m/z: 519 (M+1).

Additional Examples

TABLE 1

The following examples were prepared from 2-chloro-6-trifluoromethyl-1H-benzoimidazole (Example 1c) and commercially available piperazines according to the general procedure described for the preparation of Example 1d.

| Ex. | Structure | Melt. Point (° C.) | M.S. (ESI) m/z |
|---|---|---|---|
| 205 | 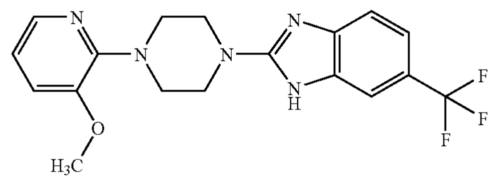 | 259 | 378 (M + 1) |
| 206 | 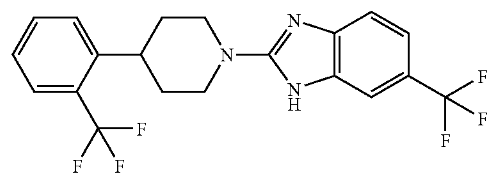 | 274-275 | 414 (M + 1) |
| 207 | 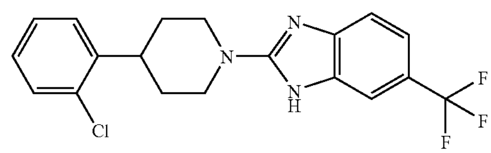 | 221-224 | 381 (M + 1) |
| 208 | 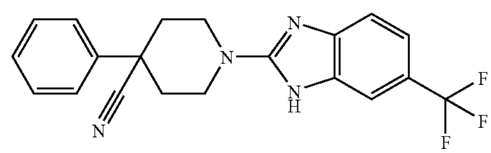 | 215-216 | 371 (M + 1) |
| 209 | 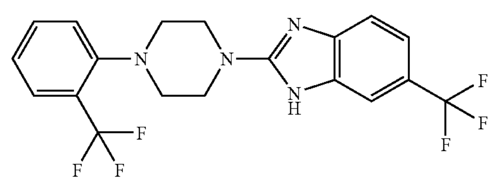 | 268-269 | 415 (M + 1) |
| 210 | 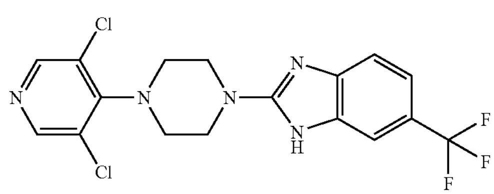 | amorphous solid | 416 (M + 1) |
| 211 | 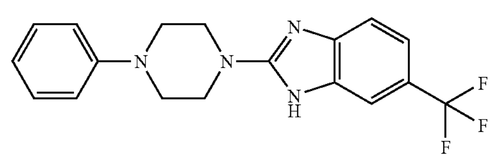 | amorphous solid | 347 (M + 1) |

TABLE 1-continued

The following examples were prepared from 2-chloro-6-trifluoromethyl-1H-benzoimidazole (Example 1c) and commercially available piperazines according to the general procedure described for the preparation of Example 1d.

| Ex. | Structure | Melt. Point (° C.) | M.S. (ESI) m/z |
|-----|-----------|--------------------|----------------|
| 212 | 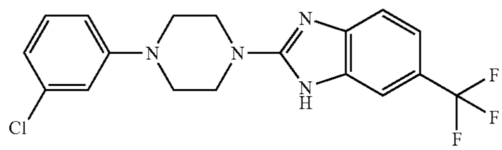 | amorphous solid | 381 (M + 1) |
| 213 | 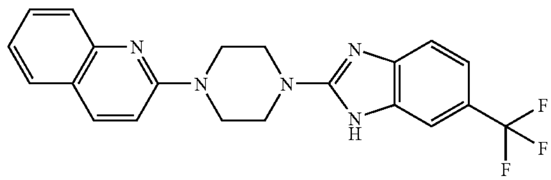 | amorphous solid | 398 (M + 1) |
| 214 | 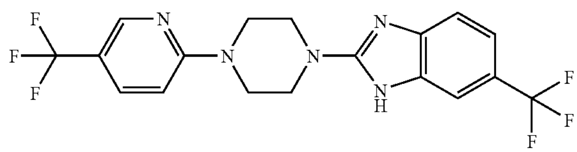 | 214 | 416 (M + 1) |
| 215 | 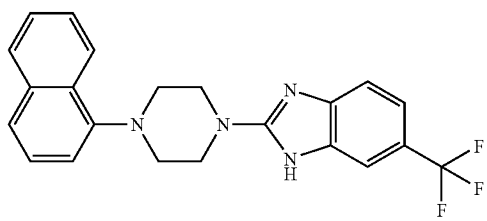 | 258-261 | 397 (M + 1) |
| 216 | 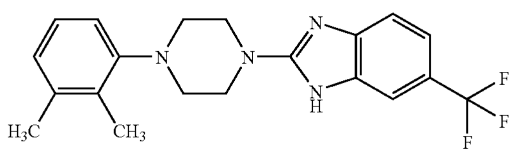 | 272-273 | 375 (M + 1) |
| 217 | 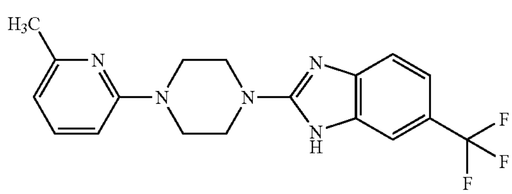 | amorphous solid | 362 (M + 1) |
| 218 | 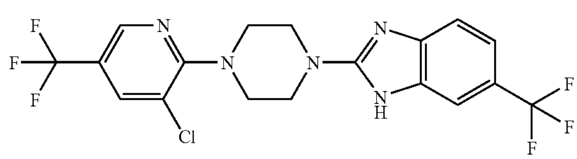 | amorphous solid | 450 (M + 1) |
| 219 | 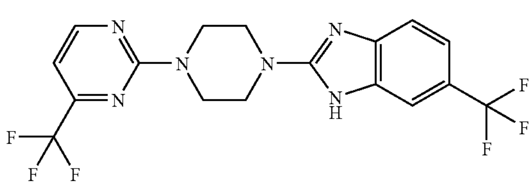 | amorphous solid | 417 (M + 1) |

TABLE 1-continued

The following examples were prepared from 2-chloro-6-trifluoromethyl-1H-benzoimidazole (Example 1c) and commercially available piperazines according to the general procedure described for the preparation of Example 1d.

| Ex. | Structure | Melt. Point (° C.) | M.S. (ESI) m/z |
|---|---|---|---|
| 220 | 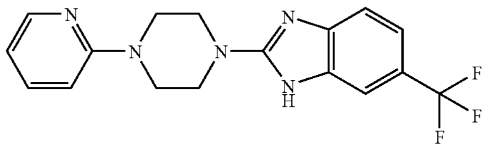 | 245 | 348 (M + 1) |
| 221 | 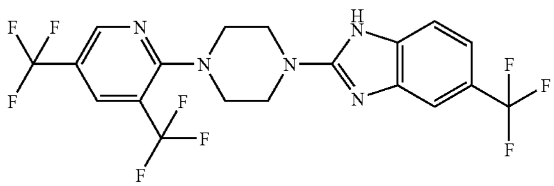 | amorphous solid | 484 (M + 1) |
| 222 | 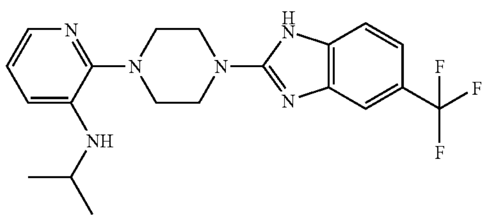 | amorphous solid | 405 (M + 1) |
| 223 | 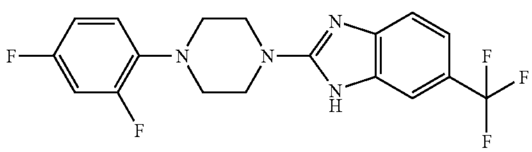 | amorphous solid | 383.4 |
| 224 | 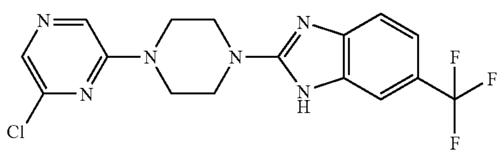 | amorphous solid | 383.6 |

TABLE 2

The following examples were prepared from 2-piperazin-1-yl-6-trifluoromethyl-1H-benzoimidazole (Example 2a) and commercially available reagents according to the general procedures described for the preparation of Example 2b and/or Example 3a.

| Ex. | Structure | Melt. Point (° C.) | M.S. (ESI) m/z |
|---|---|---|---|
| 225 | 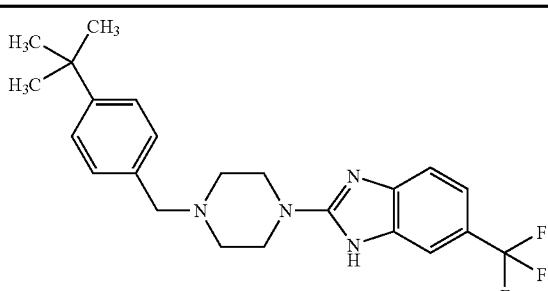 | 209-211 | 417 (M + 1) |

TABLE 2-continued

The following examples were prepared from 2-piperazin-1-yl-6-trifluoromethyl-1H-benzoimidazole (Example 2a) and commercially available reagents according to the general procedures described for the preparation of Example 2b and/or Example 3a.

| Ex. | Structure | Melt. Point (° C.) | M.S. (ESI) m/z |
|---|---|---|---|
| 226 | 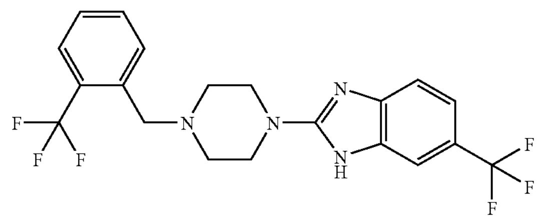 | 242-244 | 429 (M + 1) |
| 227 | 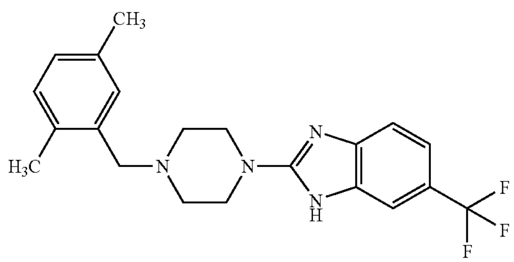 | amorphous solid | 389 (M + 1) |
| 228 | 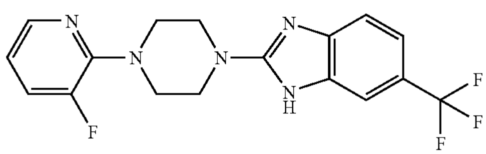 | amorphous solid | 366 (M + 1) |
| 229 | 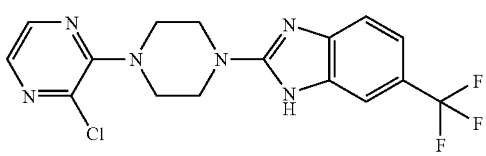 | amorphous solid | 383 (M + 1) |
| 230 | 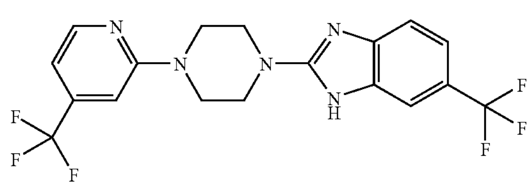 | amorphous solid | 416 (M + 1) |
| 231 | 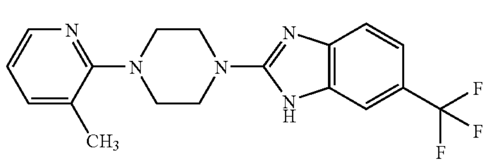 | amorphous solid | 362 (M + 1) |

TABLE 3
The following examples were prepared from commercially available 2-chloropyridines, piperazines and 2-chloro-6-trifluoromethyl-1H-benzoimidazole (Example 1c) according to the general procedure described for the preparation of Example 9.
| Ex. | Structure | Melt. Point (° C.) | M.S. (ESI) m/z |
|---|---|---|---|
| 232 | 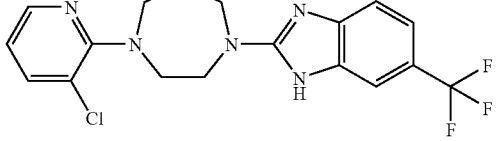 | amorphous solid | 396 (M + 1) |
| 233 | 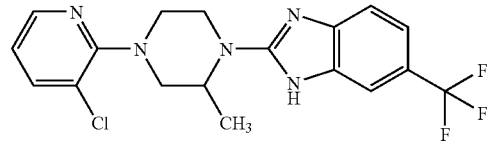 | 186-188 | 396 (M + 1) |
| 234 | 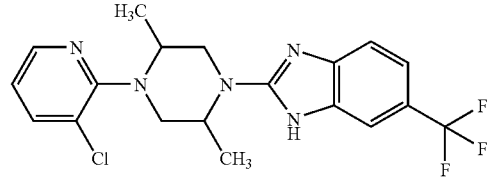 | 179-181 | 410 (M + 1) |
| 235 | 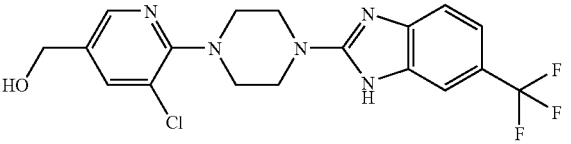 | 162-165 | 412 (M + 1) |
| 236 | 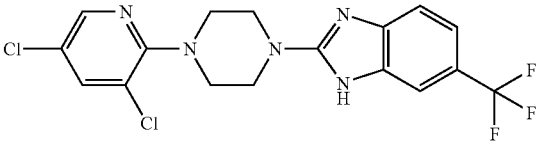 | 129-131 | 416 (M + 1) |
| 237 | 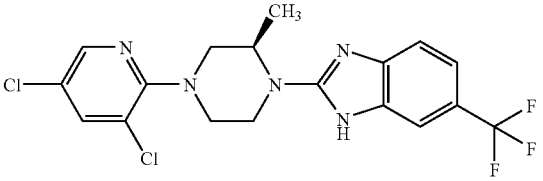 | 184-189 | 430 (M + 1) |
| 238 | 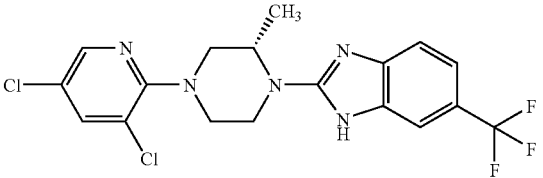 | 183-188 | 430 (M + 1) |
| 239 | 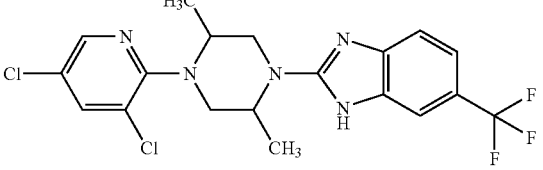 | 151-153 | 444 (M + 1) |

TABLE 3-continued

The following examples were prepared from commercially available 2-chloropyridines, piperazines and 2-chloro-6-trifluoromethyl-1H-benzoimidazole (Example 1c) according to the general procedure described for the preparation of Example 9.

| Ex. | Structure | Melt. Point (° C.) | M.S. (ESI) m/z |
|---|---|---|---|
| 240 | 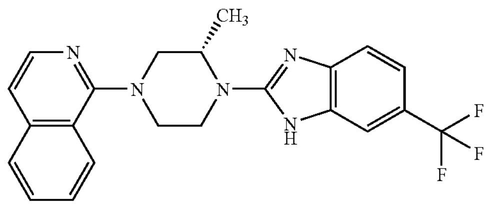 | 187-190 | 411 (M + 1) |
| 241 | 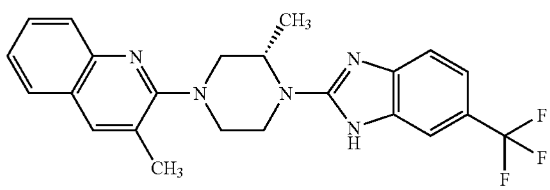 | 154 | 426 (M + 1) |
| 242 | 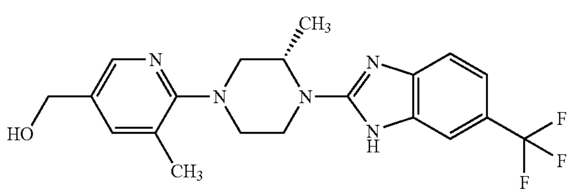 | 181 | 426 (M + 1) |
| 243 | 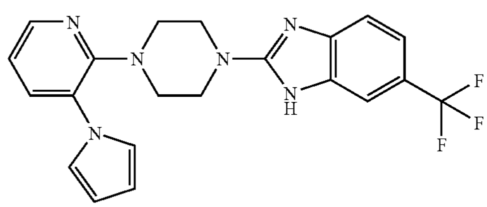 | amorphous solid | 413 (M + 1) |
| 244 | 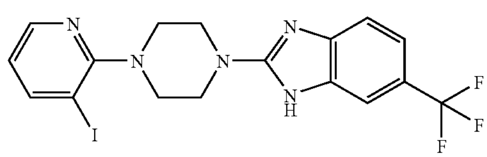 | amorphous solid | 474 (M + 1) |
| 245 | 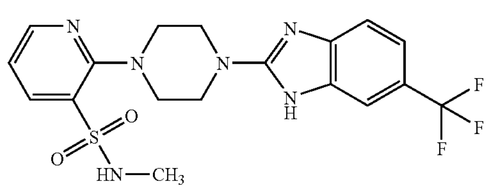 | amorphous solid | 441 (M + 1) |

TABLE 4

The following examples were prepared from commercially available 2-chloropyridines, piperazines and 4-bromo-2-chloro-6-trifluoromethyl-1H-benzoimidazole (Example 6b) according to the general procedure described for the preparation of Example 9.

| Ex. | Structure | Melt. Point (° C.) | M.S. (ESI) m/z |
|---|---|---|---|
| 246 | 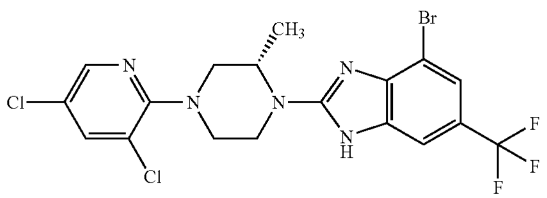 | 127-130 | 510 (M + 1) |
| 247 | 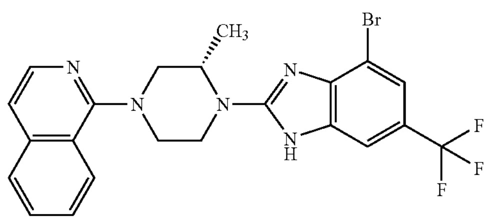 | 178-181 | 492 (M + 1) |
| 248 | 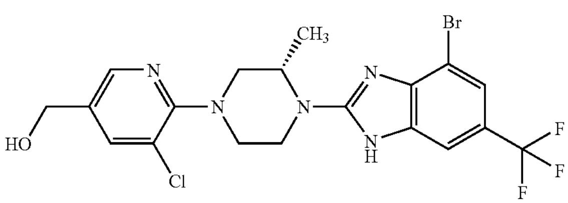 | 175 | 506 (M + 1) |

TABLE 5

The following examples were prepared from commercially available boronic acids, 4-bromo-6-trifluoromethyl-2-[4-(3-trifluoromethylpyridin-2-yl)piperazin-1-yl]-1H-benzoimidazole (Example 7) and Pd(PPh$_3$)$_4$ or PdCl$_2$(PPh$_3$)$_2$ as catalyst analogously to the general procedures described for the preparation of Example 10 or Example 51a.

| Ex. | Structure | Melt. Point (° C.) | M.S. (ESI) m/z |
|---|---|---|---|
| 249 | 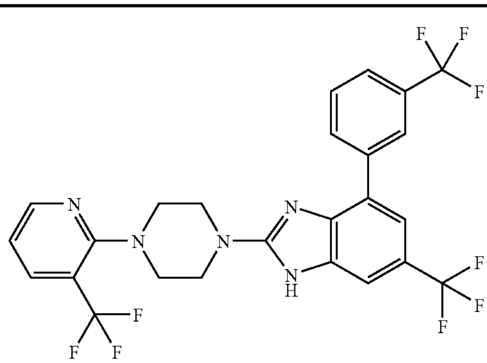 | amorphous solid | 560 (M + 1) |

TABLE 5-continued

The following examples were prepared from commercially available boronic acids, 4-bromo-6-trifluoromethyl-2-[4-(3-trifluoromethylpyridin-2-yl)piperazin-1-yl]-1H-benzoimidazole (Example 7) and Pd(PPh$_3$)$_4$ or PdCl$_2$(PPh$_3$)$_2$ as catalyst analogously to the general procedures described for the preparation of Example 10 or Example 51a.

| Ex. | Structure | Melt. Point (° C.) | M.S. (ESI) m/z |
|---|---|---|---|
| 250 | 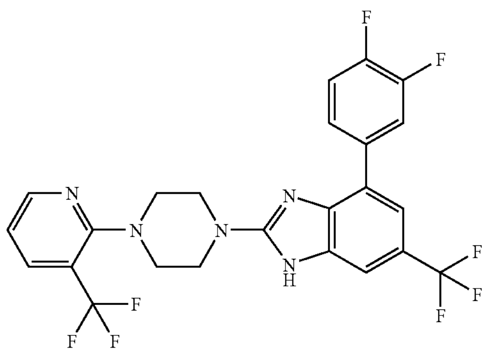 | amorphous solid | 528 (M + 1) |
| 251 | 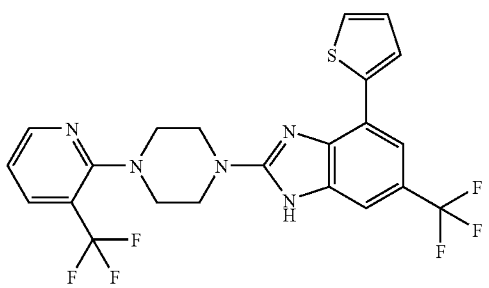 | amorphous solid | 498 (M + 1) |
| 252 | 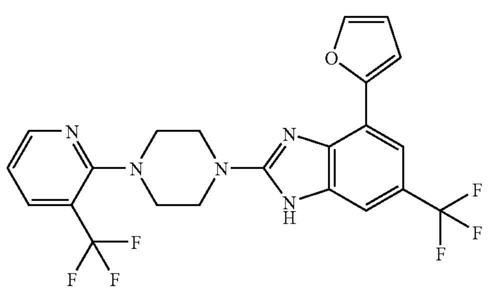 | amorphous solid | 482 (M + 1) |
| 253 | 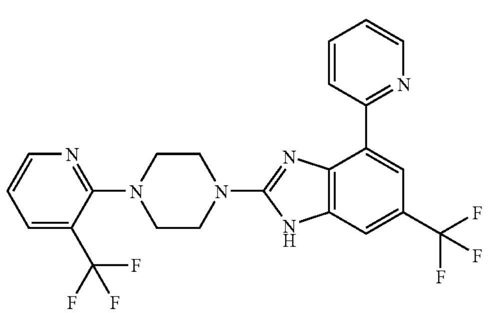 | amorphous solid | 493 (M + 1) |

TABLE 5-continued

The following examples were prepared from commercially available boronic acids, 4-bromo-6-trifluoromethyl-2-[4-(3-trifluoromethylpyridin-2-yl)piperazin-1-yl]-1H-benzoimidazole (Example 7) and Pd(PPh$_3$)$_4$ or PdCl$_2$(PPh$_3$)$_2$ as catalyst analogously to the general procedures described for the preparation of Example 10 or Example 51a.

| Ex. | Structure | Melt. Point (° C.) | M.S. (ESI) m/z |
|---|---|---|---|
| 254 | 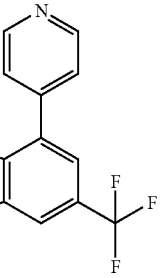 | amorphous solid | 493 (M + 1) |
| 255 | 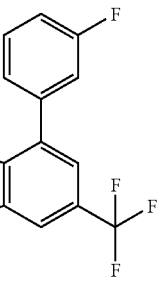 | amorphous solid | 510 (M + 1) |
| 256 | 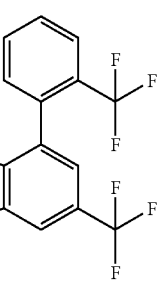 | amorphous solid | 560 (M + 1) |
| 257 | 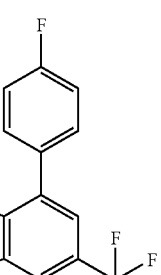 | amorphous solid | 510 (M + 1) |

TABLE 5-continued

The following examples were prepared from commercially available boronic acids, 4-bromo-6-trifluoromethyl-2-[4-(3-trifluoromethylpyridin-2-yl)piperazin-1-yl]-1H-benzoimidazole (Example 7) and Pd(PPh$_3$)$_4$ or PdCl$_2$(PPh$_3$)$_2$ as catalyst analogously to the general procedures described for the preparation of Example 10 or Example 51a.

| Ex. | Structure | Melt. Point (° C.) | M.S. (ESI) m/z |
|---|---|---|---|
| 258 | 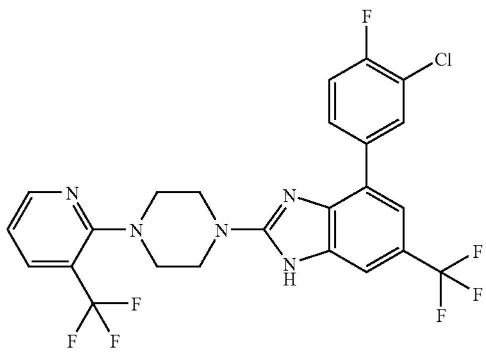 | amorphous solid | 544 (M + 1) |
| 259 | 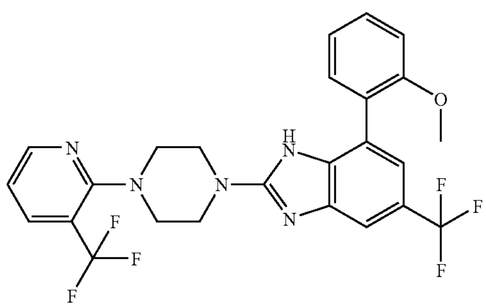 | amorphous solid | 522 (M + 1) |
| 260 | 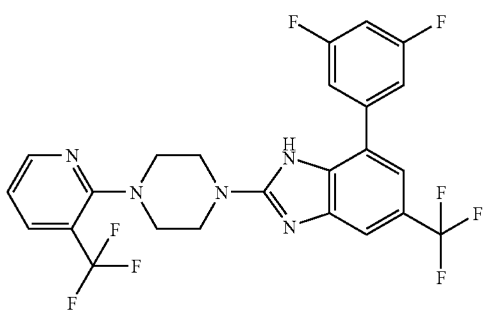 | amorphous solid | 528 (M + 1) |
| 261 | 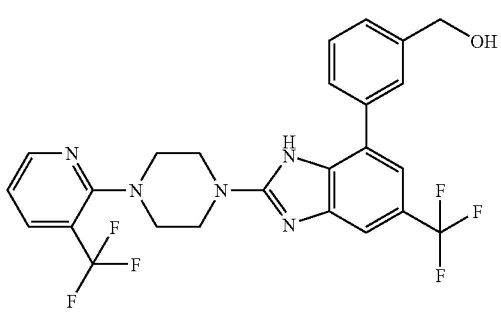 | amorphous solid | 522 (M + 1) |

TABLE 5-continued

The following examples were prepared from commercially available boronic acids, 4-bromo-6-trifluoromethyl-2-[4-(3-trifluoromethylpyridin-2-yl)piperazin-1-yl]-1H-benzoimidazole (Example 7) and Pd(PPh$_3$)$_4$ or PdCl$_2$(PPh$_3$)$_2$ as catalyst analogously to the general procedures described for the preparation of Example 10 or Example 51a.

| Ex. | Structure | Melt. Point (° C.) | M.S. (ESI) m/z |
|---|---|---|---|
| 262 | 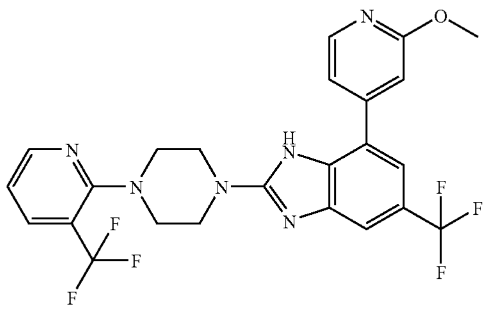 | amorphous solid | 523 (M + 1) |
| 263 | 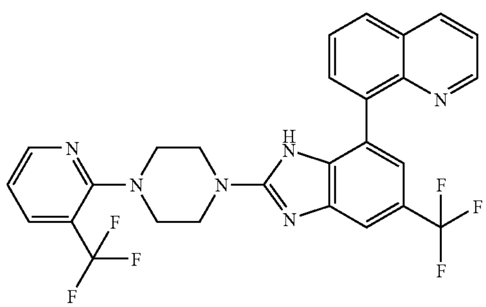 | amorphous solid | 543 (M + 1) |
| 264 | 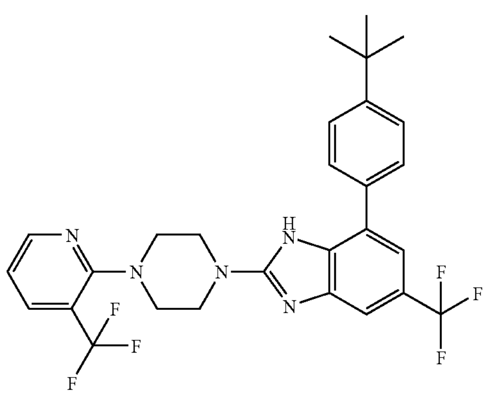 | amorphous solid | 548 (M + 1) |
| 265 | 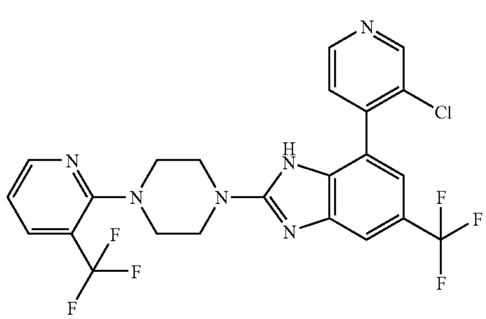 | amorphous solid | 527 (M + 1) |

TABLE 5-continued

The following examples were prepared from commercially available boronic acids, 4-bromo-6-trifluoromethyl-2-[4-(3-trifluoromethylpyridin-2-yl)piperazin-1-yl]-1H-benzoimidazole (Example 7) and Pd(PPh$_3$)$_4$ or PdCl$_2$(PPh$_3$)$_2$ as catalyst analogously to the general procedures described for the preparation of Example 10 or Example 51a.

| Ex. | Structure | Melt. Point (° C.) | M.S. (ESI) m/z |
|---|---|---|---|
| 266 | 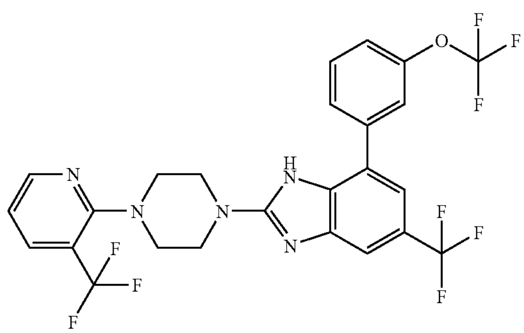 | amorphous solid | 576 (M + 1) |
| 267 | 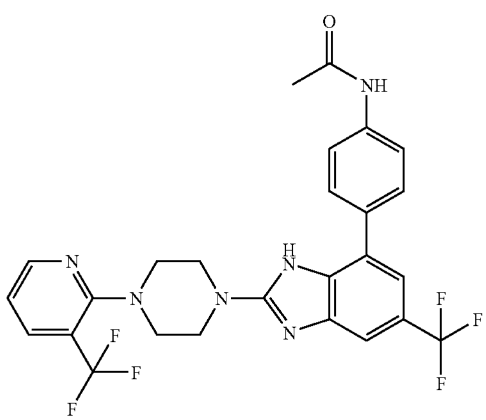 | amorphous solid | 549 (M + 1) |
| 268 | 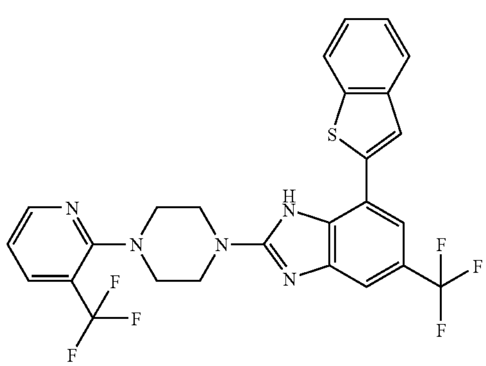 | amorphous solid | 548 (M + 1) |
| 269 | 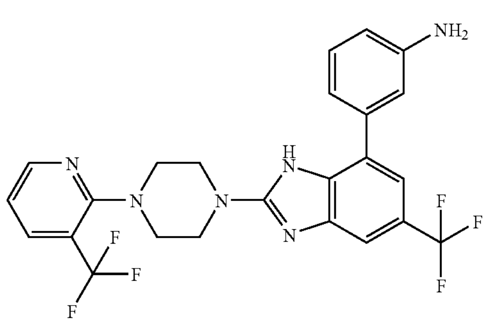 | amorphous solid | 507 (M + 1) |

TABLE 5-continued

The following examples were prepared from commercially available boronic acids, 4-bromo-6-trifluoromethyl-2-[4-(3-trifluoromethylpyridin-2-yl)piperazin-1-yl]-1H-benzoimidazole (Example 7) and Pd(PPh$_3$)$_4$ or PdCl$_2$(PPh$_3$)$_2$ as catalyst analogously to the general procedures described for the preparation of Example 10 or Example 51a.

| Ex. | Structure | Melt. Point (° C.) | M.S. (ESI) m/z |
|---|---|---|---|
| 270 | 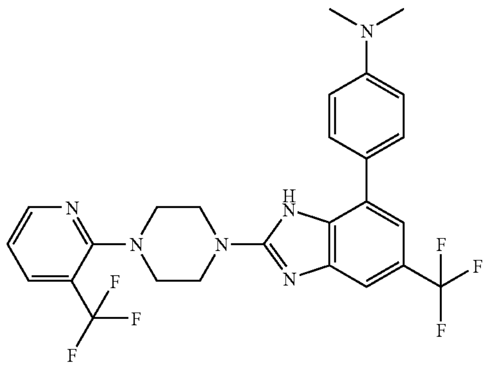 | amorphous solid | 535 (M + 1) |
| 271 | 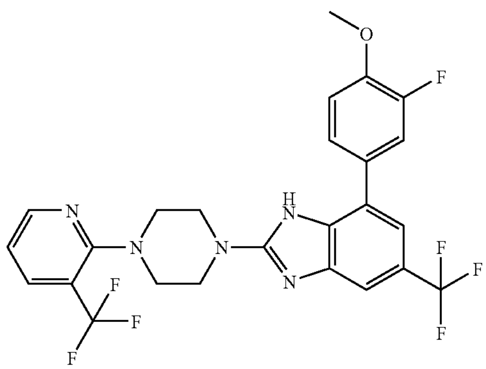 | amorphous solid | 540 (M + 1) |
| 272 | 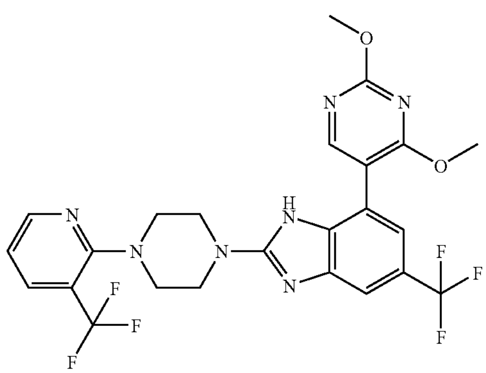 | amorphous solid | 554 (M + 1) |
| 273 | 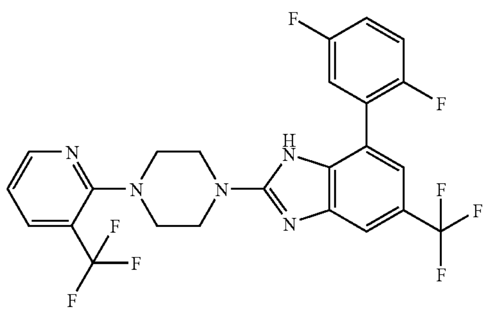 | amorphous solid | 528 (M + 1) |

TABLE 5-continued

The following examples were prepared from commercially available boronic acids, 4-bromo-6-trifluoromethyl-2-[4-(3-trifluoromethylpyridin-2-yl)piperazin-1-yl]-1H-benzoimidazole (Example 7) and Pd(PPh$_3$)$_4$ or PdCl$_2$(PPh$_3$)$_2$ as catalyst analogously to the general procedures described for the preparation of Example 10 or Example 51a.

| Ex. | Structure | Melt. Point (° C.) | M.S. (ESI) m/z |
|---|---|---|---|
| 274 | 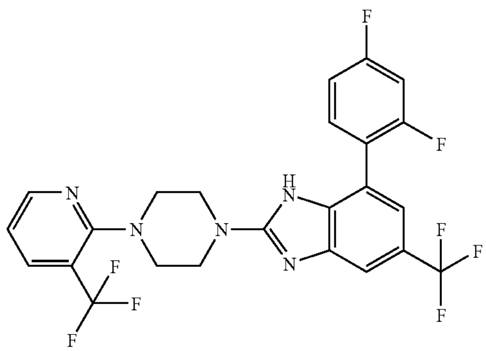 | amorphous solid | 528 (M + 1) |
| 275 | 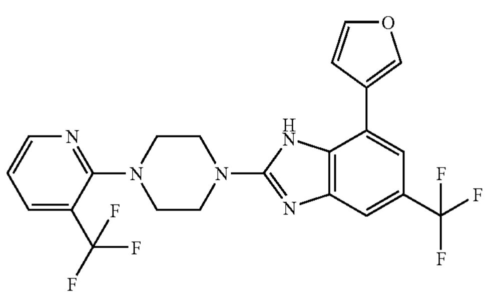 | amorphous solid | 482 (M + 1) |
| 276 | 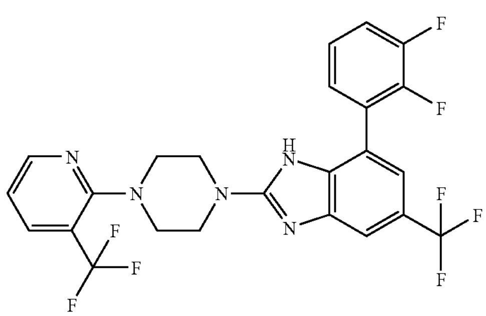 | amorphous solid | 528 (M + 1) |
| 277 | 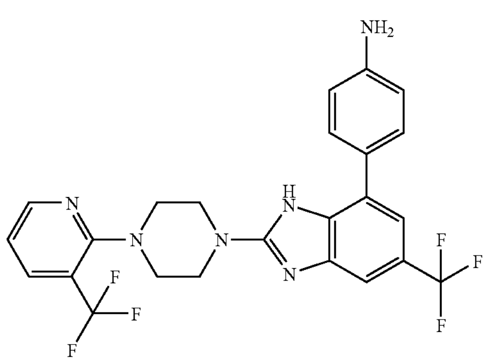 | amorphous solid | 507 (M + 1) |

TABLE 5-continued

The following examples were prepared from commercially available boronic acids, 4-bromo-6-trifluoromethyl-2-[4-(3-trifluoromethylpyridin-2-yl)piperazin-1-yl]-1H-benzoimidazole (Example 7) and Pd(PPh$_3$)$_4$ or PdCl$_2$(PPh$_3$)$_2$ as catalyst analogously to the general procedures described for the preparation of Example 10 or Example 51a.

| Ex. | Structure | Melt. Point (° C.) | M.S. (ESI) m/z |
|---|---|---|---|
| 278 | 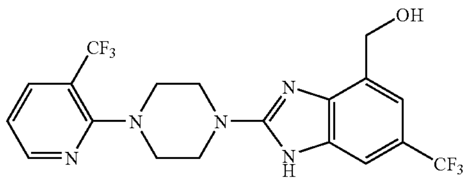 | 180-212 (decomp.) | 522 (M + 1) |
| 279 | 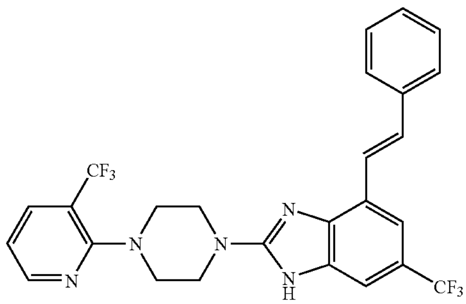 | 117.9-118 | 518 (M + 1) |
| 280 | 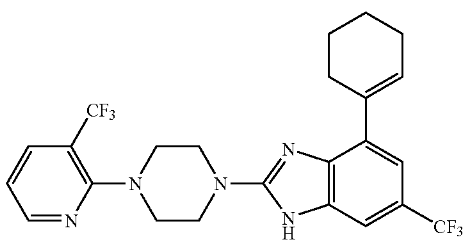 | 180-183 | 496 (M + 1) |

TABLE 6

The following examples were prepared from commercially available aldehydes and {6-[(3R)-4-(7-Amino-5-trifluoromethyl-1H-benzoimidazol-2-yl)-3-methyl-piperazin-1-yl]-5-chloro-pyridin-3-yl}-methanol methanol (Example 175b) analogously to the general procedures described for the preparation of Example 179.

| Ex. | Structure | Melt. Point (° C.) | M.S. (ESI) m/z |
|---|---|---|---|
| 281 | 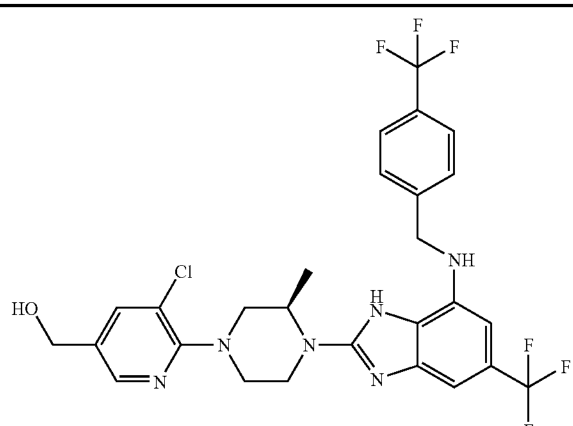 | amorphous solid | 599 (M + 1) |

TABLE 6-continued

The following examples were prepared from commercially available aldehydes and {6-[(3R)-4-(7-Amino-5-trifluoromethyl-1H-benzoimidazol-2-yl)-3-methyl-piperazin-1-yl]-5-chloro-pyridin-3-yl}-methanol methanol (Example 175b) analogously to the general procedures described for the preparation of Example 179.

| Ex. | Structure | Melt. Point (° C.) | M.S. (ESI) m/z |
|---|---|---|---|
| 282 | 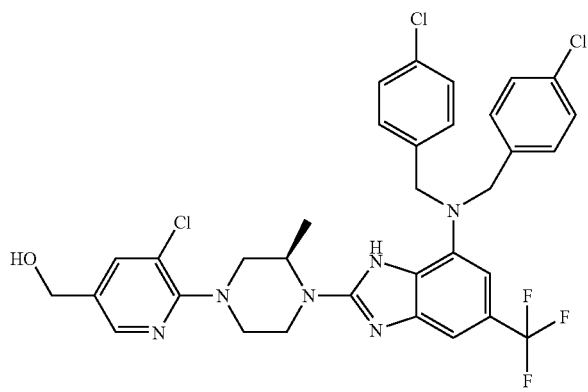 | amorphous solid | 691 (M + 1) |
| 283 | 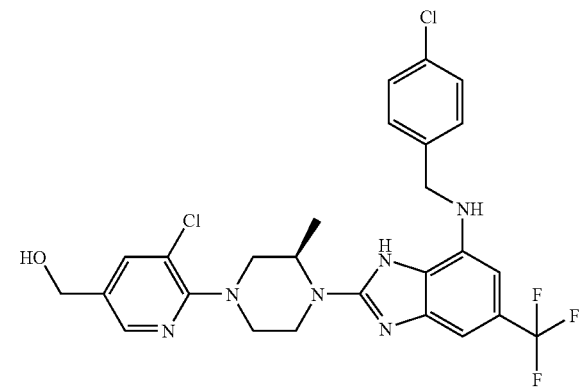 | amorphous solid | 565 (M + 1) |
| 284 | 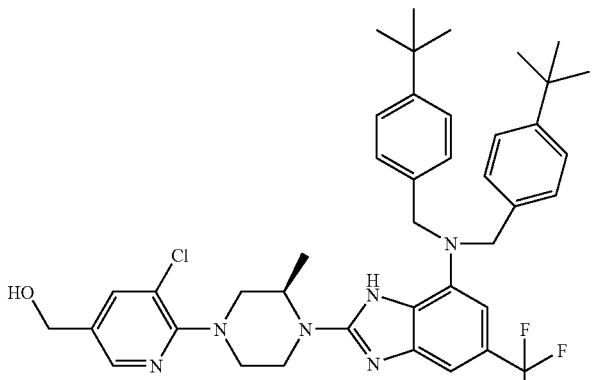 | amorphous solid | 733 (M + 1) |

TABLE 6-continued

The following examples were prepared from commercially available aldehydes and {6-[(3R)-4-(7-Amino-5-trifluoromethyl-1H-benzoimidazol-2-yl)-3-methyl-piperazin-1-yl]-5-chloro-pyridin-3-yl}-methanol methanol (Example 175b) analogously to the general procedures described for the preparation of Example 179.

| Ex. | Structure | Melt. Point (° C.) | M.S. (ESI) m/z |
|---|---|---|---|
| 285 | 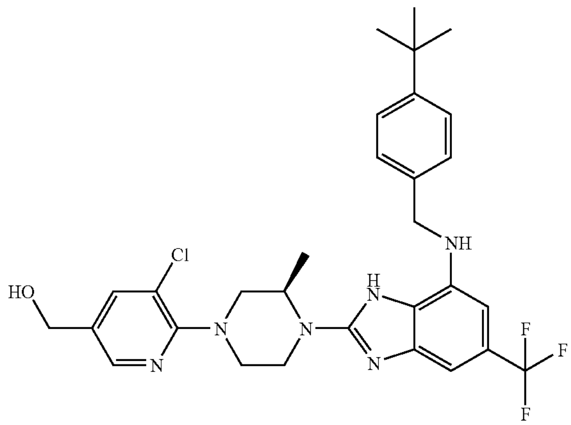 | amorphous solid | 587 (M + 1) |
| 286 | 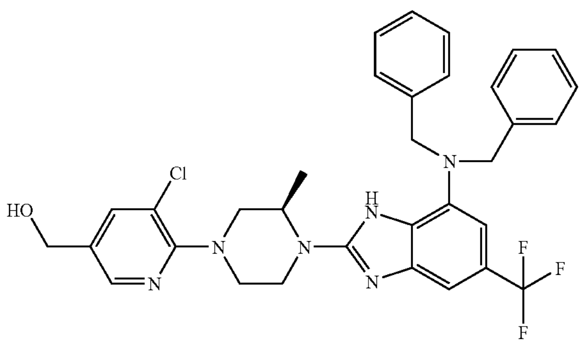 | amorphous solid | 621 (M + 1) |
| 287 | 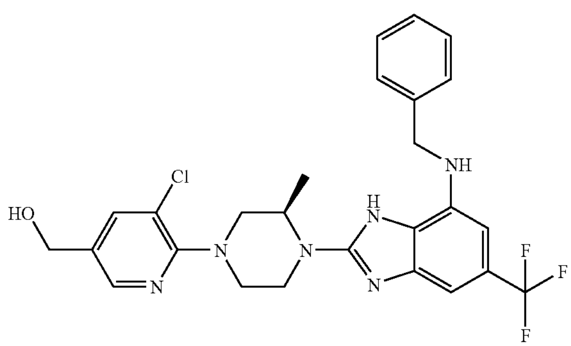 | amorphous solid | 621 (M + 1) |

Capsaicin-Induced $Ca^{2+}$ Influx in Primary Dorsal Root Ganglion Neurons

Embryonic 19 day old (E19) dorsal root ganglia (DRG) were dissected from timed-pregnant, terminally anesthetized Sprague-Dawley rats (Charles River, Wilmington, Mass.) and collected in ice-cold L-15 media (Life Technologies, Grand Island, N.Y.) containing 5% heat inactivated horse serum (Life Technologies). The DRG were then dissociated into single cell suspension using a papain dissociation system (Worthington Biochemical Corp., Freehold, N.J.). The dissociated cells were pelleted at 200×g for 5 min and re-suspended in EBSS containing 1 mg/ml ovomucoid inhibitor, 1 mg/ml ovalbumin and 0.005% DNase. Cell suspension was centrifuged through a gradient solution containing 10 mg/ml ovomucoid inhibitor, 10 mg/ml ovalbumin at 200×g for 6 min to remove cell debris; and filtered through a 88-μm nylon mesh (Fisher Scientific, Pittsburgh, Pa.) to remove any clumps. Cell number was determined with a hemocytometer and cells were seeded into poly-ornithine 100 μg/ml (Sigma) and mouse laminin 1 μg/ml (Life Technologies)-coated 96-well plates at $10 \times 10^3$ cells/well in complete medium. The complete medium consists of minimal essential medium (MEM) and Ham's F12, 1:1, penicillin (100 U/ml), and streptomycin (100 μg/ml), and nerve growth factor (10 ng/ml), 10% heat inactivated horse serum (Life Technologies). The cultures were kept at 37° C., 5% $CO_2$ and 100% humidity. For controlling the growth of non-neuronal cells, 5-fluoro-2'-deoxyuridine (75 µM) and uridine (180 µM) were included in the medium. Activation of VR1 is achieved in these cellular assays using either a capsaicin stimulus (ranging from 0.01-10 µM) or by an acid stimulus (addition of 30 mM Hepes/Mes buffered at pH 4.1). Compounds are also tested in an assay format to evaluate their agonist properties at VR1.

Capsaicin Antagonist Assay: E-19 DRG cells at 5 days in culture are incubated with serial concentrations of VR1 antagonists, in HBSS (Hanks buffered saline solution supplemented with BSA 0.1 mg/ml and 1 mM Hepes at pH 7.4) for 15 min, 37° C. Cells are then challenged with a VR1 agonist, capsaicin 200 nM, in activation buffer containing 0.1 mg/ml BSA, 15 mM Hepes, pH 7.4, and 10 µCi/ml $^{45}Ca^{2+}$ (Amersham) in Ham's F12 for 2 min at 37° C.

Acid Antagonist Assay: Compounds are pre-incubated with E-19 DRG cells for 2 minutes prior to addition of Calcium-45 in 30 mM Hepes/Mes buffer (Final Assay pH 5) and then left for an additional 2 minutes prior to compound washout. Final 45Ca (Amersham CES3-2mCi) at 10 µCi/mL.

Agonist Assay: Compounds are incubated with E-19 DRG cells for 2 minutes in the presence of Calcium-45 prior to compound washout. Final $^{45}Ca^{2+}$ (Amersham CES3-2mCi) at 10 µCi/mL.

Compound Washout and Analysis: Assay plates are washed using an ELX405 plate washer (Bio-Tek Instruments Inc.) immediately after functional assay. Wash 3× with PBS Mg2+/Ca2+ free, 0.1 mg/mL BSA. Aspirate between washes. Read plates using a MicroBeta Jet (Wallac Inc.). Compound activity is then calculated using appropriate computational algorithms.

$^{45}Calcium^{2+}$ Assay Protocol

Compounds may be assayed using Chinese Hamster Ovary cell lines stably expressing either human VR1 or rat VR1 under a CMV promoter. Cells can be cultured in Growth Medium, routinely passaged at 70% confluency using trypsin and plated in the assay plate 24 hours prior to compound evaluation.

Possible Growth Medium:
  DMEM, high glucose (Gibco 11965-084).
  10% Dialyzed serum (Hyclone SH30079.03).
  1× Non-Essential Amino Acids (Gibco 11140-050).
  1× Glutamine-Pen-Strep (Gibco 10378-016).
  Geneticin, 450 µg/mL (Gibco 10131-035).

Compounds can be diluted in 100% DMSO and tested for activity over several log units of concentration [40 µM-2 pM]. Compounds may be further diluted in HBSS buffer (pH 7.4) 0.1 mg/mL BSA, prior to evaluation. Final DMSO concentration in assay would be 0.5%. Each assay plate can be controlled with a buffer only and a known antagonist compound (either capsazepine or one of the described VR1 antagonists).

Activation of VR1 can be achieved in these cellular assays using either a capsaicin stimulus (ranging from 0.1-1 µM) or by an acid stimulus (addition of 30 mM Hepes/Mes buffered at pH 4.1). Compounds may also tested in an assay format to evaluate their agonist properties at VR1.

Capsaicin Antagonist Assay: Compounds may be pre-incubated with cells (expressing either human or rat VR1) for 2 minutes prior to addition of Calcium-45 and Capsaicin and then left for an additional 2 minutes prior to compound washout. Capsaicin (0.5 nM) can be added in HAM's F12, 0.1 mg/mL BSA, 15 mM Hepes at pH 7.4. Final $^{45}Ca$ (Amersham CES3-2mCi) at 10 µCi/mL.

Acid Antagonist Assay: Compounds can be pre-incubated with cells (expressing either human or rat VR1) for 2 minutes prior to addition of Calcium-45 in 30 mM Hepes/Mes buffer (Final Assay pH 5) and then left for an additional 2 minutes prior to compound washout. Final $^{45}Ca$ (Amersham CES3-2mCi) at 10 µCi/mL.

Agonist Assay: Compounds can be incubated with cells (expressing either human or rat VR1) for 2 minutes in the presence of Calcium-45 prior to compound washout. Final $^{45}Ca$ (Amersham CES3-2mCi) at 10 µCi/mL.

Compound Washout and Analysis: Assay plates can be washed using an ELX405 plate washer (Bio-Tek Instruments Inc.) immediately after functional assay. One can wash 3× with PBS Mg2/Ca$^{2+}$ free, 0.1 mg/mL BSA, aspirating between washes. Plates may be read using a MicroBeta Jet (Wallac Inc.). Compound activity may then calculated using appropriate computational algorithms.

Useful nucleic acid sequences and proteins may be found in U.S. Pat. Nos. 6,335,180, 6, 406,908 and 6,239,267, herein incorporated by reference in their entirety.

For the treatment of vanilloid-receptor-diseases, such as acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating vanilloid-receptor-mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, isopropoxymethyl, α-methoxyethyl, groups such as α-(($C_1$-$C_4$) alkyloxy)ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

We claim:
1. A compound having the structure:

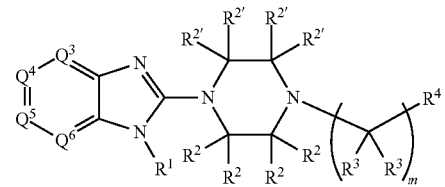

or any pharmaceutically-acceptable salt thereof, wherein:
m is independently at each instance 0, 1 or 2;
$Q^3$ is N or $C(R^5)$;
$Q^4$ is CH;
$Q^5$ is $C(CF_3)$;
$Q^6$ is N or $C(R^5)$;
$R^1$ is H or —$(C(R^2)(R^2))_m$—$R^g$;
$R^2$ is, independently, in each instance, H, $C_{1-8}$alkyl, $C_{1-4}$haloalkyl, —O($C_{1-7}$alkyl), —N($C_{1-7}$alkyl)$R^a$, or a $C_{1-6}$alkyl substituted by 1, 2 or 3 substituents selected from halo, cyano, —$OR^a$, —OC(=O)$R^b$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)N$R^aR^a$, —N($R^a$)C(=N$R^a$)N$R^aR^a$, —N($R^a$)S(=O)$_2R^b$, —$NR^aC_{2-6}$alkylN$R^aR^a$ and —$NR^aC_{2-6}$alkylO$R^a$; wherein any two geminal $R^2$ groups may additionally be oxo;
$R^{2'}$ is, independently, in each instance, H, $C_{1-8}$alkyl, $C_{1-4}$haloalkyl, —O($C_{1-7}$alkyl), —N($C_{1-7}$alkyl)$R^a$, or a $C_{1-6}$alkyl substituted by 1, 2 or 3 substituents selected from halo, cyano, —$OR^a$, —OC(=O)$R^b$, —$SR^a$, —S(=O)$R^b$, —S(=O)$_2R^b$, —S(=O)$_2NR^aR^a$, —$NR^aR^a$, —N($R^a$)C(=O)$R^b$, —N($R^a$)C(=O)$OR^b$, —N($R^a$)C(=O)N$R^aR^a$, —N($R^a$)C(=N$R^a$)N$R^aR^a$, —N($R^a$)S(=O)$_2R^b$, —$NR^aC_{2-6}$alkylN$R^aR^a$ and —NR$^a$C$_{2-6}$alkylOR$^a$; wherein any two geminal R$^{2'}$ groups may additionally be oxo;

R$^3$ is, independently, in each instance, H, C$_{1-8}$alkyl, C$_{1-4}$haloalkyl, —O(C$_{1-7}$alkyl), —N(C$_{1-7}$alkyl)R$^a$, or a C$_{1-6}$alkyl substituted by 0, 1, 2 or 3 substituents selected from halo, cyano, —OR$^a$, —OC(=O)R$^b$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —NR$^a$C$_{2-6}$alkylNR$^a$R$^a$ and —NR$^a$C$_{2-6}$alkylOR$^a$; wherein any two geminal R$^3$ groups may additionally be oxo;

R$^4$ is phenyl, wherein the phenyl and naphthyl are substituted by 1, 2, 3 or 4 substituents selected from C$_{1-8}$alkyl, C$_{1-4}$haloalkyl, halo, cyano, nitro, —C(=O)R$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$ and R$^e$; R$^5$ is independently, at each instance, H, C$_{1-8}$alkyl, C$_{1-4}$haloalkyl, halo, cyano, —C(=O)R$^b$, —C(=O)OR$^b$, —C(=O)NR$^b$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, C$_{1-3}$alkylR$^c$, C$_{1-3}$alkylR$^f$ and R$^e$; or R$^5$ is a saturated or unsaturated 5-, 6 or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2, 3 or 4 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$ and R$^b$;

R$^6$ is independently, at each instance, H, C$_{1-8}$alkyl, C$_{1-4}$haloalkyl, halo, cyano, —C(=O)R$^b$, —C(=O)OR$^b$, —C(=O)NR$^a$R$^a$, —C(=NR$^a$)NR$^a$R$^a$, —OH, —OC$_{2-6}$alkyl, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —NR$^a$R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$ and R$^e$;

R$^a$ is independently, at each instance, H or R$^b$;

R$^b$ is independently, at each instance, phenyl, benzyl or C$_{1-6}$alkyl, the phenyl, benzyl and C$_{1-6}$alkyl being substituted by 0, 1, 2 or 3 substituents selected from halo, C$_{1-4}$alkyl, C$_{1-3}$haloalkyl, —OC$_{1-4}$alkyl, —NH$_2$, —NHC$_{1-4}$alkyl, —N(C$_{1-4}$alkyl)C$_{1-4}$alkyl;

R$^c$ is independently at each instance a saturated or unsaturated 5-, 6- or 7-membered monocyclic or 6-, 7-, 8-, 9-, 10- or 11-membered bicyclic ring containing 1, 2, 3 or 4 atoms selected from N, O and S, wherein the carbon atoms of the ring are substituted by 0, 1 or 2 oxo groups;

R$^d$ is independently at each instance

R$^e$ is independently at each instance C$_{1-6}$alkyl substituted by 1, 2 or 3 substituents independently selected from R$^d$;

R$^f$ is independently at each instance R$^c$ substituted by 1, 2 or 3 substituents independently selected from R$^d$; and R$^g$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$.

2. The compound according to claim 1, wherein:
Q$^3$ is C(R$^5$); and
Q$^6$ is C(R$^5$).

3. The compound according to claim 1, wherein R$^1$ is H.

4. The compound according to claim 1, wherein R$^1$ is —(C(R$^2$)(R$^2$))$_m$—R$^g$.

5. The compound according to claim 1, wherein R$^2$ is, in each instance H.

6. The compound according to claim 1, wherein at least one R$^2$ group is selected from C$_{1-8}$alkyl, C$_{1-4}$haloalkyl, —O(C$_{1-7}$alkyl), —N(C$_{1-7}$alkyl)R$^a$, oxo and C$_{1-6}$alkyl substituted by 0, 1, 2 or 3 substituents selected from halo, cyano, —OR$^a$, —OC(=O)R$^b$, —SR$^a$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —NR$^a$C$_{2-6}$alkylNR$^a$R$^a$ and —NR$^a$C$_{2-6}$alkylOR$^a$.

7. The compound according to claim 1, wherein R$^3$ is, in each instance, H.

8. The compound according to claim 1, wherein at least one R$^3$ group is selected from C$_{1-8}$alkyl, C$_{1-4}$haloalkyl, —O(C$_{1-7}$alkyl), —N(C$_{1-7}$alkyl)R$^a$, oxo and C$_{1-6}$alkyl substituted by 0, 1, 2 or 3 substituents selected from halo, cyano, —OR$^a$, —OC(=O)R$^b$, —SR$^a$, —S(=O)R$^b$, —S(=O)$_2$R$^b$, —S(=O)$_2$NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —NR$^a$C$_{2-6}$alkylNR$^a$R$^a$ and —NR$^a$C$_{2-6}$alkylOR$^a$.

9. The compound according to claim 1, wherein R$^4$ is phenyl substituted by 1, 2, 3 or 4 substituents selected from C$_{1-8}$alkyl, C$_{1-4}$haloalkyl, halo, cyano, nitro, —C(=O)R$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)

$R^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$ and R$^e$.

10. The compound according to claim 1, wherein R$^5$ is independently, at each instance, H, C$_{1-8}$alkyl, C$_{1-4}$haloalkyl, halo, cyano, —C(=O)R$^b$, —C(=NR$^a$)NR$^a$R$^a$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —C$_{1-3}$alkylR$^c$, C$_{1-3}$alkylR$^f$ and R$^e$; or R$^5$ is a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2, 3 or 4 substituents selected from C$_{1-8}$alkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)W, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$ and R$^e$.

11. The compound according to claim 1, wherein R$^5$ is, at each instance, H.

12. The compound according to claim 1, wherein at least one R$^3$ is C$_{1-8}$alkyl, C$_{1-4}$haloalkyl, halo, cyano, —C(=O)R$^b$, —C(=NR$^a$)NR$^a$R$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkyl OR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, C$_{1-3}$alkylR$^c$ C$_{1-3}$alkylR$^f$ and R$^e$.

13. The compound according to claim 1, wherein at least one R$^5$ is a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2, 3 or 4 substituents selected from C$_{1-5}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(=O)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$ and R$^e$.

14. The compound according to claim 1, wherein at least one R$^5$ is an unsaturated 5-, 6- or 7-membered monocyclic ring containing 0, 1, 2 or 3 atoms selected from N, O and S, wherein the carbon atoms of the ring are substituted by 0, 1 or 2 oxo groups and the ring is substituted by 0, 1, 2, 3 or 4 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)N(R$^a$)S(=O)$_2$R$^b$, —OC$_{2-6}$alkylNR$^a$R$^a$, —OC$_{2-6}$alkylOR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$ and R$^e$.

15. The compound according to claim 1, wherein at least one R$^5$ is an unsaturated 6-membered monocyclic ring containing 0, 1 or 2 N atoms, wherein the ring is substituted by 0, 1, 2, 3 or 4 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$ and R$^e$.

16. The compound according to claim 1, wherein at least one R$^5$ is a saturated or unsaturated 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2, 3 or 4 substituents selected from C$_{1-8}$alkyl, C$_{1-4}$haloalkyl, halo, cyano, nitro, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$ and R$^e$.

17. The compound according to claim 1, wherein the compound is selected from:

2-[4-(2,6-dichlorophenyl)piperazin-1-yl]-6-trifluoromethyl-1H-benzoimidazole,

2-[4-(2,6-dichlorobenzyl)piperazin-1-yl]-6-trifluoromethyl-1H-benzoimidazole, 4-chloro-6-trifluoromethyl-2-[4-(3-trifluoromethylpyridin-2-yl)piperazin-1-yl]-1H -benzoimidazole, 2-[4-(2-chlorophenyl)piperazin-1-yl]-6-trifluoromethyl-1H-benzoimidazole, 6-trifluoromethyl-2-[4-(3-trifluoromethylphenyl)piperazin-1-yl]-1H-benzoimidazole, 2-(4-phenylpiperazin-1-yl)-6-trifluoromethyl-1H-benzoimidazole, 2-[4-(3-chlorophenyl)piperazin-1-yl]-6-trifluoromethyl-1H-benzoimidazole 2-[4-(naphthtalen-1-yl)piperazin-1-yl]-6-trifluoromethyl-1H-benzoimidazole, 2-[4-(2,3-dimethylphenyl)piperazin-1-yl]-6-trifluoromethyl-1H-benzoimidazole,
6-trifluoromethyl-2-[4-(4-trifluoromethylbenzyl)piperazin-1-yl]-1H-benzoimidazole,
6-trifluoromethyl-2-[4-(2-trifluoromethylbenzyl)piperazin-1-yl]-1H-benzoimidazole,
2-[4-(2,5-dimethylbenzyl)piperazin-1-yl]-6-trifluoromethyl-1H-benzoimidazole, 6-trifluoromethyl-4-(3-trifluoromethylphenyl)-2-[4-(3-trifluoromethylpyridin-2-yl)-2-methylpiperazin-1-yl]-1H-benzoimidazole, and
4-(3,4-difluorophenyl)-6-trifluoromethyl-2-[4-(3-trifluoromethylpyridin-2-yl)-2-methylpiperazin-1-yl]-1H-benzoimidazole.

\* \* \* \* \*